US007087225B2

(12) United States Patent
Yu et al.

(10) Patent No.: US 7,087,225 B2
(45) Date of Patent: Aug. 8, 2006

(54) METHODS AND COMPOSITIONS FOR TREATING METABOLIC BONE DISEASES RELATING TO HUMAN ENDOKINE ALPHA

(75) Inventors: Guo-Liang Yu, Berkeley, CA (US); Jian Ni, Germantown, MD (US); Craig A. Rosen, Laytonsville, MD (US); Bernadetta Nardelli, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 427 days.

(21) Appl. No.: 10/218,547

(22) Filed: Aug. 15, 2002

(65) Prior Publication Data

US 2003/0100074 A1 May 29, 2003

Related U.S. Application Data

(60) Provisional application No. 60/330,761, filed on Oct. 30, 2001, provisional application No. 60/312,542, filed on Aug. 16, 2001.

(51) Int. Cl.
*A61K 45/00* (2006.01)
*A61K 38/19* (2006.01)
*C07K 14/715* (2006.01)

(52) U.S. Cl. .................. 424/85.1; 424/192.1; 530/351; 514/12

(58) Field of Classification Search ................ 530/351; 536/23.5; 424/85.1, 185.1, 192.1; 514/12
See application file for complete search history.

(56) References Cited

U.S. PATENT DOCUMENTS

| 5,288,852 | A | 2/1994 | Yamada et al. |
| 5,998,171 | A | 12/1999 | Yu et al. |
| 6,406,867 | B1 | 6/2002 | Yu et al. |
| 6,521,742 | B1 | 6/2002 | Yu et al. |
| 2002/0099198 | A1 | 7/2002 | Yu et al. |
| 2002/0146389 | A1* | 10/2002 | Ashkenazi et al. ........ 424/85.1 |
| 2002/0168729 | A1 | 11/2002 | Yu et al. |

FOREIGN PATENT DOCUMENTS

| EP | 0 212 489 A2 | 3/1987 |
| EP | 0 218 868 A2 | 4/1987 |
| EP | 0 288 088 A2 | 11/1988 |
| WO | WO 96/14328 A1 | 5/1996 |
| WO | WO 00/50620 | 8/2000 |

OTHER PUBLICATIONS

See Locksley et al., Cell, vol. 104, pp. 487-501, Feb. 23, 2001.*
U.S. Appl. No. 09/912,293, Rosen et al., Not Published.
Aggarwal, B.B., and Natarajan, K., "Tumor necrosis factors: Developments during the last decade," *Eur. Cytokine Netw.* 7:93-124, John Libbey Eurotext (Apr.-Jun. 1996).
Beutler, B., et al., "Passive Immunization Against Cachectin/Tumor Necrosis Factor Protects Mice from Lethal Effect of Endotoxin," *Science* 229:869-871, American Association for the Advancement of Science (1985).
Bowie, J.U., et al., "Deciphering the Message in Protein Sequences: Tolerance to Amino Acid Substitutions," *Science* 247:1306-1310, American Association for the Advancement of Science (1990).
Bringman, T.S., and Aggarwal, B.B., "Monoclonal Antibodies to Human Tumor Necrosis Factors Alpha and Beta: Application for Affinity Purification, Immunoassays, and as Structural Probes," *Hybridoma* 6:489-507, Mary Ann Liebert, Inc. (1987).
Doerks, T., et al., "Protein annotation:detective work for function prediction," *Trends Genet.* 14:248-250, Elsevier Science B. V. (Jun. 1998).
Elliott, M.J., and Maini, R.N., "Anti-cytokine therapy in rheumatoid arthritis," *Baillière's Clin. Rheum.* 9:633-652, Baillière Tindall (Nov. 1995).
Feldmann, M., et al., "TNFα Is an Effective Therapeutic Target for Rheumatoid Arthritis," *Ann. N.Y. Acad. Sci.* 766:272-278, New York Academy of Sciences (Nov. 1995).
Fendly, B.M., et al., "Murine Monoclonal Antibodies Defining Neutralizing Epitopes on Tumor Necrosis Factor," *Hybridoma* 6:359-370, Mary Ann Liebert, Inc. (1987).
Gruss, H-J., and Dower, S.K., "Tumor Necrosis Factor Ligand Superfamily: Involvement in the Pathology of Malignant Lymphomas," *Blood* 85:3378-3404, W.B. Saunders Co. (Jun. 1995).
Gurney, A.L., et al., "Identification of a new member of the tumor necrosis factor family and its receptor, a human ortholog of mouse GITR," *Curr. Biol.* 9:251-218, Elsevier Science Ltd. (1999).
Hillier, L., et al. Database EST-STN on MASPAR search, WashU-Merck EST Project, (St. Louis, Mo, USA), No. R38487, "yf60c04.s1 Homo sapiens cDNA clone 26749 3'," (May 1995).

(Continued)

*Primary Examiner*—Eileen B. O'Hara
(74) *Attorney, Agent, or Firm*—Human Genome Sciences, Inc.

(57) ABSTRACT

The present invention concerns methods for diagnosis and treatment of metabolic bone diseases and disorders using a novel member of the tumor necrosis factor (TNF) family of cytokines. In particular the invention provides methods of using the Endokine alpha protein and/or homomultimeric and/or heteromultimeric polypeptide complexes containing Endokine alpha, in the diagnosis, prognosis and treatment of metabolic bone diseases and disorders. Also provided by the invention are methods of using the Endokine alpha protein and/or homomultimeric and/or heteromultimeric polypeptide complexes containing Endokine alpha, in the diagnosis, prognosis and treatment of diseases and/or disorders associated with aberrant osteoclast development and/or activity. The present invention also provides isolated polynucleotides encoding polypeptides of the invention, antibodies thereto, and agonists and antagonists thereof, for use in the diagnosis, prognosis and treatment of metabolic bone diseases and disorders.

25 Claims, 11 Drawing Sheets

OTHER PUBLICATIONS

Hillier, L., et al. Database EST-STN on MASPAR search, WashU-Merck EST Project, (St. Louis, MO., USA) No. R41403, "yf94c12.s1 Homo sapiens cDNA clone 30225 3'," (May 1995).

Hinshaw, L.B., et al., "Survival of Primates in $LD_{100}$ Septic Shock Following Therapy With Antibody to Tumor Necrosis Factor (TNFα)," *Circ. Shock* 30:279-292, Wiley-Liss, Inc. (1990).

Hirai, M., et al., "Production and characterization of monoclonal antibodies to human tumor necrosis factor," *J. Immunol. Methods* 96:57-62, Elsevier Science B.V. (1987).

Kriegeler, M., et al., "A Novel Form of TNF/Cachectin Is a Cell Surface Cytotoxic Transmembrane Protein: Ramifications for the Complex Physiology of TNF," *Cell* 53:45-53, Cell Press (1988).

Kwon, B., et al., "Identification of a Novel Activation-inducible Protein of the Tumor Necrosis Factor Receptor Superfamily and Its Ligand," *J. Biol. Chem.* 274:6056-6061, American Society for Biochemistry and Molecular Biology, Inc. (1999).

Liang, C-M., et al., "Production and Characterization of Monoclonal Antibodies Against Recombinant Human Tumor Necrosis Factor/Cachectin," *Biochem. Biophys. Res. Comm.* 137:847-854, Academic Press, Inc. (1986).

Mathison, J.C., et al., "Participation of Tumor Necrosis Factor in the Mediation of Gram Negative Bacterial Lipopolysaccharide-induced Injury in Rabbits," *J. Clin. Invest.* 81:1925-1937, Rockefeller University Press (1988).

Meager, A., et al., "Preparation and Charcterization of Monoclonal Antibodies Directed Against Antigenic Determinants of Recombinant Human Tumour Necrosis Factor (rTNF)," *Hybridoma* 6:305-311, Mary Ann Liebert, Inc. (1987).

Mikayama, T., et al., "Molecular cloning and functional expression of a cDNA encoding glycosylation-inhibiting factor," *Proc. Natl. Acad. Sci. USA* 90:10056-10060, National Academy of Sciences of the USA (1993).

Miki, Y., et al., Database EST-STN on MASPAR search, GenBank No. S78214, "Disruption of the APC gene by retrotransposal insertion of L1 sequence in a colon cancer,"0 *Cancer Research* 52:643-5 (1992).

Möller, A., et al., "Monoclonal Antibodies to Human Tumor Necrosis Factor α: In Vitro and In Vivo Application," *Cytokine* 2:162-169, W.B. Saunders Co. (1990).

Opal, S.M., et al., "Efficacy of a Monoclonal Antibody Directed against Tumor Necrosis Factor in Protecting Neutropenic Rats from Lethal Infection with *Pseudomonas aeruginosa,*" *J. Infect. Dis.* 161:1148-1152, University of Chicago Press (1990).

Shimamoto, Y., et al., "Monoclonal antibodies against human recombinant tumor necrosis factor: prevention of endotoxic shock," *Immunol. Letters* 17:311-318, Elsevier Science B.V. (1988).

Silva, A.T., et al., "Prophylactic and Therapeutic Effects of a Monoclonical Antibody to Tumor Necrosis Factor-α in Experimental Gram-Negative Shock," *J. Infect. Dis.* 162:421-427, University of Chicago Press (1990).

Smith, R.A., and Baglioni, C., "The Active Form of Tumor Necrosis Factor Is a Trimer," *J. Biol. Chem.* 262:6951-6954, American Society of Biological Chemists, Inc. (1987).

Tracey, K.J. et al., "Anti-cachetin/TNF monoclonal antibodies prevent septic shock during lethal bacteraemia," *Nature* 330:662-664, Macmillan Journals Ltd. (1987).

Tracey, K.J., and Cerami, A., "Tumor necrosis factor: An updated review of its biology," *Crit. Care Med.* 21:S415-S422, Williams & Wilkins (1993).

Van Der Poll, T., and Lowry, S.F., "Tumor Necrosis Factor in Sepsis: Mediator of Multiple Organ Failure or Essential Part of Host Defense?" *Shock* 3:1-12, BioMedical Press (Jan. 1995).

Voet, D., and Voet, J.G., "Sickle-Cell Anemia: The Influence of Nature Selection," and "Abnormal Hemoglobins," in *Biochemistry*, Voet, D., and Voet, J.G., eds., John Wiley & Sons, Inc., New York, NY, pp. 126-128 and 228-234 (1990).

Wherry, J.C., et al., "Tumor necrosis factor and the therapeutic potential of anti-tumor necrosis factor antibodies," *Crit. Care Med.* 21:S436-S440, Williams & Wilkins (1993).

Wiley, S.R., et al, "Identification and Characterization of a New Member of the TNF Family that Induces Apoptosis," *Immunity* 3:673-682, Cell Press (Dec. 1995).

Wood, D.O. EMBL/Genbank/DDBJ Data Banks, No. P41086, EMBL U02603, "Putative Succinate Dehydrogenase 15 KD Hydrophobic Protein" (May 1995).

International Search Report for Application No. PCT/US96/13282, mailed Nov. 1996.

* cited by examiner

```
  1 GTTTTCCACAGCTCTCATTTCTCCAAAAATGTGTTTGAGCCACTTGGAAA
 51 ATATGCCTTTAAGCCATTCAAGAACTCAAGGAGCTCAGAGATCATCCTGG
     M  P  L  S  H  S  R  T  Q  G  A  Q  R  S  S  W
101 AAGCTGTGGCTCTTTTGCTCAATAGTTATGTTGCTATTTCTTTGCTCCTT
     K  L  W  L  F  C  S  I  V  M  L  L  F  L  C  S  F
151 CAGTTGGCTAATCTTTATTTTTCTCCAATTAGAGACTGCTAAGGAGCCCT
     S  W  L  I  F  I  F  L  Q  L  E  T  A  K  E  P  C
201 GTATGGCTAAGTTTGGACCATTACCCTCAAAATGGCAAATGGCATCTTCT
     M  A  K  F  G  P  L  P  S  K  W  Q  M  A  S  S
251 GAACCTCCTTGCGTGAATAAGGTGTCTGACTGGAAGCTGGAGATACTTCA
     E  P  P  C  V  N  K  V  S  D  W  K  L  E  I  L  Q
301 GAATGGCTTATATTTAATTTATGGCCAAGTGGCTCCCAATGCAAACTACA
     N  G  L  Y  L  I  Y  G  Q  V  A  P  N  A  N  Y  N
351 ATGATGTAGCTCCTTTTGAGGTGCGGCTGTATAAAAACAAAGACATGATA
     D  V  A  P  F  E  V  R  L  Y  K  N  K  D  M  I
401 CAAACTCTAACAAACAAATCTAAAATCCAAAATGTAGGAGGGACTTATGA
     Q  T  L  T  N  K  S  K  I  Q  N  V  G  G  T  Y  E
451 ATTGCATGTTGGGGACACCATAGACTTGATATTCAACTCTGAGCATCAGG
     L  H  V  G  D  T  I  D  L  I  F  N  S  E  H  Q  V
501 TTCTAAAAAATAATACCTACTGGGGTATCATTTTACTAGCAAATCCCCAA
     L  K  N  N  T  Y  W  G  I  I  L  L  A  N  P  Q
551 TTCATCTCCTAGAGACTTGATTTGATCTCCTCATTCCCTTCAGCACATGT
     F  I  S
601 AGAGGTGCCAGTGGGTGGATTGGAGGGAGAAGATATTCAATTTCTAGAGT
651 TTGTCTGTCTACAAAAATCAACACAAACAGAACTCCTCTGCACGTGAATT
701 TTCATCTATCATGCCTATCTGAAAGAGACTCAGGGGAAAAGCCAAAGACT
751 TTTGGTTGGATCTGCAGAGATACTTCATTAATCCATGATAAAACAAATAT
801 GGATGACAGAGGACATGTGCTTTTCAAAGAATCTTTATCTAATTCTTGAA
851 TTCATGAGTGGAAAAATGGAGTTCTATTCCCATGGAAGATTTACCTGGTA
901 TGCAAAAAGGATCTGGGGCAGTAGCCTGGCTTTGTTCTCATATTCTTGGG
951 CTGCTGTAATTCATTCTTCTCATACTCCCATCTTCTGAGACCCTCCCAAT
1001 AAAAAGTAGACTGATAGGATGGCCACAGATATGCCTACCATACCCTACTT
1051 TAGATATGGTGGTGTTAGAAGATAAAGAACAATCTGAGAACTATTGGAAT
1101 AGAGGTACAAGTGGCATAAAATGGAATGTACGCTATCTGGAAATTTCTCT
1151 TGGTTTTATCTTCCTCAGGATGCAGGGTGCTTTAAAAAGCCTTATCAAAG
1201 GAGTCATTCCGAACCCTCACGTAGAGCTTTGTGAGAACTTACTGTTGGTG
1251 TGTGTGTCTAAACATTGCTAATTGTAAAGAAAGAGTAACCATTAGTAATC
1301 ATTAGGTTTAACCCCAGAATGGTATTATCATTACTGGATTATGTCATGTA
1351 ATGATTTAGTATTTTTAGCTAGCTTTCCACAGTTTGCAAAGTGCTTTCGT
1401 AAAACAGTTAGCAATTCTATGAAGTTAATTGGGCAGGCATTTGGGGAAA
1451 ATTTTAGTGATGAGAATGTGATAGCATAGCATAGCCAACTTTCCTCAACT
1501 CATAGGACAAGTGACTACAAGAGGCAATGGGTAGTCCCCTGCATTGCACT
1551 GTCTCAGCTTTAGAATTGTTATTTCTGCTATCGTGTTATAAGACTCTAAA
1601 ACTTAGCGAATTCACTTTTCAGGAAGCATATTCCCCTTTAGCCCAAGGTG
1651 AGCAGAGTGAAGCTACAACAGATCTTTCCTTTACCAGCACACTTTTTTTT
1701 TTTTCCTGCCTGAATCAGGGAGATCCAGGATGCTGTTCAGGCCTTATCCC
1751 AACCAAATTCCCCTCTTCACTTTGCAGGGCCCATCTTAGTCAAATGTGCT
1801 AACTTCTAAAATAATAAATAGCACTAATTCAAAAAAAAAAAAAAAAAAA
```

```
MS-TESMIRDVELAEEALPKKTG----------GPQGSRRCLFL-----SLFSFLIV--A  TNFalpha
MT-PPERL--------FLERVCG----------TT--------LHL-----LLLGLILVLLP  TNFbeta
MPLSHSRT--------QGAQRSSWKLWLFCSIVML------LFLCSFSWLIFIFIQL--E  Endokine alpha GATTLFCLLHFGVIGPQREESPRDLSLISPLAQAVRSSSRT----PSDKPVAHVVANPQA  TNFalpha
GAQGL-----------------EGVGLTPSAAQTARQHPKMHLAHSTLKPAAHLIGDPSK  TNFbeta
TAKE--------------LCMAKFGPLP----SKWQM----ASSEP-------ECV     Endokine alpha EGQLQWLNRRANALLANGVELRDNQLVVFSEGLYLIYSQVLFKGQG----QPSTHVLLDF  TNFalpha
QNSLLWRANTDRAFLQDGFSLSNNSLLVFTSGLYFVWSQVVFSGKAYSPKAPSSPLYLAH  TNFbeta
NKVSDWKLEILQ------------------NGLYLIYGQV---------ALNAN-----  Endokine alpha TISRIAVSYQTKVNLLSAIKSPCQRETPEGAEAKPWYEPIYLGGVFQLEKGDRLSAEINR  TNFalpha
EVQLFSSQYPFHVPLLSSQK------MVYPGLQEPWLHSMYHGAAFQLTQGDQLSTHTDG  TNFbeta
----YNDVAPFEVRLYKNKD------MIQTLTNKSKIQNV--GGTYELHVGDTIDLIFNS  Endokine alpha PDYLDFAESGQVYFGIIAL                                          TNFalpha
IPHLVLS-PSTVFFGAFAL                                          TNFbeta
-EHQVLK-NMTYWGILLLANPQFIS                                    Endokine alpha
```

METHODS AND COMPOSITIONS FOR TREATING METABOLIC BONE DISEASES RELATING TO HUMAN ENDOKINE ALPHA

CROSS-REFERENCE TO RELATED APPLICATIONS

This application claims the benefit of priority under 35 U.S.C. § 119(e) of U.S. Provisional Application Nos. 60/312,542, filed Aug. 16, 2001, and 60/330,761, filed Oct. 30, 2001, each of which is hereby incorporated by reference in its entirety.

FIELD OF THE INVENTION

The present invention concerns methods for diagnosis and treatment of metabolic bone diseases and disorders using a novel member of the tumor necrosis factor (TNF) family of cytokines. In particular the invention provides methods of using the Endokine alpha protein in the diagnosis, prognosis and treatment of metabolic bone diseases and disorders. Furthermore, the invention provides methods of using homomultimeric and heteromultimeric polypeptide complexes containing Endokine alpha, in the diagnosis, prognosis and treatment of metabolic bone diseases and disorders. Also provided by the invention are methods of using the Endokine alpha protein and/or homomultimeric or heteromultimeric polypeptide complexes containing Endokine alpha, in the diagnosis, prognosis and treatment of diseases and/or disorders associated with metabolic bone diseases and disorders. Also provided by the invention are methods of using the Endokine alpha protein and/or homomultimeric or heteromultimeric polypeptide complexes containing Endokine alpha, in the diagnosis, prognosis and treatment of diseases and/or disorders associated with aberrant osteoclast development and/or activity, including, for example, excessive bone resorption.

BACKGROUND OF THE INVENTION

TNF Ligand Family

The cytokine known as tumor necrosis factor-α (TNFα; also termed cachectin) is a protein secreted primarily by monocytes and macrophages in response to endotoxin or other stimuli as a soluble homotrimer of 17 kD protein subunits (Smith, R. A. et al., *J. Biol. Chem.* 262:6951–6954 (1987)). A membrane-bound 26 kD precursor form of TNF has also been described (Kriegler, M. et al., *Cell* 53:45–53 (1988)).

Accumulating evidence indicates that TNF is a regulatory cytokine with pleiotropic biological activities. These activities include: inhibition of lipoprotein lipase synthesis ("cachectin" activity) (Beutler, B. et al., *Nature* 316:552 (1985)), activation of polymorphonuclear leukocytes (Klebanoff, S. J. et al, *J. Immunol.* 136:4220 (1986); Perussia, B., et al., *J. Immunol.* 138:765 (1987)), inhibition of cell growth or stimulation of cell growth (Vilcek, J. et al., *J. Exp. Med.* 163:632 (1986); Sugarman, B. J. et al., *Science* 230:943 (1985); Lachman, L. B. et al., *J. Immunol.* 138:2913 (1987)), cytotoxic action on certain transformed cell types (Lachman, L. B. et al., supra; Darzynkiewicz, Z. et al., *Canc. Res.* 44:83 (1984)), antiviral activity (Kohase, M. et al., *Cell* 45:659 (1986); Wong, G. H. W. et al., *Nature* 323:819 (1986)), stimulation of bone resorption (Bertolini, D. R. et al., *Nature* 319:516 (1986); Saklatvala, J., *Nature* 322:547 (1986)), stimulation of collagenase and prostaglandin E2 production (Dayer, J.-M. et al., *J. Exp. Med.* 162:2163 (1985)); and immunoregulatory actions, including activation of T cells (Yokota, S. et al., *J. Immunol.* 140:531 (1988)), B cells (Kehrl, J. H. et al., *J. Exp. Med.* 166:786 (1987)), monocytes (Philip, R. et al., *Nature* 323:86 (1986)), thymocytes (Ranges, G. E. et al., *J. Exp. Med.* 167:1472 (1988)), and stimulation of the cell-surface expression of major histocompatibility complex (MHC) class I and class II molecules (Collins, T. et al., *Proc. Natl. Acad. Sci. USA* 83:446 (1986); Pujol-Borrel, R. et al., *Nature* 326:304 (1987)).

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J. Surg.* 76:670–671 (1989); Debets, J. M. H. et al., *Second Vienna Shock Forum*, p.463–466 (1989); Simpson, S. Q. et al., *Crit. Care Clin.* 5:27–47 (1989)), including fever, malaise, anorexia, and cachexia. Endotoxin is a potent monocyte/macrophage activator which stimulates production and secretion of TNF (Kornbluth, S. K. et al., *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., *N. Eng. J. Med.* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161: 982–987 (1990)).

Passive immunotherapy directed at neutralizing TNF may have a beneficial effect in Gram-negative sepsis and endotoxemia, based on the increased TNF production and elevated TNF levels in these pathology states, as discussed above.

Antibodies to a "modulator" material which was characterized as cachectin (later found to be identical to TNF) were disclosed by Cerami et al. (EPO Patent Publication 0,212,489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., *Shonica (Pediatrics)* 26:935 (1985)) were said to contain elevated TNF levels which were related to progress of the pathology (Yone et al., supra).

Other investigators have described mAbs specific for recombinant human TNF which had neutralizing activity in vitro (Liang, C-M. et al. *Biochem. Biophys. Res. Comm.* 137:847–854 (1986); Meager, A. et al., *Hybridoma* 6:305–311 (1987); Fendly et al., *Hybridoma* 6:359–369 (1987); Bringman, T. S. et al., *Hybridoma* 6:489–507 (1987); Hirai, M. et al., *J. Immunol. Meth.* 96:57–62 (1987); Moller, A. et al. (*Cytokine* 2:162–169 (1990)). Some of these mAbs were used to map epitopes of human TNF and develop enzyme immunoassays (Fendly et al., supra; Hirai et al., supra; Moller et al., supra) and to assist in the purification of recombinant TNF (Bringman et al., supra). However, these studies do not provide a basis for producing TNF neutralizing antibodies that can be used for in vivo diagnostic or therapeutic uses in humans, due to immunogenicity, lack of specificity and/or pharmaceutical suitability.

Neutralizing antisera or mAbs to TNF have been shown in mammals other than man to abrogate adverse physiological changes and prevent death after lethal challenge in experimental endotoxemia and bacteremia. This effect has been demonstrated, e.g., in rodent lethality assays and in primate pathology model systems (Mathison, J. C. et al., *J. Clin. Invest.* 81:1925–1937 (1988); Beutler, B. et al., *Science* 229:869–871 (1985); Tracey, K. J. et al., *Nature* 330:662–664 (1987); Shimamoto, Y. et al., *Immunol. Lett.* 17:311–318 (1988); Silva, A. T. et al., *J. Infect. Dis.* 162:421–427 (1990); Opal, S. M. et al., *J. Infect. Dis.* 161:1148–1152 (1990); Hinshaw, L. B. et al., *Circ. Shock* 30:279–292 (1990)).

To date, experience with anti-TNF mAb therapy in humans has been limited but shows beneficial therapeutic results, e.g., in arthritis and sepsis. See, e.g., Elliott, M. J. et al., *Baillieres Clin. Rheumatol.* 9:633–52 (1995); Feldmann M, et al., *Ann. N.Y. Acad. Sci. USA* 766:272–8 (1995); van der Poll, T. et al., *Shock* 3:1–12 (1995); Wherry et al., *Crit. Care. Med.* 21:S436–40 (1993); Tracey K. J., et al., *Crit. Care Med.* 21:S415–22 (1993).

Sequence analysis of cytokine receptors has defined several subfamilies of membrane proteins (1) the Ig superfamily, (2) the hematopoietin (cytokine receptor superfamily and (3) the tumor necrosis factor (TNF)/nerve growth factor (NGF) receptor superfamily (for review of TNF superfamily see, Gruss and Dower, *Blood* 85(12):3378–3404 (1995) and Aggarwal and Natarajan, *Eur. Cytokine Netw.*, 7(2):93–124 (1996)). The TNF/NGF receptor superfamily contains at least 10 different proteins. Gruss and Dower, supra. Ligands for these receptors have been identified and belong to at least two cytokine superfamilies. Gruss and Dower, supra.

The Musculoskeletal System

The Human Musculoskeletal System is comprised of skeleton (e.g., bone), muscle, tendon, ligament, and other components of joints, which constitute the basic structural framework of the body. Together, the components of this system provide the strength, stability, frame, and elasticity necessary for movement. Additionally, the musculoskeletal system protects the internal organs, stores minerals, and produces blood.

The primary component of the musculoskeletal system is the skeleton itself. The skeleton is a highly organized connection of bones responsible for many functions, including supporting the body against gravity, providing sites for muscle attachment, producing blood cells, protecting the organs and other soft body tissues, and permitting flexible movement.

Anatomically, two types of bones can be distinguished in the skeleton: flat bones (e.g., skull bones, scapula, mandible, and ileum) and long bones (e.g., tibia, femur, and humerus). The long bone is composed of two wider extremities (e.g., the epiphyses), a cylindrical tube in the middle (e.g., the midshaft or diaphysis), and a developmental zone (e.g., the metaphysis) between them. In a growing long bone, the epiphysis and the metaphysis are separated by a layer of cartilage (e.g., epiphyseal cartilage or growth plate), responsible for the longitudinal growth of the bones. The external part of the bones is formed by a layer of calcified tissue (e.g., the cortex or compact bone). In the diaphyisis, the cortex encloses the medullary cavity, the location of the hematopoietic bone marrow. Toward the metaphysis and epiphysis, the cortex becomes progressively thinner, containing a network of thin, calcified trabeculae (e.g., trabecular bone or spongy bone) and hematopoietic bone marrow. At the center of most bones is yellow marrow, which is used to store fats. Therefore, the cortical bone fulfills mainly a mechanical and protective function, and the trabecular bone fulfills a metabolic function.

Joints are formed when two bones come together and allow for bending and movement. Tough bands of connective tissue, called ligaments, surround the joints, join the two bones together, and keep the bones properly aligned. The joint capsule is lined by a synovial membrane, which produces synovial fluid for lubricating the joint. Joints may also contain fluid-filled sacs (e.g., bursa) that reduce friction in areas where skin, muscles, tendons, and ligaments rub over bones. Most joints are freely moving synovial joints; however, some joints (e.g, vertebrae) are partly movable and allow some degree of flexibility with cartilage, or menisci, between the bones, while other joints (e.g., skull sutures) do not allow movement at all.

Composed of striated bundles of myosin and actin fibers, skeletal muscles have very long fiber-like cells that contract quickly, but only when stimulated by nerve cells. Muscle is attached to the bone by tough connective tissue, called tendons, and arranged in opposing, balancing groups around joints that facilitate balanced movement.

Although the musculoskeletal system was designed for strength and endurance, the components of this system can become worn, injured, or inflamed. These disorders can range from mild to severe and from acute to chronic. Generally, the treatment depends on the type and severity of the disorder.

Bone Metabolism

Bone is formed by collagen fibers, comprising approximately 90% type I collagen, together with non-collagenous proteins. Orientation of these collagen fibers alternates between layers giving adult bone a characteristic lamellar structure. Crystals of hydroxyapatite [$3Ca_3(PO_4)_2 \cdot (OH)_2$] are found on collagen fibers, within them and in the ground substance of the bone. Ground substance, primarily composed of glycoproteins and proteoglycans, is a highly anionic complex which is believed to play a role in hydroxyapatite binding and calcification of the bone tissue.

Bone is a balanced, dynamic system, constantly degrading and regenerating. Initial bone development relies on the osteoblast, a cell responsible for production of the bone matrix, i.e., collagen fibers and ground substance. After formation of the bone matrix, the osteoblast reaches the end of its secreting life and differentiates into a flat bone lining cell or an osteocyte. As calcification occurs, the osteocyte then differentiates into cortical bone or trabecular bone within small osteoclast lacunae throughout the calcified collagen fiber matrix. Blood vessels penetrate the newly calcified bone, bringing the blood supply that will form the hematopoietic bone marrow.

Bone is degraded by cells called osteoclasts that are responsible for resorption of bone matrix. Osteoclasts develop from pluripotent mononuclear precursor cells found in the bone marrow. As these cells commit to the osteoclast lineage they lose proliferative potential and eventually they fuse to form multinuclear immature osteoclasts. In the presence of bone, mature osteoclasts become polarized, develop a ruffled border and begin to resorb bone. A tight seal is formed between the osteoclast and the surface or the bone to be resorbed. The osteoclast secretes lysosomal and non-lysosomal enzymes, via its ruffled border, into the extracellular bone-resorbing compartment. The osteoclast acidifies this extracellular compartment by secreting protons. The reduced pH facilitates exposure of the bone matrix by dissolving crystals and also provides conditions suitable for the function of lysosomal enzymes in matrix degradation. Digestion products of this resorption process may be internalized by the osteoclast, transported through the osteoclast by transcytosis to be released at the basolateral domain of the cell or released through relapse of the seal created between the osteoclast and the bone surface. Bone resorption by osteoclasts serves to remove bone matrix from the center of the bone, forming the central cavity of the long bones during bone formation, and also to allow bone remodeling in the adult.

Diseases and Disorders of the Bone

Several types of bone disorders occur from an imbalance of the growth and breakdown cycles of bone. The most common, osteoporosis, is a metabolic bone disease characterized by a low bone mass and microarchitectural deterioration of bone tissue leading to progressive decrease in the density of bones, causing them to weaken. A distinguishing characteristic of osteoporosis is the normal mineral/collagen ration in affected tissues, in contrast to the disease osteomalacia in which a mineral deficiency relative to collagen is observed. Osteoporosis occurs in several different types and is seen more often in older women. Postmenopausal osteoporosis is generally found in women between the ages 51 and 75 and is caused by the lack of estrogen. Senile osteoporosis results not only from the imbalance between growth and breakdown but also from the calcium deficiency associated with age. Secondary osteoporosis is caused by secondary effects of another medical condition (e.g., chronic renal failure, hormonal disorders) or by drugs (e.g., barbiturates, anticonvulsants). Idiopathic juvenile osteoporosis is a rare form that occurs in children and young adults who, for no obvious reason, have weak bones. Treatment for all forms of osteoporosis is aimed at increasing bone density (e.g., estrogen intake, bisphosphonates, fluoride supplements).

Paget's Disease also results from an imbalance of the growth and breakdown of bone. The turnover rate is areas affected by Paget's Disease increases tremendously; resulting in abnormal, enlarged bone that is soft and weak. Although no specific genetic pattern has been determined, Paget's Disease tends to appear in family lineages. There is no direct treatment for Paget's Disease, rather treatment is given only alleviate pain and discomfort.

Bone disorders can also result from infection. Bone can be infected through three routes: bloodstream, direct invasion, and adjacent soft tissue infections. Osteomyelitis is a bone infection usually caused by bacteria (e.g., *Staphylococcus aureus*) which results in swelling of the soft bone marrow tissue, compression of the blood vessels, and possibly death of parts of bone. Pott's disease is an infection of the vertebrae by the bacteria that cause tuberculosis (e.g., *Mycobacterium tuberculosis, M. bovis*, or *M. africanum*.) For acute infections, antibiotics are generally the most effective treatment for this disease. However, if the infection is severe or chronic, surgery may also be required to remove the infected tissue and replaced with healthy bone, muscle, or skin.

Most bone carcinomas are benign. The most common type of benign bone tumor, usually occurring in people aged 10 to 20, is osteochrondroma. Osteochrondromas are growths on the surface of a bone that protrude as hard lumps. Benign chondromas, usually occurring in people aged 10 to 30, develop in the central part of the bone. Chrondroblastomas, usually occurring in people aged 10 to 20, are rare, painful tumors that grow in the ends of bones. Osteoid osteomas are very small tumors that commonly develop in the arms or legs but can occur in any bone. Giant cell tumors, usually occurring in people aged 20–40, most commonly originate in the ends of the bones and may extend into adjacent tissue. Treatment of these tumors generally involves pain management and, possibly, surgery to remove the tumor.

Although rare, malignant bone tumors may be primary or metastatic. In children, most malignant bone tumors are primary; in adults, most are metastatic. The most common type of malignant primary tumor, multiple myeloma, originates in the red bone marrow cells and most commonly occurs in older people. Osteosarcoma, usually occurring in people aged 10–20, commonly occurs in or around the knee and cause pain and swelling. These tumors tend to spread to the lungs. Chrondrosarcomas are slow-growing tumors composed of cancerous cartilage cells. Ewing's sarcoma, occurring most commonly in males aged 10 to 20, develop most often in arms and legs. These tumors can become large and can affect the entire length of a bone. Metastatic bone tumors most often originate from breast, lung, prostate, kidney and thyroid cancers.

Treatment for bone tumors depends on the type of cancer. Most treatments are complex and involve a combination of chemotherapy, radiotherapy, and surgery. Prompt treatment is especially important for malignant bone tumors.

Accordingly, there is a need to provide methods for use in the diagnosis and treatment of metabolic bone diseases and disorders. Such methods may also be used in the diagnosis, prognosis and treatment of diseases and/or disorders associated with metabolic bone diseases and disorders and/or aberrant osteoclast development and/or activity.

SUMMARY OF THE INVENTION

The present invention relates to the detection, diagnosis, prognosis and/or treatment of metabolic bone diseases and disorders, including but not limited to osteoporosis, using compositions comprising polynucleotides encoding Endokine alpha, the polypeptides encoded by these polynucleotides and antibodies that immunospecifically bind these polypeptides. More specifically, isolated Endokine alpha nucleic acid molecules are provided encoding Endokine alpha polypeptides. Endokine alpha polypeptides and antibodies that bind to these polypeptides are provided. Also provided are vectors, host cells, and recombinant and synthetic methods for producing Endokine polynucleotides, polypeptides, and/or antibodies. The invention further relates to diagnostic and therapeutic methods useful for diagnosing, treating, preventing and/or prognosing disorders of bone metabolism, and therapeutic methods for treating such disorders. The invention further relates to screening methods for identifying agonists and antagonists of polynucleotides and polypeptides of the invention. The invention further relates to methods and/or compositions for inhibiting or promoting the production and/or function of the polypeptides of the invention. The invention is based in part on the ability of Endokine alpha to inhibit osteoclast differentiation and thus prevent osteoclast-mediated bone degradation, as demonstrated in Example 20, below.

In accordance with one embodiment of the present invention, there is provided an extracellular domain of an Endokine alpha polypeptide, as well as biologically active fragments, analogs and derivatives thereof together with fragments, analogs and derivatives thereof which may be useful in the diagnosis or treatment of metabolic bone diseases or disorders.

In accordance with a further embodiment of the present invention, there is provided a multimeric complex of Endokine alpha polypeptides or biologically active fragments, analogs and derivatives thereof which may be useful in the diagnosis or treatment of metabolic bone diseases or disorders.

In accordance with a further embodiment, the multimeric polypeptide complex of the invention, used to detect, diagnose, prognose and/or treat metabolic bone disorders, may be a homodimer, a homotrimer, a homotetramer or a higher homomultimeric complex of Endokine alpha polypeptides, or biologically active fragments, analogs or derivatives thereof.

In accordance with a further embodiment, the multimeric polypeptide complex of the invention, used to detect, diagnose, prognose and/or treat metabolic bone disorders, may be a heterodimer, a heterotrimer, a heterotetramer or a higher heteromultimeric complex of Endokine alpha polypeptides, or biologically active fragments, analogs or derivatives thereof.

In specific embodiments, the present invention provides heteromultimeric complexes, particularly heterotrimeric complexes, comprising Endokine alpha polypeptides, wherein said Endokine alpha polypeptides may be full length polypeptides or extracellular polypeptide domains as described herein.

In further specific embodiments the present invention provides heteromultimeric complexes, particularly heterotrimeric complexes, comprising polypeptides at least 80% identical, more preferably at least 85% or 90% identical, and still more preferably 95%, 96%, 97%, 98% or 99% identical to Endokine alpha, wherein said Endokine alpha polypeptides may full length polypeptides or extracellular polypeptide domains as described herein.

In specific embodiments heterotrimeric polypeptide complexes of the present invention, contain three full-length Endokine alpha polypeptides; three Endokine alpha extracellular portion polypeptides; one full-length Endokine alpha polypeptide together with two Endokine alpha extracellular portion polypeptides; or two full-length Endokine alpha polypeptides together with one Endokine alpha extracellular portion polypeptide.

In further specific embodiments heterotrimeric polypeptide complexes of the present invention contain two full-length Endokine alpha polypeptides together with one full-length TNF family member ligand polypeptide; two Endokine alpha extracellular portion polypeptides together with one full-length TNF family member ligand polypeptide; two full-length Endokine alpha polypeptides together with one TNF family member ligand extracellular domain polypeptide; two Endokine alpha extracellular portion polypeptides together with one TNF family member ligand extracellular domain polypeptide; one full-length Endokine alpha polypeptide together with two full-length TNF family member ligand polypeptides; one Endokine alpha extracellular portion polypeptide together with two full-length TNF family member ligand polypeptides; one full-length Endokine alpha polypeptide together with two TNF family member ligand extracellular domain polypeptides; or one Endokine alpha extracellular portion polypeptide together with two TNF family member ligand extracellular domain polypeptides, wherein a TNF family member ligand polypeptide may be any of the polypeptides identified in Table 1.

In further embodiments heteromultimeric complexes of the present invention, comprise polypeptides of two (2), or three (3) distinct TNF family member ligands in addition to Endokine alpha, for example, as described herein, wherein said TNF family ligand polypeptides may be full length polypeptides or extracellular polypeptide domains as described herein.

In accordance with another embodiment of the present invention, there are provided isolated nucleic acid molecules encoding human Endokine alpha, including mRNAs, DNAs, cDNAs, genomic DNAs as well as analogs and biologically active and diagnostically or therapeutically useful fragments and derivatives thereof.

The present invention provides isolated nucleic acid molecules comprising, or alternatively, consisting of, a polynucleotide encoding a cytokine that is structurally similar to TNF and related cytokines and has similar biological effects and activities. This cytokine is named Endokine alpha and the invention includes Endokine alpha polypeptides having at least a portion of the amino acid sequence in FIG. 1 (SEQ ID NO:40) or amino acid sequence encoded by the cDNA clone deposited as ATCC Deposit Number 97640 on Jun. 27, 1996. The nucleotide sequence, which was determined by sequencing the deposited Endokine alpha cDNA clone as shown in FIG. 1 (SEQ ID NO:39), contains an open reading frame encoding a polypeptide of about 169 amino acid residues including an N-terminal methionine, an intracellular domain of about 17 amino acid residues, a transmembrane domain of about 26 amino acids, an extracellular domain of about 126 amino acids, and a deduced molecular weight for the complete protein of about 19 kDa. As for other type II transmembrane proteins, soluble forms of Endokine alpha include all or a portion of the extracellular domain cleaved from the transmembrane domain and a polypeptide comprising the complete Endokine alpha polypeptide lacking the transmembrane domain, i.e., the extracellular domain linked to the intracellular domain. In alternative embodiments, the Endokine alpha protein may expressed using the initial ATG codon of SEQ ID NO:39 to produce an intracellular domain that contains an additional eight amino acids at the N-terminus (MCLSHLEN; SEQ ID NO:58) preceding the initial methionine residue shown in SEQ ID NO:40. Thus, the alternative full-length Endokine alpha protein containing this longer (25 amino acids) intracellular domain is 177 amino acids long.

A further aspect of the invention provides an isolated nucleic acid molecule comprising a polynucleotide having a nucleotide sequence selected from the group consisting of: (a) a nucleotide sequence encoding the Endokine alpha polypeptide having the complete amino acid sequence in SEQ ID NO:40; (b) a nucleotide sequence encoding the Endokine alpha polypeptide having the complete amino acid sequence in SEQ ID NO:40 but minus the N-terminal methionine residue; (c) a nucleotide sequence encoding the Endokine alpha polypeptide having the complete amino acid sequence encoded by the cDNA clone contained in ATCC Deposit No. 97640; and (d) a nucleotide sequence complementary to any of the nucleotide sequences in (a), (b) or (c) above.

Further embodiments of the invention include isolated nucleic acid molecules that comprise or, alternatively, consist of, a polynucleotide having a nucleotide sequence at least 80%, 85%, 90%, 92%, or 95% identical, and more preferably at least 96%, 97%, 98% or 99% identical, to any of the nucleotide sequences in (a), (b), (c), or (d), above, or a polynucleotide which hybridizes under stringent hybridization conditions to a polynucleotide in (a), (b), (c), or (d), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a Endokine alpha polypeptide having an amino acid sequence in (a), (b), (c), or (d), above.

In additional embodiments, the nucleic acid molecules of the invention comprise, or alternatively consist of, a polynucleotide which encodes the amino acid sequence of an epitope-bearing portion of an Endokine alpha polypeptide having an amino acid sequence in (a), (b), (c) or (d) above. A further nucleic acid embodiment of the invention relates to an isolated nucleic acid molecule comprising, or alternatively consisting of, a polynucleotide which encodes the amino acid sequence of an Endokine alpha polypeptide having an amino acid sequence which contains at least one amino acid addition, substitution, and/or deletion but not more than 50 amino acid additions, substitutions and/or deletions, even more preferably, not more than 40 amino acid additions, substitutions, and/or deletions, still more preferably, not more than 30 amino acid additions, substitutions, and/or deletions, and still even more preferably, not more than 20 amino acid additions, substitutions, and/or deletions. Of course, in order of ever-increasing preference, it is highly preferable for a polynucleotide which encodes the amino acid sequence of an Endokine alpha polypeptide to have an amino acid sequence which contains not more than 10, 9, 8, 7, 6, 5, 4, 3, 2 or 1 or 1–100, 1–50, 1–25, 1–20, 1–15, 1–10, or 1–5 amino acid additions, substitutions and/or deletions. Conservative substitutions are preferable.

The invention is further directed to nucleic acid fragments of the nucleic acid molecules described herein. Preferred nucleic acid fragments include nucleic acid molecules which encode: a polypeptide comprising the Endokine alpha intracellular domain (amino acid residues from about 1 to about 17 in FIG. 1 (SEQ ID NO:40); or alternatively, the 25 amino acid intracellular domain that includes the additional amino acids of SEQ ID NO:58 at the N-terminus when translation is initiated at the initial ATG codon of SEQ ID NO:39); a polypeptide comprising the Endokine alpha transmembrane domain (amino acid residues from about 18 to about 43 in FIG. 1 (SEQ ID NO:40)); and a polypeptide comprising the Endokine alpha extracellular domain (amino acid residues from about 44 to about 169 in FIG. 1 (SEQ ID NO:40)).

The present invention also relates to recombinant vectors, which include the isolated nucleic acid molecules of the present invention, and to host cells containing the recombinant vectors, as well as to methods of making such vectors and host cells and for using them for production of Endokine alpha polypeptides or peptides by recombinant techniques.

In accordance with a further embodiment of the present invention, there is provided a process for producing such polypeptides by recombinant techniques comprising culturing recombinant prokaryotic and/or eukaryotic host cells, containing an Endokine alpha nucleic acid sequence of the invention, under conditions promoting expression of said polypeptide and subsequent recovery of said polypeptide.

The invention further provides an isolated Endokine alpha polypeptide having an amino acid sequence selected from the group consisting of: (a) the complete 169 amino acid sequence in SEQ ID NO:40; (b) the complete 169 amino acid sequence in SEQ ID NO:40 but minus the N-terminal methionine residue; (c) the complete amino acid sequence encoded by the cDNA clone contained in ATCC Deposit No. 97640; and (d) the amino acid sequence of an epitope-bearing portion of any one of the polypeptides of (a), (b), or (c). The polypeptides of the present invention also include polypeptides having an amino acid sequence at least 80%, 85%, 90%, 92%, or 95% identical, more preferably at least 96%, 97%, 98% or 99% identical to those above.

The present invention also encompasses the above polynucleotide sequences fused to a heterologous polynucleotide sequence. Polypeptides encoded by these polynucleotides and nucleic acid molecules are also encompassed by the invention.

In one embodiment, the heterotrimeric complex of the present invention comprises full-length or extracellular portions of Endokine alpha polypeptides of SEQ ID NO:40, together with full-length or extracellular portions of other TNF ligand family member polypeptides, as described herein.

In one embodiment, the heterotrimeric complex of the present invention comprises full-length or extracellular portions of Endokine alpha polypeptides of SEQ ID NO:40, together with full-length or extracellular portions of Lymphotoxin-alpha ides of SEQ ID NO:2.

In one embodiment, the heterotrimeric complex of the present invention comprises full-length or extracellular portions of Endokine alpha polypeptides of SEQ ID NO:40, together with full-length or extracellular portions of TNF-alpha polypeptides of SEQ ID NO:4.

In one embodiment, the heterotrimeric complex of the present invention comprises full-length or extracellular portions of Endokine alpha polypeptides of SEQ ID NO:40, together with full-length or extracellular portions of Lymphotoxin-beta polypeptides of SEQ ID NO:6.

In one embodiment, the heterotrimeric complex of the present invention comprises full-length or extracellular portions of Endokine alpha polypeptides of SEQ ID NO:40, together with full-length or extracellular portions of OX40L polypeptides of SEQ ID NO:8.

In one embodiment, the heterotrimeric complex of the present invention comprises full-length or extracellular portions of Endokine alpha polypeptides of SEQ ID NO:40, together with full-length or extracellular portions of CD40L polypeptides of SEQ ID NO:10.

In one embodiment, the heterotrimeric complex of the present invention comprises full-length or extracellular portions of Endokine alpha polypeptides of SEQ ID NO:40, together with full-length or extracellular portions of FasL polypeptides of SEQ ID NO:12.

In one embodiment, the heterotrimeric complex of the present invention comprises full-length or extracellular portions of Endokine alpha polypeptides of SEQ ID NO:40, together with full-length or extracellular portions of CD70 polypeptides of SEQ ID NO:14.

In one embodiment, the heterotrimeric complex of the present invention comprises full-length or extracellular portions of Endokine alpha polypeptides of SEQ ID NO:40, together with full-length or extracellular portions of CD30LG polypeptides of SEQ ID NO:16.

In one embodiment, the heterotrimeric complex of the present invention comprises full-length or extracellular portions of Endokine alpha polypeptides of SEQ ID NO:40, together with full-length or extracellular portions of 4-1BB-L polypeptides of SEQ ID NO:18.

In one embodiment, the heterotrimeric complex of the present invention comprises full-length or extracellular portions of Endokine alpha polypeptides of SEQ ID NO:40, together with full-length or extracellular portions of TRAIL polypeptides of SEQ ID NO:20.

In one embodiment, the heterotrimeric complex of the present invention comprises full-length or extracellular portions of Endokine alpha polypeptides of SEQ ID NO:40, together with full-length or extracellular portions of RANKL polypeptides of SEQ ID NO:22.

In one embodiment, the heterotrimeric complex of the present invention comprises full-length or extracellular portions of Endokine alpha polypeptides of SEQ ID NO:40, together with full-length or extracellular portions of TWEAK polypeptides of SEQ ID NO:24.

In one embodiment, the heterotrimeric complex of the present invention comprises full-length or extracellular portions of Endokine alpha polypeptides of SEQ ID NO:40, together with full-length or extracellular portions of APRIL polypeptides of SEQ ID NO:26.

In one embodiment, the heterotrimeric complex of the present invention comprises fill-length or extracellular portions of Endokine alpha polypeptides of SEQ ID NO:40, together with full-length or extracellular portions of APRIL-SV polypeptides of SEQ ID NO:28.

In one embodiment, the heterotrimeric complex of the present invention comprises full-length or extracellular portions of Endokine alpha polypeptides of SEQ ID NO:40, together with full-length or extracellular portions of polypeptides of SEQ ID NO:30.

In one embodiment, the heterotrimeric complex of the present invention comprises full-length or extracellular portions of Endokine alpha polypeptides of SEQ ID NO:40, together with full-length or extracellular portions of BLyS™-SV polypeptides of SEQ ID NO:32.

In one embodiment, the heterotrimeric complex of the present invention comprises full-length or extracellular portions of Endokine alpha polypeptides of SEQ ID NO:40, together with full-length or extracellular portions of LIGHT polypeptides of SEQ ID NO:34.

In one embodiment, the heterotrimeric complex of the present invention comprises full-length or extracellular portions of Endokine alpha polypeptides of SEQ ID NO:40, together with full-length or extracellular portions of VEGI polypeptides of SEQ ID NO:36.

In one embodiment, the heterotrimeric complex of the present invention comprises full-length or extracellular portions of Endokine alpha polypeptides of SEQ ID NO:40, together with full-length or extracellular portions of VEGI-SV polypeptides of SEQ ID NO:38.

In one embodiment, the heterotrimeric complex of the present invention comprises full-length or extracellular portions of Endokine alpha polypeptides of SEQ ID NO:40, together with full-length or extracellular portions of EDA polypeptides of SEQ ID NO:42.

In further embodiments the present invention also provides heteromultimeric complexes, particularly heterotrimeric complexes, comprising polypeptides of TNF ligand family members as described herein, fused to one or more heterologous polypeptide sequences.

In further embodiments the present invention also provides heteromultimeric complexes, particularly heterotrimeric complexes, comprising polypeptides at least 80% identical, more preferably at least 85% or 90% identical, and still more preferably 95%, 96%, 97%, 98% or 99% identical to TNF ligand family members as described herein, fused to one or more heterologous polypeptide sequences.

The present invention further provides for isolating antibodies that bind specifically to heteromultimeric complexes, particularly heterotrimeric complexes, as described above. Such antibodies are useful diagnostically or therapeutically as described below.

Peptides or polypeptides having the amino acid sequence of an epitope-bearing portion of a Endokine alpha polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to an Endokine alpha polypeptide having an amino acid sequence described in (a), (b), (c), or (d) above.

Preferred polypeptide fragments according to the present invention include a polypeptide comprising: the Endokine alpha intracellular domain, the Endokine alpha transmembrane domain, and most preferably the Endokine alpha extracellular domain.

The invention further provides methods for isolating antibodies that bind specifically to an Endokine alpha polypeptide having an amino acid sequence as described above. Such antibodies may be useful diagnostically and/or therapeutically as agonists and/or as antagonists in the treatment of metabolic bone diseases and disorders. The invention also provides a diagnostic method for determining the presence of metabolic bone diseases and disorders.

The present invention also provides pharmaceutical compositions comprising Endokine alpha polypeptides, as described above, which may be used for instance, to treat, prevent, prognose and/or diagnose metabolic bone diseases or disorders and/or conditions associated with such diseases or disorders.

The invention further provides compositions comprising heteromultimeric polypeptide complexes, particularly heterotrimeric polypeptide complexes, and/or anti-heteromultimeric complex antibodies, for administration to cells in vitro, to cells ex vivo, and to cells in vivo, or to a multicellular organism. In preferred embodiments, the compositions of the invention comprise Endokine alpha encoding polynucleotides for expression of a heteromultimeric polypeptide complex in a host organism for treatment of disease. In a most preferred embodiment, the compositions of the invention comprise Endokine alpha encoding polynucleotides for expression of a heteromultimeric polypeptide complex in a host organism for treatment of a metabolic bone disease or disorder and/or conditions associated with a metabolic bone disease or disorder. Particularly preferred in this regard is expression in a human patient for treatment of a metabolic bone disease or disorder and/or conditions associated with a metabolic bone disease or disorder.

The present invention further encompasses methods and compositions for preventing, treating and/or ameliorating diseases or disorders associated with aberrant or inappropriate osteoclast differentiation, proliferation, activation and/or function (e.g., excessive bone resorption) in an animal, preferably a mammal, and most preferably a human, comprising, or alternatively consisting of, administering to an animal in which such treatment, prevention or amelioration is desired one or more compositions of the invention (including Endokine alpha polypeptides, and/or polypeptide complexes which comprise, or alternatively consist of, Endokine alpha polypeptides including fragments or variants thereof) in an amount effective to treat prevent or ameliorate the disease or disorder.

The present invention further encompasses methods and compositions for preventing activation of osteoclasts, comprising, or alternatively consisting of, contacting compositions of the invention with osteoclasts.

The present invention further encompasses methods and compositions for preventing activation of osteoclasts, comprising, or alternatively consisting of, administering to an animal in which such prevention is desired, one or more compositions of the invention in an amount effective to prevent activation of osteoclasts.

The present invention further encompasses methods and compositions for increasing activation of osteoclasts, comprising, or alternatively consisting of, contacting compositions of the invention with osteoclasts.

The present invention further encompasses methods and compositions for increasing activation of osteoclasts, comprising, or alternatively consisting of, administering to an animal in which such an increase is desired, one or more compositions of the invention in an amount effective to increase activation of osteoclasts.

The present invention further encompasses methods and compositions for killing osteoclasts, comprising, or alternatively consisting of, contacting compositions of the invention with osteoclasts.

The present invention further encompasses methods and compositions for killing osteoclasts, comprising, or alternatively consisting of, administering to an animal in which such killing is desired, one or more compositions of the invention in an amount effective to kill osteoclasts.

The present invention further encompasses methods and compositions for promoting survival of osteoclasts, comprising, or alternatively consisting of, contacting compositions of the invention with osteoclasts.

The present invention further encompasses methods and compositions for promoting survival of osteoclasts, comprising, or alternatively consisting of, administering to an animal in which such increased survival is desired, one or more compositions of the invention in an amount effective to promote survival of osteoclasts.

The present invention further encompasses methods and compositions for increasing proliferation of osteoclast precursor cells, comprising, or alternatively consisting of, contacting compositions of the invention with osteoclast precursor cells.

The present invention further encompasses methods and compositions for increasing proliferation of osteoclast precursor cells, comprising, or alternatively consisting of, administering to an animal in which such increased proliferation is desired, one or more compositions of the invention in an amount effective to increase proliferation of osteoclast precursor cells.

The present invention further encompasses methods and compositions for stimulating differentiation of osteoclasts, comprising, or alternatively consisting of, contacting compositions of the invention with osteoclast precursor cells.

The present invention further encompasses methods and compositions for stimulating differentiation of osteoclasts, comprising, or alternatively consisting of, administering to an animal in which such stimulation of differentiation is desired, one or more compositions of the invention in an amount effective to stimulate differentiation of osteoclasts.

The present invention further encompasses methods and compositions for increasing the lifespan of osteoclasts, comprising, or alternatively consisting of, contacting compositions of the invention with osteoclasts.

The present invention further encompasses methods and compositions for increasing the lifespan of osteoclasts, comprising, or alternatively consisting of, administering to an animal in which such increase of osteoclast lifespan is desired, one or more compositions of the invention in an amount effective to increase the lifespan of osteoclasts.

The present invention further encompasses methods and compositions for decreasing the lifespan of osteoclasts, comprising, or alternatively consisting of, contacting compositions of the invention with osteoclasts.

The present invention further encompasses methods and compositions for decreasing the lifespan of osteoclasts, comprising, or alternatively consisting of, administering to an animal in which such decrease of osteoclast lifespan is desired, one or more compositions of the invention in an amount effective to decrease the lifespan of osteoclasts.

The present invention further encompasses methods and compositions for inhibiting bone resorption, comprising, or alternatively consisting of, contacting an effective amount of one or more compositions of the invention with osteoclasts, wherein the effective amount of the composition of the invention inhibits bone resorption.

The present invention further encompasses methods and compositions for inhibiting bone resorption comprising, or alternatively consisting of, administering to an animal in which such inhibition is desired, one or more compositions of the invention in an amount effective to inhibit bone resorption.

The present invention further encompasses methods and compositions for stimulating bone resorption, comprising, or alternatively consisting of, contacting an effective amount of one or more compositions of the invention with osteoclasts, wherein the effective amount of the composition of the invention stimulates bone resorption.

The present invention further encompasses methods and compositions for stimulating bone resorption comprising, or alternatively consisting of, administering to an animal in which such stimulation is desired, one or more compositions of the invention in an amount effective to stimulate bone resorption.

The present invention also provides a screening method for identifying compounds capable of enhancing or inhibiting a cellular response induced by Endokine alpha and/or heteromultimeric polypeptide complexes of the invention which involves contacting cells which express polypeptide compositions of the invention with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another embodiment, a method for identifying receptors which bind compositions of the invention is provided, as well as a screening assay for agonists and antagonists using such receptors. This assay involves determining the effect a candidate compound on binding of composition of the invention to its receptor. In particular, the method involves contacting a receptor with a composition of the invention and a candidate compound and determining whether binding to the receptor is increased or decreased due to the presence of the candidate compound. The antagonists may be employed to prevent or treat metabolic bone diseases or disorders and conditions associated with such diseases or disorders.

The present invention also provides pharmaceutical compositions comprising Endokine alpha polypeptides, as described above, which may be used for instance, to treat, prevent, prognose and/or diagnose metabolic bone diseases or disorders and/or conditions associated with such diseases or disorders.

In certain embodiments, polypeptides and polypeptide complexes, particularly heterotrimeric complexes, of the invention, or agonists thereof, are administered, to treat, prevent, prognose and/or diagnose diseases and/or disorders of the musculoskeletal system, including but not limited to, disorders of the bone, joints, ligaments, tendons, bursa, muscle, and/or neoplasms and cancers associated with musculoskeletal tissue.

In certain embodiments, polypeptides and polypeptide complexes, particularly heterotrimeric complexes, of the invention, or agonists thereof, are administered, to treat, prevent, prognose and/or diagnose diseases and/or disorders associated with diseases and/or disorders of the musculoskeletal system, including but not limited to, disorders of the bone, joints, ligaments, tendons, bursa, muscle, and/or neoplasms and cancers associated with musculoskeletal tissue.

In certain embodiments, polypeptides and polypeptide complexes, particularly heterotrimeric complexes, of the invention, or agonists thereof, are administered, to treat, prevent, prognose and/or diagnose diseases and/or disorders which may lead to and/or cause diseases and/or disorders of the musculoskeletal system, including but not limited to, disorders of the bone, joints, ligaments, tendons, bursa, muscle, and/or neoplasms and cancers associated with musculoskeletal tissue.

Diseases or disorders of the bone, diseases or disorders associated with diseases or disorders of the bone, and diseases or disorders which may lead to and/or cause diseases or disorders of the bone, which may be treated, prevented, prognosed and/or diagnosed, include, but are not limited to, osteoporosis and Paget's disease, and other disorders associated with aberrant bone resorption. Thus, in a specific embodiment, one or more compositions of the invention, or agonists thereof, are administered to treat, prevent, prognose and/or diagnose osteoporosis or Paget's disease. In addition, diseases that result from excessive bone resorption, such as arterial calcification and atherosclerosis, may also be treated, prevented, prognosed and/or diagnosed in accordance with the invention. Additional such diseases or disorders of the bone include, but are not limited to acromegaly; acute pancreatitis; acute rhabdomyolysis; acute severe illness; Addison's disease; Albers-Schönberg disease; alcoholism; aluminum intoxication; amyloidosis; ankylosing spondylitis; arterial calcification; arterial aneurysms; atherosclerosis; autoimmune hypoparathyroidism; axial osteomalacia; benign chondromas; biliary atresia; bone fractures; bowlegs; breast cancer; Buschke-Ollendorff syndrome; Caffey's disease; calcinosis circumscripta; calcinosis universalis; carbonic anhydrase II deficiency; carcinoma (e.g., of lung, esophagus, head and neck, renal cell, ovary or bladder); celiac sprue; childhood dermatomyositis; chondroblastomas; chondromyxoid fibromas; chondrosarcomas; chronic anemias; coccidioidomycosis; craniodiaphyseal dysplasia; craniometaphyseal dysplasia; Crohn's disease; Cushing syndrome; cystic fibrosis; diffuse bony metastases; DiGeorge syndrome; discoid lupus erythematosis; disorders or disease requiring treatment by anticancer agents (e.g., asparaginase, cisplatinum, cytosine arabinoside, doxorubicin or WR 2721); disorders or disease requiring treatment by foscarnet; disorders or disease requiring treatment by hypocalcemic agents (e.g., bisphosphonates, plicamycin, calcitonin, gallium nitrate or phosphate); disorders or disease requiring treatment by ketaconazole; disorders or disease requiring treatment by pentamidine; dysosteosclerosis; Ehlers-Danlos syndrome; endocrine disorders; endosteal hyperostosis; Engelmann's disease; epiphyseal dysplasia; estrogen deficiency; Ewing's sarcoma; extraskeletal (ectopic) calcification; extraskeletal (ectopic) ossification; familial hypocalciuric hypercalcemia; familial Vitamin D resistance; Fanconi syndrome; fibrodysplasia (myositis) ossificans progressiva; fibrogenesis imperfecta osseum; fibrosarcoma; fibrous dysplasia; fluorosis; frontometaphyseal dysplasia; Gaucher's disease; Giant cell tumors; gluten enteropathy; gout; granulomatous diseases; heavy metal poisoning; heel spurs; hemochromatosis; hemoglobinopathies; heparin treatment; hepatic osteodystrophy; hepatitis A; hepatitis B; hepatitis C; hepatitis C-associated osteosclerosis; high-turnover bone disease; histoplasmosis; histiocytosis-X; homocystinuria; hungry bone syndrome; hypoalbuminemia; hyperalbuminemia; hypercalcemia; hypocalcemia; hypogonadism; hypermagnesemia; hypomagnesemia; hyperostosis corticalis; hyperparathyroidism; hypoparathyroidism; hypophosphatasia; hyperphosphatasia; hypophosphatemic osteomalacia; hyperprolactinemia; hypoproteinemia; hyperproteinemia; hyperthyroidism; hypothyroidism; hypervitaminosis A, D; idiopathic hypercalciuria; immobilization; infantile cortical hyperostosis; inflammatory bowel disease; intestinal disease; intestinal resection; intestinal bypass; ischemic bone disease; juvenile rheumatoid arthritis; kidney failure; Köhler's bone disease; knock-knees; Legg-Calvé-Perthes disease; leprosy; liver failure; low-turnover bone disease; lymphoproliferative disorders; lymphoma; magnesium deficiency; malignant fibrous histiocytomas; malignant lymphoma of bone; malnutrition; Marfan's syndrome; mastocytosis; McCune-Albright syndrome; melorheostosis; metabolic acidosis; metaphyseal dysplasia; metastatic carcinoma; milk-alkali syndrome; mixed sclerosing bone dystrophy; mucopolysaccharidosis; multiple myeloma; myelofibrosis; myeloproliferative disorders; myositis ossificans; neonatal hypocalcemia; oculodento-osseous dysplasia; Osgood-Schlatter disease; osteitis fibrosa; osteoarthritis; osteoblastic metastases; osteochondritis dissecans; osteochondromas; osteochondrosis; osteochondrosis of lunate; osteochondrodysplasia; osteodysplasia of Melnick and Needles; osteoectasia with hyperphosphatasia; osteogenesis imperfecta; osteoid osteomas; osteolytic metastases; osteomalacia; osteomyelitis; osteonecrosis; osteopathia striata; osteopetroses; osteopenia; osteopoikilosis; osteoporosis (e.g., juvenile, postmenopausal, senile, severe, glucocorticoid-induced, drug-induced, as a result of ethanol abuse, as a result of testosterone deficiency, as a result of Vitamin D deficiency or as a result of malnutrition); osteosarcoma; osteosclerosis; pancreatitis; pancreatic insufficiency; pseudohypoparathyroidism; patellofemoral stress syndrome; periodontal disease; pheochromocytoma; phosphate wasting syndromes; postgastrectomy bone disease; postsurgical hypoparathyroidism; primary biliary cirrhosis; progressive diaphyseal dysplasia; psoriatic arthritis; pycnodysostosis; Pyle's disease; renal osteodystrophy; renal tubular acidosis; reticulum cell sarcoma; rheumatic fever; rheumatoid arthritis; Rickets; sarcoidosis; Scheuermann's disease; scleroderma; sclerostosis; scoliosis; secondary hyperparathyroidism; Sever's disease; sickle cell anemia; Sjogren's syndrome; skeletal sarcoidosis; spondyloepiphyseal dysplasia; spondyloepimetaphyseal dysplasia; spondylometaphyseal dysplasia; Still's disease; sunlight exposure deficiency; systemic lupus erythematosis; thalassemia; thyrotoxicosis; tobacco smoking; toxic shock syndrome; tuberculosis; tuberous sclerosis; tumor-associated hepercalcemia; tumor lysis; tumoral calcinosis; van Buchem disease; vascular disease; vasoactive intestinal polypeptide-producing tumors; vertebral metastases; Vitamin D deficiency; Vitamin D malabsorption; Vitamin D-dependent rickets, type I (1α-hydroxylase deficiency); Vitamin D-dependent rickets, type II (resistance to 1,25(OH)$_2$D); Vitamin D-resistant rickets; and Wilson's disease.

In a specific embodiment, one or more compositions of the invention, or agonists or antagonists thereof, are administered to treat, prevent, prognose and/or diagnose Albers-Schönberg disease.

In a specific embodiment, one or more compositions of the invention, or agonists or antagonists thereof, are administered to treat, prevent, prognose and/or diagnose ankylosing spondylitis.

In a specific embodiment, one or more compositions of the invention, or agonists or antagonists thereof, are administered to treat, prevent, prognose and/or diagnose arterial calcification.

In a specific embodiment, one or more compositions of the invention, or agonists or antagonists thereof, are administered to treat, prevent, prognose and/or diagnose carbonic anhydrase II deficiency.

In a specific embodiment, one or more compositions of the invention, or agonists or antagonists thereof, are administered to treat, prevent, prognose and/or diagnose childhood dermatomyositis.

In a specific embodiment, one or more compositions of the invention, or agonists or antagonists thereof, are administered to treat, prevent, prognose and/or diagnose craniodiaphyseal dysplasia.

In a specific embodiment, one or more compositions of the invention, or agonists or antagonists thereof, are administered to treat, prevent, prognose and/or diagnose craniometaphyseal dysplasia.

In a specific embodiment, one or more compositions of the invention, or agonists or antagonists thereof, are administered to treat, prevent, prognose and/or diagnose dysosteosclerosis.

In a specific embodiment, one or more compositions of the invention, or agonists or antagonists thereof, are administered to treat, prevent, prognose and/or diagnose Ehlers-Danlos syndrome.

In a specific embodiment, one or more compositions of the invention, or agonists or antagonists thereof, are administered to treat, prevent, prognose and/or diagnose Fanconi syndrome.

In a specific embodiment, one or more compositions of the invention, or agonists or antagonists thereof, are administered to treat, prevent, prognose and/or diagnose hepatic osteodystrophy.

In a specific embodiment, one or more compositions of the invention, or agonists or antagonists thereof, are administered to treat, prevent, prognose and/or diagnose hepatitis C-associated osteosclerosis.

In a specific embodiment, one or more compositions of the invention, or agonists or antagonists thereof, are administered to treat, prevent, prognose and/or diagnose high-turnover bone disease.

In a specific embodiment, one or more compositions of the invention, or agonists or antagonists thereof, are administered to treat, prevent, prognose and/or diagnose histiocytosis-X.

In a specific embodiment, one or more compositions of the invention, or agonists or antagonists thereof, are administered to treat, prevent, prognose and/or diagnose hungry bone syndrome.

In a specific embodiment, one or more compositions of the invention, or agonists or antagonists thereof, are administered to treat, prevent, prognose and/or diagnose hypercalcemia.

In a specific embodiment, one or more compositions of the invention, or agonists or antagonists thereof, are administered to treat, prevent, prognose and/or diagnose hypocalcemia.

In a specific embodiment, one or more compositions of the invention, or agonists or antagonists thereof, are administered to treat, prevent, prognose and/or diagnose hyperparathyroidism.

In a specific embodiment, one or more compositions of the invention, or agonists or antagonists thereof, are administered to treat, prevent, prognose and/or diagnose hypoparathyroidism.

In a specific embodiment, one or more compositions of the invention, or agonists or antagonists thereof, are administered to treat, prevent, prognose and/or diagnose hyperthyroidism.

In a specific embodiment, one or more compositions of the invention, or agonists or antagonists thereof, are administered to treat, prevent, prognose and/or diagnose hypothyroidism.

In a specific embodiment, one or more compositions of the invention, or agonists or antagonists thereof, are administered to treat, prevent, prognose and/or diagnose ischemic bone disease.

In a specific embodiment, one or more compositions of the invention, or agonists or antagonists thereof, are administered to treat, prevent, prognose and/or diagnose Köhler's bone disease.

In a specific embodiment, one or more compositions of the invention, or agonists or antagonists thereof, are administered to treat, prevent, prognose and/or diagnose knock-knees.

In a specific embodiment, one or more compositions of the invention, or agonists or antagonists thereof, are administered to treat, prevent, prognose and/or diagnose Legg-Calvé-Perthes disease.

In a specific embodiment, one or more compositions of the invention, or agonists or antagonists thereof, are administered to treat, prevent, prognose and/or diagnose low-turnover bone disease.

In a specific embodiment, one or more compositions of the invention, or agonists or antagonists thereof, are administered to treat, prevent, prognose and/or diagnose malignant fibrous histiocytomas.

In a specific embodiment, one or more compositions of the invention, or agonists or antagonists thereof, are administered to treat, prevent, prognose and/or diagnose malignant lymphoma of bone.

In a specific embodiment, one or more compositions of the invention, or agonists or antagonists thereof, are administered to treat, prevent, prognose and/or diagnose Marfan's syndrome.

In a specific embodiment, one or more compositions of the invention, or agonists or antagonists thereof, are administered to treat, prevent, prognose and/or diagnose mastocytosis.

In a specific embodiment, one or more compositions of the invention, or agonists or antagonists thereof, are administered to treat, prevent, prognose and/or diagnose McCune-Albright syndrome.

In a specific embodiment, one or more compositions of the invention, or agonists or antagonists thereof, are administered to treat, prevent, prognose and/or diagnose melorheostosis.

In a specific embodiment, one or more compositions of the invention, or agonists or antagonists thereof, are administered to treat, prevent, prognose and/or diagnose metabolic acidosis.

In a specific embodiment, one or more compositions of the invention, or agonists or antagonists thereof, are administered to treat, prevent, prognose and/or diagnose metaphyseal dysplasia.

In a specific embodiment, one or more compositions of the invention, or agonists or antagonists thereof, are administered to treat, prevent, prognose and/or diagnose milk-alkali syndrome.

In a specific embodiment, one or more compositions of the invention, or agonists or antagonists thereof, are administered to treat, prevent, prognose and/or diagnose mixed sclerosing bone dystrophy.

In a specific embodiment, one or more compositions of the invention, or agonists or antagonists thereof, are administered to treat, prevent, prognose and/or diagnose mucopolysaccharidosis.

In a specific embodiment, one or more compositions of the invention, or agonists or antagonists thereof, are administered to treat, prevent, prognose and/or diagnose myelofibrosis.

In a specific embodiment, one or more compositions of the invention, or agonists or antagonists thereof, are administered to treat, prevent, prognose and/or diagnose myositis ossificans.

In a specific embodiment, one or more compositions of the invention, or agonists or antagonists thereof, are administered to treat, prevent, prognose and/or diagnose neonatal hypocalcemia.

In a specific embodiment, one or more compositions of the invention, or agonists or antagonists thereof, are administered to treat, prevent, prognose and/or diagnose oculo-dento-osseous dysplasia.

In a specific embodiment, one or more compositions of the invention, or agonists or antagonists thereof, are administered to treat, prevent, prognose and/or diagnose Osgood-Schlatter disease.

In a specific embodiment, one or more compositions of the invention, or agonists or antagonists thereof, are administered to treat, prevent, prognose and/or diagnose osteitis fibrosa.

In a specific embodiment, one or more compositions of the invention, or agonists or antagonists thereof, are administered to treat, prevent, prognose and/or diagnose osteoarthritis.

In a specific embodiment, one or more compositions of the invention, or agonists or antagonists thereof, are administered to treat, prevent, prognose and/or diagnose osteoblastic metastases.

In a specific embodiment, one or more compositions of the invention, or agonists or antagonists thereof, are administered to treat, prevent, prognose and/or diagnose osteochondritis dissecans.

In a specific embodiment, one or more compositions of the invention, or agonists or antagonists thereof, are administered to treat, prevent, prognose and/or diagnose osteochondromas.

In a specific embodiment, one or more compositions of the invention, or agonists or antagonists thereof, are administered to treat, prevent, prognose and/or diagnose osteochondrosis.

In a specific embodiment, one or more compositions of the invention, or agonists or antagonists thereof, are administered to treat, prevent, prognose and/or diagnose osteochondrodysplasia.

In a specific embodiment, one or more compositions of the invention, or agonists or antagonists thereof, are administered to treat, prevent, prognose and/or diagnose osteodysplasia of Melnick and Needles.

In a specific embodiment, one or more compositions of the invention, or agonists or antagonists thereof, are administered to treat, prevent, prognose and/or diagnose osteoectasia with hyperphosphatasia.

In a specific embodiment, one or more compositions of the invention, or agonists or antagonists thereof, are administered to treat, prevent, prognose and/or diagnose osteogenesis imperfecta.

In a specific embodiment, one or more compositions of the invention, or agonists or antagonists thereof, are administered to treat, prevent, prognose and/or diagnose osteoid osteomas.

In a specific embodiment, one or more compositions of the invention, or agonists or antagonists thereof, are administered to treat, prevent, prognose and/or diagnose osteolytic metastases.

In a specific embodiment, one or more compositions of the invention, or agonists or antagonists thereof, are administered to treat, prevent, prognose and/or diagnose osteomalacia.

In a specific embodiment, one or more compositions of the invention, or agonists or antagonists thereof, are administered to treat, prevent, prognose and/or diagnose osteomyelitis.

In a specific embodiment, one or more compositions of the invention, or agonists or antagonists thereof, are administered to treat, prevent, prognose and/or diagnose osteonecrosis.

In a specific embodiment, one or more compositions of the invention, or agonists or antagonists thereof, are administered to treat, prevent, prognose and/or diagnose osteopathia striata.

In a specific embodiment, one or more compositions of the invention, or agonists or antagonists thereof, are administered to treat, prevent, prognose and/or diagnose osteopetroses.

In a specific embodiment, one or more compositions of the invention, or agonists or antagonists thereof, are administered to treat, prevent, prognose and/or diagnose osteopenia.

In a specific embodiment, one or more compositions of the invention, or agonists or antagonists thereof, are administered to treat, prevent, prognose and/or diagnose osteopoikilosis.

In a specific embodiment, one or more compositions of the invention, or agonists or antagonists thereof, are administered to treat, prevent, prognose and/or diagnose juvenile osteoporosis.

In a specific embodiment, one or more compositions of the invention, or agonists or antagonists thereof, are administered to treat, prevent, prognose and/or diagnose postmenopausal osteoporosis.

In a specific embodiment, one or more compositions of the invention, or agonists or antagonists thereof, are administered to treat, prevent, prognose and/or diagnose senile osteoporosis.

In a specific embodiment, one or more compositions of the invention, or agonists or antagonists thereof, are administered to treat, prevent, prognose and/or diagnose severe osteoporosis.

In a specific embodiment, one or more compositions of the invention, or agonists or antagonists thereof, are administered to treat, prevent, prognose and/or diagnose glucocorticoid-induced osteoporosis.

In a specific embodiment, one or more compositions of the invention, or agonists or antagonists thereof, are administered to treat, prevent, prognose and/or diagnose drug-induced osteoporosis.

In a specific embodiment, one or more compositions of the invention, or agonists or antagonists thereof, are administered to treat, prevent, prognose and/or diagnose osteoporosis caused by alcohol abuse.

In a specific embodiment, one or more compositions of the invention, or agonists or antagonists thereof, are administered to treat, prevent, prognose and/or diagnose osteoporosis caused by testosterone deficiency.

In a specific embodiment, one or more compositions of the invention, or agonists or antagonists thereof, are administered to treat, prevent, prognose and/or diagnose osteoporosis caused by a Vitamin D deficiency.

In a specific embodiment, one or more compositions of the invention, or agonists or antagonists thereof, are administered to treat, prevent, prognose and/or diagnose osteoporosis due to malnutrition.

In a specific embodiment, one or more compositions of the invention, or agonists or antagonists thereof, are administered to treat, prevent, prognose and/or diagnose osteosarcoma.

In a specific embodiment, one or more compositions of the invention, or agonists or antagonists thereof, are administered to treat, prevent, prognose and/or diagnose osteosclerosis.

In a specific embodiment, one or more compositions of the invention, or agonists or antagonists thereof, are administered to treat, prevent, prognose and/or diagnose Paget's disease.

In a specific embodiment, one or more compositions of the invention, or agonists or antagonists thereof, are administered to treat, prevent, prognose and/or diagnose pseudohypoparathyroidism.

In a specific embodiment, one or more compositions of the invention, or agonists or antagonists thereof, are administered to treat, prevent, prognose and/or diagnose patellofemoral stress syndrome.

In a specific embodiment, one or more compositions of the invention, or agonists or antagonists thereof, are administered to treat, prevent, prognose and/or diagnose periodontal disease.

In a specific embodiment, one or more compositions of the invention, or agonists or antagonists thereof, are administered to treat, prevent, prognose and/or diagnose pheochromocytoma.

In a specific embodiment, one or more compositions of the invention, or agonists or antagonists thereof, are administered to treat, prevent, prognose and/or diagnose phosphate wasting syndromes.

In a specific embodiment, one or more compositions of the invention, or agonists or antagonists thereof, are administered to treat, prevent, prognose and/or diagnose postgastrectomy bone disease.

In a specific embodiment, one or more compositions of the invention, or agonists or antagonists thereof, are administered to treat, prevent, prognose and/or diagnose postsurgical hypoparathyroidism.

In a specific embodiment, one or more compositions of the invention, or agonists or antagonists thereof, are administered to treat, prevent, prognose and/or diagnose progressive diaphyseal dysplasia.

In a specific embodiment, one or more compositions of the invention, or agonists or antagonists thereof, are administered to treat, prevent, prognose and/or diagnose psoriatic arthritis.

In a specific embodiment, one or more compositions of the invention, or agonists or antagonists thereof, are administered to treat, prevent, prognose and/or diagnose pycnodysostosis.

In a specific embodiment, one or more compositions of the invention, or agonists or antagonists thereof, are administered to treat, prevent, prognose and/or diagnose Pyle's disease.

In a specific embodiment, one or more compositions of the invention, or agonists or antagonists thereof, are administered to treat, prevent, prognose and/or diagnose renal osteodystrophy.

In a specific embodiment, one or more compositions of the invention, or agonists or antagonists thereof, are administered to treat, prevent, prognose and/or diagnose renal tubular acidosis.

In a specific embodiment, one or more compositions of the invention, or agonists or antagonists thereof, are administered to treat, prevent, prognose and/or diagnose reticulum cell sarcoma.

In a specific embodiment, one or more compositions of the invention, or agonists or antagonists thereof, are administered to treat, prevent, prognose and/or diagnose rheumatoid arthritis.

In a specific embodiment, one or more compositions of the invention, or agonists or antagonists thereof, are administered to treat, prevent, prognose and/or diagnose rickets.

In a specific embodiment, one or more compositions of the invention, or agonists or antagonists thereof, are administered to treat, prevent, prognose and/or diagnose sarcoidosis.

In a specific embodiment, one or more compositions of the invention, or agonists or antagonists thereof, are administered to treat, prevent, prognose and/or diagnose Scheuermann's disease.

In a specific embodiment, one or more compositions of the invention, or agonists or antagonists thereof, are administered to treat, prevent, prognose and/or diagnose scleroderma.

In a specific embodiment, one or more compositions of the invention, or agonists or antagonists thereof, are administered to treat, prevent, prognose and/or diagnose sclerostosis.

In a specific embodiment, one or more compositions of the invention, or agonists or antagonists thereof, are administered to treat, prevent, prognose and/or diagnose scoliosis.

In a specific embodiment, one or more compositions of the invention, or agonists or antagonists thereof, are administered to treat, prevent, prognose and/or diagnose secondary hyperparathyroidism.

In a specific embodiment, one or more compositions of the invention, or agonists or antagonists thereof, are administered to treat, prevent, prognose and/or diagnose Sever's disease.

In a specific embodiment, one or more compositions of the invention, or agonists or antagonists thereof, are administered to treat, prevent, prognose and/or diagnose spondyloepiphyseal dysplasia.

In a specific embodiment, one or more compositions of the invention, or agonists or antagonists thereof, are administered to treat, prevent, prognose and/or diagnose spondyloepimetaphyseal dysplasia.

In a specific embodiment, one or more compositions of the invention, or agonists or antagonists thereof, are administered to treat, prevent, prognose and/or diagnose spondylometaphyseal dysplasia.

In a specific embodiment, one or more compositions of the invention, or agonists or antagonists thereof, are administered to treat, prevent, prognose and/or diagnose Still's disease.

In a specific embodiment, one or more compositions of the invention, or agonists or antagonists thereof, are administered to treat, prevent, prognose and/or diagnose thyrotoxicosis.

In a specific embodiment, one or more compositions of the invention, or agonists or antagonists thereof, are administered to treat, prevent, prognose and/or diagnose tuberous sclerosis.

In a specific embodiment, one or more compositions of the invention, or agonists or antagonists thereof, are administered to treat, prevent, prognose and/or diagnose tumor-associated hepercalcemia.

In a specific embodiment, one or more compositions of the invention, or agonists or antagonists thereof, are administered to treat, prevent, prognose and/or diagnose tumoral calcinosis.

In a specific embodiment, one or more compositions of the invention, or agonists or antagonists thereof, are administered to treat, prevent, prognose and/or diagnose van Buchem disease.

In a specific embodiment, one or more compositions of the invention, or agonists or antagonists thereof, are administered to treat, prevent, prognose and/or diagnose vertebral metastases.

In a specific embodiment, one or more compositions of the invention, or agonists or antagonists thereof, are administered to treat, prevent, prognose and/or diagnose Vitamin D deficiency.

In a specific embodiment, one or more compositions of the invention, or agonists or antagonists thereof, are administered to treat, prevent, prognose and/or diagnose Vitamin D malabsorption.

In a specific embodiment, one or more compositions of the invention, or agonists or antagonists thereof, are administered to treat, prevent, prognose and/or diagnose Vitamin D-dependent rickets, type I (1α-hydroxylase deficiency).

In a specific embodiment, one or more compositions of the invention, or agonists or antagonists thereof, are administered to treat, prevent, prognose and/or diagnose Vitamin D-dependent rickets, type II (resistance to 1,25(OH)$_2$D).

In a specific embodiment, one or more compositions of the invention, or agonists or antagonists thereof, are administered to treat, prevent, prognose and/or diagnose Vitamin D-resistant rickets.

In a specific embodiment, one or more compositions of the invention, or agonists or antagonists thereof, are administered to treat, prevent, prognose and/or diagnose Wilson's disease.

BRIEF DESCRIPTION OF THE FIGURES

FIG. 1 shows the nucleotide (SEQ ID NO:39) and deduced amino acid (SEQ ID NO:40) sequences of the Endokine alpha protein. Amino acids 1 to 17 represent the intracellular domain (an alternative 25 amino acid intracellular domain includes the additional amino acids of SEQ ID NO:58 at the N-terminus when translation is initiated at the initial ATG codon of SEQ ID NO:39, i.e. nucleotides 29–31 of FIG. 1), amino acids 18 to 43 the transmembrane domain (the underlined sequence), and amino acids 44 to 169 the extracellular domain (the remaining sequence).

FIG. 2 shows the regions of similarity between the amino acid sequences of the Endokine alpha protein (SEQ ID NO:40), tissue necrosis factor α (TNF-α) (SEQ ID NO:4), and Lymphotoxin-alpha (SEQ ID NO:2). The J. Hein method was used with PAM 250 residue weight table. Shading with solid black indicates residues that match consensus exactly.

DETAILED DESCRIPTION OF THE INVENTION

Figure 3:
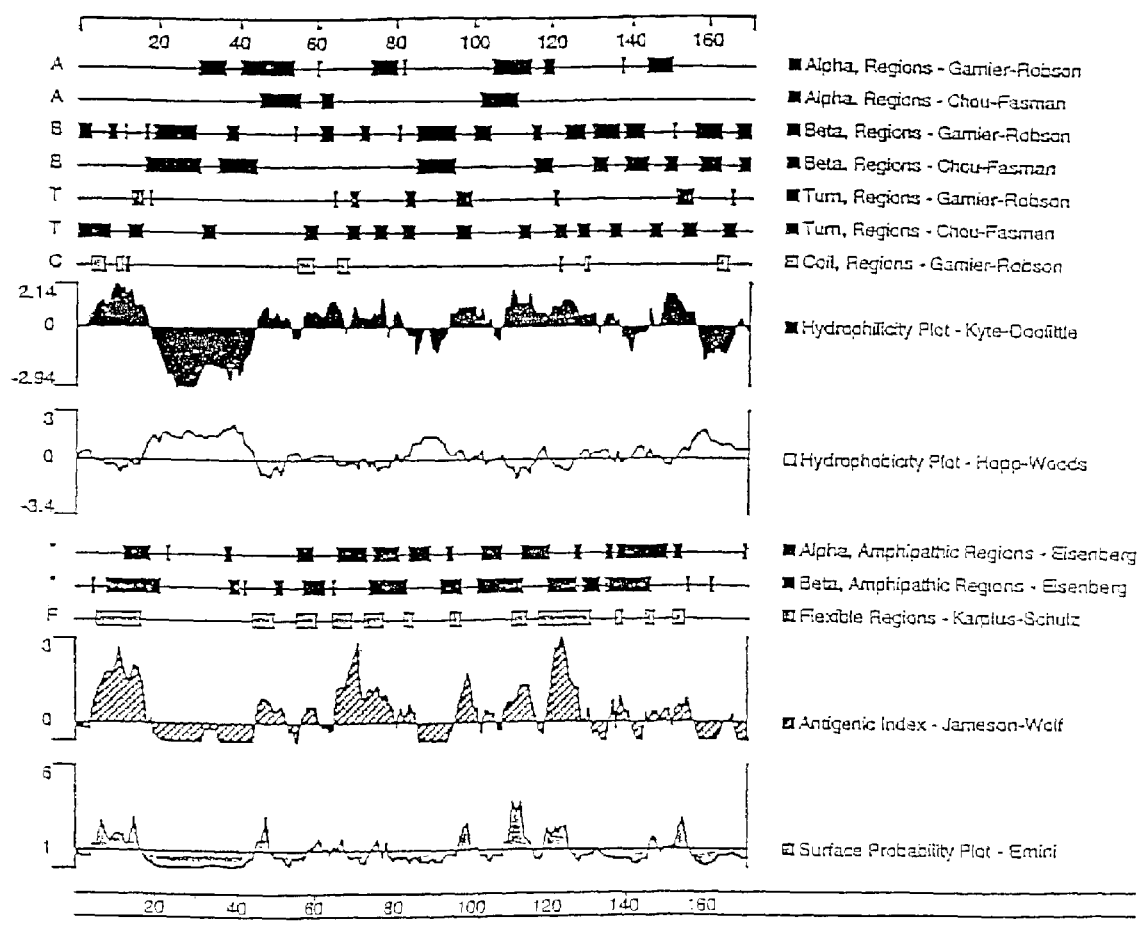
FIG. 3 provides an analysis of the Endokine alpha amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 44–54, 57–68, 69–78, 94–105, 108–132 and 148–158 in FIG. 1 correspond to the shown highly antigenic regions of the Endokine alpha protein.
Figure 4B:
FIG. 4 provides experimental results from a lacunar bone resorption assay. Monocytes grown in the presence of M-CSF differentiate to macrophages, consequently no resorption lacunae are observed on the bone disk (4A). Cells grown in presence of M-CSF and RANK-L differentiate to osteoclasts and large lacunae are visible on the bone disk (4B). When Endokine alpha is added to the culture at 1000 ng/ml lacunae formation is completely inhibited (4C). Only small lacunae are observed when Endokine alpha is added at 300 ng/ml (4D).
Figure 4A:
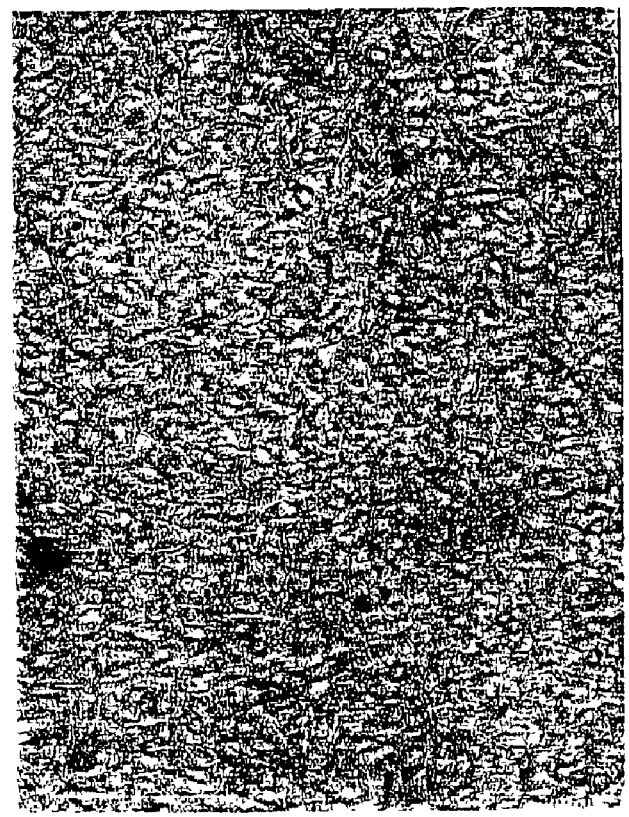
Figure 4D:
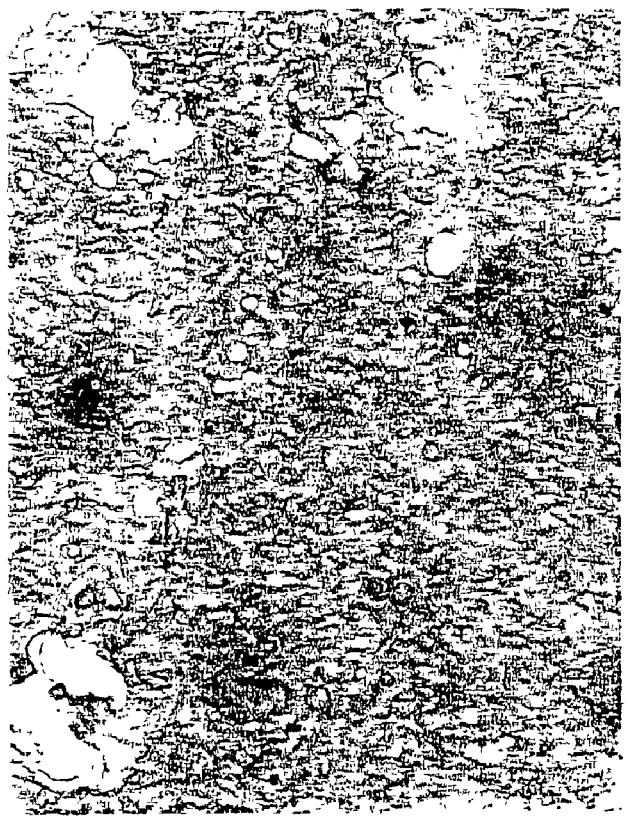
Figure 4C:
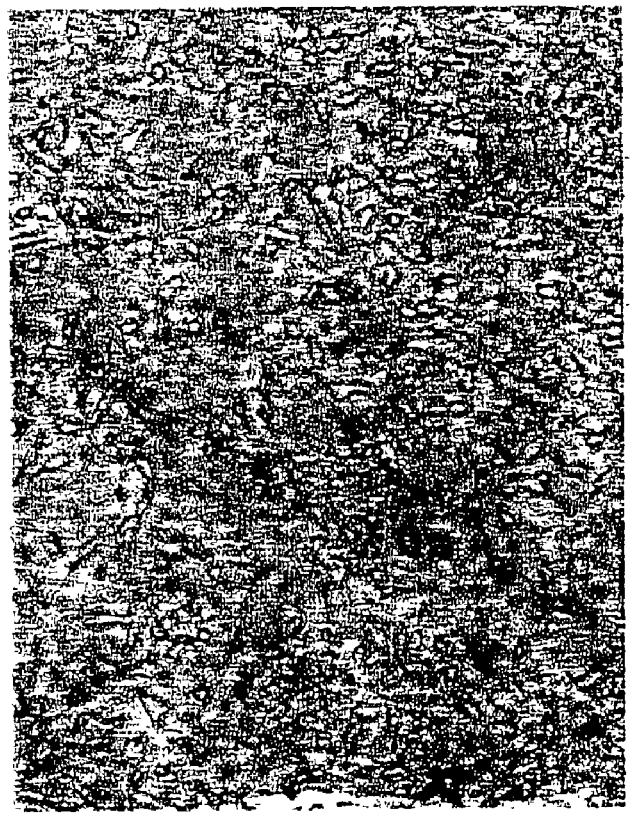
Figure 5B:
FIG. 5 provides experimental results from a lacunar bone resorption assay. Monocytes of a second donor (different from the donor used to purify monocytes used in experiments presented in FIG. 1) were cultured with M-CSF and RANK-L and in presence of 1000 ng/ml Endokine alpha (5A), or APRIL (5B), or LIGHT (5C), or BLyS™ (5D). While no bone resorption was caused by the cells cultured in presence of Endokine alpha, extensive bone resorption was observed on the disks from the cultures with the other cytokines.
Figure 5D:
Figure 5A:
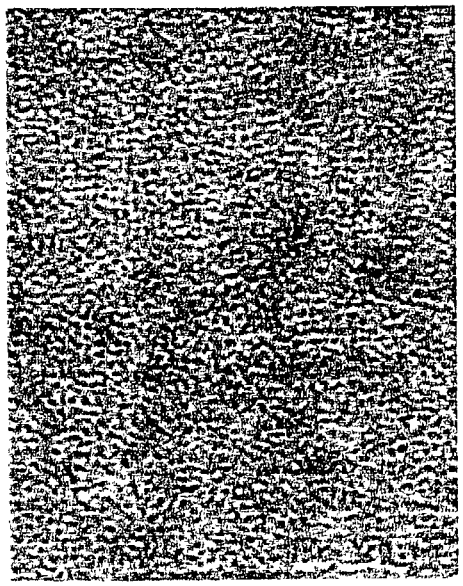
Figure 5C:

The present invention provides methods and compositions comprising the cytokine Endokine alpha in the detection, diagnosis, prognosis, treatment and/or prevention of metabolic bone disorders, conditions leading to and/or causing metabolic bone disorders and/or conditions resulting from metabolic bone disorders. The present invention provides heteromultimeric polypeptide complexes, particularly heterotrimers, of Endokine alpha in combination with known TNF ligand family member polypeptides, including, for example, those having the amino acid sequences SEQ ID NOs:2, 4, 6, 8, 10, 12, 14, 16, 18, 20, 22, 24, 26, 28, 30, 32, 34, 36, 38, and 42, as described in Table 1. Endokine alpha and other TNF ligand family member polypeptides are thought to play roles in regulating bone homeostasis through bone formation by osteoblasts and bone resorption by osteoclasts. The present invention further provides methods of using the compositions of the present invention in the detection, diagnosis, prognosis, treatment and/or prevention of disease associated with factors involved in bone homeostasis, including, for example, regulation of bone matrix deposition by osteoblasts, regulation of bone resorption by osteoclasts, proliferation of osteoblasts, proliferation of osteoclasts, differentiation of osteoblasts, differentiation of osteoclasts, activation of osteoblasts or activation of osteoclasts.

While the invention is described for illustrative purposes with respect to TNF ligand sequences contained in SEQ ID NOs:1–42, other forms of the TNF ligand family members known in the art may also be used in accordance with the invention as described herein.

Nucleic Acid Molecules

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as, for example, the nucleotide sequences of SEQ ID NOs:1, 3, 5, 7, 9, 11, 13, 15, 17, 19, 21, 23, 25, 27, 29, 31, 33, 35, 37, 39, and 41, a nucleic acid molecule of the present invention encoding a TNF ligand family member polypeptide may be obtained using standard cloning and screening procedures, such as those for cloning cDNAs using mRNA as starting material. For example, using the nucleotide information provided, a nucleic acid molecule of the present invention encoding a TNF ligand family member polypeptide may be obtained using standard cloning and screening procedures, such as those for cloning cDNAs using mRNA as starting material. Illustrative of the invention, the nucleic acid molecule of SEQ ID NO:31 was discovered in a cDNA library derived from primary dendritic cells, while the nucleic acid molecule described in FIG. 1 (SEQ ID NO:39) was discovered in a cDNA library derived from human brain striatum. Expressed sequence tags corresponding to a portion of the Endokine alpha cDNA were also found in several endothelial libraries and a fetal liver library.

TABLE 1

Exemplary TNF ligands.

| TNF Ligand | Aliases | Exemplary Identifiers | Exemplary PCT/Patent References | Exemplary trimerisation partners | Exemplary Extracellular Portions |
|---|---|---|---|---|---|
| EDA | | NM_001399; NP_001390 | | APRIL; BLyS | Glu 63 to Ser 391 (NM_001399) |

TABLE 1-continued

Exemplary TNF ligands.

| TNF Ligand | Aliases | Exemplary Identifiers | Exemplary PCT/Patent References | Exemplary trimerisation partners | Exemplary Extracellular Portions |
|---|---|---|---|---|---|
| APRIL | TL-3; TALL-2; TRIDL; TNF-delta; TNF-epsilon; TNFSF13 | NM_003808; NP_003799 | WO9733902 | BLyS; EDA | Thr 50 to Leu 250 (NP_003799) Ala 88 to Leu 233 (SEQ ID 2) Ala 105 to Leu 250 (SEQ ID 11) Ala 39 to Leu 168 (SEQ ID 4) Ala 105 to Leu 234 (SEQ ID 13) |
| BLyS™ | Neutrokine-a; TL7; BAFF; TALL1; THANK; TNFSF13B | AF132600; AAD21092 | WO9818921 WO0050597 | APRIL; EDA | Gln 73 to Leu 285 (SEQ ID 2) Gln 73 to Leu 266 (SEQ ID 19) |
| CD30L | TNFSF8 | L09753; AAA74594; AAR45009 | WO9324135 | GITRL | Gln 63 to Asp 234 (AAR45009) |
| AITRL | GITRL; TL6; Endokine; TNFSF18 | AF125303; AAD22634 | WO9807880 WO0050620 | CD30L | Glu 44 to Ser 169 (SEQ ID 2) |
| 4-1BBL | TNFSF9 | U03398; AAA53134; AAR64190 | WO9426290 | TWEAK; CD70 | Ala 50 to Glu 254 (AAR64190) |
| TWEAK | TL-9; APO3L; DR3LG; TNFSF12 | AF030099; AAC51923; AAY95338 | WO0037638 | 4-1BBL; CD70; VEGI | Val 41 to His 249 (AAY95338) |
| CD70 | CD27L; CD27LG; TNFSF7 | L08096; AAA36175; AAR50121 | WO9405691 | TWEAK; 4-1BBL | Gln 39 to Pro 193 (AAA36175) |
| LTa | TNF-beta; LT; TNFSF1 | X01393; CAA25649; AAP50055 | EP164965 | LIGHT; TNF-alpha; LT-beta | Leu 35 to Leu 205 (CAA25649) |
| TNFa | TNF; DIF; TNFSF2 | X01394; CAA25650; AAP50096 | EP155549 | LT-alpha | Val 77 to Leu 233 (CAA26669) |
| FasL | APT1LG1; TNFSF6 | U11821; AAC50124; I38707; AAR77281 | WO9518819 | LIGHT; VEGI | Gln 103 to Leu 281 (I38707) |
| LTb | TNFC; p33; TNFSF3 | L11015; AAA99888; Q06643; AAR56865 | WO9413808 | LT-alpha; LIGHT | Gln 49 to Gly 244 (Q06643) |
| LIGHT | LT-gamma; TL5; AIM2; TNFSF14; HVEML | AF036581; AAC39563 | WO9734911 WO0053223 | FasL; LT-alpha; LT-beta; VEGI | Gln 60 to Val 240 (SEQ ID 240) |
| TRAIL | Apo-2L; TL2; AIM1; TNFSF10 | U37518; AAC50332; P50591 | WO9733899 | RANKL; CD40L | Thr 39 to Gly 281 (P50591) |
| RANKL | TRANCE; OPGL; ODF; TNFSF11; TL-8 | AF053712; AAC39731; O14788; AAW83195 | WO9846751 | TRAIL; CD40L | Tyr 69 to Asp 317 (O14788) |
| CD40L | CD40LG; CD154; gp39; IMD3; HIGM1; TRAP | X67878; CAA48077; AAR36701 | WO9308207 | TRAIL; RANKL | His 47 to Leu 261 (CAA48077) |
| VEGI | TNF-gamma; TL1; TNFSF15 | AF039390; AAD08783 | WO9614328 WO0066608 | FasL; TWEAK; LIGHT | Thr 28 to Leu 147 (SEQ ID 2) Gln 62 to Leu 251 (SEQ ID 20) Arg 60 to Leu 251 (SEQ ID 20) |

TABLE 1-continued

Exemplary TNF ligands.

| TNF Ligand | Aliases | Exemplary Identifiers | Exemplary PCT/Patent References | Exemplary trimerisation partners | Exemplary Extracellular Portions |
|---|---|---|---|---|---|
| OX40L | gp34; TXGP1; TNFSF4 | D90224; BAA14259; AAR79903 | WO9521915 | | Gln 51 to Leu 183 (D90224) |

The present invention provides, for example, compositions comprising Endokine alpha together with one or more copies of the polypeptide encoded by the nucleic acid sequence of SEQ ID NO:1, comprising an open reading frame which encodes the TNF ligand family member polypeptide Lymphotoxin-alpha of SEQ ID NO:2. The Lymphotoxin-alpha open reading frame (nucleotides 80 to about 697 of SEQ ID NO:1) encodes a protein of about 205 amino acid residues, which comprises a predicted signal peptide of about 34 amino acids (amino acid residues from about 1 to about 34 of SEQ ID NO:2), a predicted extracellular domain of about 171 amino acids (amino acid residues from about 35 to about 205 of SEQ ID NO:2), and a predicted molecular weight of about 22.5 kDa.

The present invention provides, for example, compositions comprising Endokine alpha together with one or more copies of the polypeptide encoded by the nucleic acid sequence of SEQ ID NO:3, comprising an open reading frame which encodes the TNF ligand family member polypeptide TNF-alpha of SEQ ID NO:4. The TNF-alpha open reading frame (nucleotides 153 to about 854 of SEQ ID NO:3) encodes a protein of about 233 amino acid residues, which comprises a predicted signal peptide of about 76 amino acids (amino acid residues from about 1 to about 76 of SEQ ID NO:4), a predicted extracellular domain of about 157 amino acids (amino acid residues from about 77 to about 233 of SEQ ID NO:4), and a predicted molecular weight of about 26 kDa.

The present invention provides, for example, compositions comprising Endokine alpha together with one or more copies of the polypeptide encoded by the nucleic acid sequence of SEQ ID NO:5, comprising an open reading frame which encodes the TNF ligand family member polypeptide Lymphotoxin-beta of SEQ ID NO:6. The Lymphotoxin-beta open reading frame (nucleotides 9 to about 743 of SEQ ID NO:5) encodes a protein of about 244 amino acid residues, which comprises a predicted signal peptide of about 48 amino acids (amino acid residues from about 1 to about 48 of SEQ ID NO:6), a predicted extracellular domain of about 196 amino acids (amino acid residues from about 49 to about 244 of SEQ ID NO:6), and a predicted molecular weight of about 25 kDa.

The present invention provides, for example, compositions comprising Endokine alpha together with one or more copies of the polypeptide encoded by the nucleic acid sequence of SEQ ID NO:7, comprising an open reading frame which encodes the TNF ligand family member polypeptide OX-40L of SEQ ID NO:8. The OX-40L open reading frame (nucleotides 37 to about 588 of SEQ ID NO:7) encodes a protein of about 183 amino acid residues, which comprises a predicted intracellular domain of about 23 amino acids (amino acid residues from about 1 to about 23 of SEQ ID NO:8), a predicted transmembrane domain of about 27 amino acids (amino acid residues from about 24 to about 50 of SEQ ID NO:8), a predicted extracellular domain of about 133 amino acids (amino acid residues from about 51 to about 183 of SEQ ID NO:8), and a predicted molecular weight of about 21 kDa.

The present invention provides, for example, compositions comprising Endokine alpha together with one or more copies of the polypeptide encoded by the nucleic acid sequence of SEQ ID NO:9, comprising an open reading frame which encodes the TNF ligand family member polypeptide CD40L of SEQ ID NO:10. The CD40L open reading frame (nucleotides 46 to about 831 of SEQ ID NO:9) encodes a protein of about 261 amino acid residues, which comprises a predicted intracellular domain of about 22 amino acids (amino acid residues from about 1 to about 22 of SEQ ID NO:10), a predicted transmembrane domain of about 24 amino acids (amino acid residues from about 23 to about 46 of SEQ ID NO:10), a predicted extracellular domain of about 215 amino acids (amino acid residues from about 47 to about 261 of SEQ ID NO:10), and a predicted molecular weight of about 29 kDa.

The present invention provides, for example, compositions comprising Endokine alpha together with one or more copies of the polypeptide encoded by the nucleic acid sequence of SEQ ID NO:11, comprising an open reading frame which encodes the TNF ligand family member polypeptide FasL of SEQ ID NO:12, which may comprise heteromultimeric polypeptide complexes with other TNF ligand family member polypeptides. The FasL open reading frame (nucleotides 65 to about 910 of SEQ ID NO:11) encodes a protein of about 281 amino acid residues, which comprises a predicted intracellular domain of about 79 amino acids (amino acid residues from about 1 to about 79 of SEQ ID NO:12), a predicted transmembrane domain of about 23 amino acids (amino acid residues from about 80 to about 102 of SEQ ID NO:12), a predicted extracellular domain of about 179 amino acids (amino acid residues from about 103 to about 281 of SEQ ID NO:12), and a predicted molecular weight of about 31 kDa.

The present invention provides, for example, compositions comprising Endokine alpha together with one or more copies of the polypeptide encoded by the nucleic acid sequence of SEQ ID NO:13, comprising an open reading frame which encodes the TNF ligand family member polypeptide CD70 of SEQ ID NO:14. The CD70 open reading frame (nucleotides 151 to about 732 of SEQ ID NO:13) encodes a protein of about 193 amino acid residues, which comprises a predicted intracellular domain of about 20 amino acids (amino acid residues from about 1 to about 20 of SEQ ID NO:14), a predicted transmembrane domain of about 18 amino acids (amino acid residues from about 21 to about 38 of SEQ ID NO:14), a predicted extracellular domain of about 155 amino acids (amino acid residues from about 39 to about 193 of SEQ ID NO:14), and a predicted molecular weight of about 21 kDa.

The present invention provides, for example, compositions comprising Endokine alpha together with one or more copies of the polypeptide encoded by the nucleic acid sequence of SEQ ID NO:15, comprising an open reading frame which encodes the TNF ligand family member polypeptide CD30L of SEQ ID NO:16. The CD30L open reading frame (nucleotides 115 to about 819 of SEQ ID NO:15) encodes a protein of about 234 amino acid residues, which comprises a predicted intracellular domain of about 37 amino acids (amino acid residues from about 1 to about 37 of SEQ ID NO:16), a predicted transmembrane domain of about 25 amino acids (amino acid residues from about 38 to about 62 of SEQ ID NO:16), a predicted extracellular domain of about 172 amino acids (amino acid residues from about 63 to about 234 of SEQ ID NO:16), and a predicted molecular weight of about 26 kDa.

The present invention provides, for example, compositions comprising Endokine alpha together with one or more copies of the polypeptide encoded by the nucleic acid sequence of SEQ ID NO:17, comprising an open reading frame which encodes the TNF ligand family member polypeptide 4-1BB-L of SEQ ID NO:18. The 4-1BB-L open reading frame (nucleotides 4 to about 768 of SEQ ID NO:17) encodes a protein of about 254 amino acid residues, which comprises a predicted intracellular domain of about 25 amino acids (amino acid residues from about 1 to about 25 of SEQ ID NO:18), a predicted transmembrane domain of about 23 amino acids (amino acid residues from about 26 to about 48 of SEQ ID NO:18), a predicted extracellular domain of about 206 amino acids (amino acid residues from about 49 to about 254 of SEQ ID NO:18), and a predicted molecular weight of about 27 kDa.

The present invention provides, for example, compositions comprising Endokine alpha together with one or more copies of the polypeptide encoded by the nucleic acid sequence of SEQ ID NO:19, comprising an open reading frame which encodes the TNF ligand family member polypeptide TRAIL of SEQ ID NO:20. The TRAIL open reading frame (nucleotides 88 to about 933 of SEQ ID NO:19) encodes a protein of about 281 amino acid residues, which comprises a predicted intracellular domain of about 17 amino acids (amino acid residues from about 1 to about 17 of SEQ ID NO:20), a predicted transmembrane domain of about 21 amino acids (amino acid residues from about 18 to about 38 of SEQ ID NO:20), a predicted extracellular domain of about 243 amino acids (amino acid residues from about 39 to about 281 of SEQ ID NO:20), and a predicted molecular weight of about 33 kDa.

The present invention provides, for example, compositions comprising Endokine alpha together with one or more copies of the polypeptide encoded by the nucleic acid sequence of SEQ ID NO:21, comprising an open reading frame which encodes the TNF ligand family member polypeptide RANKL of SEQ ID NO:22. The RANKL open reading frame (nucleotides 185 to about 1138 of SEQ ID NO:21) encodes a protein of about 317 amino acid residues, which comprises a predicted intracellular domain of about 47 amino acids (amino acid residues from about 1 to about 47 of SEQ ID NO:22), a predicted transmembrane domain of about 21 amino acids (amino acid residues from about 48 to about 68 of SEQ ID NO:22), a predicted extracellular domain of about 249 amino acids (amino acid residues from about 69 to about 317 of SEQ ID NO:22), and a predicted molecular weight of about 35 kDa.

The present invention provides, for example, compositions comprising Endokine alpha together with one or more copies of the polypeptide encoded by the nucleic acid sequence of SEQ ID NO:23, comprising an open reading frame which encodes the TNF ligand family member polypeptide TWEAK of SEQ ID NO:24. The TWEAK open reading frame (nucleotides 18 to about 767 of SEQ ID NO:23) encodes a protein of about 249 amino acid residues, which comprises a predicted signal peptide of about 40 amino acids (amino acid residues from about 1 to about 40 of SEQ ID NO:24), a predicted extracellular domain of about 209 amino acids (amino acid residues from about 41 to about 249 of SEQ ID NO:24), and a predicted molecular weight of about 27 kDa.

The present invention provides, for example, compositions comprising Endokine alpha together with one or more copies of the polypeptide encoded by the nucleic acid sequence of SEQ ID NO:25, comprising an open reading frame which encodes the TNF ligand family member polypeptide APRIL of SEQ ID NO:26. The APRIL open reading frame (nucleotides 282 to about 1034 of SEQ ID NO:25) encodes a protein of about 250 amino acid residues, which comprises a predicted signal peptide of about 49 amino acids (amino acid residues from about 1 to about 49 of SEQ ID NO:26), a predicted extracellular domain of about 201 amino acids (amino acid residues from about 50 to about 250 of SEQ ID NO:26), a predicted mature secreted domain of about 146 amino acids (amino acid residues from about 105 to about 250 of SEQ ID NO:26), and a predicted molecular weight of about 27 kDa.

The present invention provides, for example, compositions comprising Endokine alpha together with one or more copies of the polypeptide encoded by the nucleic acid sequence of SEQ ID NO:27, comprising an open reading frame which encodes the TNF ligand family member polypeptide APRIL-SV of SEQ ID NO:28. The APRIL-SV open reading frame (nucleotides 108 to about 812 of SEQ ID NO:27) encodes a protein of about 234 amino acid residues, which comprises a predicted signal peptide of about 104 amino acids (amino acid residues from about 1 to about 104 of SEQ ID NO:28), a predicted extracellular domain of about 130 amino acids (amino acid residues from about 105 to about 234 of SEQ ID NO:28), and a predicted molecular weight of about 26 kDa.

The present invention provides, for example, compositions comprising Endokine alpha together with one or more copies of the polypeptide encoded by the nucleic acid sequence of SEQ ID NO:29, comprising an open reading frame which encodes the TNF ligand family member polypeptide BLyS™ of SEQ ID NO:30. The BLyS open reading frame (nucleotides 1 to about 858 of SEQ ID NO:29) encodes a protein of about 285 amino acid residues, which comprises a predicted signal peptide of about 72 amino acids (amino acid residues from about 1 to about 72 of SEQ ID NO:30), a predicted extracellular domain of about 213 amino acids (amino acid residues from about 73 to about 285 of SEQ ID NO:30), and a predicted molecular weight of about 31 kDa.

The present invention provides, for example, compositions comprising Endokine alpha together with one or more copies of the polypeptide encoded by the nucleic acid sequence of SEQ ID NO:31, comprising an open reading frame which encodes the TNF ligand family member polypeptide BLyS-SV of SEQ ID NO:32. The BLyS-SV open reading frame (nucleotides 1 to about 798 of SEQ ID NO:31) encodes a protein of about 266 amino acid residues, which comprises a predicted signal peptide of about 72 amino acids (amino acid residues from about 1 to about 72 of SEQ ID NO:32), a predicted extracellular domain of about 194 amino acids (amino acid residues from about 73 to about 266 of SEQ ID NO:32), and a predicted molecular weight of about 29 kDa.

The present invention provides, for example, compositions comprising Endokine alpha together with one or more copies of the polypeptide encoded by the nucleic acid sequence of SEQ ID NO:33, comprising an open reading frame which encodes the TNF ligand family member polypeptide LIGHT of SEQ ID NO:34. The LIGHT open reading frame (nucleotides 49 to about 771 of SEQ ID NO:33) encodes a protein of about 240 amino acid residues, which comprises a predicted intracellular domain of about 37 amino acids (amino acid residues from about 1 to about 37 of SEQ ID NO:34), a predicted transmembrane domain of about 21 amino acids (amino acid residues from about 38 to about 58 of SEQ ID NO:34), a predicted extracellular domain of about 162 amino acids (amino acid residues from about 59 to about 240 of SEQ ID NO:34), and a predicted molecular weight of about 26 kDa.

The present invention provides, for example, compositions comprising Endokine alpha together with one or more copies of the polypeptide encoded by the nucleic acid sequence of SEQ ID NO:35, comprising an open reading frame which encodes the TNF ligand family member polypeptide VEGI of SEQ ID NO:36. The VEGI open reading frame (nucleotides 1124 to about 1648 of SEQ ID NO:35) encodes a protein of about 174 amino acid residues, which comprises a predicted signal peptide of about 27 amino acids (amino acid residues from about 1 to about 27 of SEQ ID NO:36), a predicted extracellular domain of about 147 amino acids (amino acid residues from about 28 to about 174 of SEQ ID NO:36), and a predicted molecular weight of about 20 kDa.

The present invention provides, for example, compositions comprising Endokine alpha together with one or more copies of the polypeptide encoded by the nucleic acid sequence of SEQ ID NO:37, comprising an open reading frame which encodes the TNF ligand family member polypeptide VEGI-SV of SEQ ID NO:38. The VEGI-SV open reading frame (nucleotides 1 to about 756 of SEQ ID NO:37) encodes a protein of about 251 amino acid residues, which comprises a predicted signal peptide of about 59 amino acids (amino acid residues from about 1 to about 59 of SEQ ID NO:38), a predicted extracellular domain of about 192 amino acids (amino acid residues from about 60 to about 251 of SEQ ID NO:38), and a predicted molecular weight of about 28 kDa.

The present invention provides, for example, compositions comprising one or more Endokine alpha polypeptides encoded by the nucleic acid sequence of SEQ ID NO:39, comprising an open reading frame which encodes the TNF ligand family member polypeptide Endokine alpha of SEQ ID NO:40, which may comprise heteromultimeric polypeptide complexes with other TNF ligand family member polypeptides. The two alternative Endokine alpha open reading frames (169 amino acids and 177 amino acids) are detailed above in, for example, the brief description of FIG. 1.

The present invention provides, for example, compositions comprising Endokine alpha together with one or more copies of the polypeptide encoded by the nucleic acid sequence of SEQ ID NO:41, comprising an open reading frame which encodes the TNF ligand family member polypeptide EDA of SEQ ID NO:42. The EDA open reading frame (nucleotides 243 to about 1418 of SEQ ID NO:41) encodes a protein of about 391 amino acid residues, which comprises a predicted signal peptide of about 43 amino acids (amino acid residues from about 1 to about 43 of SEQ ID NO:42), a predicted extracellular domain of about 329 amino acids (amino acid residues from about 63 to about 391 of SEQ ID NO:42), and a predicted molecular weight of about 41 kDa.

It will be appreciated that, the polypeptide domains described herein have been predicted by computer analysis, and accordingly, that depending on the analytical criteria used for identifying various functional domains, the exact "address" of the extracellular, intracellular and transmembrane domains and signal peptides of the TNF ligand family member polypeptides may differ slightly. For example, the exact location of the Endokine alpha extracellular domain described above, may vary slightly (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus and/or C-terminus of the complete polypeptides, including polypeptides lacking one or more amino acids from the N-termini of the extracellular domains described herein, which constitute soluble forms of the extracellular domains of the TNF ligand family member polypeptides.

Nucleic acid molecules and polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule (DNA or RNA), which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread", as in a karyotype), is not "isolated" for the purposes of this invention. As discussed further herein, isolated nucleic acid molecules according to the present invention may be produced naturally, recombinantly, or synthetically.

The present invention provides isolated nucleic acid molecules comprising, or alternatively consisting of, for example, a sequence encoding the Lymphotoxin-alpha polypeptide having an amino acid sequence encoded by SEQ ID NO:1; a sequence encoding the TNF-alpha polypeptide having an amino acid sequence encoded by SEQ ID NO:3; a sequence encoding the Lymphotoxin-beta polypeptide having an amino acid sequence encoded by SEQ ID NO:5; a sequence encoding the OX-40L polypeptide having an amino acid sequence encoded by SEQ ID NO:7; a sequence encoding the CD40L polypeptide having an amino acid sequence encoded by SEQ ID NO:9; a sequence encoding the FasL polypeptide having an amino acid sequence encoded by SEQ ID NO:11; a sequence encoding the CD70 polypeptide having an amino acid sequence encoded by SEQ ID NO:13; a sequence encoding the CD30LG polypeptide having an amino acid sequence encoded by SEQ ID NO:15; a sequence encoding the 4-1BB-L polypeptide having an amino acid sequence encoded by SEQ ID NO:17; a sequence encoding the TRAIL polypeptide having an amino acid sequence encoded by SEQ ID NO:19; a sequence encoding the RANKL polypeptide having an amino acid sequence encoded by SEQ ID NO:21; a sequence encoding the TWEAK polypeptide having an amino acid sequence encoded by SEQ ID NO:23; a sequence encoding the APRIL polypeptide having an amino acid sequence encoded by SEQ ID NO:25; a sequence encoding the APRIL-SV polypeptide having an amino acid sequence encoded by SEQ ID NO:27; a sequence encoding the BLyS polypeptide having an amino acid sequence encoded by SEQ ID NO:29; a sequence encoding the BLyS-SV polypeptide having an amino acid sequence encoded by SEQ ID NO:31; a sequence encoding the LIGHT polypeptide having an amino acid sequence encoded by SEQ ID NO:33; a sequence encoding the VEGI polypeptide having an amino acid sequence encoded by SEQ ID NO:35; a sequence encoding the VEGI-SV polypeptide having an amino acid sequence encoded by SEQ ID NO:37; a sequence encoding the AITRL polypeptide having an amino acid sequence encoded by SEQ ID NO:39; or a sequence encoding the EDA polypeptide having an amino acid sequence encoded by SEQ ID NO:41.

Isolated nucleic acid molecules of the present invention include, for example, DNA molecules comprising, or alternatively consisting of, an open reading frame (ORF) with an initiation codon at positions 80–82 of SEQ ID NO:1; positions 153–155 of SEQ ID NO:3; positions 9–11 of SEQ ID NO:5; positions 37–39 of SEQ ID NO:7; positions 46–48 of SEQ ID NO:9; positions 65–67 of SEQ ID NO:11; positions 151–153 of SEQ ID NO:13; positions 115–117 of SEQ ID NO:15; positions 4–6 of SEQ ID NO:17; positions 88–90 of SEQ ID NO:19; positions 185–187 of SEQ ID NO:21; positions 18–20 of SEQ ID NO:23; positions 282–284 of SEQ ID NO:25; positions 108–110 of SEQ ID NO:27; positions 1–3 of SEQ ID NO:29; positions 1–3 of SEQ ID NO:31; positions 49–51 of SEQ ID NO:33; positions 1124–1126 of SEQ ID NO:35; positions 1–3 of SEQ ID NO:37; positions 1–3 of SEQ ID NO:39; or positions 243–245 of SEQ ID NO:41.

In addition, isolated nucleic acid molecules of the invention include, for example, DNA molecules which comprise, or alternatively consist of, a sequence substantially different from SEQ ID NO:1, but which due to the degeneracy of the genetic code, still encodes the Lymphotoxin-alpha protein of SEQ ID NO:2; a sequence substantially different from SEQ ID NO:3, but which due to the degeneracy of the genetic code, still encodes the TNF-alpha protein of SEQ ID NO:4; a sequence substantially different from SEQ ID NO:5, but which due to the degeneracy of the genetic code, still encodes the Lymphotoxin-beta protein of SEQ ID NO:6; a sequence substantially different from SEQ ID NO:7, but which due to the degeneracy of the genetic code, still encodes the OX-40L protein of SEQ ID NO:8; a sequence substantially different from SEQ ID NO:9, but which due to the degeneracy of the genetic code, still encodes the CD40L protein of SEQ ID NO:10; a sequence substantially different from SEQ ID NO:11, but which due to the degeneracy of the genetic code, still encodes the FasL protein of SEQ ID NO:12; a sequence substantially different from SEQ ID NO:13, but which due to the degeneracy of the genetic code, still encodes the CD70 protein of SEQ ID NO:14; a sequence substantially different from SEQ ID NO:15, but which due to the degeneracy of the genetic code, still encodes the CD30LG protein of SEQ ID NO:16; a sequence substantially different from SEQ ID NO:17, but which due to the degeneracy of the genetic code, still encodes the 4-1BB-L protein of SEQ ID NO:18; a sequence substantially different from SEQ ID NO:19, but which due to the degeneracy of the genetic code, still encodes the TRAIL protein of SEQ ID NO:20; a sequence substantially different from SEQ ID NO:21, but which due to the degeneracy of the genetic code, still encodes the RANKL protein of SEQ ID NO:22; a sequence substantially different from SEQ ID NO:23, but which due to the degeneracy of the genetic code, still encodes the TWEAK protein of SEQ ID NO:24; a sequence substantially different from SEQ ID NO:25, but which due to the degeneracy of the genetic code, still encodes the APRIL protein of SEQ ID NO:26; a sequence substantially different from SEQ ID NO:27, but which due to the degeneracy of the genetic code, still encodes the APRIL-SV protein of SEQ ID NO:28; a sequence substantially different from SEQ ID NO:29, but which due to the degeneracy of the genetic code, still encodes the BLyS protein of SEQ ID NO:30; a sequence substantially different from SEQ ID NO:31, but which due to the degeneracy of the genetic code, still encodes the BLyS-SV protein of SEQ ID NO:32; a sequence substantially different from SEQ ID NO:33, but which due to the degeneracy of the genetic code, still encodes the LIGHT protein of SEQ ID NO:34; a sequence substantially different from SEQ ID NO:35, but which due to the degeneracy of the genetic code, still encodes the VEGI protein of SEQ ID NO:36; a sequence substantially different from SEQ ID NO:37, but which due to the degeneracy of the genetic code, still encodes the VEGI-SV protein of SEQ ID NO:38; a sequence substantially different from SEQ ID NO:39, but which due to the degeneracy of the genetic code, still encodes the Endokine alpha protein of SEQ ID NO:40; or a sequence substantially different from SEQ ID NO:41, but which due to the degeneracy of the genetic code, still encodes the EDA protein of SEQ ID NO:42. Of course, the genetic code is well known in the art. Thus, it would be routine for one skilled in the art to generate the degenerate variants described above.

In another embodiment, the invention provides isolated nucleic acid molecules comprising, or alternatively consisting of, for example, a sequence encoding a polypeptide sequence that is at least 80%, 85%, 90%, 92%, 95%, 96%, 97%, 98%, or 99% identical to the Lymphotoxin-alpha amino acid sequence of SEQ ID NO:2; at least 80%, 85%, 90%, 92%, 95%, 96%, 97%, 98%, or 99% identical to the TNF-alpha amino acid sequence of SEQ ID NO:4; at least 80%, 85%, 90%, 92%, 95%, 96%, 97%, 98%, or 99% identical to the Lymphotoxin-beta amino acid sequence of SEQ ID NO:6; at least 80%, 85%, 90%, 92%, 95%, 96%, 97%, 98%, or 99% identical to the OX-40L amino acid sequence of SEQ ID NO:8; at least 80%, 85%, 90%, 92%, 95%, 96%, 97%, 98%, or 99% identical to the CD40L amino acid sequence of SEQ ID NO:10; at least 80%, 85%, 90%, 92%, 95%, 96%, 97%, 98%, or 99% identical to the FasL amino acid sequence of SEQ ID NO:12; at least 80%, 85%, 90%, 92%, 95%, 96%, 97%, 98%, or 99% identical to the CD70 amino acid sequence of SEQ ID NO:14; at least 80%, 85%, 90%, 92%, 95%, 96%, 97%, 98%, or 99% identical to the CD30LG amino acid sequence of SEQ ID NO:16; at least 80%, 85%, 90%, 92%, 95%, 96%, 97%, 98%, or 99% identical to the 4-1BB-L amino acid sequence of SEQ ID NO:18; at least 80%, 85%, 90%, 92%, 95%, 96%, 97%, 98%, or 99% identical to the TRAIL amino acid sequence of SEQ ID NO:20; at least 80%, 85%, 90%, 92%, 95%, 96%, 97%, 98%, or 99% identical to the RANKL amino acid sequence of SEQ ID NO:22; at least 80%, 85%, 90%, 92%, 95%, 96%, 97%, 98%, or 99% identical to the TWEAK amino acid sequence of SEQ ID NO:24; at least 80%, 85%, 90%, 92%, 95%, 96%, 97%, 98%, or 99% identical to the APRIL amino acid sequence of SEQ ID NO:26; at least 80%, 85%, 90%, 92%, 95%, 96%, 97%, 98%, or 99% identical to the APRIL-SV amino acid sequence of SEQ ID NO:28; at least 80%, 85%, 90%, 92%, 95%, 96%, 97%, 98%, or 99% identical to the BLyS amino acid sequence of SEQ ID NO:30; at least 80%, 85%, 90%, 92%, 95%, 96%, 97%, 98%, or 99% identical to the BLyS-SV amino acid sequence of SEQ ID NO:32; at least 80%, 85%, 90%, 92%, 95%, 96%, 97%, 98%, or 99% identical to the LIGHT amino acid sequence of SEQ ID NO:34; at least 80%, 85%, 90%, 92%, 95%, 96%, 97%, 98%, or 99% identical to the VEGI amino acid sequence of SEQ ID NO:36; at least 80%, 85%, 90%, 92%, 95%, 96%, 97%, 98%, or 99% identical to the VEGI-SV amino acid sequence of SEQ ID NO:38; at least 80%, 85%, 90%, 92%, 95%, 96%, 97%, 98%, or 99% identical to the Endokine alpha amino acid sequence of SEQ ID NO:40; or at least 80%, 85%, 90%, 92%, 95%, 96%, 97%, 98%, or 99% identical to the EDA amino acid sequence of SEQ ID NO:42.

Preferably, this nucleic acid molecule comprises, or alternatively consists of, for example, a sequence encoding the extracellular domain, the mature or soluble polypeptide sequence of the polypeptide encoded by SEQ ID NO:1; SEQ ID NO:3; SEQ ID NO:5; SEQ ID NO:7; SEQ ID NO:9; SEQ ID NO:11; SEQ ID NO:13; SEQ ID NO:15; SEQ ID NO:17; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; or SEQ ID NO:41.

The invention further provides isolated nucleic acid molecules comprising, or alternatively consisting of, nucleic acid molecules having a sequence complementary to, for example, any one of the above described sequences.

The present invention is further directed to fragments of nucleic acid molecules (i.e. polynucleotides) encoding TNF ligand family members, including, for example, those polynucleotides described herein. By a fragment of a nucleic acid molecule having, for example, the nucleotide sequence of SEQ ID NO:1, a nucleotide sequence encoding the polypeptide sequence of SEQ ID NO:2, the nucleotide sequence of SEQ ID NO:3, a nucleotide sequence encoding the polypeptide sequence of SEQ ID NO:4, the nucleotide sequence of SEQ ID NO:5, a nucleotide sequence encoding the polypeptide sequence of SEQ ID NO:6, the nucleotide sequence of SEQ ID NO:7, a nucleotide sequence encoding the polypeptide sequence of SEQ ID NO:8, the nucleotide sequence of SEQ ID NO:9, a nucleotide sequence encoding the polypeptide sequence of SEQ ID NO:10, the nucleotide sequence of SEQ ID NO:11, a nucleotide sequence encoding the polypeptide sequence of SEQ ID NO:12, the nucleotide sequence of SEQ ID NO:13, a nucleotide sequence encoding the polypeptide sequence of SEQ ID NO:14, the nucleotide sequence of SEQ ID NO:15, a nucleotide sequence encoding the polypeptide sequence of SEQ ID NO:16, the nucleotide sequence of SEQ ID NO:17, a nucleotide sequence encoding the polypeptide sequence of SEQ ID NO:18, the nucleotide sequence of SEQ ID NO:19, a nucleotide sequence encoding the polypeptide sequence of SEQ ID NO:20, the nucleotide sequence of SEQ ID NO:21, a nucleotide sequence encoding the polypeptide sequence of SEQ ID NO:22, the nucleotide sequence of SEQ ID NO:23, a nucleotide sequence encoding the polypeptide sequence of SEQ ID NO:24, the nucleotide sequence of SEQ ID NO:25, a nucleotide sequence encoding the polypeptide sequence of SEQ ID NO:26, the nucleotide sequence of SEQ ID NO:27, a nucleotide sequence encoding the polypeptide sequence of SEQ ID NO:28, the nucleotide sequence of SEQ ID NO:29, a nucleotide sequence encoding the polypeptide sequence of SEQ ID NO:30, the nucleotide sequence of SEQ ID NO:31, a nucleotide sequence encoding the polypeptide sequence of SEQ ID NO:32, the nucleotide sequence of SEQ ID NO:33, a nucleotide sequence encoding the polypeptide sequence of SEQ ID NO:34, the nucleotide sequence of SEQ ID NO:35, a nucleotide sequence encoding the polypeptide sequence of SEQ ID NO:36, the nucleotide sequence of SEQ ID NO:37, a nucleotide sequence encoding the polypeptide sequence of SEQ ID NO:38, the nucleotide sequence of SEQ ID NO:39, a nucleotide sequence encoding the polypeptide sequence of SEQ ID NO:40, the nucleotide sequence of SEQ ID NO:41, or a nucleotide sequence encoding the polypeptide sequence of SEQ ID NO:42, or the complementary strand thereto, is intended fragments at least 15 nt, and more preferably at least 20 nt or at least 25 nt, still more preferably at least 30 nt, and even more preferably, at least 40, 50, 100, 150, 200, 250, 300, 325, 350, 375, 400, 450, or 500 nt in length. These fragments have numerous uses which include, but are not limited to, diagnostic probes and primers as discussed herein. Of course, larger fragments, such as those of 501–1500 nt in length are also useful according to the present invention.

Preferred nucleic acid fragments of the present invention include, for example, nucleic acid molecules encoding polypeptides comprising, or alternatively, consisting of, portions of the TNF ligand family member polypeptides as identified in Table 1, which comprise heteromultimeric polypeptide complexes, and are described in more detail below. Polypeptides encoded by these polynucleotide fragments are also encompassed by the invention.

Also by a fragment of a nucleic acid molecule having, for example, the nucleotide sequence of SEQ ID NO:1, a nucleotide sequence encoding the polypeptide sequence of SEQ ID NO:2, the nucleotide sequence of SEQ ID NO:3, a nucleotide sequence encoding the polypeptide sequence of SEQ ID NO:4, the nucleotide sequence of SEQ ID NO:5, a nucleotide sequence encoding the polypeptide sequence of SEQ ID NO:6, the nucleotide sequence of SEQ ID NO:7, a nucleotide sequence encoding the polypeptide sequence of SEQ ID NO:8, the nucleotide sequence of SEQ ID NO:9, a nucleotide sequence encoding the polypeptide sequence of SEQ ID NO:10, the nucleotide sequence of SEQ ID NO:11, a nucleotide sequence encoding the polypeptide sequence of SEQ ID NO:12, the nucleotide sequence of SEQ ID NO:13, a nucleotide sequence encoding the polypeptide sequence of SEQ ID NO:14, the nucleotide sequence of SEQ ID NO:15, a nucleotide sequence encoding the polypeptide sequence of SEQ ID NO:16, the nucleotide sequence of SEQ ID NO:17, a nucleotide sequence encoding the polypeptide sequence of SEQ ID NO:18, the nucleotide sequence of SEQ ID NO:19, a nucleotide sequence encoding the polypeptide sequence of SEQ ID NO:20, the nucleotide sequence of SEQ ID NO:21, a nucleotide sequence encoding the polypeptide sequence of SEQ ID NO:22, the nucleotide sequence of SEQ ID NO:23, a nucleotide sequence encoding the polypeptide sequence of SEQ ID NO:24, the nucleotide sequence of SEQ ID NO:25, a nucleotide sequence encoding the polypeptide sequence of SEQ ID NO:26, the nucleotide sequence of SEQ ID NO:27, a nucleotide sequence encoding the polypeptide sequence of SEQ ID NO:28, the nucleotide sequence of SEQ ID NO:29, a nucleotide sequence encoding the polypeptide sequence of SEQ ID NO:30, the nucleotide sequence of SEQ ID NO:31, a nucleotide sequence encoding the polypeptide sequence of SEQ ID NO:32, the nucleotide sequence of SEQ ID NO:33, a nucleotide sequence encoding the polypeptide sequence of SEQ ID NO:34, the nucleotide sequence of SEQ ID NO:35, a nucleotide sequence encoding the polypeptide sequence of SEQ ID NO:36, the nucleotide sequence of SEQ ID NO:37, a nucleotide sequence encoding the polypeptide sequence of SEQ ID NO:38, the nucleotide sequence of SEQ ID NO:39, a nucleotide sequence encoding the polypeptide sequence of SEQ ID NO:40, the nucleotide sequence of SEQ ID NO:41, or a nucleotide sequence encoding the polypeptide sequence of SEQ ID NO:42, or the complementary strands thereof, is intended fragments at least 15 nt, and more preferably at least 20 nt or at least 25 nt, still more preferably at least 30 nt, and even more preferably, at least 40, 50, 100, 150, 200, 250, 300, 325, 350, 375, 400, 450, or 500 nt in length. These fragments have numerous uses which include, but are not limited to, diagnostic probes and primers as discussed herein. Of course, larger fragments, such as those of 501–1500 nt in length are also useful according to the present invention. Polypeptides encoded by these polynucleotide fragments are also encompassed by the invention.

Representative examples of TNF ligand family member polynucleotide fragments of the invention include, for example, fragments that comprise, or alternatively, consist of, a sequence from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, and/or 1301 to 1325, of SEQ ID NO:1; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, and/or 1601 to 1643, of SEQ ID NO:3; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, and/or 851 to 894 of SEQ ID NO:5; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, 2251 to 2300, 2301 to 2350, 2351 to 2400, 2401 to 2450, 2451 to 2500, 2501 to 2550, 2551 to 2600, 2601 to 2650, 2651 to 2700, 2701 to 2750, 2751 to 2800, 2801 to 2850, 2851 to 2900, 2901 to 2950, 2951 to 3000, 3001 to 3050, 3051 to 3100, 3101 to 3150, 3151 to 3200, 3201 to 3250, 3251 to 3300, 3301 to 3350 and/or 3351 to 3362, of SEQ ID NO:7; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, and/or 1801 to 1803 of SEQ ID NO:9; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, and/or 951 to 972 of SEQ ID NO:11; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, and/or 901 to 926 of SEQ ID NO:13; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, and/or 1901 to 1906 of SEQ ID NO:15; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, and/or 1601 to 1619 of SEQ ID NO:17; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, and/or 1751 to 1769 of SEQ ID NO:19; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, and/or 2251 to 2271 of SEQ ID NO:21; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, and/or 1301 to 1306 of SEQ ID NO:23; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, and/or 1301 to 1348 of SEQ ID NO:25; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, and/or 1101 to 1126 of SEQ ID NO:27; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, and/or 800 to 858 of SEQ ID NO:29; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, and/or 751 to 798 of SEQ ID NO:31; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, and/or 1151 to 1169 of SEQ ID NO:33; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, 2251 to 2300, 2301 to 2350, 2351 to 2400, 2401 to 2450, 2451 to 2500, 2501 to 2550, 2551 to 2600, 2601 to 2650, 2651 to 2700, 2701 to 2750, and/or 2751 to 2785 of SEQ ID NO:35; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, and/or 1101 to 1116 of SEQ ID NO:37; from about nucleotide 1 to 50, 51 to 100, 101 to 146, 147 to 200, 201 to 250, 251 to 300, 301 to 350, 351 to 400, 401 to 450, 451 to 500, and/or 501 to 534 of SEQ ID NO:39; from about nucleotide 1 to 50, 51 to 100, 101 to 146, 147 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, 2251 to 2300, 2301 to 2350, 2351 to 2400, 2401 to 2450, 2451 to 2500, 2501 to 2550, 2551 to 2600, 2601 to 2650, 2651 to 2700, 2701 to 2750, 2751 to 2800, 2801 to 2850, 2851 to 2900, 2901 to 2950, 2951 to 3000, 3001 to 3050, 3051 to 3100, 3101 to 3150, 3151 to 3200, 3201 to 3250, 3251 to 3300, 3301 to 3350, 3351 to 3400, 3401 to 3450, 3451 to 3500, 3501 to 3550, 3551 to 3600, 3601 to 3650, 3651 to 3700, 3701 to 3750, 3751 to 3800, 3801 to 3850, 3851 to 3900, 3901 to 3950, 3951 to 4000, 4001 to 4050, 4051 to 4100, 4101 to 4150, 4151 to 4200, 4201 to 4250, 4251 to 4300, 4301 to 4350, 4351 to 4400, 4401 to 4450, 4451 to 4500, 4501 to 4550, 4551 to 4600, 4601 to 4650, 4651 to 4700, 4701 to 4750, 4751 to 4800, 4801 to 4850, 4851 to 4900, 4901 to 4950, 4951 to 5000, 5001 to 5050, 5051 to 5100, 5101 to 5150, 5151 to 5200, and/or 5251 to 5307, of SEQ ID NO:41; or the complementary strands thereto. In this context "about" includes the particularly recited ranges, and ranges that are larger or smaller by several (5, 4, 3, 2, or 1) nucleotides, at either terminus or at both termini.

Preferably, the polynucleotide fragments of the invention encode polypeptides which comprise a composition demonstrating functional activity in binding and/or activating one or more TNF receptor family members. By demonstrating "functional activity" is meant, a polypeptide or heteromultimeric polypeptide complex capable of displaying one or more known functional activities associated with a full-length and/or secreted TNF ligand polypeptides. Such functional activities include, but are not limited to, biological activity (e.g., ability to regulate osteoclast proliferation, survival, differentiation, and/or activation), antigenicity (ability to bind or compete with a TNF ligand polypeptide for binding to an anti-TNF ligand antibody), immunogenicity (ability to generate antibody which binds to a TNF ligand polypeptide and/or a heteromultimeric complex of TNF ligand polypeptides), ability to bind to a TNF receptor family member, and ability to stimulate a TNF receptor signalling cascade (e.g., to activate calcium-modulator and cyclophilin ligand ("CAML"), calcineurin, nuclear factor of activated T cells transcription factor ("NF-AT"), nuclear factor-kappa B ("NF-kappa B"), activator protein-1 (AP-1), SRF, extracellular-signal regulated kinase 1 (ERK-1), polo like kinases (PLK), ELF-1, high mobility group I (HMG-I), and/or high mobility group Y (HMG-Y)).

In additional specific embodiments, the polynucleotide fragments of the invention encode a polypeptide comprising, or alternatively, consisting of the predicted signal peptide, the predicted intracellular domain, the predicted transmembrane domain, the predicted extracellular domain, or the predicted TNF conserved domain of TNF ligand family member polypeptides including, for example, those encoded by SEQ ID NOs:1, 3, 5, 7, 9, 11, 13, 15, 17, 19, 21, 23, 25, 27, 29, 31, 33, 35, 37, 39, and 41. In additional embodiments, the polynucleotide fragments of the invention encode a polypeptide comprising, or alternatively, consisting of any combination of 1, 2, 3, 4 or all 5 of the above recited domains from each encoded polypeptide. Polypeptides encoded by these polynucleotides are also encompassed by the invention.

In additional embodiments, the polynucleotides of the invention encode polypeptides comprising, or alternatively consisting of, functional attributes of TNF ligand family member polypeptides. Preferred embodiments of the invention in this regard include fragments that comprise, or alternatively consist of, alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TNF ligand polypeptides.

Additional preferred nucleic acid fragments of the present invention include nucleic acid molecules comprising, or alternatively, consisting of a sequence encoding one or more epitope-bearing portions of TNF ligand family member polypeptides. Polypeptides encoded by these nucleic acid molecules are also encompassed by the invention. Polypeptide fragments which bear antigenic epitopes of the TNF ligand family members may be easily determined by one of skill in the art using analysis of the Jameson-Wolf antigenic index. Methods for determining other such epitope-bearing portions of TNF ligands are described in detail below.

In specific embodiments, the polynucleotides of the invention are less than 100,000 kb, 50,000 kb, 10,000 kb, 1,000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of a TNF ligand family member polypeptide coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide sequence set forth as SEQ ID NOs:1, 3, 5, 7, 9, 11, 13, 15, 17, 19, 21, 23, 25, 27, 29, 31, 33, 35, 37, 39, or 41. In further embodiments, polynucleotides of the invention comprise at least 15, at least 30, at least 50, at least 100, or at least 250, at least 500, or at least 1000 contiguous nucleotides of TNF ligand family member coding sequence, but do not comprise all or a portion of any TNF ligand family member intron. In another embodiment, the nucleic acid comprising a TNF ligand family member coding sequence does not contain coding sequences of a genomic flanking gene (i.e., 5' or 3' to the TNF ligand gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In another embodiment, the invention provides an isolated nucleic acid molecule comprising a polynucleotide which hybridizes under stringent hybridization conditions to a portion of the polynucleotide in a nucleic acid molecule of the invention described above, for instance, the sequence complementary to the coding and/or noncoding sequence of SEQ ID NOs:1, 3, 5, 7, 9, 11, 13, 15, 17, 19, 21, 23, 25, 27, 29, 31, 33, 35, 37, 39, or 41, or fragments (such as, for example, the open reading frame or a fragment thereof) of these sequences, as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 40, 50, or 60) nucleotides, and even more preferably about any integer in the range of 30–70 or 80–150 nucleotides, or the entire length of the reference polynucleotide. These have uses, which include, but are not limited to, diagnostic probes and primers as discussed above and in more detail below. By a portion of a polynucleotide of "at least about 20 nt in length," for example, is intended to include the particularly recited ranges, larger or smaller by several (i.e. 5, 4, 3, 2, 1, or 0) amino acids, at either extreme or at both extremes of the nucleotide sequence of the reference polynucleotide (e.g., SEQ ID NO:1, 3, 5, 7, 9, 11, 13, 15, 17, 19, 21, 23, 25, 27, 29, 31, 33, 35, 37, 39, or 41). Of course, a polynucleotide which hybridizes only to a poly A sequence, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

As indicated, nucleic acid molecules of the present invention which encode a TNF ligand family member polypeptide may include, but are not limited to, polynucleotides encoding the amino acid sequence of the respective extracellular domains of the polypeptides, by themselves; and the coding sequence for the extracellular domains of the respective polypeptides and additional sequences, such as those encoding the intracellular and transmembrane domain sequences, or a pre-, or pro- or prepro-protein sequence; the coding sequence of the respective extracellular domains of the polypeptides, with or without the aforementioned additional coding sequences.

Also encoded by nucleic acids of the invention are the above protein sequences together with additional, non-coding sequences, including for example, but not limited to, introns and non-coding 5' and 3' sequences, such as the transcribed, non-translated sequences that play a role in transcription, mRNA processing, including splicing and polyadenylation signals, for example, ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this embodiment of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the BLyS or the BLyS-SV polypeptides fused to Fc at the N- or C-terminus.

The present invention further relates to variants of the nucleic acid molecules of the present invention, which encode portions, analogs or derivatives of TNF ligand polypeptides as described herein and including, for example, SEQ ID NOs:2, 4, 6, 8, 10, 12, 14, 16, 18, 20, 22, 24, 26, 28, 30, 32, 34, 36, 38, 40, and 42. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells er al., *Philos. Trans. R. Soc. London* SerA 317:415 (1986)).

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TNF ligand family member polypeptides or portions thereof. Also especially preferred in this regard are conservative substitutions.

Additional embodiments of the invention are directed to isolated nucleic acid molecules comprising a polynucleotide which encodes the amino acid sequence of a TNF ligand polypeptide (e.g., a TNF ligand family member polypeptide fragment described herein) having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, 10–20 conservative amino acid substitutions, 5–10 conservative amino acid substitutions, 1–5 conservative amino acid substitutions, 3–5 conservative amino acid substitutions, or 1–3 conservative amino acid substitutions. Of course, in order of ever-increasing preference, it is highly preferable for a polynucleotide which encodes the amino acid sequence of a TNF ligand polypeptide to have an amino acid sequence which contains not more than 10, 9, 8, 7, 6, 5, 4, 3, 2 or 1 conservative amino acid substitutions.

Further embodiments include an isolated nucleic acid molecule comprising, or alternatively consisting of, a polynucleotide having a nucleotide sequence at least 80%, 85%, or 90% identical, and more preferably at least 95%, 96%, 97%,-98% or 99% identical to a polynucleotide selected from the group consisting of: (a) a nucleotide sequence encoding a TNF ligand family member polypeptide (e.g., SEQ ID NOs:2, 4, 6, 8, 10, 12, 14, 16, 18, 20, 22, 24, 26, 28, 30, 32, 34, 36, 38, 40, or 42); (b) a nucleotide sequence encoding a TNF ligand family member polypeptide (e.g., SEQ ID NOs:2, 4, 6, 8, 10, 12, 14, 16, 18, 20, 22, 24, 26, 28, 30, 32, 34, 36, 38, 40, or 42), excepting the N-terminal methionine; (c) a fragment of the polypeptide of (b) having TNF ligand functional activity (e.g., antigenic or biological activity); (d) a nucleotide sequence encoding the predicted extracellular domain of a TNF ligand polypeptide (e.g., SEQ ID NOs:2, 4, 6, 8, 10, 12, 14, 16, 18, 20, 22, 24, 26, 28, 30, 32, 34, 36, 38, 40, or 42); and (e) a nucleotide sequence complementary to any of the nucleotide sequences in (a), (b), (c), (d), or (e) above. The present invention also encompasses the above polynucleotide sequences fused to a heterologous polynucleotide sequence. Polypeptides encoded by these polynucleotides and nucleic acid molecules are also encompassed by the invention.

Highly preferred embodiments of the invention are directed to nucleic acid molecules comprising, or alternatively consisting of polynucleotides having nucleotide sequences at least 0.80%, 85%, 90% identical and more preferably at least 95%, 96%, 97%, 98%, 99% or 100% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42. Preferred embodiments of the invention are directed to nucleic acid molecules comprising, or alternatively consisting of polynucleotides having nucleotide sequences at least 90% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42. More preferred embodiments of the invention are directed to nucleic acid molecules comprising, or alternatively consisting of polynucleotides having nucleotide sequences at least 95% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42. More preferred embodiments of the invention are directed to nucleic acid molecules comprising, or alternatively consisting of polynucleotides having nucleotide sequences at least 96% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42.

Additionally, more preferred embodiments of the invention are directed to nucleic acid molecules comprising, or alternatively consisting of polynucleotides having nucleotide sequences at least 97% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42. Additionally, more preferred embodiments of the invention are directed to nucleic acid molecules comprising, or alternatively consisting of polynucleotides having nucleotide sequences at least 98% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42. Additionally, more preferred embodiments of the invention are directed to nucleic acid molecules comprising, or alternatively consisting of polynucleotides having nucleotide sequences at least 99% identical to polynucleotide sequences encoding TNF ligand family member polypeptides including, for example, SEQ ID NOs:2, 4, 6, 8, 10, 12, 14, 16, 18, 20, 22, 24, 26, 28, 30, 32, 34, 36, 38, 40, or 42.

A further embodiment of the invention relates to an isolated nucleic acid molecule comprising a polynucleotide which encodes the amino acid sequence of a TNF ligand family member polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a TNF ligand polypeptide to have an amino acid sequence which contains not more than 7–10, 5–10, 3–7, 3–5, 2–5, 1–5, 1–3, 10, 9, 8, 7, 6, 5, 4, 3, 2 or 1 conservative amino acid substitutions.

By a polynucleotide having a nucleotide sequence at least, for example, 95% "identical" to a reference nucleotide sequence encoding a TNF ligand polypeptide is intended that the nucleotide sequence of the polynucleotide is identical to the reference sequence except that the polynucleotide sequence may include up to five mismatches per each 100 nucleotides of the reference nucleotide sequence encoding the TNF ligand polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire nucleotide sequence encoding a TNF ligand family member polypeptide, or any TNF ligand polynucleotide fragment as described herein.

As a practical matter, whether any particular nucleic acid molecule is at least 80%, 85%, 90%, 95%, 96%, 97%, 98% or 99% identical to, for instance, any TNF ligand polynucleotide such as, for example, the polynucleotides shown as SEQ ID NOs:1, 3, 5, 7, 9, 11, 13, 15, 17, 19, 21, 23, 25, 27, 29, 31, 33, 35, 37, 39, or 41, or fragments thereof, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

Preferred embodiments of the present invention include nucleic acid molecules having sequences at least 80%, 85%, 90%, 92%, 95%, 96%, 97%, 98% or 99% identical to the nucleic acid sequences disclosed herein, which encode polypeptides comprising heteromultimeric polypeptide complexes having TNF ligand functional activity (e.g., biological activity).

By "a polypeptide having TNF ligand functional activity" (e.g., biological activity), are intended polypeptides exhibiting activity similar, but not necessarily identical, to an activity of the extracellular domain or the full-length TNF ligand polypeptides of the invention, as measured in a particular functional assay (e.g., immunological or biological assay). For example, functional activity can be measured by the ability of a polypeptide sequence described herein to form multimers (e.g., homodimers and homotrimers) with full-length or the extracellular domain of TNF ligand family members. TNF ligand polypeptide functional activity can be also be measured by determining the ability of a polypeptide of the invention to induce lymphocyte (e.g., B cell) proliferation, differentiation or activation and/or to extend B cell survival. These functional assays can be routinely performed using techniques described herein (e.g., see Example 6) and otherwise known in the art. Additionally, TNF ligand polypeptides of the present invention modulate cell proliferation, cytotoxicity, cell survival and cell death. An in vitro cell proliferation, cytotoxicity, cell survival, and cell death assay for measuring the effect of a protein on certain cells can be performed by using reagents well known and commonly available in the art for detecting cell replication and/or death. For instance, numerous such assays for TNF-related protein activities are described in the various references in this disclosure. Briefly, an example of such an assay involves collecting human or animal (e.g., mouse) cells and mixing with (1) transfected host cell-supernatant containing TNF ligand protein (or a candidate polypeptide) or (2) nontransfected host cell-supernatant control, and measuring the effect on cell numbers or viability after incubation of certain period of time. Such cell proliferation and/or survival modulation activities as can be measured in this type of assay are useful for treating tumor, tumor metastasis, infections, autoimmune diseases, inflammation and other immune-related diseases.

TNF ligand family members exhibit activity on leukocytes including, for example, monocytes, lymphocytes (e.g., B cells) and neutrophils. Heteromultimeric polypeptide complexes of the invention are active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art.

For example, see Peters et al., Immun. Today 17:273 (1996); Young et al., J. Exp. Med. 182:1111 (1995); Caux et al., Nature 390:258 (1992); and Santiago-Schwarz et al., Adv. Exp. Med. Biol. 378:7 (1995).

Of course, due to the degeneracy of the genetic code, one of ordinary skill in the art will immediately recognize that a large number of nucleic acid molecules having a sequence at least 80%, 85%, 90%, 92%, 95%, 96%, 97%, 98%, or 99% identical to nucleic acid sequences encoding TNF ligand polypeptides, including, for example, those encoded by SEQ ID NO:1, 3, 5, 7, 9, 11, 13, 15, 17, 19, 21, 23, 25, 27, 29, 31, 33, 35, 37, 39, or 41, or fragments thereof, will encode polypeptides "having TNF ligand polypeptide functional activity" (e.g., biological activity). In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TNF ligand activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules encoding polypeptides which comprised by the present invention, host cells which are genetically engineered with the recombinant vectors, and the production of Endokine alpha polypeptides and heteromultimeric complexes comprising Endokine alpha polypeptides or portions thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids. See, e.g., Ausubel, infra; Sambrook, infra.

The DNA insert should be operatively linked to an appropriate promoter, such as the phage lambda PL promoter, the E. coli: lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will include a translation initiating AUG at the beginning and a termination codon appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223–3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods in Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. In a further example, a region of additional amino acids, particularly charged amino acids, may be added to the N-terminus of the polypeptide to improve stability and persistence in the host cell, during purification or during subsequent handling and storage. Also, as indicated, a region(s) also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP A 0,464,533 (also, Canadian counterpart 2,045,869) discloses fusion proteins comprising various portions of constant region of immunoglobin molecules together with another human protein or part thereof. In many cases, the Fc part in the fusion protein is thoroughly advantageous for use in therapy and diagnosis and thus results, for example, in improved pharmacokinetic properties (EP A 0,232,262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fe portions for the purpose of high-throughput screening assays to identify antagonists (for example, hIL-5). See, D. Bennett et al., *Journal of Molecular Recognition* 8:52–58 (1995) and K. Johanson et al., *The Journal of Biological Chemistry* 270(16):9459–9471 (1995).

The Endokine alpha protein together with heteromultimeric complexes comprising the Endokine alpha polypeptide, can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., Endokine alpha coding sequence), and/or to include genetic material (e.g., heterologous polynucleotide sequences) that is operably associated with, for example, Endokine alpha polynucleotides of the invention, and which activates, alters, and/or amplifies endogenous Endokine alpha polynucleotides. For example, techniques known in the art may be used to operably associate heterologous control regions (e.g., promoter and/or enhancer) and endogenous Endokine alpha polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

Endokine Alpha Polypeptides and Peptides

The invention further provides isolated Endokine alpha polypeptides and heteromultimeric complexes comprising Endokine alpha polypeptides having the amino acid sequence encoded by the deposited cDNA, or the amino acid sequence in FIG. 1 (SEQ ID NO:40), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

By "isolated" polypeptide or protein is intended a polypeptide or protein removed from its native environment. For example, recombinantly produced polypeptides and proteins expressed in recombinant host cells are considered isolated for purposes of the invention as are native or recombinant polypeptides and proteins which have been substantially purified by any suitable technique such as, for example, the one-step method described in Smith and Johnson, *Gene* 67:31–40 (1988).

It will be recognized in the art that some amino acid sequence of the Endokine alpha polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes heteromultimeric complexes comprising variations of the Endokine alpha polypeptide which show substantial Endokine alpha polypeptide activity or which include regions of Endokine alpha protein such as the protein fragments discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," Science 247:1306–1310 (1990).

Thus, the fragment, derivative or analog of the polypeptide of SEQ ID NO:40, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the Endokine alpha protein. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331–340 (1967); Robbins et al., Diabetes 36:838–845 (1987); Cleland et al. Crit. Rev. Therapeutic Drug Carrier Systems 10:307–377 (1993)).

The replacement of amino acids can also change the selectivity of binding to cell surface receptors. Ostade et al., Nature 361:266–268 (1993) describes certain mutations resulting in selective binding of TNF-α to only one of the two known types of TNF receptors. Thus, the Endokine alpha of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 2).

TABLE 2

| Conservative Amino Acid Substitutions. | |
| --- | --- |
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |

TABLE 2-continued

| Conservative Amino Acid Substitutions. | |
| --- | --- |
| Acidic | Aspartic Acid |
|  | Glutamic Acid |
| Small | Alanine |
|  | Serine |
|  | Threonine |
|  | Methionine |
|  | Glycine |

Of course, the number of amino acid substitutions a skilled artisan would make depends on many factors, including those described above. Generally speaking, the number of substitutions for any given Endokine alpha polypeptide will not be more than 50, 40, 30, 20, 10, 5, or 3, depending on the objective.

Amino acids in the Endokine alpha protein of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., J. Mol. Biol. 224: 899–904 (1992) and de Vos et al. Science 255:306–312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the Endokine alpha polypeptide can be substantially purified by the one-step method described in Smith and Johnson, Gene 67:31–40 (1988).

The heteromultimeric polypeptide complexes of the present invention and the polypeptides of the present invention include the polypeptides comprising or, alternatively, consisting of: (a) the complete amino acid sequence as shown in FIG. 1 (SEQ ID NO:40); (b) the complete amino acid sequence as shown in FIG. 1 (SEQ ID NO:40), but minus the N-terminal methionine residue; (c) the amino acid sequence of the Endokine alpha polypeptide having the amino acid sequence encoded by the cDNA clone contained in ATCC Deposit No. 97640; and (d) the amino acid sequence of an epitope-bearing portion of any one of the polypeptides of (a), (b), or (c), as well as polypeptides which are at least 80%, 85%, 90%, 92% or 95% identical, more preferably at least 96%, 97%, 98% or 99% identical to a polypeptide described herein, and also include portions of such polypeptides with at least 30 amino acids and more preferably at least 50 amino acids.

By a polypeptide having an amino acid sequence at least, for example, 95% "identical" to a reference amino acid sequence of an Endokine alpha polypeptide is intended that the amino acid sequence of the polypeptide is identical to the reference sequence except that the polypeptide sequence may include up to five amino acid alterations per each 100 amino acids of the reference amino acid sequence of the Endokine alpha polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide comprises or, alternatively, consists of, a sequence at least 80%, 85%, 90%, 92%, 95%, 96%, 97%,98% or 99% identical to, for instance, the amino acid sequence shown in FIG. 1 (SEQ ID NO:40) or to the amino acid sequence encoded by deposited cDNA clone can be determined conventionally using known computer programs such the BESTFIT program (Wisconsin Sequence Analysis Package, Version 8 for Unix, Genetics Computer Group, University Research Park, 575 Science Drive, Madison, Wis. 53711. When using BESTFIT or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present inventors have discovered that the Endokine alpha protein is a 169 residue protein exhibiting three main structural domains. The intracellular domain was identified within residues from about 1 to about 17 in FIG. 1 (SEQ ID NO:40); or, alternatively, the 25 amino acid intracellular domain that includes additionally the eight amino acids of SEQ ID NO:58 at the N-terminus when translation is initiated at the initial ATG codon of SEQ ID NO:39. The transmembrane domain was identified within residues from about 18 to about 43 in FIG. 1 (SEQ ID NO:40). The extracellular domain was identified within residues from about 44 to about 169 in FIG. 1 (SEQ ID NO:40). Thus, the invention further provides preferred Endokine alpha protein fragments and heteromultimeric polypeptide complexes comprising such fragments, comprising a polypeptide selected from: the Endokine alpha intracellular domain, the transmembrane domain and the Endokine alpha extracellular domain.

The extracellular domain of the Endokine alpha protein can be combined with parts of the constant domain of immunoglobulins (IgG), resulting in chimeric polypeptides. These fusion proteins show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86 (1988)). Fusion proteins that have a disulfide-linked dimeric structure due to the IgG part can also be more efficient in binding and neutralizing the ligands than the monomeric extracellular domains alone (Fountoulakis et al., *J. Biochem.* 270:3958–3964 (1995)).

Polypeptide fragments of the present invention include polypeptides comprising or alternatively, consisting of, an amino acid sequence contained in SEQ ID NO:40, encoded by the cDNA contained in the deposited clone, or encoded by nucleic acids which hybridize (e.g., under stringent hybridization conditions) to the nucleotide sequence contained in the deposited clone, or shown in FIG. 1 (SEQ ID NO:39) or the complementary strand thereto. Protein fragments maybe "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: 1 to 50, 51 to 100, 101 to 150 and/or 151 to 169 of SEQ ID NO:40. In this context, "about" includes the particularly recited ranges and ranges larger or smaller, by several (5, 4, 3, 2, or 1) amino acids, at either terminus or both termini. Moreover, polypeptide fragments can be at least 10, 20, 30, 40, 50, 60, 70, 80, 90, 100, 110, 120, 130, 140, 150 or 168 amino acids in length. Polynucleotides encoding these polypeptides are also encompassed by the invention. Polynucleotides that hybridize to the complement of these encoding polynucleotides are also encompassed by the invention, as are the polypeptides encoded by these hybridizing polynucleotides.

Among the especially preferred fragments of the invention are fragments characterized by structural or functional attributes of Endokine alpha. Such fragments include amino acid residues that comprise alpha-helix and alpha-helix-forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of full-length Endokine alpha (SEQ ID NO:40). Certain preferred regions are those set out in FIG. 3 and include, but are not limited to, regions of the aforementioned types identified by analysis of the amino acid sequence depicted in FIG. 1 (SEQ ID NO:40), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolfhigh antigenic index regions, as predicted using the default parameters of these computer programs. Polynucleotides encoding these polypeptides are also encompassed by the invention.

The data representing the structural or functional attributes of Endokine alpha set forth in FIG. 3 and/or Table 2, as described above, was generated using the various modules and algorithms of the DNA*STAR set on default parameters. In a preferred embodiment, the data presented in columns VIII, IX, XIII, and XIV of Table 2 can be used to determine regions of Endokine alpha which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table 2, be represented or identified by using tabular representations of the data presented in FIG. 3. The DNA*STAR computer algorithm used to generate FIG. 3 (set on the original default parameters) was used to present the data in FIG. 3 in a tabular format (See Table 2). The tabular format of the data in FIG. 3 may be used to easily determine specific boundaries of a preferred region.

The above-mentioned preferred regions set out in FIG. 3 and in Table 2 include, but are not limited to, regions of the aforementioned types identified by analysis of the amino acid sequence set out in FIG. 3. As set out in FIG. 3 and in Table 2, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

Amino and Carboxy Terminal Deletions.

As mentioned above, even if deletion of one or more amino acids from the N-terminus of a protein results in modification or loss of one or more biological functions of the protein, other biological activities may still be retained. Thus, the ability of shortened Endokine alpha molecules to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an Endokine alpha mutein with a large number of deleted N-terminal amino acid residues may retain some biological or immunogenic activities. In fact, peptides composed of as few as six Endokine alpha amino acid residues may often evoke an immune response.

Accordingly, the present invention further provides Endokine alpha polypeptides and heteromultimeric polypeptide complexes comprising Endokine alpha polypeptides having one or more residues deleted from the amino terminus of the Endokine alpha amino acid sequence shown in FIG. 1 (i.e., SEQ ID NO:40), up to the asparagine residue at position number 164 and polynucleotides encoding such polypeptides. In particular, the present invention provides polypeptides comprising the amino acid sequence of residues n-169 of FIG. 1 (SEQ ID NO:40), where n is an integer in the range of 2 to 164, and 165 is the position of the first residue from the N-terminus of the complete Endokine alpha polypeptide believed to be required for at least immunogenic activity of the Endokine alpha polypeptide.

More in particular, the invention provides polynucleotides encoding polypeptides comprising, or alternatively consisting of, the amino acid sequence of a member selected from the group consisting of: residues P-2 to S-169; L-3 to S-169; S-4 to S-169; H-5 to S-169; S-6 to S-169; R-7 to S-169; T-8 to S-169; Q-9 to S-169; G-10 to S-169; A-11 to S-169; Q-12 to S-169; R-13 to S-169; S-14 to S-169; S-15 to S-169; W-16 to S-169; K-17 to S-169; L-18 to S-169; W-19 to S-169; L-20 to S-169; F-21 to S-169; C-22 to S-169; S-23 to S-169; I-24 to S-169; V-25 to S-169; M-26 to S-169; L-27 to S-169; L-28 to S-169; F-29 to S-169; L-30 to S-169; C-31 to S-169; S-32 to S-169; F-33 to S-169; S-34 to S-169; W-35 to S-169; L-36 to S-169; I-37 to S-169; F-38 to S-169; I-39 to S-169; F-40 to S-169; L-41 to S-169; Q-42 to S-169; L-43 to S-169; E-44 to S-169; T-45 to S-169; A-46 to S-169; K-47 to S-169; E-48 to S-169; P-49 to S-169; C-50 to S-169; M-51 to S-169; A-52 to S-169; K-53 to S-169; F-54 to S-169; G-55 to S-169; P-56 to S-169; L-57 to S-169; P-58 to S-169; S-59 to S-169; K-60 to S-169; W-61 to S-169; Q-62 to S-169; M-63 to S-169; A-64 to S-169; S-65 to S-169; S-66 to S-169; E-67 to S-169; P-68 to S-169; P-69 to S-169; C-70 to S-169; V-71 to S-169; N-72 to S-169; K-73 to S-169; V-74 to S-169; S-75 to S-169; D-76 to S-169; W-77 to S-169; K-78 to S-169; L-79 to S-169; E-80 to S-169; I-81 to S-169; L-82 to S-169; Q-83 to S-169; N-84 to S-169; G-85 to S-169; L-86 to S-169; Y-87 to S-169; L-88 to S-169; I-89 to S-169; Y-90 to S-169; G-91 to S-169; Q-92 to S-169; V-93 to S-169; A-94 to S-169; P-95 to S-169; N-96 to S-169; A-97 to S-169; N-98 to S-169; Y-99 to S-169; N-100 to S-169; D-101 to S-169; V-102 to S-169; A-103 to S-169; P-104 to S-169; F-105 to S-169; E-106 to S-169; V-107 to S-169; R-108 to S-169; L-109 to S-169; Y-110 to S-169; K-111 to S-169; N-112 to S-169; K-113 to S-169; D-114 to S-169; M-115 to S-169; I-116 to S-169; Q-117 to S-169; T-118 to S-169; L-119 to S-169; T-120 to S-169; N-121 to S-169; K-122 to S-169; S-123 to S-169; K-124 to S-169; I-125 to S-169; Q-126 to S-169; N-127 to S-169; V-128 to S-169; G-129 to S-169; G-130 to S-169; T-131 to S-169; Y-132 to S-169; E-133 to S-169; L-134 to S-169; H-135 to S-169; V-136 to S-169; G-137 to S-169; D-138 to S-169; T-139 to S-169; I-140 to S-169; D-141 to S-169; L-142 to S-169; I-143 to S-169; F-144 to S-169; N-145 to S-169; S-146 to S-169; E-147 to S-169; H-148 to S-169; Q-149 to S-169; V-150 to S-169; L-151 to S-169; K-152 to S-169; N-153 to S-169; N-154 to S-169; T-155 to S-169; Y-156 to S-169; W-157 to S-169; G-158 to S-169; I-159 to S-169; I-160 to S-169; L-161 to S-169; L-162 to S-169; A-163 to S-169; and N-164 to S-169 of the Endokine alpha sequence shown in FIG. 1. In addition, the invention provides polynucleotides that encode polypeptides segments of the 177 amino acid alternative Endokine alpha protein that contains the 25 amino acid intracellular domain that includes additionally the eight amino acids of SEQ ID NO:58 at the N-terminus when translation is initiated at the initial ATG codon of SEQ ID NO:39, in the same manner as detailed for the 169 amino acid Endokine alpha protein detailed above. The present invention is also directed to nucleic acid molecules comprising or, alternatively, consisting of, a polynucleotide sequence at least 80%, 85%, 90%, 92%, 95%, 96%, 97%, 98% or 99% identical to the polynucleotide sequences encoding the Endokine alpha polypeptides described above. The present invention also encompasses the above polynucleotide sequences fused to a heterologous polynucleotide sequence. Polypeptides encoded by these polynucleotide sequences are also encompassed by the invention.

Also as mentioned above, even if deletion of one or more amino acids from the C-terminus of a protein results in modification or loss of one or more biological functions of the protein, other biological activities may still be retained. Thus, the ability of the shortened Endokine alpha mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an Endokine alpha mutein with a large number of deleted C-terminal amino acid residues may retain some biological or immunogenic activities. In fact, peptides composed of as few as six Endokine alpha amino acid residues may often evoke an immune response.

Accordingly, the present invention further provides polypeptides and heteromultimeric polypetide complexes comprising polypeptides having one or more residues deleted from the carboxy terminus of the amino acid sequence of the Endokine alpha polypeptide shown in FIG. 1 (SEQ ID NO:40), up to the serine residue at position number 6, and polynucleotides encoding such polypeptides. In particular, the present invention provides polypeptides comprising the amino acid sequence of residues 1-m of FIG. 1 (i.e., SEQ ID NO:40), where m is an integer in the range of 6 to 169, and 6 is the position of the first residue from the C-terminus of the complete Endokine alpha polypeptide believed to be required for at least immunogenic activity of the Endokine alpha polypeptide.

More in particular, the invention provides polynucleotides encoding polypeptides comprising, or alternatively consisting of, the amino acid sequence of a member selected from the group consisting of: residues M-1 to I-168; M-1 to F-167; M-1 to Q-166; M-1 to P-165; M-1 to N-164; M-1 to A-163; M-1 to L-162; M-1 to L-161; M-1 to I-160; M-1 to I-159; M-1 to G-158; M-1 to W-157; M-1 to Y-156; M-1 to T-155; M-1 to N-154; M-1 to N-153; M-1 to K-152; M-1 to L-151; M-1 to V-150; M-1 to Q-149; M-1 to H-148; M-1 to E-147; M-1 to S-146; M-1 to N-145; M-1 to F-144; M-1 to 1–143; M-1 to L-142; M-1 to D-141; M-1 to I-140; M-1 to T-139; M-1 to D-138; M-1 to G-137; M-1 to V-136; M-1 to H-135; M-1 to L-134; M-1 to E-133; M-1 to Y-132; M-1 to T-131; M-1 to G-130; M-1 to G-129; M-1 to V-128; M-1 to N-127; M-1 to Q-126; M-1 to I-125; M-1 to K-124; M-1 to S-123; M-1 to K-122; M-1 to N-121; M-1 to T-120; M-1 to L-119; M-1 to T-118; M-1 to Q-117; M-1 to I-116; M-1 to M-115; M-1 to D-114; M-1 to K-113; M-1 to N-112; M-1 to K-111; M-1 to Y-110; M-1 to L-109; M-1 to R-108; M-1 to V-107; M-1 to E-106; M-1 to F-105; M-1 to P-104; M-1 to A-103; M-1 to V-102; M-1 to D-101; M-1 to N-100; M-1 to Y-99; M-1 to N-98; M-1 to A-97; M-1 to N-96; M-1 to P-95; M-1 to A-94; M-1 to V-93; M-1 to Q-92; M-1 to G-91; M-1 to Y-90; M-1 to I-89; M-1 to L-88; M-1 to Y-87; M-1 to L-86; M-1 to G-85; M-1 to N-84; M-1 to Q-83; M-1 to L-82; M-1 to I-81; M-1 to E-80; M-1 to L-79; M-1 to K-78; M-1 to W-77; M-1 to D-76; M-1 to S-75; M-1 to V-74; M-1 to K-73; M-1 to N-72; M-1 to V-71; M-1 to C-70; M-1 to P-69; M-1 to P-68; M-1 to E-67; M-1 to S-66; M-1 to S-65; M-1 to A-64; M-1 to M-63; M-1 to Q-62; M-1 to W-61; M-1 to K-60; M-1 to S-59; M-1 to P-58; M-1 to L-57; M-1 to P-56; M-1 to G-55; M-1 to F-54; M-1 to K-53; M-1 to A-52; M-1 to M-51; M-1 to C-50; M-1 to P-49; M-1 to E-48; M-1 to K-47; M-1 to A-46; M-1 to T-45; M-1 to E-44; M-1 to L-43; M-1 to Q-42; M-1 to L-41; M-1 to F-40; M-1 to I-39; M-1 to F-38; M-1 to I-37; M-1 to L-36; M-1 to W-35; M-1 to S-34; M-1 to F-33; M-1 to S-32; M-1 to C-31; M-1 to L-30; M-1 to F-29; M-1 to L-28; M-1 to L-27; M-1 to M-26; M-1 to V-25; M-1 to I-24; M-1 to S-23; M-1 to C-22; M-1 to F-21; M-1 to L-20; M-1 to W-19; M-1 to L-18; M-1 to K-17; M-1 to W-16; M-1 to S-15; M-1 to S-14; M-1 to R-13; M-1 to Q-12; M-1 to A-11; M-1 to G-10; M-1 to Q-9; M-1 to T-8; M-1 to R-7; and M-1 to S-6 of the sequence of the Endokine alpha sequence shown in FIG. 1. In addition, the invention provides polynucleotides that encode polypeptides segments of the 177 amino acid alternative Endokine alpha protein that contains the 25 amino acid intracellular domain that includes additionally the eight amino acids of SEQ ID NO:58 at the N-terminus when translation is initiated at the initial ATG codon of SEQ ID NO:39, in the same manner as detailed for the 169 amino acid Endokine alpha protein detailed above. The present invention is also directed to nucleic acid molecules comprising or, alternatively, consisting of, a polynucleotide sequence at least 80%, 85%, 90%, 92%, 95%, 96%, 97%, 98% or 99% identical to the polynucleotide sequences encoding the Endokine alpha polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of an Endokine alpha polypeptide, which may be described generally as having residues n-m of FIG. 1 (i.e., SEQ ID NO:40), where n and m are integers as described above.

The Endokine alpha polypeptides of the invention may be in monomers or multimers (i.e., dimers, trimers, tetramers and higher multimers). Accordingly, the present invention relates to monomers and multimers of the Endokine alpha polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only Endokine alpha polypeptides of the invention (including Endokine alpha fragments, variants, and fusion proteins, as described herein). These homomers may contain Endokine alpha polypeptides having identical or different amino acid sequences. In a specific embodiment, a homomer of the invention is a multimer containing only Endokine alpha polypeptides having an identical amino acid sequence. In another specific embodiment, a homomer of the invention is a multimer containing Endokine alpha polypeptides having different amino acid sequences. In specific embodiments, the multimer of the invention is a homodimer (e.g., containing Endokine alpha polypeptides having identical or different amino acid sequences) or a homotrimer (e.g., containing Endokine alpha polypeptides having identical or different amino acid sequences). In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the Endokine alpha fragments and Endokine alpha polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the Endokine alpha polypeptides of the invention. Such covalent associations may involve one or more amino acid residues contained in the polypeptide sequence (e.g., that recited in SEQ ID NO:40, or contained in the polypeptide encoded by the clone 97640). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an Endokine alpha fusion protein. In one example, covalent associations are between the heterologous sequence contained in a fusion protein of the invention (see, e.g., U.S. Pat. No. 5,478,925). In a specific example, the covalent associations are between the heterologous sequence contained in a Endokine alpha-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety).

In another embodiment, two or more Endokine alpha polypeptides of the invention are joined through peptide linkers. Examples include those peptide linkers described in U.S. Pat. No. 5,073,627 (hereby incorporated by reference). Proteins comprising multiple Endokine alpha polypeptides separated by peptide linkers may be produced using conventional recombinant DNA technology.

Another method for preparing multimer Endokine alpha polypeptides of the invention involves use of Endokine alpha polypeptides fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric Endokine alpha proteins are those described in PCT application WO 94/10308, hereby incorporated by reference. Recombinant fusion proteins comprising a soluble Endokine alpha polypeptide fused to a peptide that dimerizes or trimerizes in solution are expressed in suitable host cells, and the resulting soluble multimeric Endokine alpha is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric Endokine alpha may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric Endokine alpha.

In another example, proteins of the invention are associated by interactions between Flag® polypeptide sequence contained in Flag®-Endokine alpha fusion proteins of the invention. In a further embodiment, associations proteins of the invention are associated by interactions between a heterologous polypeptide sequence contained in Flag®-Endokine alpha fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, polypeptides of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105–111). For example, a peptide corresponding to a fragment of the Endokine alpha polypeptides of the invention can be synthesized by use of a peptide synthesizer. Furthermore, if desired, nonclassical amino acids or chemical amino acid analogs can be introduced as a substitution or addition into the Endokine alpha polynucleotide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses Endokine alpha polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of Endokine alpha which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

Protein Modification

In addition, proteins of the invention can be chemically synthesized using techniques known in the art (see, e.g., Creighton, *Proteins: Structures and Molecular Principles*, W.H. Freeman & Co., N.Y. (1983), and Hunkapiller, M., et al., *Nature* 310:105–111 (1984)). For example, a peptide corresponding to a fragment of the Endokine-alpha polypeptides of the invention can be synthesized by use of a peptide synthesizer. Furthermore, if desired, nonclassical amino acids or chemical amino acid analogs can be introduced as a substitution or addition into the Endokine-alpha polypeptide sequence. Non-classical amino acids include, but are not limited to, to the D-isomers of the common amino acids, 2,4-diaminobutyric acid, alpha-amino isobutyric acid, 4-aminobutyric acid, Abu, 2-amino butyric acid, alpha-Abu, alpha-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alpha-alanine, fluoro-amino acids, designer amino acids such as alpha-methyl amino acids, Ca-methyl amino acids, Na-methyl amino acids, and amino acid analogs in general. Furthermore, the amino acids can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), and restriction selection mutagenesis (see, e.g., Wells et al., *Philos. Trans. R. Soc. London SerA* 317:415 (1986)).

The invention additionally, encompasses Endokine-alpha polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of Endokine alpha which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on the functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

Antibodies and Epitopes

As described in detail below, the polypeptides and polypeptide complexes of the present invention can be used to raise polyclonal and monoclonal antibodies, which are useful in diagnostic assays for detecting Endokine alpha protein expression as described below or as agonists and antagonists capable of inhibiting Endokine alpha protein function. Further, such polypeptides can be used in the yeast two-hybrid system to "capture" Endokine alpha protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., *Proc. Natl. Acad. Sci. USA* 81:3998–4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein.

See, for instance, Sutcliffe, J. G. et al., *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 30 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes posttranslational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides that can be used to generate Endokine-specific polyclonal and monoclonal antibodies include a polypeptide comprising or, alternatively, consisting of one, two, three or more of any of the following amino acid sequences and polynucleotides encoding these polypeptides: amino acid residues from about 44 to about 158 in FIG. 1 (SEQ ID NO:40); amino acid residues from about 44 to about 54 in FIG. 1 (SEQ ID NO:40); amino acid residues from about 57 to about 68 in FIG. 1 (SEQ ID NO:40); amino acid residues from about 69 to about 78 in FIG. 1 (SEQ ID NO:40); amino acid residues from about 94 to about 105 in FIG. 1 (SEQ ID NO:40); amino acid residues from about 108 to about 132 in FIG. 1 (SEQ ID NO:40); and amino acid residues from about 148 to about 158 in FIG. 1 (SEQ ID NO:40). As indicated above, the inventors have determined that the above polypeptide fragments are antigenic regions of the Endokine alpha protein.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. See, Houghten, R. A., *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354(1985). Generally, animals maybe immunized with free peptide; however, anti-peptide antibody titer may be boosted by coupling of the peptide to a macromolecular carrier, such as keyhole limpet hemocyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde.

Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al. (1984), supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art.

For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention which include, but are not limited to, Fab, Fab' and F(ab')2, Fd, single-chain Fvs (scFv), single-chain antibodies, disulfide-linked Fvs (sdfv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes monoclonal, polyclonal, chimeric, humanized, and human monoclonal and polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991) J. Immunol. 147:60–69; U.S. Pat. Nos. 5,573,920, 4,474,893, 5,601,819, 4,714,681, 4,925,648; Kostelny, S. A. et al. (1992) J. Immunol. 148:1547–1553.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; and WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "monoclonal antibody" refers to an antibody that is derived from a single clone, including any eukaryotic, prokaryotic, or phage clone, and not to the method by which it is produced. Monoclonal antibodies can be prepared using a wide variety of techniques known in the art including the use of hybridoma, recombinant and phage display technology.

Hybridoma techniques include those known in the art and taught in Harlow et al., *Antibodies: A Laboratory Manual* (Cold Spring Harbor Laboratory Press, 2nd ed. 1988); Hammerling, et al., in: *Monoclonal Antibodies and T-cell Hybridomas*, pp. 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995) J. Immunol. Methods 182:41–50; Ames, R. S. et al. (1995) J. Immunol. Methods 184:177–186; Kettleborough, C. A. et al. (1994) Eur. J. Immunol. 24:952–958; Persic, L. et al. (1997) Gene 187 9–18; Burton, D. R. et al. (1994) Advances in Immunology 57:191–280; PCT/GB91/01134; WO 90/02809; WO 91/10737; WO 92/01047; WO 92/18619; WO 93/11236; WO 95/15982; and WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12(6):864–869 (1992); and Sawai, H. et al., *AJRI* 34:26–34 (1995); and Better, M. et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu, L. et al., *PNAS* 90:7995–7999 (1993); and Skerra, A. et al., *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al., *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. No. 5,530,101; and 5,585, 089), veneering or resurfacing (EP 0 592 106; EP 0 519 596; Padlan E. A., *Molecular Immunology* 28(4/5):489–498 (1991); Studnicka G. M. et al., *Protein Engineering* 7(6): 805–814 (1994); Roguska M. A. et al., *PNAS* 91:969–973 (1994)), and chain shuffling (U.S. Pat. No. 5,565,332). Human antibodies can be made by a variety of methods known in the art including phage display methods described above. See also U.S. Pat. Nos. 4,444,887, 4,716,111, 5,545, 806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al., *Immunol. Lett.* 39:91–99 (1994); U.S. Pat. No. 5,474, 981; Gillies, S. O. et al., *PNAS* 89:1428–1432 (1992); Fell, H. P. et al., *J. Immunol.* 146:2446–2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fe portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al., *PNAS* 88:10535–10539 (1991); Zheng, X. X. et al., *J. Immunol.* 154:5590–5600 (1994); and Vil, H. et al., *PNAS* 89:11337–11341 (1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al., *Blood* 92(6):1981–1988 (1998); Chen, Z. et al., *Cancer Res.* 58(16):3668–3678 (1998); Harrop, J. A. et al., *J. Immunol.* 161(4):1786–1794 (1998); Zhu, Z. et al., *Cancer Res.* 58(15):3209–3214 (1998); Yoon, D. Y. et al., *J. Immunol.* 160(7):3170–3179 (1998); Prat, M. et al., *J. Cell. Sci.* 111(Pt2):237–247 (1998); Pitard, V. et al., *J. Immunol. Methods* 205(2):177–190 (1997); Liautard, J. et al., *Cytokine* 9(4):233–241 (1997); Carlson, N. G. et al., *J. Biol. Chem.* 272(17):11295–11301 (1997); Taryman, R. E. et al., *Neuron* 14(4):755–762 (1995); Muller, Y. A. et al., *Structure* 6(9):1153–1167 (1998); Bartunek, P. et al., *Cytokine* 8(1):14–20 (1996)(said references incorporated by reference in their entireties).

The entire disclosure of each document cited in this section on "Polypeptides and Peptides" is hereby incorporated herein by reference.

Epitopes

The present invention encompasses polypeptides comprising, or alternatively consisting of, an epitope of the polypeptide having an amino acid sequence of SEQ ID NO:40, or an epitope of the polypeptide sequence encoded by a polynucleotide sequence contained in deposited clone [Deposit information] or encoded by a polynucleotide that hybridizes to the complement of the sequence of SEQ ID NO:39 or contained in the clone deposited as ATCC Deposit Number 97640 on Jun. 27, 1996 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:39), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding, but does not necessarily exclude cross-reactivity with other antigens. Antigenic epitopes need not necessarily be immunogenic.

Fragments that function as epitopes may be produced by any conventional means. (See, e.g., Houghten, *Proc. Natl. Acad. Sci. USA* 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, e.g., Wilson et al., *Cell* 37:767–778 (1984); Sutcliffe et al., *Science* 219:660–666 (1983)).

Similarly, immunogenic epitopes can be used, for example, to induce antibodies according to methods well known in the art. (See, e.g., Sutcliffe et al., supra; Wilson et al., supra; Chow et al., *Proc. Natl. Acad. Sci. USA* 82:910–914; and Bittle et al., *J. Gen. Virol.* 66:2347–2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.* 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimido-benzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected by, for example, ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, and IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature* 331:84–86 (1988). IgG fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., *J. Biochem.* 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., *Proc. Natl. Acad. Sci. USA* 88:8972–897 (1991)). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., *Curr. Opinion Biotechnol.* 8:724–33 (1997); Harayama, *Trends Biotechnol.* 16(2):76–82 (1998); Hansson, et al., *J. Mol. Biol.* 287:265–76 (1999); and Lorenzo and Blasco, *Biotechniques* 24(2):308–13 (1998) (each of these patents and publications are hereby incorporated by reference in its entirety). In one embodiment, alteration of polynucleotides corresponding to SEQ ID NO:39 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be mono-specific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; and WO 92/05793; Tutt, et al., *J. Immunol.* 147:60–69 (1991); U.S. Pat. Nos. 4,474,893; 4,714,681; 4,925,648; 5,573,920; and 5,601,819; Kostelny et al., *J. Immunol.* 148:1547–1553 (1992).

Antibodies of the present invention may be described or specified in terms of the epitope(s) or portion(s) of a polypeptide or polypeptide complex of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $5 \times 10^{7}$M, $10^{-7}$M, $5 \times 10^{-8}$M, $10^{-8}$M, $5 \times 10^{-9}$M, $10^{-9}$M, $5 \times 10^{-10}$M, $10^{-11}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides and/or polypeptide complexes of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding, but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6): 1981–1988 (1998); Chen, et al., *Cancer Res.* 58(16):3668–3678 (1998); Harrop et al., *J. Immunol.* 161(4):1786–1794 (1998); Zhu et al., *Cancer Res.* 58(15):3209–3214 (1998); Yoon, et al., *J. Immunol.* 160(7):3170–3179 (1998); Prat et al., *J. Cell. Sci.* 111(Pt2):237–247 (1998); Pitard et al., *J. Immunol. Methods* 205(2):177–190 (1997); Liautard et al., *Cytokine* 9(4):233–241 (1997); Carlson et al., *J. Biol. Chem.* 272(17): 11295–11301 (1997); Taryman et al., *Neuron* 14(4):755–762 (1995); Muller et al., *Structure* 6(9):1153–1167 (1998); Bartunek et al., *Cytokine* 8(1): 14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual* (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; and WO 89/12624; U.S. Pat. No. 5,314,995; and EP 396,387.

The antibodies of the invention include derivatives that are modified, e.g., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/ blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual* (Cold Spring Harbor Laboratory Press, 2nd ed. 1988); Hammerling, et al., in: *Monoclonal Antibodies and T-Cell Hybridomas* 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art and are discussed in detail in Example 3. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986);

Gillies et al., *J. Immunol. Methods* 125:191–202 (1989); U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, *Molecular Immunology* 28(4/5): 489–498 (1991); Studnicka et al., *Protein Engineering* 7(6): 805–814 (1994); Roguska. et al., *PNAS* 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (*Int. Rev. Immunol.* 13:65–93 (1995)). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899–903 (1988)).

Further, antibodies to the polypeptides and/or polypeptide complexes of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444 (1989) and Nissinoff, *J. Immunol.* 147(8): 2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:40.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated therefrom, or nucleic acid, preferably poly A+ RNA, isolated therefrom, or any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (See, for example, the techniques described in Sambrook et al., *Molecular Cloning, A Laboratory Manual,* 2d Ed., Cold Spring Harbor Laboratory, Cold Spring Harbor, N.Y. (1990) and Ausubel et al., eds., *Current Protocols in Molecular Biology,* John Wiley & Sons, NY (1998), which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions maybe made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851–855 (1984); Neuberger et al., *Nature* 312:604–608 (1984); Takeda et al., *Nature* 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., *Proc. Natl. Acad. Sci. USA* 85:5879–5883 (1988); and Ward et al., *Nature* 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science* 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101–3109 (1985); Van Heeke & Schuster, *J. Biol. Chem.* 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355–359 (1984)).

Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293,3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 (*Clinical Pharmacy* 12:488–505; Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); *TIB TECH* 11(5):155–215 (May 1993)); and hygro, which confers resistance to hygromycin (Santerre et al., 1984, Gene 30:147). Methods commonly known in the art of recombinant DNA technology which can be used are described in Ausubel et al., eds., *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al., eds, *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells," in *DNA Cloning*, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, *Nature* 322:52 (1986); Köhler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides and/or polypeptide complexes of the present invention fused or conjugated to antibody domains other than the variable regions. For example, polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides and/or polypeptide complexes of the present invention may be fused or conjugated to the above antibody portions to increase the in vivo half-life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988)). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270:9459–9471 (1995).

Moreover, the antibodies or fragments thereof of the present invention can be fused to marker sequences, such as a peptide to facilitates their purification. In preferred embodiments, the marker amino acid sequence is a hexahistidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. eds., pp. 243–56 (Alan R. Liss, Inc. 1985); Hellstrom et al., "Antibodies For Drug Delivery", in *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. eds., pp. 475–506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. eds., pp. 303–16 (Academic Press 1985), and Thorpe et al., "The Preparation And Cytotoxic Properties Of Antibody-Toxin Conjugates", *Immunol. Rev.* 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays for Antibody Binding

The antibodies of the invention may be assayed for immunospecific binding by any method known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, Vol. 1, John Wiley & Sons, Inc., New York (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel (et al., eds, *Current Protocols in Molecular Biology*, Vol. 1, John Wiley & Sons, Inc., New York (19914) at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel, et al., eds, *Current Protocols in Molecular Biology*, Vol. 1, John Wiley & Sons, Inc., New York (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel, et al., eds, *Current Protocols in Molecular Biology*, Vol. 1, John Wiley & Sons, Inc., New York (1994) at 1 1.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Endokine Alpha Related Disorder Diagnosis

Endokine alpha is a new member of the TNF family of cytokines. For Endokine alpha related disorders, it is believed that substantially altered (increased or decreased) levels of Endokine alpha gene expression can be detected in tissue or other cells or bodily fluids (e.g., sera, plasma, urine, synovial fluid, spinal fluid or bone marrow) taken from an individual having such a disorder, relative to a "standard" Endokine alpha gene expression level, that is, the Endokine alpha expression level in tissue or bodily fluids from an individual not having the disorder. Thus, the invention provides a diagnostic method useful during diagnosis of an Endokine alpha-related disorder, which involves measuring the expression level of the gene encoding the Endokine alpha protein in tissue or other cells or body fluid from an individual and comparing the measured gene expression level with a standard Endokine alpha gene expression level, whereby an increase or decrease in the gene expression level compared to the standard is indicative of an Endokine alpha related disorder.

By individual is intended mammalian individuals, preferably humans. By "measuring the expression level of the gene encoding the Endokine alpha protein" is intended qualitatively or quantitatively measuring or estimating the level of the Endokine alpha protein or the level of the mRNA encoding the Endokine alpha protein in a first biological sample either directly (e.g., by determining or estimating absolute protein level or mRNA level) or relatively (e.g., by comparing to the Endokine alpha protein level or mRNA level in a second biological sample). Preferably, the Endokine alpha protein level or mRNA level in the first biological sample is measured or estimated and compared to a standard Endokine alpha protein level or mRNA level, the standard being taken from a second biological sample obtained from an individual not having the disorder or being determined by averaging levels from a population of individuals not having a disorder involving Endokine alpha. As will be appreciated in the art, once a standard Endokine alpha protein level or mRNA level is known, it can be used repeatedly as a standard for comparison.

By "biological sample" is intended any biological sample obtained from an individual, body fluid, cell line, tissue culture, or other source which contains Endokine alpha protein or mRNA. As indicated, biological samples include body fluids (such as sera, plasma, urine, synovial fluid and spinal fluid) which contain secreted mature Endokine alpha protein, or tissue sources found to express Endokine alpha. Methods for obtaining tissue biopsies and body fluids from mammals are well known in the art. Where the biological sample is to include mRNA, a tissue biopsy is the preferred source.

The present invention is useful for diagnosis of various Endokine alpha-related disorders in mammals, preferably humans, as similar to TNF-like disorders known in the art or as presented herein. Such disorders include metabolic bone diseases or disorders and/or conditions associated with such diseases or disorders, specifically diseases and/or disorders of the musculoskeletal system, including but not limited to, disorders of the bone, joints, ligaments, tendons, bursa, muscle, and/or neoplasms and cancers associated with musculoskeletal tissue.

Diseases or disorders of the bone, diseases or disorders associated with diseases or disorders of the bone, and diseases or disorders which may lead to and/or cause diseases or disorders of the bone, which may be detected and/or diagnosed using compositions of the present invention, include, but are not limited to, acromegaly; acute pancreatitis; acute rhabdomyolysis; acute severe illness; Addison's disease; Albers-Schönberg disease; alcoholism; aluminum intoxication; amyloidosis, ankylosing spondylitis; arterial calcification; arterial aneurysms; atherosclerosis; autoimmune hypoparathyroidism; axial osteomalacia; benign chondromas; biliary atresia; bone fractures; bowlegs; breast cancer; Buschke-Ollendorff syndrome; Caffey's disease; calcinosis circumscripta; calcinosis universalis; carbonic anhydrase II deficiency; carcinoma (e.g., of lung, esophagus, head and neck, renal cell, ovary or bladder); celiac sprue; childhood dermatomyositis; chondroblastomas; chondromyxoid fibromas; chondrosarcomas; chronic anemias; coccidioidomycosis; craniodiaphyseal dysplasia; craniometaphyseal dysplasia; Crohn's disease; Cushing syndrome; cystic fibrosis; diffuse bony metastases; DiGeorge syndrome; discoid lupus erythematosis; disorders or disease requiring treatment by anticancer agents (e.g., asparaginase, cisplatinum, cytosine arabinoside, doxorubicin or WR 2721); disorders or disease requiring treatment by foscarnet; disorders or disease requiring treatment by hypocalcemic agents (e.g., bisphosphonates, plicamycin, calcitonin, gallium nitrate or phosphate); disorders or disease requiring treatment by ketaconazole; disorders or disease requiring treatment by pentamidine; dysosteosclerosis; Ehlers-Danlos syndrome; endocrine disorders; endosteal hyperostosis; Engelmann's disease; epiphyseal dysplasia; estrogen deficiency; Ewing's sarcoma; extraskeletal (ectopic) calcification; extraskeletal (ectopic) ossification; familial hypocalciuric hypercalcemia; familial Vitamin D resistance; Fanconi syndrome; fibrodysplasia (myositis) ossificans progressiva; fibrogenesis imperfecta osseum; fibrosarcoma; fibrous dysplasia; fluorosis; frontometaphyseal dysplasia; Gaucher's disease; Giant cell tumors; gluten enteropathy; gout; granulomatous diseases; heavy metal poisoning; heel spurs; hemochromatosis; hemoglobinopathies; heparin treatment; hepatic osteodystrophy; hepatitis A; hepatitis B; hepatitis C; hepatitis C-associated osteosclerosis; high-turnover bone disease; histoplasmosis; histiocytosis-X; homocystinuria; hungry bone syndrome; hypoalbuminemia; hyperalbuminemia; hypercalcemia; hypocalcemia; hypogonadism; hypermagnesemia; hypomagnesemia; hyperostosis corticalis; hyperparathyroidism; hypoparathyroidism; hypophosphatasia; hyperphosphatasia; hypophosphatemic osteomalacia; hyperprolactinemia; hypoproteinemia; hyperproteinemia; hyperthyroidism; hypothyroidism; hypervitaminosis A, D; idiopathic hypercalciuria; immobilization; infantile cortical hyperostosis; inflammatory bowel disease; intestinal disease; intestinal resection; intestinal bypass; ischemic bone disease; juvenile rheumatoid arthritis; kidney failure; Köhler's bone disease; knock-knees; Legg-Calvé-Perthes disease; leprosy; liver failure; low-turnover bone disease; lymphoproliferative disorders; lymphoma; magnesium deficiency; malignant fibrous histiocytomas; malignant lymphoma of bone; malnutrition; Marfan's syndrome; mastocytosis; McCune-Albright syndrome; melorheostosis; metabolic acidosis; metaphyseal dysplasia; metastatic carcinoma; milk-alkali syndrome; mixed sclerosing bone dystrophy; mucopolysaccharidosis; multiple myeloma; myelofibrosis; myeloproliferative disorders; myositis ossificans; neonatal hypocalcemia; oculo-dento-osseous dysplasia; Osgood-Schlatter disease; osteitis fibrosa; osteoarthritis; osteoblastic metastases; osteochondritis dissecans; osteochondromas; osteochondrosis; osteochondrosis of lunate; osteochondrodysplasia; osteodysplasia of Melnick and Needles; osteoectasia with hyperphosphatasia; osteogenesis imperfecta; osteoid osteomas; osteolytic metastases; osteomalacia; osteomyelitis; osteonecrosis; osteopathia striata; osteopetroses; osteopenia; osteopoikilosis; osteoporosis (e.g., juvenile, postmenopausal, senile, severe, glucocorticoid-induced, drug-induced, as a result of ethanol abuse, as a result of testosterone deficiency, as a result of Vitamin D deficiency or as a result of malnutrition); osteosarcoma; osteosclerosis; Paget's disease; pancreatitis; pancreatic insufficiency; pseudohypoparathyroidism; patellofemoral stress syndrome; periodontal disease; pheochromocytoma; phosphate wasting syndromes; postgastrectomy bone disease; postsurgical hypoparathyroidism; primary biliary cirrhosis; progressive diaphyseal dysplasia; psoriatic arthritis; pycnodysostosis; Pyle's disease; renal osteodystrophy; renal tubular acidosis; reticulum cell sarcoma; rheumatic fever; rheumatoid arthritis; Rickets; sarcoidosis; Scheuermann's disease; scleroderma; sclerostosis; scoliosis; secondary hyperparathyroidism; Sever's disease; sickle cell anemia; Sjogren's syndrome; skeletal sarcoidosis; spondyloepiphyseal dysplasia; spondyloepimetaphyseal dysplasia; spondylometaphyseal dysplasia; Still's disease; sunlight exposure deficiency; systemic lupus erythematosis; thalassemia; thyrotoxicosis; tobacco smoking; toxic shock syndrome; tuberculosis; tuberous sclerosis; tumor-associated hepercalcemia; tumor lysis; tumoral calcinosis; van Buchem disease; vascular disease; vasoactive intestinal polypeptide-producing tumors; vertebral metastases; Vitamin D deficiency; Vitamin D malabsorption; Vitamin D-dependent rickets, type I (1α-hydroxylase deficiency); Vitamin D-dependent rickets, type II (resistance to 1,25(OH)$_2$D); Vitamin D-resistant rickets; and Wilson's disease.

Total cellular RNA can be isolated from a biological sample using any suitable technique such as the single-step-guanidinium-thiocyanate-phenol-chloroform method described in Chomczynski and Sacchi, *Anal. Biochem.* 162: 156–159 (1987). Levels of mRNA encoding an Endokine alpha polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Endokine alpha protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Endokine alpha protein). Northern blot analysis can be performed as described above.

Preferably, levels of mRNA encoding the polypeptides of the invention are assayed using the RT-PCR method described in Makino et al., *Technique* 2:295–301(1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the Endokine alpha protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying protein levels in a biological sample can occur using any art-known method. For example, preferred for assaying Endokine alpha protein levels in a biological sample are antibody-based techniques. For example, Endokine alpha protein expression in tissues can be studied with classical immunohistological methods. In these, the specific recognition is provided by the primary antibody (polyclonal or monoclonal), but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of Endokine alpha protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of Endokine alpha protein can be accomplished using isolated Endokine alpha protein as a standard. This technique can also be applied to body fluids. With these samples, a molar concentration of Endokine alpha protein will aid to set standard values of Endokine alpha protein content for different body fluids, like serum, plasma, urine, synovial fluid, spinal fluid, etc. The normal appearance of Endokine alpha protein amounts can then be set using values from healthy individuals, which can be compared to those obtained from a test subject.

Other antibody-based methods useful for detecting protein levels include immunoassays, such as the enzyme linked immunosorbent assay (ELISA) and the radioimmunoassay (RIA). For example, Endokine alpha protein-specific monoclonal antibodies can be used both as an immunoadsorbent and as an enzyme-labeled probe to detect and quantify the Endokine alpha protein. The amount of Endokine alpha protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In another ELISA assay, two distinct specific monoclonal antibodies can be used to detect Endokine alpha protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting Endokine alpha protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying protein levels in a biological sample obtained from an individual, protein can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

An antibody specific for a polypeptide complex or polypeptide of the invention or antibody portion which has been labeled with an appropriate detectable imaging moiety, such as a radioisotope (for example, $^{131}$I, $^{111}$In, $^{99m}$Tc), a radio-opaque substance, or a material detectable by nuclear magnetic resonance, is introduced (for example, parenterally, subcutaneously or intraperitoneally) into the mammal to be examined for a disorder. It will be understood in the art that the size of the subject and the imaging system used will determine the quantity of imaging moieties needed to produce diagnostic images. In the case of a radioisotope moiety, for a human subject, the quantity of radioactivity injected will normally range from about 5 to 20 millicuries of $^{99m}$Tc. The labeled antibody or antibody portion will then preferentially accumulate at the location of cells which contain Endokine alpha protein. In vivo tumor imaging is described in S. W. Burchiel et al., "Immunopharmacokinetics of Radiolabeled Antibodies and Their Portions" (Chapter 13 in *Tumor Imaging: The Radiochemical Detection of Cancer*, Burchiel, S. W. and Rhodes, B. A. eds., Masson Publishing Inc. (1982)).

Specific antibodies for use in the present invention can be raised against the intact Endokine alpha protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to Endokine alpha protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316–325 (1983)). Thus, these portions are preferred.

The antibodies of the present invention may be prepared by any of a variety of methods. For example, cells expressing the Endokine alpha protein or an antigenic portion thereof can be administered to an animal in order to induce the production of sera containing polyclonal antibodies. In a preferred method, a preparation of Endokine alpha protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies. Such monoclonal antibodies can be prepared using hybridoma technology (see, e.g., Colligan, *Current Protocols in Immunology*, Wiley Interscience, New York (1990–1996); Harlow & Lane, *Antibodies: A Laboratory Manual*, Chs. 6–9, Cold Spring Harbor Press, Cold Spring Harbor, N.Y. (1988); Ausubel, infra, at Chapter 11, these references entirely incorporated herein by reference).

In general, such procedures involve immunizing an animal (preferably a mouse) with an Endokine alpha polypeptide antigen or with an Endokine alpha polypeptide-expressing cell. Suitable cells can be recognized by their capacity to bind anti-Endokine alpha protein antibody. Such cells may be cultured in any suitable tissue culture medium (e.g., Earle's modified Eagle's medium supplemented with 10% fetal bovine serum (inactivated at about 56° C.), supplemented with about 10 μg/l of nonessential amino acids, about 1,000 U/ml of penicillin, and about 100 μg/ml of streptomycin). The splenocytes of such mice are extracted and fused with a suitable myeloma cell line. Any suitable myeloma cell line may be employed in accordance with the present invention (e.g., parent myeloma cell line (SP$_2$O), available from the American Type Culture Collection (ATCC) (Manassas, Va., USA)). After fusion, the resulting hybridoma cells are selectively maintained in HAT medium, and then cloned by limiting dilution as described by Wands et al., *Gastroenterology* 80:225–232 (1981); Harlow & Lane, infra, Chapter 7. The hybridoma cells obtained through such a selection are then assayed to identify clones which secrete antibodies capable of binding the Endokine alpha antigen.

Alternatively, additional antibodies capable of binding to the compositions of the invention may be produced in a two-step procedure through the use of anti-idiotypic antibodies. Such a method makes use of the fact that antibodies are themselves antigens, and therefore it is possible to obtain an antibody which binds to a second antibody. In accordance with this method, Endokine alpha protein specific antibodies are used to immunize an animal, preferably a mouse. The splenocytes of such an animal are then used to produce hybridoma cells, and the hybridoma cells are screened to identify clones which produce an antibody whose ability to bind to the Endokine alpha protein-specific antibody can be blocked by the Endokine alpha protein antigen. Such antibodies comprise anti-idiotypic antibodies to the Endokine alpha protein-specific antibody and can be used to immunize an animal to induce formation of further Endokine alpha protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, Endokine alpha protein-binding portions can be produced through the application of recombinant DNA technology or through synthetic chemistry.

Where in vivo imaging is used to detect enhanced levels of polypeptides and/or polypeptide complexes of the invention for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In and $^{99m}$Tc are preferred isotopes where in vivo imaging is used since they avoid the problem of dehalogenation of the $^{125}$I or $^{131}$I-labeled monoclonal antibody by the liver. In addition, these radionucleotides have a more favorable gamma emission energy for imaging (Perkins et al., *Eur. J. Nucl. Med.* 10:296–301 (1985); Carasquillo et al., *J. Nucl. Med.* 28:281–287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (*Clin. Chim. Acta* 70:1–31 (1976)), and Schurs et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The present invention further relates to antibodies and T-cell antigen receptors (TCR) which specifically bind the polypeptides and polypeptide complexes of the present invention. The antibodies of the present invention include IgG (including IgG1, IgG2, IgG3, and IgG4), IgA (including IgA1 and IgA2), IgD, IgE, IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies which specifically bind the polypeptides of the present invention. The present invention further includes antibodies which are anti-idiotypic to the antibodies of the present invention.

The antibodies of the present invention maybe monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al., *J. Immunol.* 147:60–69 (1991); U.S. Pat. Nos. 5,573,920, 4,474,893, 5,601,819, 4,714,681, 4,925,648; Kostelny, S. A. et al., *J. Immunol.* 148:1547–1553 (1992). Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{12}$M, $10^{-12}$M, $5 \times 10^{-13}$M, $10^{-13}$M, $5 \times 10^{-14}$M, $10^{-14}$M, $5 \times 10^{15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: A Laboratory Manual*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. Monoclonal antibodies can be prepared using a wide of techniques known in the art including the use of hybridoma and recombinant technology. See, e.g., Harlow et al., *Antibodies: A Laboratory Manual*, (Cold Spring Harbor Laboratory Press, 2nd ed. 1988); Hammerling, et al., in: *Monoclonal Antibodies and T-cell Hybridomas*, pp. 563–681 (Elsevier, N.Y., 1981) (said references incorporated by reference in their entireties).

Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al., *J. Immunol. Methods* 182:41–50 (1995); Ames, R. S. et al., *J. Immunol. Methods* 184:177–186 (1995); Kettleborough, C. A. et al., *Eur. J. Immunol.* 24:952–958 (1994); Persic, L. et al., *Gene* 187:9–18 (1997); Burton, D. R. et al., *Advances in Immunology* 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax, R. L. et al., *BioTechniques* 12(6):864–869 (1992); and Sawai, H. et al., *AJRI* 34:26–34 (1995); and Better, M. et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al. (1991) Methods in Enzymology 203:46–88; Shu, L. et al., *PNAS* 90:7995–7999 (1993); and Skerra, A. et al., *Science* 240: 1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, *Science* 229:1202 (1985); Oi et al., *BioTechniques* 4:214 (1986); Gillies, S. D. et al., *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E. A., *Molecular Immunology* 28(4/5):489–498 (1991); Studnicka G. M. et al., *Protein Engineering* 7(6): 805–814 (1994); Roguska M. A. et al., *PNAS* 91:969–973) (1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura, M. et al., *Immunol. Lett.* 39:91–99 (1994); U.S. Pat. No. 5,474,981; Gillies, S. O. et al., *PNAS* 89:1428–1432 (1992); Fell, H. P. et al., *J. Immunol.* 146:2446–2452 (1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al., *PNAS* 88:10535–10539 (1991); Zheng, X. X. et al., *J. Immunol.* 154:5590–5600 (1995); and Vil, H. et al., *PNAS* 89:11337–11341 (1992) (said references incorporated by reference in their entireties).

The invention further relates to antibodies which act as agonists or antagonists of the polypeptides and/or polypeptide complexes of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding, but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. see e.g., WO 96/40281; U.S. Pat. No. 5,811,097; Deng, B. et al., *Blood* 92(6):1981–1988 (1998); Chen, Z. et al., *Cancer Res.* 58(16):3668–3678 (1998); Harrop, J. A. et al., *J. Immunol.* 161(4): 1786–1794 (1998); Zhu, Z. et al., *Cancer Res.* 58(15):3209–3214 (1998); Yoon, D. Y. et al., *J. Immunol.* 160(7):3170–3179 (1998); Prat, M. et al., *J. Cell. Sci.* 111(Pt2):237–247 (1998); Pitard, V. et al., *J. Immunol. Methods* 205(2):177–190 (1997); Liautard, J. et al., *Cytokinde* 9(4):233–241 (1997); Carlson, N. G. et al., *J. Biol. Chem.* 272(17):11295–11301 (1997); Taryman, R. E. et al. *Neuron* 14(4):755–762 (1995); Muller, Y. A. et al., *Structure*

6(9):1153–1167 (1998); Bartunek, P. et al., *Cytokine* 8(1): 14–20 (1996) (said references incorporated by reference in their entireties).

Transgenic Animals

The polypeptides and/or polypeptide complexes of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology (NY)* 11: 1263–1270 (1993); Wright et al., *Biotechnology (NY)* 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, *Intl. Rev. Cytol.* 115:171–229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of Endokine alpha polypeptides, studying conditions and/or disorders associated with aberrant Endokine alpha expression, and in screening for compounds effective in ameliorating such conditions and/or disorders.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety. See also U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antagonists

In specific embodiments, antagonists according to the present invention are nucleic acids corresponding to the sequences contained in SEQ ID NO:39, or the complementary strand thereof, and/or to nucleotide sequences contained in the deposited clone 97640. In one embodiment, antisense sequence is generated internally by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the Endokine alpha antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the Endokine alpha antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding Endokine alpha, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of an Endokine alpha gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded Endokine alpha antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an Endokine alpha RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of the nucleotide sequence shown in FIG. 1 could be used in an antisense approach to inhibit translation of endogenous Endokine alpha mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of Endokine alpha mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci.* 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (see, e.g., Krol et al., *BioTechniques* 6:958–976 (1988)) or intercalating agents. (see, e.g., Zon, *Pharm. Res.* 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)). The oligonucleotide is a 2'-0-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448–7451 (1988)), etc.

While antisense nucleotides complementary to the Endokine alpha coding region sequence could be used, those complementary to the transcribed untranslated region are most preferred.

Potential antagonists according to the invention also include catalytic RNA, or a ribozyme (see, e.g., PCT International Publication WO 90/11364, published Oct. 4, 1990; Sarver et al., *Science* 247:1222–1225 (1990). While ribozymes that cleave mRNA at site specific recognition sequences can be used to destroy Endokine alpha mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of Endokine alpha (FIG. 1). Preferably, the ribozyme is engineered so that the cleavage recognition site is located near the 5' end of the Endokine alpha mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express Endokine alpha in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous Endokine alpha messages and inhibit translation. Since ribozymes unlike antisense molecules, are catalytic, a lower intracellular concentration is required for efficiency.

Endogenous gene expression can also be reduced by inactivating or "knocking out" the Endokine alpha gene and/or its promoter using targeted homologous recombination. (e.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of Endokine alpha (e.g., fragments of the Endokine alpha polypeptide shown in FIG. 1 that include the ligand binding domain from the extracellular region of the full length receptor). Such soluble forms of Endokine alpha, which may be naturally occurring or synthetic, antagonize Endokine alpha mediated signaling by competing with the cell surface bound forms of the receptor for binding to TNF-family ligands. Antagonists of the present invention also include antibodies specific for TNF-family ligands and Endokine alpha-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-a, lymphotoxin-a (LT-a, also known as TNF-b), LT-b (found in complex heterotrimer LT-a2-b), FasL, CD40L, CD27L, CD30L, 4-1BBL, OX40L and nerve growth factor (NGF).

TNF-α has been shown to protect mice from infection with herpes simplex virus type 1 (HSV-1). Rossol-Voth et al., J .Gen. Virol. 72:143–147 (1991). The mechanism of the protective effect of TNF-α is unknown but appears to involve neither interferons nor NK cell killing. One member of the TNFR family has been shown to mediate HSV-1 entry into cells. Montgomery et al., Eur. Cytokine Newt. 7:159 (1996). Further, antibodies specific for the extracellular domain of this TNFR block HSV-1 entry into cells. Thus, Endokine alpha antagonists of the present invention include both Endokine alpha amino acid sequences and antibodies capable of preventing TNFR mediated viral entry into cells. Such sequences and antibodies can function by either competing with cell surface localized TNFR for binding to virus or by directly blocking binding of virus to cell surface receptors.

Antibodies according to the present invention may be prepared by any of a variety of standard methods using Endokine alpha receptor immunogens of the present invention. Such Endokine alpha receptor immunogens include the Endokine alpha receptor protein shown in FIG. 1 (SEQ ID NO:40) (which may or may not include a leader sequence) and polypeptide fragments of the receptor comprising the ligand binding, extracellular, transmembrane, the intracellular domains of the Endokine alpha receptors, or any combination thereof.

Polyclonal and monoclonal antibody agonists or antagonists according to the present invention can be raised according to the methods disclosed herein and/or known in the art, such as, for example, those methods described in Tartaglia and Goeddel, J. Biol. Chem. 267(7):4304–4307(1992)); Tartaglia et al., Cell 73:213–216 (1993)), and PCT Application WO 94/09137 (the contents of each of these three applications are herein incorporated by reference in their entireties), and are preferably specific to polypeptides of the invention having the amino acid sequence of SEQ ID NO:40.

As one of skill in the art will appreciate, Endokine alpha polypeptides of the present invention and the epitope-bearing fragments thereof described above can be combined with heterologous polypeptide sequences. For example, the polypeptides of the present invention may be fused with the constant domain of immunoglobulins (IgA, IgE, IgG, and IgM) or portions thereof (CH1, CH2, CH3, and any combination thereof, including both entire domains and portions thereof), resulting in chimeric polypeptides. These fusion proteins facilitate purification and show an increased half-life.

The techniques of gene-shuffling, motif-shuffling, exon-shuffling, and/or codon-shuffling (collectively referred to as "DNA shuffling") may be employed to modulate the activities of Endokine alpha thereby effectively generating agonists and antagonists of Endokine alpha. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2): 76–82 (1998); Hansson, L. O., et al., J. Mol. Biol. 287: 265–76 (1999); and Lorenzo, M. M. and Blasco, R. Biotechniques 24(2):308–13 (1998) (each of these patents and publications are hereby incorporated by reference). In one embodiment, alteration of Endokine alpha polynucleotides and corresponding polypeptides may be achieved by DNA shuffling. DNA shuffling involves the assembly of two or more DNA segments into a desired Endokine alpha molecule by homologous, or site-specific, recombination. In another embodiment, Endokine alpha polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of Endokine alpha may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185–1190), Endokine-alpha (International Publication Nos. WO 98/07880 and WO 98/18921), OPG, OX40, nerve growth factor (NGF), and soluble forms of Fas, CD30, CD27, CD40 and 4-IBB, DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202),312C2 (International Publication No. WO 98/06842), TR12, and TNF-R1, TRAMP/DR3/APO-3/ WSL/LARD, TRAIL-R1/DR4/APO-2, TRAIL-R2/DR5, DcR1/TRAIL-R3/TRID/LIT, DcR2/TRAIL-R4, CAD, TRAIL, TRAMP, and v-FLIP.

In further preferred embodiments, the heterologous molecules are any member of the TNF family.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an Endokine alpha protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Therapeutic and Diagnostic Uses

Polypeptides, polypeptide complexes, antibodies, agonists or antagonists of the invention may be used in developing treatments for any disorder mediated (directly or indirectly) by defective, or insufficient amounts of one or more polypeptides and/or polypeptide complexes of the invention. Polypeptides, polypeptide complexes, antibodies, agonists or antagonists of the invention may be administered to a patient (e.g., mammal, preferably human) afflicted with such a disorder. Alternatively, a gene therapy approach may be applied to treat such disorders. Disclosure herein of polypeptides, polypeptide complexes, of the invention, together with polynucleotides which encode such polypeptides, permits the detection of defective polynucleotides encoding compositions of the invention, and the replacement thereof with normal polynucleotides. Defective polynucleotides maybe detected in in vitro diagnostic assays, and by comparison of the nucleotide sequences disclosed herein with those of polynucleotides derived from a patient suspected of harboring a defect in such a polynucleotide.

The inventors of the present invention have discovered that compositions of the present invention may be used in the functional and developmental regulation of cells and processes responsible for bone homeostasis.

The invention is based in part on the discovery, detailed in Example 20, below, that Endokine alpha is a potent inhibitor of osteoclast differentiation and activity. Furthermore, as described in Example 21, below, the biological effects of Endokine alpha on osteoclast precursor cells may be blocked by the soluble endokine alpha receptor TR11 but not by the soluble receptor TR1 (osteoprotegerin, see e.g., International Publication No. WO 98/12344, the contents of which are hereby incorporated in their entirety), which can block osteoclast differentiation stimulated by TL8 (RANK ligand, see e.g., International Publication No. WO 97/33899, the contents of which are hereby incorporated in their entirety) binding to TR8 (RANK, see e.g., International Publication No. WO 98/54201, the contents of which are hereby incorporated in their entirety). The inventors of the present invention have also discovered, as described in Example 22, below, that osteoclast precursor cells, after Endokine alpha treatment, show no detectable expression of TR8, a cell surface molecule whose activation by TL8 stimulates osteoclast differentiation and activation. These data indicate that the effects of Endokine alpha on osteoclast differentiation and activation are specific, reversible and upstream of the known effects of TR1, TR8 and TL8 on osteoclast function. These characteristics show the usefulness of compositions of the present invention in the diagnosis, imaging, prevention and/or treatment of metabolic bone diseases and/or disorders associated with such diseases.

Therefore, while not being limited to any particular underlying mechanism, the present invention is directed to methods of detection, diagnosis, prevention and therapy for metabolic bone disorders, which involve administering compositions of the invention to a mammalian, preferably human, patient for treating one or more metabolic bone disorders, including, but not limited to, osteoporosis, Paget's disease, and arterial calcification. Methods for producing polypeptides, polypeptide complexes, antibodies, agonists and antagonists of the invention are described in detail above. Such embodiments of the invention may be provided in pharmaceutically acceptable compositions as known in the art or as described herein.

Polypeptides and/or polypeptide complexes of the invention, and/or polynucleotides encoding polypeptide components thereof, and/or antibodies thereto, and/or agonists and/or antagonists thereof, are useful in the diagnosis and treatment or prevention of a wide range of metabolic bone diseases and/or conditions including but not limited to, disorders of the bone, joints, ligaments, tendons, bursa, muscle, and/or neoplasms and cancers associated with musculoskeletal tissue.

Polypeptides and/or polypeptide complexes of the invention, and/or polynucleotides encoding polypeptide components thereof, and/or antibodies thereto, and/or agonists and/or antagonists thereof, are useful in the diagnosis and treatment or prevention of a wide range of metabolic bone diseases and/or conditions. Diseases or disorders of the bone, diseases or disorders associated with diseases or disorders of the bone, and diseases or disorders which may lead to and/or cause diseases or disorders of the bone, which may be treated, prevented, prognosed and/or diagnosed using compositions of the present invention, include but are not limited to, acromegaly; acute pancreatitis; acute rhabdomyolysis; acute severe illness; Addison's disease; Albers-Schönberg disease; alcoholism; aluminum intoxication; amyloidosis, ankylosing spondylitis; arterial calcification; arterial aneurysms; atherosclerosis; autoimmune hypoparathyroidism; axial osteomalacia; benign chondromas; biliary atresia; bone fractures; bowlegs; breast cancer; Buschke-Ollendorff syndrome; Caffey's disease; calcinosis circumscripta; calcinosis universalis; carbonic anhydrase II deficiency; carcinoma (e.g., of lung, esophagus, head and neck, renal cell, ovary or bladder); celiac sprue; childhood dermatomyositis; chondroblastomas; chondromyxoid fibromas; chondrosarcomas; chronic anemias; coccidioidomycosis; craniodiaphyseal dysplasia; craniometaphyseal dysplasia; Crohn's disease; Cushing syndrome; cystic fibrosis; diffuse bony metastases; DiGeorge syndrome; discoid lupus erythematosis; disorders or disease requiring treatment by anticancer agents (e.g., asparaginase, cisplatinum, cytosine arabinoside, doxorubicin or WR 2721); disorders or disease requiring treatment by foscarnet; disorders or disease requiring treatment by hypocalcemic agents (e.g., bisphosphonates, plicamycin, calcitonin, gallium nitrate or phosphate); disorders or disease requiring treatment by ketaconazole; disorders or disease requiring treatment by pentamidine; dysosteosclerosis; Ehlers-Danlos syndrome; endocrine disorders; endosteal hyperostosis; Engelmann's disease; epiphyseal dysplasia; estrogen deficiency; Ewing's sarcoma; extraskeletal (ectopic) calcification; extraskeletal (ectopic) ossification; familial hypocalciuric hypercalcemia; familial Vitamin D resistance; Fanconi syndrome; fibrodysplasia (myositis) ossificans progressiva; fibrogenesis imperfecta osseum; fibrosarcoma; fibrous dysplasia; fluorosis; frontometaphyseal dysplasia; Gaucher's disease; Giant cell tumors; gluten enteropathy; gout; granulomatous diseases; heavy metal poisoning; heel spurs; hemochromatosis; hemoglobinopathies; heparin treatment; hepatic osteodystrophy; hepatitis A; hepatitis B; hepatitis C; hepatitis C-associated osteosclerosis; high-turnover bone disease; histoplasmosis; histiocytosis-X; homocystinuria; hungry bone syndrome; hypoalbuminemia; hyperalbuminemia; hypercalcemia; hypocalcemia; hypogonadism; hypermagnesemia; hypomagnesemia; hyperostosis corticalis; hyperparathyroidism; hypoparathyroidism; hypophosphatasia; hyperphosphatasia; hypophosphatemic osteomalacia; hyperprolactinemia; hypoproteinemia; hyperproteinemia; hyperthyroidism; hypothyroidism; hypervitaminosis A, D; idiopathic hypercalciuria; immobilization; infantile cortical hyperostosis; inflammatory bowel disease; intestinal disease; intestinal resection; intestinal bypass; ischemic bone disease; juvenile rheumatoid arthritis; kidney failure; Köhler's bone disease; knock-knees; Legg-Calvé-Perthes disease; leprosy; liver failure; low-turnover bone disease; lymphoproliferative disorders; lymphoma; magnesium deficiency; malignant fibrous histiocytomas; malignant lymphoma of bone; malnutrition; Marfan's syndrome; mastocytosis; McCune-Albright syndrome; melorheostosis; metabolic acidosis; metaphyseal dysplasia; metastatic carcinoma; milk-alkali syndrome; mixed sclerosing bone dystrophy; mucopolysaccharidosis; multiple myeloma; myelofibrosis; myeloproliferative disorders; myositis ossificans; neonatal hypocalcemia; oculodento-osseous dysplasia; Osgood-Schlatter disease; osteitis fibrosa; osteoarthritis; osteoblastic metastases; osteochondritis dissecans; osteochondromas; osteochondrosis; osteochondrosis of lunate; osteochondrodysplasia; osteodysplasia of Melnick and Needles; osteoectasia with hyperphosphatasia; osteogenesis imperfecta; osteoid osteomas; osteolytic metastases; osteomalacia; osteomyelitis; osteonecrosis; osteopathia striata; osteopetroses; osteopenia; osteopoikilosis; osteoporosis (e.g., juvenile, postmenopausal, senile, severe, glucocorticoid-induced, drug-induced, as a result of ethanol abuse, as a result of testosterone deficiency, as a result of Vitamin D deficiency or as a result of malnutrition); osteosarcoma; osteosclerosis; Paget's disease; pancreatitis; pancreatic insufficiency; pseudohypoparathyroidism; patellofemoral stress syndrome; periodontal disease; pheochromocytoma; phosphate wasting syndromes; postgastrectomy bone disease; postsurgical hypoparathyroidism; primary biliary cirrhosis; progressive diaphyseal dysplasia; psoriatic arthritis; pycnodysostosis; Pyle's disease; renal osteodystrophy; renal tubular acidosis; reticulum cell sarcoma; rheumatic fever; rheumatoid arthritis; Rickets; sarcoidosis; Scheuermann's disease; scleroderma; sclerostosis; scoliosis; secondary hyperparathyroidism; Sever's disease; sickle cell anemia; Sjogren's syndrome; skeletal sarcoidosis; spondyloepiphyseal dysplasia; spondyloepimetaphyseal dysplasia; spondylometaphyseal dysplasia; Still's disease; sunlight exposure deficiency; systemic lupus erythematosis; thalassemia; thyrotoxicosis; tobacco smoking; toxic shock syndrome; tuberculosis; tuberous sclerosis; tumor-associated hepercalcemia; tumor lysis; tumoral calcinosis; van Buchem disease; vascular disease; vasoactive intestinal polypeptide-producing tumors; vertebral metastases; Vitamin D deficiency; Vitamin D malabsorption; Vitamin D-dependent rickets, type I (1α-hydroxylase deficiency); Vitamin D-dependent rickets, type II (resistance to 1,25(OH)$_2$D); Vitamin D-resistant rickets; and Wilson's disease.

Polypeptides and/or polypeptide complexes of the invention, and/or polynucleotides encoding polypeptide components thereof, and/or antibodies thereto, and/or agonists and/or antagonists thereof are useful in regulating bone formation and treating osteoporosis.

Polypeptides and/or polypeptide complexes of the invention, and/or polynucleotides encoding polypeptide components thereof, and/or antibodies thereto, and/or agonists and/or antagonists thereof are useful in regulating bone resorption and treating osteoporosis.

A summary of the ways in which the antibodies of the present invention may be used therapeutically includes binding polypeptides and/or polypeptide complexes of the invention locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The pharmaceutical compositions of the present invention may be administered by any means that achieve their intended purpose. Amounts and regimens for the administration of antibodies, their fragments or derivatives can be determined readily by those with ordinary skill in the clinical art of treating metabolic bone diseases and/or disorders.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 µg/kg body weight to about 5000 mg/kg body weight. The preferred dosages comprise 0.1 to 500 mg/kg body wt.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations contain from about 0.01 to 99 percent, preferably from about 20 to 75 percent of active compound(s), together with the excipient.

Similarly, preparations of an Endokine alpha antibody or fragment of the present invention for parenteral administration, such as in detectably labeled form for imaging or in a free or conjugated form for therapy, include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, antioxidants, chelating agents, and inert gases and the like. See, generally, *Remington's Pharmaceutical Science,* 16th ed., Mack Publishing Co., Easton, Pa., 1980.

In particular, the antibodies, fragments and derivatives of the present invention are useful for treating a subject having or developing metabolic bone disorders as described herein. Such treatment comprises parenterally administering single or multiple doses of the antibody, a fragment or derivative, or a conjugate thereof.

The antibodies of this invention may be advantageously utilized in combination with other monoclonal or chimeric antibodies, or with lymphokines or hemopoietic growth factors, etc., which serve to increase the number or activity of effector cells which interact with the antibodies.

Since circulating concentrations of TNF ligand family polypeptides tend to be extremely low, in the range of about 10 pg/ml in normal individuals, and reaching, for example, about 50 pg/ml in septic patients and above 100 pg/ml in the sepsis syndrome for TNF (Hammerle, A. F. et al., 1989, supra) or it is preferred to use high affinity and/or potent in vivo inhibiting and/or neutralizing antibodies, fragments or regions thereof, for both detection and diagnosis immunoassays and preventive and therapeutic uses of the invention. Such antibodies, fragments, or regions, will preferably have an affinity for human Endokine alpha, expressed as Ka, of at least $10^8$ $M^{-1}$, more preferably, at least $10^9$ $M^{-1}$, such as $5\times10^8$ $M^{-1}$, $8\times10^8$ $M^{-1}$, $2\times10^9$ $M^{-1}$, $4\times10^9$ $M^{-1}$, $6\times10^9$ $M^{-1}$, $8\times10^9$ $M^{-1}$.

Preferred for human therapeutic use are high affinity murine and murine/human or human/human chimeric antibodies, and fragments, regions and derivatives having potent in vivo inhibiting and/or neutralizing activity, according to the present invention, e.g., that block osteoclast precursor proliferation, osteoclast differentiation, osteoclast formation, osteoclast maturation and/or osteoclast activation in vivo, in situ, and in vitro. Additional preferred embodiments of the invention include, but are not limited to, the use of one or more polypeptides and/or polypeptide complexes of the invention, and/or polynucleotides encoding one or more polypeptide components thereof, and/or functional agonists thereof, in the following applications:

As a treatment for metabolic bone disorders.

As a promoter of bone homeostasis.

As an inhibitor of bone resorption.

As an inhibitor of osteoclast formation.

As an agent that prevents a bone metabolic disorder in an individual.

As an agent to accelerate recovery of an individual suffering from a metabolic bone disorder.

As an agent to prevent bone degeneration among aged populations.

As an agent to prevent bone resorption.

As an agent to promote bone formation.

As a therapy for generation and/or regeneration of bone tissues following surgery, trauma or genetic defect.

As a therapy for promotion of bone healing following fractures.

As a gene-based therapy for genetically inherited disorders resulting in bone defects such as observed, for example, among Paget's disease patients.

As a means of preventing metabolic bone disorders resulting from infection by bacteria, fungi, parasites and/or viruses, as seen, for example, in osteomyelitis due to infection by *Staphylococcus aureus.*

As a means of preventing metabolic bone disorders resulting from cancer, for example, multiple myeloma.

As a means of preventing metabolic bone disorders resulting from disorders of the endocrine system, for example, hypoparathyroidism.

As a means of preventing metabolic bone disorders resulting from autoimmune disorders, for example, rheumatoid arthritis.

As a means of preventing disorders, diseases or conditions resulting from disorders of bone metabolism, for example, arterial calcification.

As a means of regulating secreted cytokines that are elicited by compositions of the invention and regulate bone metabolism.

All of the above described applications as they may apply to veterinary medicine.

Antagonists of the invention include binding and/or inhibitory antibodies, antisense nucleic acids, ribozymes or soluble forms of the receptor(s) which bind polypeptides and/or polypeptide complexes of the invention. These would be expected to reverse many of the activities of the ligand described above as well as find clinical or practical application as:

As a treatment for metabolic bone disorders.

As a promoter of bone homeostasis.

As a promoter of bone resorption.

As a stimulator of osteoclast formation.

As an agent that prevents a bone metabolic disorder in an individual.

As an agent to accelerate recovery of an individual suffering from a metabolic bone disorder.

As an agent to prevent inappropriate bone formation, as seen for example, in osteopetrosis.

As an agent to promote bone resorption.

As an agent to prevent bone formation.

As a therapy for generation and/or regeneration of bone tissues following surgery, trauma or genetic defect.

As a therapy for promotion of bone healing following fractures.

As a gene-based therapy for genetically inherited disorders resulting in bone defects such as observed, for example, among Paget's disease patients.

As a means of preventing metabolic bone disorders resulting from infection by bacteria, fungi, parasites and/or viruses, as seen, for example, in osteomyelitis due to infection by Staphylococcus aureus.

As a means of preventing metabolic bone disorders resulting from cancer, for example, multiple myeloma.

As a means of preventing metabolic bone disorders resulting from disorders of the endocrine system, for example, hypoparathyroidism.

As a means of preventing metabolic bone disorders resulting from autoimmune disorders, for example, rheumatoid arthritis.

As a means of preventing disorders, diseases or conditions resuting from disorders of bone metabolism, for example, arterial calcification.

As a means of regulating secreted cytokines that are elicited by compositions of the invention and regulate bone metabolism.

All of the above described applications as they may apply to veterinary medicine.

The agonists and antagonists may be employed in a composition with a pharmaceutically acceptable carrier, e.g., as described above.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), Endokine-alpha (International Publication No. WO 98/07880), TR6 (International Publication No. WO 98/30694), OPG, and neutrokine-alpha (International Publication No. WO 98/18921), OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to. Glioma Derived Growth Factor (GDGF), as disclosed in European Patent Number EP-399816; Platelet Derived Growth Factor-A (PDGF-A), as disclosed in European Patent Number EP-6821 10; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., *Growth Factors,* 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference.

In an additional embodiment, the compositions of the invention are administered in combination with Fibroblast Growth Factors. Fibroblast Growth Factors tha may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example, as an emulsion in an acceptable oil) or ion exchange resins, and sparingly soluble derivatives (such as, for example, a sparingly soluble salt).

Sustained-release matrices include polylactides (U.S. Pat. No. 3,773,919, and EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer,* Lopez-Berestein and Fidler (eds.), Liss, New York, pp. 317–327 and 353–365 (1989)). Liposomes containing Endokine alpha polypeptide may be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the Endokine alpha polypeptide therapy.

In another embodiment sustained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). Other controlled release systems are discussed in the review by Langer (Science 249:1527–1533 (1990)).

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, monophosphoryl lipid immunomodulator, AdjuVax 100a, QS-21, QS-18, CRL1005, aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diphtheria, hepatitis A, hepatitis B, *Haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately, but simultaneously or concurrently; or sequentially. This includes presentations in which the combined agents are administered together as a therapeutic mixture, and also procedures in which the combined agents are administered separately, but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23™ to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram-positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23™ to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae*.

The compositions of the invention may be administered alone or in combination with other therapeutic agents, including, but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately, but simultaneously or concurrently; or sequentially. This includes presentations in which the combined agents are administered together as a therapeutic mixture, and also procedures in which the combined agents are administered separately, but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911 and WO 98/18921), APRIL (J. Exp. Med. 188(6): 1185–1190), Endokine-alpha (International Publication No. WO 98/07880), TR6 (International Publication No. WO 98/30694), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12.

In a preferred embodiment, the compositions of the invention are administered alone or in combination with CD40 ligand (CD40L), a soluble form of CD40L (e.g., AVREND), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVTR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that maybe administered in combination with the compositions of the invention, include, but are not limited to, TRIMETHOPRIM-SULFAMETHOXAZOLE™, DAPSONE™, PENTAMIDTNE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDTNE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that maybe administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but are not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In another embodiment, compositions of the invention may be administered with any interleukin, including, but not limited to, IL-1 alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the compositions of the invention are administered in combination with IL4 and IL10.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGENE™ (FILGRASTIM™).

In an additional embodiment, the compositions of the invention are administered in combination with fibroblast growth factors. Fibroblast growth factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the compositions of the invention may be administered alone or in combination with other therapeutic regimens, including, but not limited to, radiation therapy. Such combinatorial therapy may be administered sequentially and/or concomitantly.

Therapeutic Uses

The present invention is further directed to therapies which involve administering therapeutic compounds of the invention to an animal, preferably a mammal, and most preferably a human, patient for treating one or more of the described disorders. Therapeutic compounds of the invention include, but are not limited to, polypeptides, polypeptide complexes and antibodies of the invention (including fragments, analogs and derivatives thereof as described herein) and nucleic acids encoding the polypeptides, polypeptide complexes and antibodies of the invention (including fragments, analogs and derivatives thereof as described herein). The embodiments of the invention can be used to treat, inhibit or prevent diseases, disorders or conditions associated with aberrant bone homeostasis, including, but not limited to, any one or more of the diseases, disorders, or conditions described herein such as, for example osteoporosis, disorders, or conditions associated with such diseases or disorders (including, but not limited to, acromegaly; acute pancreatitis; acute rhabdomyolysis; acute severe illness; Addison's disease; Albers-Schönberg disease; alcoholism; aluminum intoxication; amyloidosis, ankylosing spondylitis; arterial calcification; arterial aneurysms; atherosclerosis; autoimmune hypoparathyroidism; axial osteomalacia; benign chondromas; biliary atresia; bone fractures; bowlegs; breast cancer; Buschke-Ollendorff syndrome; Caffey's disease; calcinosis circumscripta; calcinosis universalis; carbonic anhydrase II deficiency; carcinoma (e.g., of lung, esophagus, head and neck, renal cell, ovary or bladder); celiac sprue; childhood dermatomyositis; chondroblastomas; chondromyxoid fibromas; chondrosarcomas;

chronic anemias; coccidioidomycosis; craniodiaphyseal dysplasia; craniometaphyseal dysplasia; Crohn's disease; Cushing syndrome; cystic fibrosis; diffuse bony metastases; DiGeorge syndrome; discoid lupus erythematosis; disorders or disease requiring treatment by anticancer agents (e.g., asparaginase, cisplatinum, cytosine arabinoside, doxorubicin or WR 2721); disorders or disease requiring treatment by foscarnet; disorders or disease requiring treatment by hypocalcemic agents (e.g., bisphosphonates, plicamycin, calcitonin, gallium nitrate or phosphate); disorders or disease requiring treatment by ketaconazole; disorders or disease requiring treatment by pentamidine; dysosteosclerosis; Ehlers-Danlos syndrome; endocrine disorders; endosteal hyperostosis; Engelmann's disease; epiphyseal dysplasia; estrogen deficiency; Ewing's sarcoma; extraskeletal (ectopic) calcification; extraskeletal (ectopic) ossification; familial hypocalciuric hypercalcemia; familial Vitamin D resistance; Fanconi syndrome; fibrodysplasia (myositis) ossificans progressiva; fibrogenesis imperfecta osseum; fibrosarcoma; fibrous dysplasia; fluorosis; frontometaphyseal dysplasia; Gaucher's disease; Giant cell tumors; gluten enteropathy; gout; granulomatous diseases; heavy metal poisoning; heel spurs; hemochromatosis; hemoglobinopathies; heparin treatment; hepatic osteodystrophy; hepatitis A; hepatitis B; hepatitis C; hepatitis C-associated osteosclerosis; high-turnover bone disease; histoplasmosis; histiocytosis-X; homocystinuria; hungry bone syndrome; hypoalbuminemia; hyperalbuminemia; hypercalcemia; hypocalcemia; hypogonadism; hypermagnesemia; hypomagnesemia; hyperostosis corticalis; hyperparathyroidism; hypoparathyroidism; hypophosphatasia; hyperphosphatasia; hypophosphatemic osteomalacia; hyperprolactinemia; hypoproteinemia; hyperproteinemia; hyperthyroidism; hypothyroidism; hypervitaminosis A, D; idiopathic hypercalciuria; immobilization; infantile cortical hyperostosis; inflammatory bowel disease; intestinal disease; intestinal resection; intestinal bypass; ischemic bone disease; juvenile rheumatoid arthritis; kidney failure; Köhler's bone disease; knock-knees; Legg-Calvé-Perthes disease; leprosy; liver failure; low-turnover bone disease; lymphoproliferative disorders; lymphoma; magnesium deficiency; malignant fibrous histiocytomas; malignant lymphoma of bone; malnutrition; Marfan's syndrome; mastocytosis; McCune-Albright syndrome; melorheostosis; metabolic acidosis; metaphyseal dysplasia; metastatic carcinoma; milk-alkali syndrome; mixed sclerosing bone dystrophy; mucopolysaccharidosis; multiple myeloma; myelofibrosis; myeloproliferative disorders; myositis ossificans; neonatal hypocalcemia; oculodento-osseous dysplasia; Osgood-Schlatter disease; osteitis fibrosa; osteoarthritis; osteoblastic metastases; osteochondritis dissecans; osteochondromas; osteochondrosis; osteochondrosis of lunate; osteochondrodysplasia; osteodysplasia of Melnick and Needles; osteoectasia with hyperphosphatasia; osteogenesis imperfecta; osteoid osteomas; osteolytic metastases; osteomalacia; osteomyelitis; osteonecrosis; osteopathia striata; osteopetroses; osteopenia; osteopoikilosis; osteoporosis (e.g., juvenile, postmenopausal, senile, severe, glucocorticoid-induced, drug-induced, as a result of ethanol abuse, as a result of testosterone deficiency, as a result of Vitamin D deficiency or as a result of malnutrition); osteosarcoma; osteosclerosis; Paget's disease; pancreatitis; pancreatic insufficiency; pseudohypoparathyroidism; patellofemoral stress syndrome; periodontal disease; pheochromocytoma; phosphate wasting syndromes; postgastrectomy bone disease; postsurgical hypoparathyroidism; primary biliary cirrhosis; progressive diaphyseal dysplasia; psoriatic arthritis; pycnodysostosis; Pyle's disease; renal osteodystrophy; renal tubular acidosis; reticulum cell sarcoma; rheumatic fever; rheumatoid arthritis; Rickets; sarcoidosis; Scheuermann's disease; scleroderma; sclerostosis; scoliosis; secondary hyperparathyroidism; Sever's disease; sickle cell anemia; Sjogren's syndrome; skeletal sarcoidosis; spondyloepiphyseal dysplasia; spondyloepimetaphyseal dysplasia; spondylometaphyseal dysplasia; Still's disease; sunlight exposure deficiency; systemic lupus erythematosis; thalassemia; thyrotoxicosis; tobacco smoking; toxic shock syndrome; tuberculosis; tuberous sclerosis; tumor-associated hepercalcemia; tumor lysis; tumoral calcinosis; van Buchem disease; vascular disease; vasoactive intestinal polypeptide-producing tumors; vertebral metastases; Vitamin D deficiency; Vitamin D malabsorption; Vitamin D-dependent rickets, type I (1α-hydroxylase deficiency); Vitamin D-dependent rickets, type II (resistance to 1,25(OH)$_2$D); Vitamin D-resistant rickets; and Wilson's disease.

In a specific embodiment, one or more compositions of the invention, or agonists or antagonists thereof, are administered to treat, prevent, prognose and/or diagnose osteoporosis.

In a specific embodiment, one or more compositions of the invention, or agonists or antagonists thereof, are administered to treat, prevent, prognose and/or diagnose osteoarthritis.

In a specific embodiment, one or more compositions of the invention, or agonists or antagonists thereof, are administered to treat, prevent, prognose and/or diagnose osteomyelitis.

In a specific embodiment, one or more compositions of the invention, or agonists or antagonists thereof, are administered to treat, prevent, prognose and/or diagnose rheumatoid arthritis.

In a specific embodiment, one or more compositions of the invention, or agonists or antagonists thereof, are administered to treat, prevent, prognose and/or diagnose rickets.

In a specific embodiment, one or more compositions of the invention, or agonists or antagonists thereof, are administered to treat, prevent, prognose and/or diagnose Vitamin D deficiency.

In a specific embodiment, one or more compositions of the invention, or agonists or antagonists thereof, are administered to treat, prevent, prognose and/or diagnose arterial calcification.

In a specific embodiment, one or more compositions of the invention, or agonists or antagonists thereof, are administered to treat, prevent, prognose and/or diagnose Albers-Schönberg disease.

In a specific embodiment, one or more compositions of the invention, or agonists or antagonists thereof, are administered to treat, prevent, prognose and/or diagnose ankylosing spondylitis.

In a specific embodiment, one or more compositions of the invention, or agonists or antagonists thereof, are administered to treat, prevent, prognose and/or diagnose carbonic anhydrase II deficiency.

In a specific embodiment, one or more compositions of the invention, or agonists or antagonists thereof, are administered to treat, prevent, prognose and/or diagnose childhood dermatomyositis.

In a specific embodiment, one or more compositions of the invention, or agonists or antagonists thereof, are administered to treat, prevent, prognose and/or diagnose craniodiaphyseal dysplasia.

In a specific embodiment, one or more compositions of the invention, or agonists or antagonists thereof, are administered to treat, prevent, prognose and/or diagnose craniometaphyseal dysplasia.

In a specific embodiment, one or more compositions of the invention, or agonists or antagonists thereof, are administered to treat, prevent, prognose and/or diagnose dysosteosclerosis.

In a specific embodiment, one or more compositions of the invention, or agonists or antagonists thereof, are administered to treat, prevent, prognose and/or diagnose Ehlers-Danlos syndrome.

In a specific embodiment, one or more compositions of the invention, or agonists or antagonists thereof, are administered to treat, prevent, prognose and/or diagnose Fanconi syndrome.

In a specific embodiment, one or more compositions of the invention, or agonists or antagonists thereof, are administered to treat, prevent, prognose and/or diagnose hepatic osteodystrophy.

In a specific embodiment, one or more compositions of the invention, or agonists or antagonists thereof, are administered to treat, prevent, prognose and/or diagnose hepatitis C-associated osteosclerosis.

In a specific embodiment, one or more compositions of the invention, or agonists or antagonists thereof, are administered to treat, prevent, prognose and/or diagnose high-turnover bone disease.

In a specific embodiment, one or more compositions of the invention, or agonists or antagonists thereof, are administered to treat, prevent, prognose and/or diagnose histiocytosis-X.

In a specific embodiment, one or more compositions of the invention, or agonists or antagonists thereof, are administered to treat, prevent, prognose and/or diagnose hungry bone syndrome.

In a specific embodiment, one or more compositions of the invention, or agonists or antagonists thereof, are administered to treat, prevent, prognose and/or diagnose hypercalcemia.

In a specific embodiment, one or more compositions of the invention, or agonists or antagonists thereof, are administered to treat, prevent, prognose and/or diagnose hypocalcemia.

In a specific embodiment, one or more compositions of the invention, or agonists or antagonists thereof, are administered to treat, prevent, prognose and/or diagnose hyperparathyroidism.

In a specific embodiment, one or more compositions of the invention, or agonists or antagonists thereof, are administered to treat, prevent, prognose and/or diagnose hypoparathyroidism.

In a specific embodiment, one or more compositions of the invention, or agonists or antagonists thereof, are administered to treat, prevent, prognose and/or diagnose hyperthyroidism.

In a specific embodiment, one or more compositions of the invention, or agonists or antagonists thereof, are administered to treat, prevent, prognose and/or diagnose hypothyroidism.

In a specific embodiment, one or more compositions of the invention, or agonists or antagonists thereof, are administered to treat, prevent, prognose and/or diagnose ischemic bone disease.

In a specific embodiment, one or more compositions of the invention, or agonists or antagonists thereof, are administered to treat, prevent, prognose and/or diagnose Köhler's bone disease.

In a specific embodiment, one or more compositions of the invention, or agonists or antagonists thereof, are administered to treat, prevent, prognose and/or diagnose knock-knees.

In a specific embodiment, one or more compositions of the invention, or agonists or antagonists thereof, are administered to treat, prevent, prognose and/or diagnose Legg-Calvé-Perthes disease.

In a specific embodiment, one or more compositions of the invention, or agonists or antagonists thereof, are administered to treat, prevent, prognose and/or diagnose low-turnover bone disease.

In a specific embodiment, one or more compositions of the invention, or agonists or antagonists thereof, are administered to treat, prevent, prognose and/or diagnose malignant fibrous histiocytomas.

In a specific embodiment, one or more compositions of the invention, or agonists or antagonists thereof, are administered to treat, prevent, prognose and/or diagnose malignant lymphoma of bone.

In a specific embodiment, one or more compositions of the invention, or agonists or antagonists thereof, are administered to treat, prevent, prognose and/or diagnose Marfan's syndrome.

In a specific embodiment, one or more compositions of the invention, or agonists or antagonists thereof, are administered to treat, prevent, prognose and/or diagnose mastocytosis.

In a specific embodiment, one or more compositions of the invention, or agonists or antagonists thereof, are administered to treat, prevent, prognose and/or diagnose McCune-Albright syndrome.

In a specific embodiment, one or more compositions of the invention, or agonists or antagonists thereof, are administered to treat, prevent, prognose and/or diagnose melorheostosis.

In a specific embodiment, one or more compositions of the invention, or agonists or antagonists thereof, are administered to treat, prevent, prognose and/or diagnose metabolic acidosis.

In a specific embodiment, one or more compositions of the invention, or agonists or antagonists thereof, are administered to treat, prevent, prognose and/or diagnose metaphyseal dysplasia.

In a specific embodiment, one or more compositions of the invention, or agonists or antagonists thereof, are administered to treat, prevent, prognose and/or diagnose milk-alkali syndrome.

In a specific embodiment, one or more compositions of the invention, or agonists or antagonists thereof, are administered to treat, prevent, prognose and/or diagnose mixed sclerosing bone dystrophy.

In a specific embodiment, one or more compositions of the invention, or agonists or antagonists thereof, are administered to treat, prevent, prognose and/or diagnose mucopolysaccharidosis.

In a specific embodiment, one or more compositions of the invention, or agonists or antagonists thereof, are administered to treat, prevent, prognose and/or diagnose myelofibrosis.

In a specific embodiment, one or more compositions of the invention, or agonists or antagonists thereof, are administered to treat, prevent, prognose and/or diagnose myositis ossificans.

In a specific embodiment, one or more compositions of the invention, or agonists or antagonists thereof, are administered to treat, prevent, prognose and/or diagnose neonatal hypocalcemia.

In a specific embodiment, one or more compositions of the invention, or agonists or antagonists thereof, are administered to treat, prevent, prognose and/or diagnose oculo-dento-osseous dysplasia.

In a specific embodiment, one or more compositions of the invention, or agonists or antagonists thereof, are administered to treat, prevent, prognose and/or diagnose Osgood-Schlatter disease.

In a specific embodiment, one or more compositions of the invention, or agonists or antagonists thereof, are administered to treat, prevent, prognose and/or diagnose osteitis fibrosa.

In a specific embodiment, one or more compositions of the invention, or agonists or antagonists thereof, are administered to treat, prevent, prognose and/or diagnose osteoblastic metastases.

In a specific embodiment, one or more compositions of the invention, or agonists or antagonists thereof, are administered to treat, prevent, prognose and/or diagnose osteochondritis dissecans.

In a specific embodiment, one or more compositions of the invention, or agonists or antagonists thereof, are administered to treat, prevent, prognose and/or diagnose osteochondromas.

In a specific embodiment, one or more compositions of the invention, or agonists or antagonists thereof, are administered to treat, prevent, prognose and/or diagnose osteochondrosis.

In a specific embodiment, one or more compositions of the invention, or agonists or antagonists thereof, are administered to treat, prevent, prognose and/or diagnose osteochondrodysplasia.

In a specific embodiment, one or more compositions of the invention, or agonists or antagonists thereof, are administered to treat, prevent, prognose and/or diagnose osteodysplasia of Melnick and Needles.

In a specific embodiment, one or more compositions of the invention, or agonists or antagonists thereof, are administered to treat, prevent, prognose and/or diagnose osteoectasia with hyperphosphatasia.

In a specific embodiment, one or more compositions of the invention, or agonists or antagonists thereof, are administered to treat, prevent, prognose and/or diagnose osteogenesis imperfecta.

In a specific embodiment, one or more compositions of the invention, or agonists or antagonists thereof, are administered to treat, prevent, prognose and/or diagnose osteoid osteomas.

In a specific embodiment, one or more compositions of the invention, or agonists or antagonists thereof, are administered to treat, prevent, prognose and/or diagnose osteolytic metastases.

In a specific embodiment, one or more compositions of the invention, or agonists or antagonists thereof, are administered to treat, prevent, prognose and/or diagnose osteomalacia.

In a specific embodiment, one or more compositions of the invention, or agonists or antagonists thereof, are administered to treat, prevent, prognose and/or diagnose osteonecrosis.

In a specific embodiment, one or more compositions of the invention, or agonists or antagonists thereof, are administered to treat, prevent, prognose and/or diagnose osteopathia striata.

In a specific embodiment, one or more compositions of the invention, or agonists or antagonists thereof, are administered to treat, prevent, prognose and/or diagnose osteopetroses.

In a specific embodiment, one or more compositions of the invention, or agonists or antagonists thereof, are administered to treat, prevent, prognose and/or diagnose osteopenia.

In a specific embodiment, one or more compositions of the invention, or agonists or antagonists thereof, are administered to treat, prevent, prognose and/or diagnose osteopoikilosis.

In a specific embodiment, one or more compositions of the invention, or agonists or antagonists thereof, are administered to treat, prevent, prognose and/or diagnose juvenile osteoporosis.

In a specific embodiment, one or more compositions of the invention, or agonists or antagonists thereof, are administered to treat, prevent, prognose and/or diagnose post-menopausal osteoporosis.

In a specific embodiment, one or more compositions of the invention, or agonists or antagonists thereof, are administered to treat, prevent, prognose and/or diagnose senile osteoporosis.

In a specific embodiment, one or more compositions of the invention, or agonists or antagonists thereof, are administered to treat, prevent, prognose and/or diagnose severe osteoporosis.

In a specific embodiment, one or more compositions of the invention, or agonists or antagonists thereof, are administered to treat, prevent, prognose and/or diagnose glucocorticoid-induced osteoporosis.

In a specific embodiment, one or more compositions of the invention, or agonists or antagonists thereof, are administered to treat, prevent, prognose and/or diagnose drug-induced osteoporosis.

In a specific embodiment, one or more compositions of the invention, or agonists or antagonists thereof, are administered to treat, prevent, prognose and/or diagnose osteoporosis caused by alcohol abuse.

In a specific embodiment, one or more compositions of the invention, or agonists or antagonists thereof, are administered to treat, prevent, prognose and/or diagnose osteoporosis caused by testosterone deficiency.

In a specific embodiment, one or more compositions of the invention, or agonists or antagonists thereof, are administered to treat, prevent, prognose and/or diagnose osteoporosis caused by a Vitamin D deficiency.

In a specific embodiment, one or more compositions of the invention, or agonists or antagonists thereof, are administered to treat, prevent, prognose and/or diagnose osteoporosis due to malnutrition.

In a specific embodiment, one or more compositions of the invention, or agonists or antagonists thereof, are administered to treat, prevent, prognose and/or diagnose osteosarcoma.

In a specific embodiment, one or more compositions of the invention, or agonists or antagonists thereof, are administered to treat, prevent, prognose and/or diagnose osteosclerosis.

In a specific embodiment, one or more compositions of the invention, or agonists or antagonists thereof, are administered to treat, prevent, prognose and/or diagnose Paget's disease.

In a specific embodiment, one or more compositions of the invention, or agonists or antagonists thereof, are administered to treat, prevent, prognose and/or diagnose pseudohypoparathyroidism.

In a specific embodiment, one or more compositions of the invention, or agonists or antagonists thereof, are administered to treat, prevent, prognose and/or diagnose patellofemoral stress syndrome.

In a specific embodiment, one or more compositions of the invention, or agonists or antagonists thereof, are administered to treat, prevent, prognose and/or diagnose periodontal disease.

In a specific embodiment, one or more compositions of the invention, or agonists or antagonists thereof, are administered to treat, prevent, prognose and/or diagnose pheochromocytoma.

In a specific embodiment, one or more compositions of the invention, or agonists or antagonists thereof, are administered to treat, prevent, prognose and/or diagnose phosphate wasting syndromes.

In a specific embodiment, one or more compositions of the invention, or agonists or antagonists thereof, are administered to treat, prevent, prognose and/or diagnose postgastrectomy bone disease.

In a specific embodiment, one or more compositions of the invention, or agonists or antagonists thereof, are administered to treat, prevent, prognose and/or diagnose postsurgical hypoparathyroidism.

In a specific embodiment, one or more compositions of the invention, or agonists or antagonists thereof, are administered to treat, prevent, prognose and/or diagnose progressive diaphyseal dysplasia.

In a specific embodiment, one or more compositions of the invention, or agonists or antagonists thereof, are administered to treat, prevent, prognose and/or diagnose psoriatic arthritis.

In a specific embodiment, one or more compositions of the invention, or agonists or antagonists thereof, are administered to treat, prevent, prognose and/or diagnose pycnodysostosis.

In a specific embodiment, one or more compositions of the invention, or agonists or antagonists thereof, are administered to treat, prevent, prognose and/or diagnose Pyle's disease.

In a specific embodiment, one or more compositions of the invention, or agonists or antagonists thereof, are administered to treat, prevent, prognose and/or diagnose renal osteodystrophy.

In a specific embodiment, one or more compositions of the invention, or agonists or antagonists thereof, are administered to treat, prevent, prognose and/or diagnose renal tubular acidosis.

In a specific embodiment, one or more compositions of the invention, or agonists or antagonists thereof, are administered to treat, prevent, prognose and/or diagnose reticulum cell sarcoma.

In a specific embodiment, one or more compositions of the invention, or agonists or antagonists thereof, are administered to treat, prevent, prognose and/or diagnose sarcoidosis.

In a specific embodiment, one or more compositions of the invention, or agonists or antagonists thereof, are administered to treat, prevent, prognose and/or diagnose Scheuermann's disease.

In a specific embodiment, one or more compositions of the invention, or agonists or antagonists thereof, are administered to treat, prevent, prognose and/or diagnose scleroderma.

In a specific embodiment, one or more compositions of the invention, or agonists or antagonists thereof, are administered to treat, prevent, prognose and/or diagnose sclerostosis.

In a specific embodiment, one or more compositions of the invention, or agonists or antagonists thereof, are administered to treat, prevent, prognose and/or diagnose scoliosis.

In a specific embodiment, one or more compositions of the invention, or agonists or antagonists thereof, are administered to treat, prevent, prognose and/or diagnose secondary hyperparathyroidism.

In a specific embodiment, one or more compositions of the invention, or agonists or antagonists thereof, are administered to treat, prevent, prognose and/or diagnose Sever's disease.

In a specific embodiment, one or more compositions of the invention, or agonists or antagonists thereof, are administered to treat, prevent, prognose and/or diagnose spondyloepiphyseal dysplasia.

In a specific embodiment, one or more compositions of the invention, or agonists or antagonists thereof, are administered to treat, prevent, prognose and/or diagnose spondyloepimetaphyseal dysplasia.

In a specific embodiment, one or more compositions of the invention, or agonists or antagonists thereof, are administered to treat, prevent, prognose and/or diagnose spondylometaphyseal dysplasia.

In a specific embodiment, one or more compositions of the invention, or agonists or antagonists thereof, are administered to treat, prevent, prognose and/or diagnose Still's disease.

In a specific embodiment, one or more compositions of the invention, or agonists or antagonists thereof, are administered to treat, prevent, prognose and/or diagnose thyrotoxicosis.

In a specific embodiment, one or more compositions of the invention, or agonists or antagonists thereof, are administered to treat, prevent, prognose and/or diagnose tuberous sclerosis.

In a specific embodiment, one or more compositions of the invention, or agonists or antagonists thereof, are administered to treat, prevent, prognose and/or diagnose tumor-associated hepercalcemia.

In a specific embodiment, one or more compositions of the invention, or agonists or antagonists thereof, are administered to treat, prevent, prognose and/or diagnose tumoral calcinosis.

In a specific embodiment, one or more compositions of the invention, or agonists or antagonists thereof, are administered to treat, prevent, prognose and/or diagnose van Buchem disease.

In a specific embodiment, one or more compositions of the invention, or agonists or antagonists thereof, are administered to treat, prevent, prognose and/or diagnose vertebral metastases.

In a specific embodiment, one or more compositions of the invention, or agonists or antagonists thereof, are administered to treat, prevent, prognose and/or diagnose Vitamin D malabsorption.

In a specific embodiment, one or more compositions of the invention, or agonists or antagonists thereof, are administered to treat, prevent, prognose and/or diagnose Vitamin D-dependent rickets, type I (1α-hydroxylase deficiency).

In a specific embodiment, one or more compositions of the invention, or agonists or antagonists thereof, are administered to treat, prevent, prognose and/or diagnose Vitamin D-dependent rickets, type II (resistance to $1,25(OH)_2D$).

In a specific embodiment, one or more compositions of the invention, or agonists or antagonists thereof, are administered to treat, prevent, prognose and/or diagnose Vitamin D-resistant rickets.

In a specific embodiment, one or more compositions of the invention, or agonists or antagonists thereof, are administered to treat, prevent, prognose and/or diagnose Wilson's disease.

The treatment and/or prevention of diseases and disorders associated with aberrant bone metabolism includes, but is not limited to, alleviating symptoms associated with those diseases and disorders. Compositions of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

Compounds of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the compounds.

Compounds of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$ M, $10^{-6}$ M, $5\times10^{-7}$ M, $10^{-7}$M, $5\times10^{-8}$ M, $10^{-8}$ M, $5\times10^{-8}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

In one embodiment, the invention provides a method of delivering compositions containing the polypeptides and/or polypeptide complexes of the invention (e.g., compositions containing Endokine alpha polypeptides or anti-Endokine alpha antibodies associated with heterologous polypeptides, heterologous nucleic acids, toxins, or prodrugs) to targeted cells, expressing the membrane-bound form of a TNF ligand family polypeptide on their surface, or alternatively, a TNF receptor family polypeptide (e.g., TR11) on its surface. Polypeptides, polypeptide complexes or antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides, polypeptide complexes and/or antibodies of the invention that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of osteoclasts) by administering polypeptides of the invention (e.g., Endokine alpha polypeptides or anti-Endokine alpha antibodies) in association with toxins or cytotoxic prodrugs.

In a specific embodiment, the invention provides a method for the specific destruction of cells expressing TNF receptor family polypeptides on their surface by administering compositions of the invention in association with toxins or cytotoxic prodrugs.

In another specific embodiment, the invention provides a method for the specific destruction of cells expressing the membrane-bound form of TNF ligand family polypeptides on their surface by administering antibodies of the invention in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuc lease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label proteins (including antibodies) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

The compositions of the invention may be administered to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO 98/24893, WO 96/34096, WO 96/33735, and WO 91/10741). Compositions of the invention include, but are not limited to, polypeptides and polypeptide complexes and polynucleotides and agonists and antagonists thereof, antibodies, anti-antibodies, etc., as described herein.

The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

Gene Therapy

In a specific embodiment, nucleic acids comprising sequences encoding polypeptides and/or antibodies of the invention, or functional derivatives thereof, are administered to treat, inhibit or prevent a disease or disorder associated with aberrant bone metabolism, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); *TIBTECH* 11(5):155–215 (May 1993)). Methods commonly known in the art of recombinant DNA technology which can be used are described in Ausubel et al., eds., *Current Protocols in Molecular Biology*, John Wiley & Sons, NY (1993); and Kriegler, *Gene Transfer and Expression, A Laboratory Manual*, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, *Proc. Natl. Acad. Sci. USA* 86:8932–8935 (1989); Zijlstra et al., *Nature* 342:435–438 (1989)). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where they are expressed to produce the encoded product. This can be accomplished by any of numerous methods known in the art, e.g., by constructing them as part of an appropriate nucleic acid expression vector and administering them so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/ 20316 dated Nov. 26, 1992 (Findeis et al.); WO 93/14188 dated Jul. 22, 1993 (Clarke et al.); and WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932–8935 (1989); Zijlstra et al., *Nature* 342:435–438 (1989)).

In a specific embodiment, viral vectors that contain nucleic acid sequences encoding an antibody of the invention are used. For example, a retroviral vector can be used (see Miller et al., *Meth. Enzymol.* 217:581–599 (1993)). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434 (1991); Rosenfeld et al., *Cell* 68:143–155 (1992); Mastrangeli et al., *J. Clin. Invest.* 91:225–234 (1993); PCT Publication WO94/12649; and Wang, et al., *Gene Therapy* 2:775–783 (1995). In a preferred embodiment, adenovirus vectors are used.

Adeno-associated virus (AAV) has also been proposed for use in gene therapy (Walsh et al., *Proc. Soc. Exp. Biol. Med.* 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to osteoclast precursor cells, osteoclasts, osteoblast precursor cells, osteoblasts, epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cells used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, *Cell* 71:973–985 (1992); Rheinwald, *Meth. Cell Bio.* 21A:229 (1980); and Pittelkow and Scott, *Mayo Clinic Proc.* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, osteoclastogenesis assays and bone resorption assays. Assays that may be used in determining the effects of compounds of the invention are described in Examples 20, 21 and 22, below, and are well known to those of skill in the art. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429–4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527–1533 (1990); Treat et al., in Liposomes in the Therapy of Infectious Disease and Cancer, Lopez-Berestein and Fidler, eds., Liss, New York, pp. 353–365 (1989); Lopez-Berestein, ibid., pp. 317–327).

In yet another embodiment, the compound or composition can be delivered in a controlled release system. In one embodiment, a pump may be used (see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise, eds., CRC Pres., Boca Raton, Fla. (1974); *Controlled Drug Bioavailability, Drug Product Design and Performance*, Smolen and Ball, eds., Wiley, N.Y. (1984); Ranger and Peppas, J., *Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115–138 (1984)).

Other controlled release systems are discussed in the review by Langer (*Science* 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide or polypeptide complex of interest can be used for diagnostic purposes to detect, diagnose, or monitor diseases and/or disorders associated with the aberrant expression and/or activity of a polypeptide or polypeptide complex of the invention. The invention provides for the detection of aberrant expression of a polypeptide or polypeptide complex of interest, comprising (a) assaying the expression of the polypeptide or polypeptide complex of interest in cells or body fluid of an individual using one or more antibodies specific to the polypeptide or polypeptide complex of interest and (b) comparing the level of expression with a standard expression level, whereby an increase or decrease in the assayed expression level compared to the standard expression level is indicative of aberrant expression.

The invention provides a diagnostic assay for diagnosing a metabolic bone disorder, comprising (a) assaying the expression of a polypeptide or polypeptide complex of interest in cells or body fluid of an individual using one or more antibodies specific to the polypeptide or polypeptide complex of interest and (b) comparing the level of expression with a standard expression level, whereby an increase or decrease in the assayed expression level compared to the standard expression level is indicative of a particular metabolic bone disorder. A more definitive diagnosis of this type may allow health professionals to employ preventative measures or aggressive treatment earlier thereby preventing the development or further progression of the metabolic bone disease.

Antibodies of the invention can be used to assay protein levels in a biological sample using classical immunohistological methods known to those of skill in the art (e.g., see Jalkanen, M., et al., *J. Cell. Biol.* 101:976–985 (1985); Jalkanen, M., et al., *J. Cell. Biol.* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide or polypeptide complex of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide or polypeptide complex of interest; b) waiting for a time interval following such administration to permit the labeled molecule to preferentially concentrate at sites in the subject where the polypeptide or polypeptide complex of interest is expressed (and for unbound labeled molecule to be cleared to background level); c) determining background level; and d) detecting the labeled molecule in the subject, such that detection of labeled molecule above the background level indicates that the subject has a metabolic bone disease or disorder associated with aberrant expression of the polypeptide or polypeptide complex of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in *Tumor Imaging: The Radiochemical Detection of Cancer*, S. W. Burchiel and B. A. Rhodes, eds., Masson Publishing Inc. (1982)).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescence compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against polynucleotides and polypeptides or polypeptide complexes of the invention. Such a kit may include a control antibody that does not react with the molecule of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum to detect the presence of antigens of a polypeptide or polypeptide complex of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Having generally described the invention, the same will be more readily understood by reference to the following examples, which are provided by way of illustration and are not intended as limiting.

EXAMPLES

Example 1

Expression and Purification of Endokine Alpha in E. coli

The DNA sequence encoding the Endokine alpha protein in the deposited cDNA clone is amplified using PCR oligonucleotide primers specific to the amino terminal sequences of the Endokine alpha protein. Additional nucleotides containing restriction sites to facilitate cloning are added to the 5' and 3' sequences, respectively.

The 5' oligonucleotide primer has the sequence GCG CCATGG CTA AGT TTG GAC CAT (SEQ ID NO:43) containing the underlined Nco I restriction site.

The 3' primer has the sequence GCG AAGCTT TCA AGT CTC TAG GAG ATG (SEQ ID NO:44) containing the underlined HindIII restriction site.

The restriction sites are convenient to restriction enzyme sites in the bacterial expression vector pQE60, which is used for bacterial expression in M15/rep4 host cells in these examples. (Qiagen, Inc., Chatsworth, Calif., 9131–1). pQE60 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified Endokine alpha protein DNA and the vector pQE60 both are digested with NcoI and HindIII and the digested DNAs are then ligated together. Insertion of the Endokine alpha protein DNA into the restricted pQE60 vector places the Endokine alpha protein coding region downstream of and operably linked to the vector's IPTG-inducible promoter and in-frame with an initiating ATG appropriately positioned for translation of Endokine alpha protein.

The ligation mixture is transformed into competent E. coli cells using standard procedures. Such procedures are described in Sambrook et al., Molecular Cloning: A Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kan$^r$"), is used in carrying out the illustrative example described here. This strain, which is only one of many that are suitable for expressing Endokine alpha protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 NM ("OD600") of between 0.4 and 0.6. Isopropyl-β-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin, sterile filtered and stored in 2×PBS.

Example 2

Cloning and Expression of Endokine Alpha in a Baculovirus Expression System

The cDNA sequence encoding the Endokine alpha protein in the deposited clone is amplified using PCR oligonucleotide primers corresponding to 5' and 3' regions of the gene.

The 5' primer has the sequence GC GGATCC CGA GAC TGC TAA GGA GCC (SEQ ID NO:45) containing the underlined BamHI restriction enzyme site and containing nucleotides encoding a portion of the Endokine alpha protein in FIG. 1.

The 3' primer has the sequence GC GGATCC CTA GGA GAT GAA TTG GGG ATT TG (SEQ ID NO:46) containing the underlined BamHI restriction site and containing a sequence complementary to that encoding a portion of the Endokine alpha protein in FIG. 1.

The amplified fragment is isolated from a 1% agarose gel using a commercially available kit ("Geneclean," BIO 101 Inc., La Jolla, Calif.). The fragment then is digested with BamHI and again is purified on a 1% agarose gel. This fragment is designated herein F2.

The vector pA2-GP is used to express the Endokine alpha protein in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the Autographa californica nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus, the beta-galactosidase gene from E. coli is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzyme BamHI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. E. coli HB 101 cells are transformed with ligation mix and spread on culture plates. Bacteria are identified that contain the plasmid with the human Endokine alpha gene by digesting DNA from individual colonies using BamHI and then analyzing the digestion product by gel electrophoresis. The sequence of the cloned fragment is confirmed by DNA sequencing.

5 µg of the plasmid is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). 11 g of BaculoGold™ virus DNA and 5 µg of the plasmid are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted Endokine alpha is identified by DNA analysis including restriction mapping and sequencing of this plasmid.

Sf9 cells are grown in Grace's medium supplemented with 10% heat-inactivated FBS. The cells are infected with the recombinant baculovirus at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in CHO Cells

The vector pC4 is used for the expression of Endokine alpha protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., *J Biol. Chem.* 253:1357–1370 (1978), Hamlin, J. L. and Ma, C., *Biochem. et Biophys. Acta*, 1097:107–143 (1990), Page, M. J. and Sydenham, M. A., *Biotechnology* 9:64–68) (1991). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438–447 (1985)) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the Endokine alpha in a regulated way in mammalian cells (Gossen, M., & Bujard, H., *Proc. Natl. Acad. Sci. USA* 89: 5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718I and then dephosphorylated using calf intestinal phosphatase by procedures known in the art. The vector is then isolated from a 1% agarose gel.

The DNA sequence encoding the complete Endokine alpha protein including its leader sequence is amplified using PCR oligonucleotide primers corresponding to the 5' and 3' sequences of the gene.

The 5' primer has the sequence 5' GCG GGATCC GCC ATC ATG CCT TTA AGC CAT TC 3' (SEQ ID NO:47) containing the underlined BamHI restriction enzyme site followed by an efficient signal for initiation of translation in eukaryotes, as described by Kozak, M., *J. Mol. Biol.* 196:

947–950 (1987), and 17 bases of the coding sequence of Endokine alpha shown in FIG. 1 (SEQ ID NO:39).

The 3' primer has the sequence 5' GC <u>GGATCC</u> CTA GGA GAT GAA TTG GGG ATT TG 3' (SEQ ID NO:48) containing the underlined Asp718I restriction site followed by nucleotides complementary to the non-translated region of the Endokine alpha gene shown in FIG. 1 (SEQ ID NO:39).

The amplified fragment is digested with the endonucleases BamHI and Asp718I and then purified again on a 1% agarose gel. The isolated fragment and the dephosphorylated vector are then ligated with T4 DNA ligase. E. coli HB 101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 µg of the expression plasmid pC4 is cotransfected with 0.5 µg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 µM, 20 µM). The same procedure is repeated until clones are obtained which grow at a concentration of 100–200 µM. Expression of the desired gene product is analyzed, for instance, by SDS-PAGE and Western blot or by reverse phase HPLC analysis.

Example 4

Tissue Distribution of Endokine Alpha Expression

Northern blot analysis was carried out to examine the levels of expression of the gene encoding the Endokine alpha protein in human tissues, using methods described by, among others, Sambrook et al., supra. A cDNA probe containing the entire nucleotide sequence of the Endokine alpha protein of the present invention (SEQ ID NO:39) was labeled with $^{32}$P using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding the Endokine alpha protein.

Multiple Tissue Northern (MTN) blots containing various human tissues (H) or human immune system tissues (IM) were obtained from Clontech and were examined with labelled probe using ExpressHyb™ Hybridization Solution (Clontech) according to manufacturer's protocol number PT1190–1. Following hybridization and washing, the blots were mounted and exposed to film at −70° C. overnight, and films developed according to standard procedures.

Expression of the gene encoding an Endokine alpha protein of the present invention was detected in human brain striatum and pancreas tissue.

Example 5

Identification of A Novel Activation-Inducible Protein of the TNF Receptor Superfamily and its Ligand Background Members of the TNFR superfamily share similar multiple cysteine-rich pseudorepeats of the extracellular domain, each containing 30–45 amino acids with six cysteines (Smith, C. A., et al., Cell 76:959–962 (1994)). Except for the death domain-containing family which includes TNFR1 (Schall, T. J., et al., Cell 61:361–370 (1990)), Fas (Trauth, B. C., et al., Science 245:301–305 (1989), Yonehara, S., et al., J. Exp. Med. 169:1747–1756 (1989), and Oehm, A., et al., J. Biol. Chem. 267:10709–10715 (1992)), DR3 (Chinnaiyan, A. M., et al., Science 274:990–992 (1996), Kitson, J., et al., Nature 384:372–375 (1996), Bodmer, J.-L., et al., Immunity 6:79–88 (1997), and Screaton, G. R., et al., Proc. Natl. Acad. Sci. USA 94:4615–4619 (1997)), DR4 (Wiley, S. R., et al., Immunity 3:673–682 (1995), Pitti, R. M., et al., J. Biol. Chem. 271:12687–2690 (1996), and Pan, G., et al., Science 276:111–113 (1997)), DR5 (Walczak, H., et al., EMBO J. 16:5386–5397 (1997), MacFarlane, M., et al., J. Biol. Chem. 272:25417–25420 (1997), Schneider, P., et al., Immunity 7:831–836 (1997), Chaudhary, P. M., et al., Immunity 7:821–830 (1997), and Sheridan, J. P., et al., Science 277:818–821(1997)), and decoy TRAIL receptors (Marsters, S. A., et al., Cur. Biol. 7:1003–1006 (1997), Pan, G., et al., Science 277:815–815 (1997), Degli-Esposti, M. A., et al., J. Exp. Med. 186:1165–1170 (1997), and Degli-Esposti, M. A., et al., Immunity 7:813–820 (1997)), no remarkable similarity is found within the intracellular domain of these molecules. However, there is a striking homology in the cytoplasmic domains of murine and human 4-1BB, CD27, and murine GITR within TNFR superfamily members (Kwon, B. S., et al., Proc. Natl. Acad. Sci. USA 86:1963–1967 (1989), Camerimi, D., et al., J. Immunol. 147:3165–3169 (1991), and Nocentini, G., et al., Proc. Natl. Acad. Sci. USA 94:6216–6221 (1997)). Acidic amino acids are especially highly conserved in the cytoplasmic domain of this subfamily. Like other TNFR superfamily members (Smith, C. A., et al., Cell 76:959–962 (1994)), this subfamily is implicated in diverse biological functions. First of all, 4-1BB and CD27 molecules provide strong costimulatory signals for T cell proliferation when ligated with their respective ligands or with agonistic antibodies (Smith, C. A., et al., Cell 76:959–962 (1994), and Pollok, K. E., et al., J. Immunol. 150:771–781 (1993)). In addition to functioning as an accessory molecule, CD27 induces apoptosis, which is mediated by a death domain-containing molecule called Siva (Prasad, K. V. S., et al., Proc. Natl. Acad. Sci. USA 94:6346–6351 (1997)). Recently identified murine GITR is shown to inhibit TCR-induced apoptosis (Nocentini, G., et al., Proc. Natl. Acad. Sci. USA 94:6216–6221 (1997)).

Although the immunological functions of subfamily members have been relatively well defined, insights into their signal transduction pathway have only recently been revealed (Arch, R. H., et al., Mol. Cell. Biol. 18:558–565 (1998), Jang, I. K., et al., Biochem. Biophys. Res. Com. 242:613–620 (1998), Saoulli, K., et al., J. Exp. Med. 187: 1849–1862 (1998), and Akiba, H., et al., J. Biol. Chem.

273:13353–13358 (1998)). Two groups (Arch, R. H., et al., *Mol. Cell. Biol.* 18:558–565 (1998), and Jang, I. K., et al., *Biochem. Biophys. Res. Com.* 242:613–620 (1998)) have provided data indicating that association of 4-1BB with TRAF2 molecules initiates a signal cascade leading to activation of NF-κB. In the CD27 signaling pathway, both TRAF2 and TRAF5 mediate NF-κB and SAPK/JNK (stress-activated protein kinase/c-Jun N-terminal kinase) activation and NIK (NF-κB-inducing kinase) is a common downstream kinase of TRAF2 and TRAF5 (Akiba, H., et al., *J. Biol. Chem.* 273:13353–13358 (1998)).

Because the number of TNFR members is rapidly expanding, it was expected that even more numbers of the superfamily would exist. By a PCR-based strategy with murine GITR sequence and searching an EST (expressed sequence tag) database, a new member of the TNFR was discovered and named TR11. The following provides a characterization of the receptor TR11 and its ligand, Endokine alpha.

Experimental Procedures cDNA Cloning.

A database containing more than two million ESTs obtained from over 750 different cDNA libraries was generated by Human Genome Sciences, Inc., using high throughput automated DNA sequence analysis of randomly selected human cDNA clones. A specific homology and motif search using the known amino acid sequence and motif of TNFR members against this database revealed several ESTs with a translated sequence 35–55% homologous to that of the TNFR family. Several clones were identified from cDNA libraries of PHA-activated T cells, T helper cells, leukocytes, a healing abdomen wound, primary dendritic cells and adipose tissue. A full-length TR-11 cDNA clone encoding an intact N-terminal signal peptide was obtained from a human activated T-cell library and selected for further investigation (see, U.S. patent application Ser. No. 09/176,200 filed Oct. 21, 1998). The complete cDNA sequence of both strands of this clone was determined, and its homology to TNFR members was confirmed. The same gene was also identified by a PCR-based strategy with murine GITR sequence. Similarly, Endokine-α (TNF ligand 6) was identified through a systematic comparison of sequence homology with TNF ligand family members. Partial Endokine-α sequences which were 25% homologous to that of TNF ligand family members were identified from endothelial, HUVEC (human umbilical vein endothelial cell), brain, and fetal liver cDNA libraries. A full-length cDNA clone was obtained from a human brain cDNA library.

Expression Vectors.

Full-length and HA (hemaglutinin A epitope)-tagged TR-11 encoding the putative full-length TR-11 protein (amino acids 26–234) were amplified by PCR using sense (5'-CTAGCTAGCTAGVVVAGCGCCCCAC-CGGGGGTCCC-3' (SEQ ID NO:49), and 5'-CTAGCTAGCTAGCTATCCATATGATGT-TCCAGATTATGCTCAGCGCCCCACCG GGGGTCCC-3', (SEQ ID NO:50) respectively) and anti-sense (5'-AAG-GAAAAAAGC GGGCCGCTCACACCCACAGG TCTCCCAG-3' (SEQ ID NO:51))primers, cut with Nhe I/Not I, and fused in frame downstream of a CD5 leader sequence (Jang, I. K., et al., *Biochem. Biophys. Res. Com.* 242:613–620 (1998)) into the pcDNA3.1 (pcDNA3.1/CD5L-TR-11) and pcDNA3 (pcDNA3/CD5L-TR-11), respectively. Full-length Endokine-α was amplified by PCR (sense, 5'-AGACCCAAGCTTTTGAAAATGATAT-GAGACGC-3' (SEQ ID NO:52); anti-sense, 5'-AGACGG-GATCCTCCTCCTATAGTAAGAAGGC-3' (SEQ ID NO:53)), cut with HindIII/BamHI, and inserted into pcDNA3.1 (pcDNA3.1/Endokine-α) and pCEP4 (Invitrogen, Carlsbad, Calif.; pCEP4/Endokine-α). pRK5-based expression vectors encoding Flag-tagged full-length TRAF1, TRAF2, TRAF3, TRAF5, TRAF6, NIK, dominant negative TRAF2 (dnTRAF2), or dnNIK have been described (Jang, I. K., et al., *Biochem. Biophys. Res. Com.* 242:613–620 (1998), Rothe, M., et al., *Science* 269:1421–1427 (1995), Hu, H. M., et al., *J. Biol. Chem.* 269:30069–30072 (1994), Nakano, H., et al., *J. Biol. Chem.* 271:14661–14664 (1996), Takeuchi, M., et al., *J. Biol. Chem.* 271:19935–19942 (1996), Cao, Z., et al., *Nature* 383:443–446 (1996), and Song, H. Y., et al., *Proc. Natl. Acad. Sci. USA* 94:9792–9796 (1997)). The NF-κB-dependent E-selectin-luciferase reporter gene (pELAM-Luc) and pRSV-β-galactosidase (pRSV-β-gal) plasmids were also described elsewhere (Rothe, M., et al., *Science* 269:1421–1427 (1995), and Schindler, U., et al., *Mol. Cell. Biol.* 14:5820–9796 (1994)).

Northern Blot and RT (Reverse Transcriptase)-PCR Analysis.

For Northern blot analysis, cDNA probes were labeled with $^{32}P$ using the Rediprime DNA labeling system (Amersham Life Science, Arlington Height, Ill.), according to the manufacturer's instructions. Unincorporated nucleotide was removed from the labeled probe using CHROMA SPIN-100 (Clonetech, Palo Alto, Calif.). Two human multiple tissue poly (A) RNA blots containing approximately 2 µg of poly (A) RNA per lane from various human tissues were purchased from Clontech. In addition, two cell line blots containing 20 mg total RNA from different cell lines were used. Northern blotting was performed with the Expressed Hybridization Solution (Clonetech) according to the manufacturer's manual. For RT-PCR analysis, total RNA was isolated from human PBMC after stimulation with dexamethasone, PMA/ionomycin, or anti-CD3/CD28 mAbs, and from unstimulated or LPS-stimulated HUVEC cells. RT-PCR was performed under standard conditions.

Interaction of TR-11 with TRAFs.

pcDNA3/CD5L-TR-11-HA plasmid (5 µg/10 cm-plate) was co-transfected into HEK293 EBNA cells ($2\times10^6$ cells/plate) by the standard calcium phosphate precipitation method with pRK/TRAF1, 2, 3, 5, or 6-Flag vector (5 µg/plate). Twenty four-hours after transfection, cells were lysed with 1 ml of lysis buffer (50 mM HEPES [pH 7.4], 250 mM NaCl, 0.1% Nonidet P-40, 5 mM EDTA, 10% glycerol, and protease inhibitors). For immunoprecipitation, lysates were incubated with anti-Flag M2 (Eastman Kodak, Rochester, N.Y.) or control murine IgG1 mAb at 4° C. for 1 h, followed by incubation with 20 µl of a 1:1 slurry of protein G-Sepharose (PharMingen, San Diego, Calif.) for another hour. Precipitates were thoroughly washed with lysis buffer, then fractionated on a 10% SDS-polyacrylamide gel before transfer to PVDF membrane (Millipore, Bedfore, Mass.). Western blot analysis was performed with anti-HA mAb coupled with horseradish peroxidase (Boehringer Mannheim, Indianapolis, Ind.) and visualized using the enhanced chemiluminescence Western blotting detection system (Amersham).

Analysis of NF-κB by Reporter Assay.

Approximately $0.5\times10^6$ HEK293 EBNA cells/well were seeded on 6-well plates. After 24 h, cells were transfected by the standard calcium-phosphate precipitation method using various combinations of pcDNA3.1/CD5L-TR-11 plus pRK5 plasmids encoding TRAFs, dnTRAF2, NIK, or dnNIK. The total amount of plasmid was adjusted to 2.0 µg by adding empty vector. Twenty-four hours after transfection, cells were lysed in 200 µl reporter lysis buffer (Promega, Madison, Wis.). Luciferase activity was measured using 20 µl cell extract. 5 µl cell extract was used to assay β-galactosidase activity as an internal control, and luminescence values were normalized by individual β-galactosidase activity.

Recombinant Protein Production and Purification.

TR-11-Fc fusion protein was used for ligand screening and cell-binding experiments. A fragment encoding the predicted extracellular domain of TR-11 (amino acids 26–139) was amplified using a sense primer flanked by an Nhe I site (5'-AGACCC AAGCTTGTGGGCTCT-TGAAACCCGGCATG-3' (SEQ ID NO:54)) and an antisense primer flanked by a BglII site (5'-GAAA-GATCTGGGCTCTGCCGGCGGGGACCCTG GGAC-3' (SEQ ID NO:55)). The amplified fragment was cut with NheI/BglII and cloned into mammalian vector pCEP4, in frame with CD5L at the 5' end and with the Fc portion of human IgG1 at the 3' end (pCEP4/CD5L-TR-11-Fc). pCEP4/CD5L-TR-11-Fc was transfected into HEK293 EBNA cells. TR-11-Fc fusion protein was purified from pCEP4/CD5L-TR-11-Fc-transfected HEK293 EBNA cell supernatants using protein G column. To generate a Flag-tagged soluble form of Endokine-α protein (amino acids 39–169), the flag-tagged Endokine-α expression vector (pCEP4/CD5L-Endokine-α-Flag) was constructed by PCR amplification of Endokine-α coding sequences using sense (5'-CTAGCTAGCCCAGCGCCCCGACTACAAG-GACGACGATGACAAGGAGACTGCT AAGGAGCCC-3' (SEQ ID NO:56) and antisense (5'-CCGCTCGAGCTAT-AGTAAGA AGGCTCC-3' (SEQ ID NO:57) primers, digesting the product with Nhe I/Xho I and cloning into pCEP4, in frame with the CD5L sequence. The construct was expressed in HEK293 EBNA cells. Transfected cell supernatants containing secreted Endokine-α-Flag were harvested and used for binding assays. For some experiments, Endokine-α-Flag protein was purified from harvested supernatants, using anti-Flag gel (Sigma, St. Louis. Mo.) according to the manufacturer's instructions.

Binding Assay.

Protein binding assays were done essentially as described (Pan, G., et al., Science 276:111–113 (1997)). For cell-binding assays, HEK293 EBNA cells were transfected using pcDNA3.1/CD5L-TR-11 or pcDNA3.1, as described above. Forty-eight hours after transfection, cells were harvested and incubated consecutively with Endokine-α-Flag-containing supernatant, anti-Flag antibody, and FITC-conjugated anti-mouse IgG antibody (Southern Biotechnology, Birmingham, Ala.). Flow cytometry analysis was performed using the Becton Dickinson FACScan (San Jose, Calif.). Jurkat T cells were stably transfected by electroporation using linearized pcDNA3.1/CD5L-TR-11, and selected in the presence of Zeocin (Invitrogen). A binding assay for this cell line was performed as described above. To test the ability of TR-11-Fc fusion protein to bind membrane-bound Endokine-α, pCEP4/Endokine-α was stably transfected into HEK293 EBNA cells. After selection in the presence of hygromycin, Endokine-α-expressing cells were harvested and incubated with TR-11-Fc protein, followed by FITC-conjugated anti-human IgG1 antibody (Southern Biotechnology). The Becton Dickinson FACScan was used for flow cytometry analysis.

Results and Discussion

TR-11 was identified by searching an EST database and by a PCR-based strategy with murine GITR sequence. A full-length cDNA of a clone from a human activated T-cell cDNA library, which is tentatively named TR-11 (for activation-inducible TNFR family member), encodes a 234 amino acid type I transmembrane protein with a calculated MW of 25 kDa. The receptor has a signal peptide (the first 25 amino acids) and a single transmembrane region (amino acids 140–158). When compared with the extracellular domain of other TNFR family members, TR-11 displays three cysteine-rich pseudorepeats corresponding to the second, third, and fourth TNFR motif, respectively. The first cysteine pseudorepeat contains eight cysteine residues and lacks C4. Therefore, it is unlikely that the canonical pattern of C1–C2, C3–C5, and C4–C6 disulfide bridges exist in this motif. The second pseudorepeat shows some features of the third TNFR motif, but it is a typical in that C5 is not present even though it contains 7 cysteine residues. The third pseudorepeat shows extensive homologies with the fourth pseudorepeat of 4-1BB. The cytoplasmic domain contains acidic amino acids which are highly conserved in the cytoplasmic domains of 4-1BB, CD27, and GITR. Overall, TR-11 exhibits a high homology (55% identity) to murine GITR, but there is a mismatch in the first cysteine-rich pseudorepeat between GITR and TR-11, because the first pseudorepeat of GITR corresponds to the first TNFR cysteine-rich motif (Nocentini, G., et al., Proc. Natl. Acad. Sci. USA 94:6216–6221 (1997)).

The expression of TR-11 mRNA was investigated in multiple human tissues by Northern blot hybridization. 1.25-kb mRNA was detected in lymph node, PBL, and, weakly, in spleen. We also tested a variety of tumor cell lines for expression of TR-1 mRNA. 1.25-kb message was detected only in the colorectal adenocarcinoma cell line, SW480, among the cell lines tested. The expression of virtually all members of the TNFR superfamily is enhanced by antigen stimulation/lymphocyte activation (Smith, C. A., et al., Cell 76:959–962 (1994)). Consistent with this idea, TR-11 expression was upregulated in PBMC after stimulation. No TR-11 message was detectable in unstimulated PBMC when we used a sensitive RT-PCR method. TR-11 expression was clearly induced within 24 h by typical PBMC stimulation such as treatment with PMA plus ionomycin or soluble anti-CD3 plus anti-CD28 mAbs. FACS analysis for TR-11 expression, however, showed that a small population of activated PBMC expressed TR-11 on the cell surface at 48 h after stimulation, suggesting that a prolonged period of stimulation is required for maximum expression of TR-11 (BK, unpublished data). Expression of TR-11 was not induced by treatment with dexamethasone. This property was different from that of GITR (Nocentini, G., et al., Proc. Natl. Acad. Sci. USA 94:6216–6221 (1997)).

Recently it has been shown that 4-1BB molecules associate with TRAF1, TRAF2, and TRAF3 (Arch, R. H., et al., Mol. Cell. Biol. 18:558–565 (1998), Jang, I. K., et al., Biochem. Biophys. Res. Com. 242:613–620 (1998), and Saoulli, K., et al., J. Exp. Med. 187:1849–1862 (1998)). Because TR-11's cytoplasmic domain is similar to that of 4-1BB, its ability to co-precipitate five of the six known TRAFs that were overexpressed in HEK293 EBNA cells was tested. An interaction of TR-11 with TRAF1, TRAF2, and TRAF3 was observed but not with TRAF5 and TRAF6. The association of TR-11 with TRAF2 suggested that, like other members of the TNFR superfamily (Arch, R. H., et al., Mol. Cell. Biol. 18:558–565 (1998), Jang, I. K., et al., Biochem. Biophys. Res. Com. 242:613–620 (1998), Akiba, H., et al, *J. Biol. Chem.* 273:13353–13358 (1998), Rothe, M., et al., *Science* 269:1421–1427 (1995), Cheng, G., et al., *Science* 267:1494–1498 (1995), Duckett, C. S., et al., *Mol Cell. Biol.* 17:1535–1542 (1997), and VanArsdale, T. L., et al., *Proc. Natl. Acad. Sci. USA* 94:2460–2465 (1996)), TR-11 might mediate NF-κB activation through TRAF2. To test this possibility, an NF-κB reporter system in HEK293 EBNA cells was used (Rothe, M., et al., *Science* 269:1421–1427 (1995)). Co-transfection with the TR-11 expression vector typically induced greater than 3-fold higher luciferase activity when compared with the vector transfection control. When co-expressed with TRAF2, TR-11 induced greater luciferase activity than did TRAF2 alone. More importantly, overexpression of dominant-negative TRAF2, which lacked the RING and zinc finger motifs (Rothe, M., et al., *Science* 269:1421–1427 (1995)), abrogated the luciferase activity induced by TR-11. This indicates that TRAF2 is an important mediator of NF-κB activation for TR-11. A similar observation was made when the activity of NIK, which was thought to lie downstream of TRAF2 in the NF-κB signaling pathway, was blocked by overexpression of the dominant-negative NIK (Song, H. Y., et al., *Proc. Natl. Acad. Sci. USA* 94:9792–9796 (1997)), which lacked the two lysine residues of catalytic domain. Taken together, these data indicate that TR-11 mediates NF-κB activation through the TRAF2/NIK pathway. Since TRAF1 and TRAF3 were found to associate with TR-11 in HEK293 EBNA cells, the effects of TRAF1 and TRAF3 on NF-κB activation induced by TR-11 was examined. The introduction of TRAF3 nearly abolished the luciferase activity induced by TR-11 overexpression. To a lesser extent, TRAF1 overexpression diminished TR-11-induced NF-κB activation. These data suggest that TRAF 1 and especially TRAF3 downregulate TR-11-induced NF-κB activation.

To identify TR-11 ligand, a panel of Flag-tagged candidate TNF ligand proteins for binding to TR-11-Fc fusion protein was screened by immunoprecipitation. TR-11-Fc selectively bound Endokine-α-Flag among Flag-tagged TNF ligand proteins tested. In our experimental conditions, 4-1BB and TR2 (HVEM) bound their cognate ligands, 4-1BBL and LIGHT (Mauri, D. N., et al., *Immunity* 8:21–30 (1998)), respectively. Furthermore, this data clearly showed that Endokine-α-Flag protein bound TR-11 transiently expressed on the cell surface of HEK293 EBNA cells and TR-11 constitutively expressed on the cell surface of Jurkat cell. Since Endokine-α is a transmembrane protein (see below), flow cytometry to was used determine whether TR-11-Fc fusion protein was able to bind HEK293 EBNA cells that were stably transfected with full length Endokine-α. The results demonstrate that TR-11-Fc protein was capable of binding Endokine-α expressed on HEK293 EBNA cells.

Next, it was determined whether interactions between TR-11 and Endokine-α would result in NF-κB activation. In an NF-κB reporter assay, ligand-dependent NF-κB activation was demonstrated by cotransfecting transmembrane Endokine-α with TR-11 or transfecting Endokine-α-expressing HEK293 EBNA cells. In addition, when TR-11 was transiently transfected into HEK293 EBNA cells which constitutively secreted soluble Endokine-α protein, NF-κB activation markedly increased as compared to empty vector-transfected HEK293 EBNA cells. Similarly, higher NF-κB activation was induced by treating with soluble Endokine-α protein HEK293 cells which were transiently transfected with TR-11. This indicates that Endokine-α is able to trigger TR-11-specific activation of NF-κB. It appears that higher induction of NF-κB by Endokine-α is correlated with a stronger association of TR-11 with TRAF2 in HEK293 EBNA cells, since stronger association of TR-11 with TRAF2 was observed in cells which were cotransfected with Endokine-α than in cells which were transfected with TR-11 alone.

Endokine-α was one of the TNF ligand proteins initially identified by an EST database search. Hydrophilicity analysis of a full-length Endokine-α clone from a brain cDNA library predicts a single hydrophobic transmembrane domain and the absence of a signal sequence. Endokine-α contains two potential glycosylation sites in the C-terminal region. These features suggest that Endokine-α is a type II membrane protein with the C-terminal region extracellular. Northern blot analysis of human tissue RNAs revealed expression of a single 2.4-kb Endokine-α mRNA in pancreas. Various human cell lines and PBMC were also examined for Endokine-α expression. No message was detectable in either unstimulated or stimulated T-cell lines (CEM-6 and Jurkat), B-cell lines (Priess and Frev), promyelocytic cell line (HL-60), monocytic cell line (THP-1), and PBMC by RT-PCR. In contrast, HUVEC cells constitutively expressed Endokine-α and its expression was upregulated after stimulation with LPS. Therefore, it is believed that TR-11 and its ligand are important for interactions between activated T lymphocytes and blood vessels.

TR-11 has 55% identity with murine GITR at the amino acid level. The high sequence conservation between human and mouse provides evidence that TR-11 is the human homologue of murine GITR. At this point, however, the possibility remains that these two receptors may serve distinct functions from one another, based on the following facts: (1) There is a mismatch in the first cysteine-rich pseudorepeat between GITR and TR-11; (2) in contrast to GITR, TR-11 is not inducible by dexamethasone.

In summary, a novel protein of the TNFR superfamily, TR-11, which activates NF-κB through a TRAF2-mediated mechanism has identified. Expression of TR-11 is activation-inducible. The ligand for TR-11, Endokine-α, is a member of the TNF ligand family and is constitutively expressed in an endothelial cell line. This indicates that TR-11 and its ligand may be involved in activated T-cell trafficking.

Example 6

The Effects of Endokine Alpha on Monocytes

These studies disclose that treatment with Endokine-c induced TNF-α, MCP-1, IL-8 and IL-10 release from monocytes and inhibited the production of IL-12 in monocytes. (data not shown).

Methods

Monocyte Purification.

Peripheral blood mononuclear cells (PBMC) were purified from single donor leukopacks (American Red Cross, Baltimore, Md.) by centrifugation through a Histopaque gradient (Sigma). Monocytes were isolated from PBMC by counterflow centrifugal elutriation.

ELISA.

Human monocytes were incubated at a density of $5 \times 10^5$ cells/ml with increasing concentrations of Endokine-α. For IL-12 production, the cells were primed overnight with IFN-γ (100 U/ml) in presence of Endokine-α. LPS (10 ng/ml) was then added. Conditioned media was collected after 24 h and kept frozen until use. ELISA kits for the measurement of TNF-α, IL-10, MCP-1 and IL-8 were purchased from R & D Systems (Minneapolis, Minn.). Each value was the mean of triplicate samples±standard deviation.

Oxidative Burst.

Purified monocytes were plated in 96-well plate at 2–1×$10^5$ cell/well. Increasing concentrations of Endokine-α are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) was added, together with the stimulant (200 nM PMA). The plates were incubated at 37° C. for 2 hours and the reaction was stopped by adding 20 μl 1N NaOH per well. The absorbance was read at 610 nm. To calculate the amount of $H_2O_2$ produced by the macrophages, a standard curve of a $H_2O_2$ solution of known molarity was done for each experiment.

Effect of Endokine-α Treatment on IL-12 Secretion by Monocytes

| Treatment (mg/ml) | IL-12 (pg/ml) | Inhibition % |
|---|---|---|
| — | 513 | |
| TL-6 (0.2) | 600 | 0 |
| TL-6 (1.0) | 421 | 28 |
| TL-6 (5.0) | 54 | 89 |

Monocytes ($5 \times 10^5$/ml) were incubated with IFN-g (100 U/ml) and TL-6. After 16 hours, LPS (10 ng/ml) was added to the cultures. Conditioned media was collected 24 hours following LPS addition and analyzed in ELISA for IL-12 content.

Example 7

Assays to Detect Stimulation or Inhibition of B cell Proliferation and Differentiation Background Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL-10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure

In vitro Assay.

Purified Endokine-α protein, or truncated forms thereof, is assessed for its ability to induce activation, proliferation, differentiation or inhibition and/or death in B-cell populations and their precursors. The activity of Endokine-α protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220). Various dilutions of each sample are placed into individual wells of a 96-well plate to which are added $10^5$ B-cells suspended in culture medium (RPMI 1640 containing 10% FBS, $5 \times 10^{-5}$M 2ME, 100U/ml penicillin, 10 ug/ml streptomycin, and 10–5 dilution of SAC) in a total volume of 150 ul. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

In vivo Assay.

BALB/c mice are injected (i.p.) twice per day with buffer only, or 2 mg/Kg of Endokine-α protein, or truncated forms thereof. Mice receive this treatment for 4 consecutive days, at which time they are sacrificed and various tissues and serum collected for analyses. Comparison of H&E sections from normal and Endokine-α protein-treated spleens identify the results of the activity of Endokine-α protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from Endokine-α protein-treated mice is used to indicate whether Endokine-α protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and Endokine-α protein-treated mice.

Example 8

Assays to Detect Stimulation or Inhibition of T Cell Proliferation and Differentiation The anti-CD3 and/or PHA costimulation assay is used to detected the stimulation or inhibition of T cell proliferation and differentiation.

Assay Parameters
 Cells:

| | |
|---|---|
| PBMC per well: | $10^5$ |
| PBMC recovered per donor: | $200 \times 10^6$ |
| Total plates per day: | 20 |
| Supernatants per plate: | 48 (each assayed in duplicate) |
| Total supernatants per day per donor: | 960 (two donors per day) |

Need an additional 4 units of blood/week to accommodate new assay.
 Reagents:
 anti-human CD3 mAb (25 pg/mL final concentration in each well)
 PHA
 rhIL-2 (positive control)
 $^3$H-thymidine (0.5 µCi/well, 6.7 Ci/mmole)
 96-well plates
 Protocol:
 Purify PBMC.
 Prepare plates with appropriate controls.
 Incubate at 37° C. for 3–4 days.
 Add $^3$H-TdR and return to incubator for an additional 20–24 hours.
 Harvest and count.

Outcomes

This assay allows the determination of whether Endokine-α enhances or inhibits anti-CD3-dependent proliferation of PBMCs and whether Endokine-α stimulates PBMC proliferation in the absence of costimulatory signals.

Example 9

Isolation of Antibody Fragments Directed Against Polypeptides of the Present Invention from a Library of scFvs Naturally occurring V-genes isolated from human PBLs are constructed into a large library of antibody fragments which contain reactivities against polypeptides of the present invention to which the donor may or may not have been exposed (see e.g., U.S. Pat. No. 5,885,793 incorporated herein in its entirety by reference).

Rescue of the library. A library of scFvs is constructed from the RNA of human PBLs as described in WO92/01047. To rescue phage displaying antibody fragments, approximately $10^9$ E. coli harboring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU. Next $2 \times 10^8$ TU of delta gene 3 helper phage (M13 delta gene III, see WO 92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library.

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 10

Method of Determining Alterations in the Endokine Alpha Gene

RNA is isolated from entire families or individual patients presenting with a phenotype of interest (such as a disease). cDNA is then generated from these RNA samples using protocols known in the art. (see, Sambrook.) The cDNA is then used as a template for PCR, employing primers surrounding regions of interest in SEQ ID NO:39. Suggested PCR conditions consist of 35 cycles at 95° C. for 30 seconds; 60–120 seconds at 52–58° C.; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase (Epicentre Technologies). The intron-exon borders of selected exons of Endokine alpha are also determined and genomic PCR products analyzed to confirm the results. PCR products harboring suspected mutations in Endokine alpha are then cloned and sequenced to validate the results of the direct sequencing.

PCR products of Endokine alpha are cloned into T-tailed vectors as described in Holton, T. A. and Graham, M. W., *Nucleic Acids Research*, 19:1156 (1991) and sequenced with T7 polymerase (United States Biochemical). Affected individuals are identified by mutations in Endokine alpha not present in unaffected individuals.

Genomic rearrangements are also observed as a method of determining alterations in the Endokine alpha gene. Genomic clones isolated using techniques known in the art are nick-translated with digoxigenindeoxy-uridine 5'-triphosphate (Boehringer Manheim), and FISH performed as described in Johnson, C. G. et al., *Methods Cell Biol.* 35:73–99 (1991). Hybridization with the labeled probe is carried out using a vast excess of human cot-1 DNA for specific hybridization to the Endokine alpha genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, C. V. et al., *Genet. Anal. Tech. Appl.*, 8:75 (1991).) Image collection, analysis and chromosomal fractional length measurements are performed using the ISee Graphical Program System. (Inovision Corporation, Durham, N.C.) Chromosome alterations of the genomic region of Endokine alpha (hybridized by the probe) are identified as insertions, deletions, and translocations. These Endokine alpha alterations are used as a diagnostic marker for an associated disease.

Example 11

Method of Detecting Abnormal Levels of Endokine Alpha in a Biological Sample

Endokine alpha polypeptides can be detected in a biological sample, and if an increased or decreased level of Endokine alpha is detected, this polypeptide is a marker for a particular phenotype. Methods of detection are numerous, and thus, it is understood that one skilled in the art can modify the following assay to fit their particular needs.

For example, antibody-sandwich ELISAs are used to detect Endokine alpha in a sample, preferably a biological sample. Wells of a microtiter plate are coated with specific antibodies to Endokine alpha, at a final concentration of 0.2 to 10 ug/ml. The antibodies are either monoclonal or polyclonal and are produced using technique known in the art. The wells are blocked so that non-specific binding of Endokine alpha to the well is reduced.

The coated wells are then incubated for >2 hours at RT with a sample containing Endokine alpha. Preferably, serial dilutions of the sample should be used to validate results. The plates are then washed three times with deionized or distilled water to remove unbounded Endokine alpha.

Next, 50 μl of specific antibody-alkaline phosphatase conjugate, at a concentration of 25–400 ng, is added and incubated for 2 hours at room temperature. The plates are again washed three times with deionized or distilled water to remove unbounded conjugate.

Seventy-five ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The Endokine alpha polypeptide concentration in a sample is then interpolated using the standard curve based on the measured flourescence of that sample.

Example 12

Method of Treating Decreased Levels of Endokine Alpha

The present invention also relates to a method for treating an individual in need of an increased level of Endokine alpha biological activity in the body comprising administering to such an individual a composition comprising a therapeutically effective amount of Endokine alpha or an agonist thereof.

Moreover, it will be appreciated that conditions caused by a decrease in the standard or normal expression level of Endokine alpha in an individual can be treated by administering Endokine alpha, preferably in a soluble and/or secreted form. Thus, the invention also provides a method of treatment of an individual in need of an increased level of Endokine alpha polypeptide comprising administering to such an individual a pharmaceutical composition comprising an amount of Endokine alpha to increase the biological activity level of Endokine alpha in such an individual.

For example, a patient with decreased levels of Endokine alpha polypeptide receives a daily dose 0.1–100 μg/kg of the polypeptide for six consecutive days. Preferably, the polypeptide is in a soluble and/or secreted form.

Example 13

Method of Treating Increased Levels of Endokine Alpha

The present invention relates to a method for treating an individual in need of a decreased level of Endokine alpha biological activity in the body comprising, administering to such an individual a composition comprising a therapeutically effective amount of Endokine alpha antagonist. Preferred antagonists for use in the present invention are Endokine alpha-specific antibodies or Endokine alpha antisense polynucleotides.

Antisense technology is used to inhibit production of Endokine alpha. This technology is one example of a method of decreasing levels of Endokine alpha polypeptide, preferably a soluble and/or secreted form, due to a variety of etiologies, such as cancer.

For example, a patient diagnosed with abnormally increased levels of Endokine alpha is administered intravenously antisense polynucleotides at 0.5, 1.0, 1.5, 2.0 and 3.0 mg/kg day for 21 days. This treatment is repeated after a 7-day rest period if the is determined to be well tolerated.

Example 14

Method of Treatment Using Gene Therapy—Ex vivo

One method of gene therapy transplants fibroblasts, which are capable of expressing soluble and/or mature Endokine alpha polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted; the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA* 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding Endokine alpha can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted Endokine alpha.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the Endokine alpha gene is then added to the media and the packaging cells transduced with the vector. The packaging cells now produce infectious viral particles containing the Endokine alpha gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether Endokine alpha protein is produced.

The engineered fibroblasts are then transplanted onto the host, either alone or after having been grown to confluence on cytodex 3 microcarrier beads.

Example 15

Method of Treatment Using Gene Therapy—In vivo

Another aspect of the present invention is using in vivo gene therapy methods to treat disorders, diseases and conditions. The gene therapy method relates to the introduction of naked nucleic acid (DNA, RNA, and antisense DNA or RNA) Endokine alpha sequences into an animal to increase or decrease the expression of the Endokine alpha polypeptide. The Endokine alpha polynucleotide may be operatively linked to a promoter or any other genetic elements necessary for the expression of the Endokine alpha polypeptide by the target tissue. Such gene therapy and delivery techniques and methods are known in the art, see, for example, WO 90/11092, WO 98/11779; U.S. Pat. Nos. 5,693,622, 5,705,151, 5,580,859; Tabata H. et al., *Cardiovasc. Res.* 35:470–479 (1997); Chao J. et al., *Pharmacol. Res.* 35:517–522 (1997); Wolff J. A. *Neuromuscul. Disord.* 7:314–318 (1997); Schwartz B. et al., *Gene Ther.* 3:405–411 (1996); Tsurumi Y. et al., *Circulation* 94:3281–3290 (1996) (incorporated herein by reference).

The Endokine alpha polynucleotide constructs may be delivered by any method that delivers injectable materials to the cells of an animal, such as, injection into the interstitial space of tissues (heart, muscle, skin, lung, liver, intestine and the like). The Endokine alpha polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the Endokine alpha polynucleotides may also be delivered in liposome formulations (such as those taught in Felgner P. L. et al. *Ann. NY Acad. Sci.* 772:126–139 (1995), and Abdallah B. et al. *Biol. Cell* 85:1–7 (1995)) which can be prepared by methods well known to those skilled in the art.

The Endokine alpha polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The Endokine alpha polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked Endokine alpha polynucleotide injection, an effective dosage amount of DNA or RNA will be in the range of from about 0.05 µg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked Endokine alpha polynucleotide constructs can be delivered to arteries during angioplasty by the catheter used in the procedure.

The dose response effects of injected Endokine alpha polynucleotide in muscle in vivo are determined as follows. Suitable Endokine alpha template DNA for production of mRNA coding for Endokine alpha polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The Endokine alpha template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 µm cross-section of the individual quadriceps muscles is histochemically stained for Endokine alpha protein. A time course for Endokine alpha protein expression may be done in a similar fashion except that quadriceps from different mice are harvested at different times. Persistence of Endokine alpha DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using Endokine alpha naked DNA.

Example 16

Gene Therapy Using Endogenous Endokine Alpha Gene

Another method of gene therapy according to the present invention involves operably associating the endogenous Endokine alpha sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous Endokine alpha, flanking the promoter. The targeting sequence will be sufficiently near the 5' end of Endokine alpha so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous Endokine alpha sequence. This results in the expression of Endokine alpha in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are again centrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the Endokine alpha locus, plasmid pUC18 (MBI Fermentas, Amherst, N.Y.) is digested with HindIII. The CMV promoter is amplified by PCR with an XbaI site on the 5' end and a BamHI site on the 3'end. Two Endokine alpha non-coding sequences are amplified via PCR; one Endokine alpha non-coding sequence (Endokine alpha fragment 1) is amplified with a HindIII site at the 5' end and an Xba site at the 3'end; the other Endokine alpha non-coding sequence (Endokine alpha fragment 2) is amplified with a BamHI site at the 5'end and a HindIII site at the 3'end. The CMV promoter and Endokine alpha fragments are digested with the appropriate enzymes (CMV promoter—XbaI and BamHI; Endokine alpha fragment 1—XbaI; Endokine alpha fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1-5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 msec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and the cells are incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 17

Effect of Endokine Alpha on the Expression of MHC Class II Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presentation capacity and with functional maturation of the dendritic cells.

FACS analysis of surface antigens is performed as follows. Cells are treated 1–3 days with increasing concentrations of Endokine alpha or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines.

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of Endokine alpha for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the Expression of MHC Class II, Costimulatory and Adhesion Molecules.

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of Endokine alpha or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Endokine alpha, agonists, or antagonists of Endokine alpha can be screened using the three assays described below. For each of these assays, peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay.

Human peripheral blood monocytes progressively lose viability when cultured in absence of serum or other stimuli. Their death results from an internally regulated process (apoptosis). Addition to the culture of activating factors, such as TNF-alpha, dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×10$^6$/ml in PBS containing PI at a final concentration of 5 μg/ml, and then incubated at room temperature for 5 minutes before FAC Scan analysis. PI uptake has been demonstrated to correlate with DNA fragmentation in this experimental paradigm.

2. Effect on Cytokine Release.

An important function of monocytes/macrophages is their regulatory activity on other cellular populations of the immune system through the release of cytokines after stimulation. An ELISA to measure cytokine release is performed as follows. Human monocytes are incubated at a density of 5×10$^5$ cells/ml with increasing concentrations of Endokine alpha or in the absence of Endokine alpha. For IL-12 production, the cells are primed overnight with IFN-γ (100 U/ml) in presence of Endokine alpha. LPS (10 ng/ml) is then added. Conditioned media is collected after 24 h and kept frozen until use. Measurement of TNF-α, IL-10, MCP-1 and IL-8 is then performed using a commercially available ELISA kit (e.g., R & D Systems (Minneapolis, Minn.)) applying the standard protocols provided with the kit.

3. Oxidative Burst.

Purified monocytes are plated in 96-well plates at 2–1×10$^5$ cell/well. Increasing concentrations of Endokine alpha are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl; 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in Endokine alphaprotein. However, one skilled in the art could easily modify the exemplified studies to test the activity of Endokine alpha polynucleotides (e.g., gene therapy), agonists, and/or antagonists of Endokine alpha.

Example 18

Assay to Detect Stimulation or Inhibition of T Cell Proliferation

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4_C (1_g/ml in 0.05 M bicarbonate buffer, pH 9.5), then washed three times with PBS. PBMC are isolated by F/H gradient centrifugation from human peripheral blood and added to quadruplicate wells (5×10$^4$/well) of mAb coated plates in RPMI containing 10% FCS and P/S in the presence of varying concentrations of Endokine alpha protein (total volume 200_l). Relevant protein buffer and medium alone are controls. After 48 hour culture at 37_C, plates are spun for 2 min. at 1000 rpm and 100_l of supernatant is removed and stored –20_C for measurement of IL-2 (or other cytokines) if effect on proliferation is observed. Wells are supplemented with 100_l of medium containing 0.5_Ci of $^3$H-thymidine and cultured at 37_C for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of Endokine alpha proteins.

The studies described in this example tested activity in Endokine alpha protein. However, one skilled in the art could easily modify the exemplified studies to test the activity of Endokine alpha polynucleotides (e.g., gene therapy), agonists, and/or antagonists of Endokine alpha.

Example 19

Production of an Antibody a) Hybridoma Technology

The antibodies of the present invention can be prepared by a variety of methods. (see, Current Protocols, Chapter 2.) As one example of such methods, cells expressing Endokine alpha are administered to an animal to induce the production of sera containing polyclonal antibodies. In a preferred method, a preparation of Endokine alpha protein is prepared and purified to render it substantially free of natural contaminants. Such a preparation is then introduced into an animal in order to produce polyclonal antisera of greater specific activity.

Monoclonal antibodies specific for protein Endokine alpha are prepared using hybridoma technology. (Kohler et al., *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., pp. 563–681 (1981)). In general, an animal (preferably a mouse) is immunized with Endokine alpha polypeptide or, more preferably, with a secreted Endokine alpha polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the Endokine alpha polypeptide.

Alternatively, additional antibodies capable of binding to Endokine alpha polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the Endokine alpha protein-specific antibody can be blocked by Endokine alpha.

Such antibodies comprise anti-idiotypic antibodies to the Endokine alpha protein-specific antibody and are used to immunize an animal to induce formation of further Endokine alpha protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (see, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Endokine alpha from a Library of scFvs Naturally occurring V-genes isolated from human PBLs are constructed into a library of antibody fragments which contain reactivities against Endokine alpha to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E.$ $coli$ harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, $2 \times 10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 µg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E.$ $coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing Example 20

Endokine Alpha Inhibits Osteoclastogenesis

Background

The maintenance of skeletal mass is controlled by the activity within the bone of specialized cells that are responsible for bone synthesis (osteoblasts) and bone resorption (osteoclasts). Osteoclasts are large, multinucleated phagocytes that resorb both mature and newly synthesized bone upon activation. The differentiation of hemopoietic cells of the monocyte/macrophage lineage to osteoclasts is regulated by M-CSF and RANKL.

Methods

Human peripheral blood monocytes were cultured for 7 days in 24 well/plates with M-CSF and RANKL and in absence or presence of Endokine alpha. Endokine alpha activity was assessed by measurement of lacunar bone resorption in the cultures and by measurement of tartrate-resistant acid phosphatase (TRAP) in the cells differentiated in presence of the protein.

In the lacunar bone resorption assay, cells were cultured on synthetic bone disks (Becton Dickinson) in 24 well/plate. At the end of the culture, the cells were removed and the resorption pits were identified by light microscopy.

In the TRAP assay, cells were lysed and enzyme activity in the cell extract was measured by the conversion of p-nitrophenylphosphate to p-nitrophenol in presence of sodium tartrate.

In the TRAP staining procedure, the substrate (naphthols) released by the acid phosphatase present in the osteoclasts, couples with fast garnet forming insoluble maroon deposits inside the cells. Cells containing tartrate-sensitive acid phosphatase are not stained. Cells were fixed in the wells for 10 minutes in 2% formaldehyde which was then rinsed away with water. Cells were then stained at 37° C. for one hour in pre-warmed (37° C.) substrate solution containing diazotized fast garnet, naphthols phosphate, and acetate and tartrate buffers. Cells were then washed in water and cell nuclei were counter-stained in hematoxylin solution for 2 minutes.

Results

FIG. 4 provides experimental results from a lacunar bone resorption assay. Monocytes grown in the presence of M-CSF differentiate to macrophages, consequently no resorption lacunae are observed on the bone disk (4A). Cells grown in presence of M-CSF and RANIK-L differentiate to osteoclasts and large lacunae are visible on the bone disk (4B). When Endokine alpha is added to the culture at 1000 ng/ml lacunae formation is completely inhibited (4C). Only small lacunae are observed when Endokine alpha is added at 300 ng/ml (4D).

FIG. 5 provides additional experimental results from a lacunar bone resorption assay. Monocytes of a second donor (different from the donor used to purify monocytes used in experiments presented in FIG. 4) were cultured with M-CSF and RANK-L and in presence of 1000 ng/ml Endokine alpha (5A), or APRIL (5B), or LIGHT (5C), or BLyS (5D). While no bone resorption was caused by the cells cultured in presence of Endokine alpha, extensive bone resorption was observed on the disks from the cultures with the other cytokines.

Figure 6:
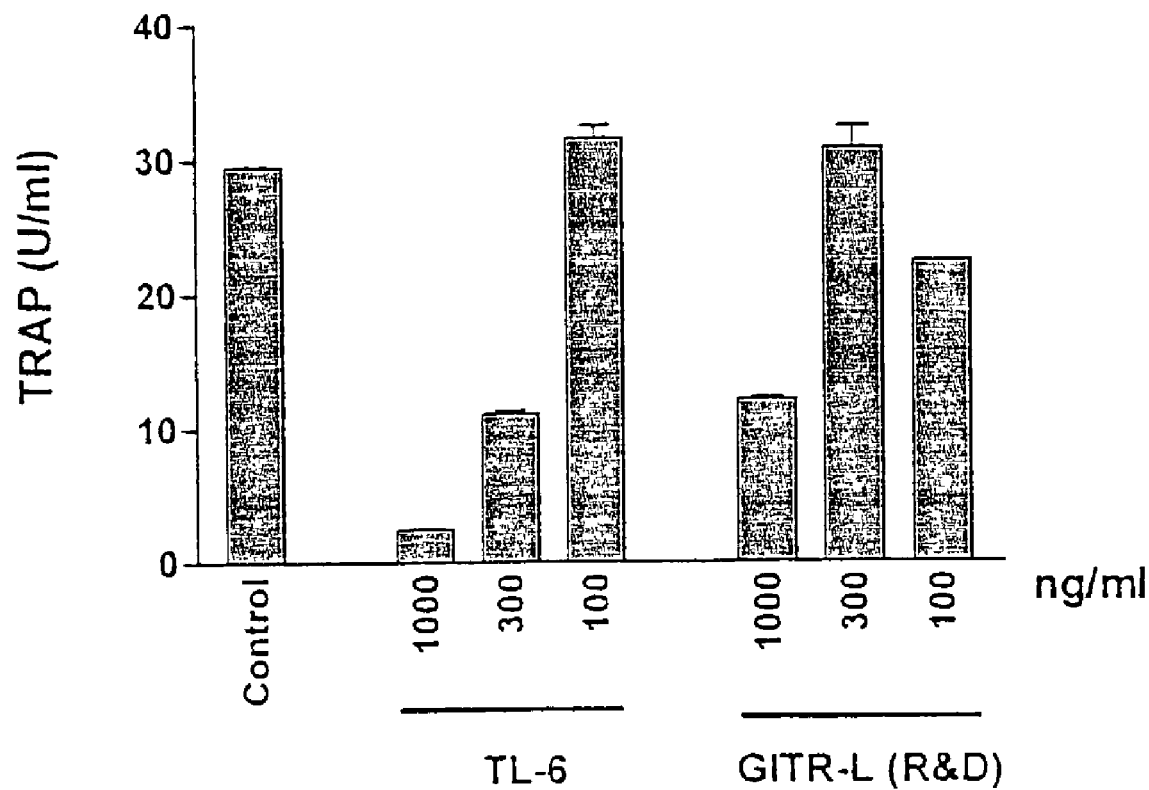
FIGS. 6 and 7 provide experimental results from TRAP assays. Endokine alpha treatment induced a strong and dose-dependent inhibition of TRAP activity, an enzyme present in osteoclasts. GITR-L (commercially available Endokine alpha, R&D Systems, Inc., Minneapolis, Minn.) had a similar effect, although higher concentrations were needed.
Figure 7:
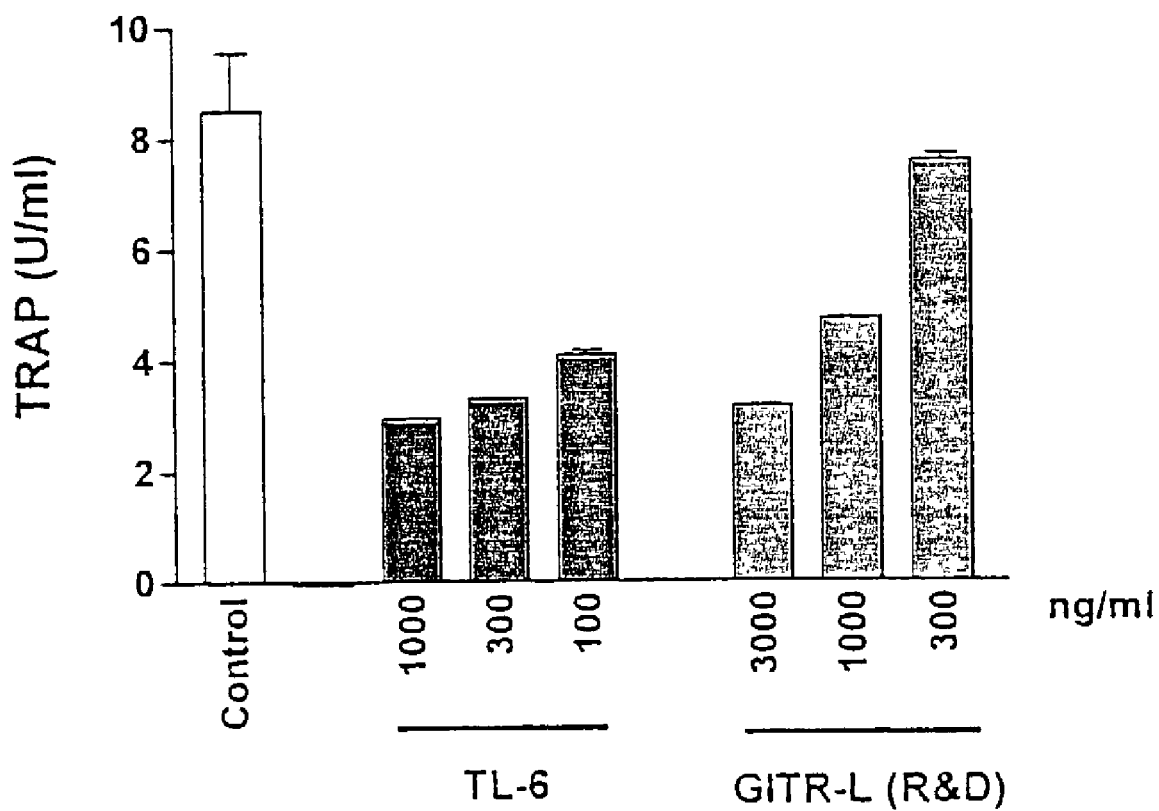

FIGS. 6 and 7 provide experimental results from TRAP assays. Endokine alpha treatment induced a strong and dose-dependent inhibition of TRAP activity, an enzyme present in osteoclasts. GITR-L (commercially available form of Endokine alpha) had a similar effect, although higher concentrations were needed.

Figure 8:
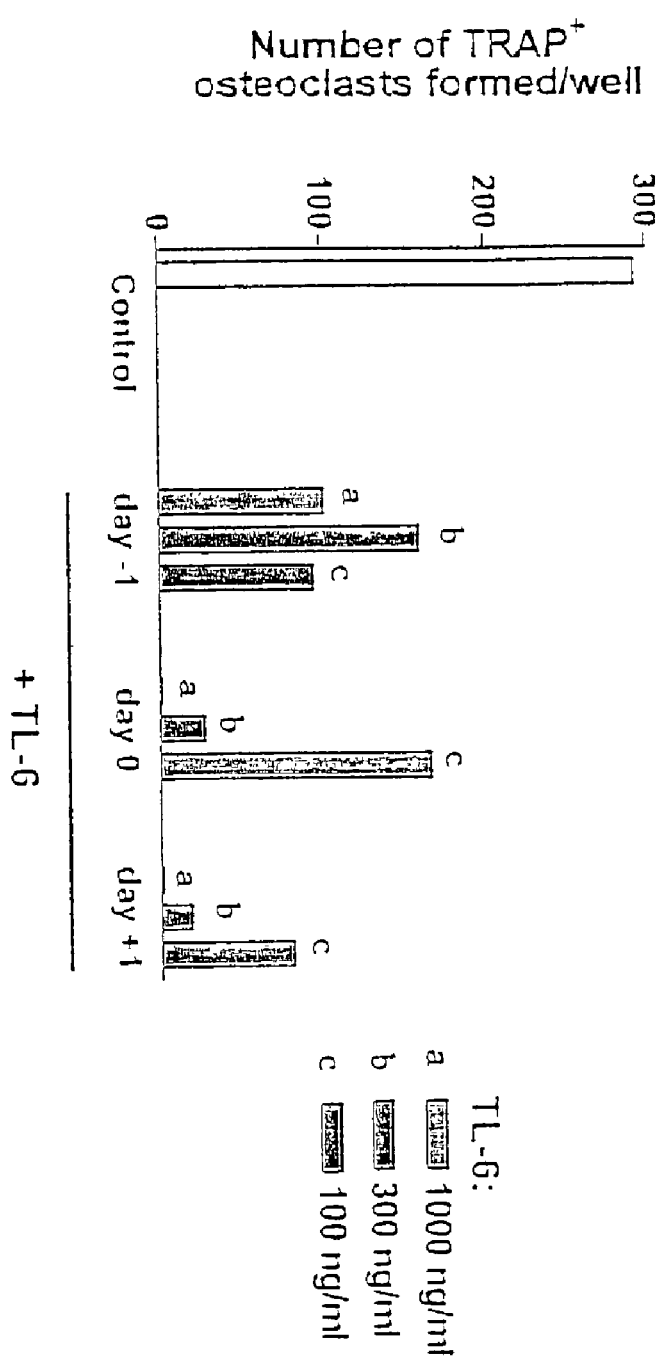
FIG. 8 provides experimental results from TRAP staining assays. Endokine alpha treatment inhibited M-CSF and RANKL-stimulated osteoclast formation in a dose-dependent fashion. Pretreatment of the cells with Endokine alpha for one day, caused a low level of inhibition, suggesting that the effects of Endokine alpha on osteoclast progenitors is not irreversible.

FIG. 8 provides experimental results from TRAP staining assays. Endokine alpha treatment inhibited M-CSF and RANKL-stimulated osteoclast formation in a dose-dependent fashion. Monocytes were cultured for seven (7) days in the presence of M-CSF and RANKL to induce osteoclast differentiation (control column). Various concentrations of Endokine alpha were added at the beginning of the culture period (day 0), or the day after (day +1). Alternatively, Endokine alpha was added to the cells for one day, on the day prior to the beginning of M-CSF and RANKL treatment, and then removed from the culture at the beginning of the M-CSF and RANKL incubation (day −1). Osteoclast formation was determined by measurement of the number of cells that stained positive for the presence of TRAP. Endokine alpha induced a dose-dependent inhibition of osteoclast formation when added to the culture on the same day (day 0) or on the day after (day +1) initiation of M-CSF and RANKL treatment of the monocytes. Pretreatment of the cells with Endokine alpha (day −1) for one day, caused a low level of inhibition, suggesting that the effects of Endokine alpha on osteoclast progenitors is not irreversible.

These results clearly demonstrate that Endokine alpha is a potent inhibitor of osteoclast differentiation and activty. Therefore, Endokine alpha is useful in the treatment, prevention, prognosis, and diagnosis of disorders associated with excessive osteoclast activity and excessive bone resorption, both as a direct result, such as osteoporosis and Paget's disease, and as an indirect result, such as arterial calcification and atherosclerosis. Also, inhibitors of Endokine alpha (e.g., antibodies) are useful in the treatment, prevention, prognosis, and diagnosis of disorders associated with inadequate osteoclast activity and/or excessive osteogenesis (e.g., excessive osteoblast activity), as detailed above.

Example 21

Endokine alpha Activity is Inhibited by TR11-Fc

Background

TNF alpha production by monocytes is a measurable marker of the biological activity of Endokine alpha.

Methods

Monocytes were treated for 1 hour with Endokine alpha (300 ng/ml) in the presence or absence of soluble receptors (1 μg/ml). Following this treatment, cells were washed and then incubated overnight. Conditioned media from the treated cells were then collected and their TNF alpha contents measured by ELISA.

Results

Figure 9:
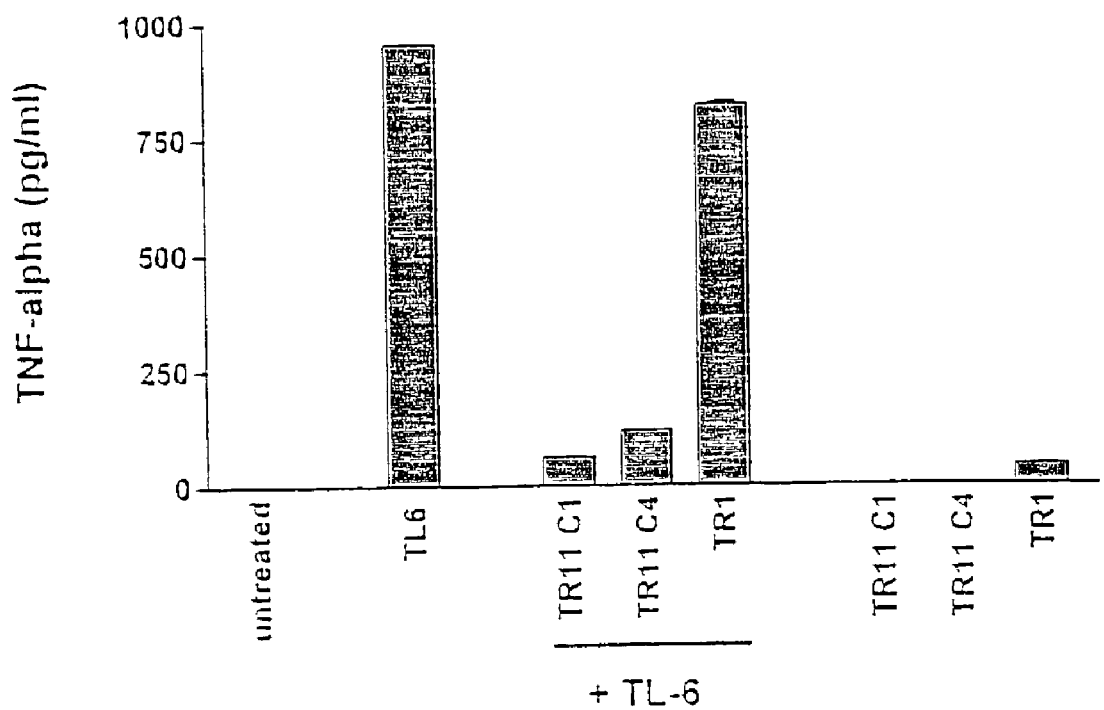
FIG. 9 provides experimental results from an assay measuring TNF alpha production by monocytes in response to treatment with Endokine alpha. Untreated monocytes did not produce detectable quantities of TNF alpha, while Endokine alpha treatment for 1 hour stimulated significant TNF alpha secretion. Endokine alpha-stimulated TNF alpha secretion was inhibited by the soluble receptor TR11, while the soluble receptor TR1 had no effect on the measured activity of Endokine alpha.

FIG. 9 provides experimental results from an assay measuring TNF alpha production by monocytes in response to treatment with Endokine alpha. Untreated monocytes did not produce detectable quantities of TNF alpha (untreated column), while Endokine alpha treatment for 1 hour stimulated significant TNF alpha secretion (endokine alpha column). Endokine alpha-stimulated TNF alpha secretion was inhibited by both C1 and C4 batches of the soluble receptor TR11-Fc (TR11C1 and TR11C4 columns), while the soluble receptor TR1-Fc had no effect on the measured activity of Endokine alpha (TR1 column). Neither soluble receptor, TR11 or TR1, stimulated TNF alpha secretion from monocytes in the absence of Endokine alpha.

Example 22

RANK Expression in Monocytes is Inhibited by Endokine alpha

Methods

Monocytes were cultured for 3 days in the absence (lane 1) or the presence of Endokine alpha (200 ng/ml; lane 2), or with M-CSF (25 ng/ml; lane 3) or M-CSF (25 ng/ml) and Endokine alpha (200 ng/ml; lane 4). Following this treatment, total cell lysates ($2 \times 10^6$ cells/lane) were resolved on 4%–20% gradient SDS-PAGE gels. RANK expression in the cells was evaluated by Western blotting using a goat anti-human RANK polyclonal antibody (R & D Systems) which was detected using Enhanced Chemiluminescence (Pierce).

Results

Figure 10:
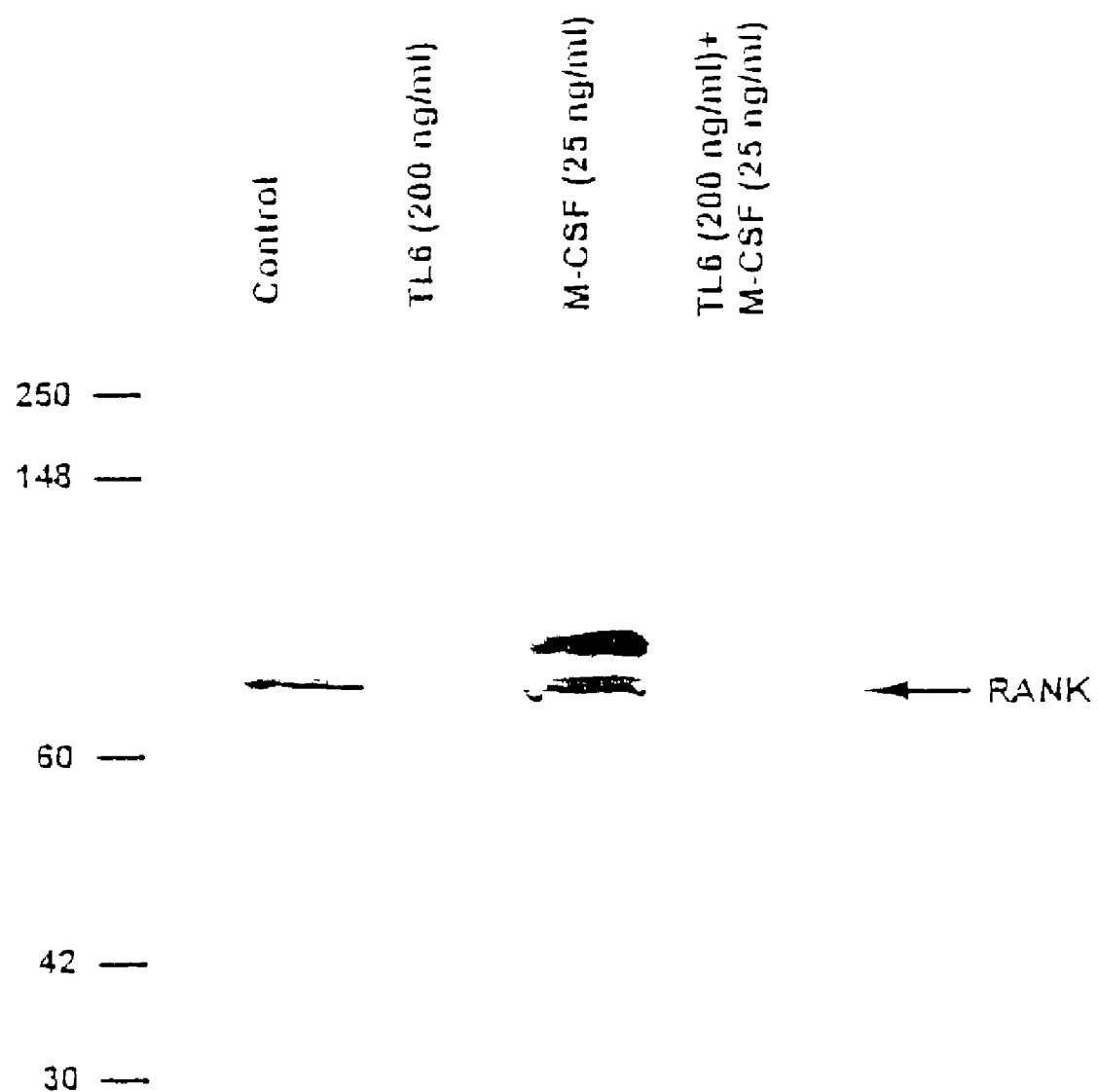
FIG. 10 provides experimental results from an assay measuring RANK expression in monocytes following treatment with Endokine alpha and/or M-CSF. Untreated monocytes expressed detectable quantities of RANK which was abolished by Endokine alpha treatment. M-CSF treatment increased RANK expression by monocytes, this increased RANK expression was also abolished on treatment with Endokine alpha.

FIG. 10 provides experimental results from an assay measuring RANK expression in monocytes following treatment with Endokine alpha and/or M-CSF. Untreated monocytes expressed detectable quantities of RANK (lane 1), whereas the detection of RANK expression was eliminated by Endokine alpha treatment (lane 2). M-CSF treatment led to increased RANK expression by monocytes (lane 3), whereas detection of this increased RANK expression was also eliminated on treatment with Endokine alpha (lane 4).

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference. Specifically, the disclosures of U.S. Provisional Patent Application Ser. Nos. 60/312,542 and 60/330,761, filed on Aug. 16, 2001 and Oct. 30, 2001 respectively, are hereby incorporated in their entireties.

Moreover, the disclosures of U.S. Provisional Patent Application Ser. Nos. 60/024,058, 60/122,099 and 60/136,788, filed on Aug. 16, 1996, Feb. 26, 1999 and May 28, 1999 respectively, and the disclosures of U.S. patent application Ser. No. 08/912,227 (now U.S. Pat. No. 5,998,171), Ser. Nos. 09/345,790, 09/513,584 (now U.S. Pat. No. 6,406,867) and Ser. No. 10/136,511, filed on Aug. 15, 1997, Jul. 1, 1999, Feb. 25, 2000 and May 2, 2002 respectively, are hereby incorporated by reference in their entireties.

What is claimed is:

1. A method of treating an individual having a disorder associated with excessive bone resorption, comprising administering to the individual a therapeutically effective amount of a composition comprising an isolated Endokine alpha polypeptide having an amino acid sequence selected from the group consisting of:
   (a) amino acids 1 to 169 of SEQ ID NO:40;
   (b) amino acids 2 to 169 of SEQ ID NO:40;
   (c) amino acids 44 to 169 of SEQ ID NO:40; and
   (d) the amino acid sequence of the Endokine alpha polypeptide having the amino acid sequence encoded by the cDNA clone contained in ATCC Deposit No. 97640.

2. The method of claim 1 wherein said amino acid sequence is (a).

3. The method of claim 1 wherein said amino acid sequence is (b).

4. The method of claim 1 wherein said amino acid sequence is (c).

5. The method of claim 1 wherein said amino acid sequence is (d).

6. The method of claim 1 wherein said Endokine alpha polypeptide further comprises an epitope tag.

7. The method of claim 1 wherein the disorder is osteoporosis.

8. The method of claim 1 wherein the disorder is Paget's disease.

9. The method of claim 1 wherein the disorder is arterial calcification.

10. A method of inhibiting RANK expression in a monocyte, macrophage, or osteoclast cell, comprising contacting the cell with an effective amount of a composition comprising an isolated Endokine alpha polypeptide having an amino acid sequence selected from the group consisting of:
   (a) amino acids 1 to 169 of SEQ ID NQ:40;
   (b) amino acids 2 to 169 of SEQ ID NO:40;
   (C) amino acids 44 to 169 of SEQ ID NO:40; and
   (d) the amino acid sequence of the Endokine alpha polypeptide having the amino acid sequence encoded by the cDNA clone contained in ATCC Deposit No. 97640.

11. The method of claim 10 wherein the cell is contacted in vivo.

12. The method of claim 10 wherein the cell is contacted in vitro.

13. A method of increasing TNF alpha production in a monocyte, macrophage, or osteoclast cell, comprising contacting the cell with an effective amount of a composition comprising an isolated Endokine alpha polypeptide having an amino acid sequence selected from the group consisting of:
   (a) ammo acids 1 to 169 of SEQ ID NO:40;
   (b) amino acids 2 to 169 of SEQ ID NO:40;
   (c) amino acids 44 to 169 of SEQ ID NO:40; and
   (d) the amino acid sequence of the Endokine alpha polypeptide having the amino acid sequence encoded by the cDNA clone contained in ATCC Deposit No. 97640.

14. The method of claim 13 wherein the cell is contacted in vivo.

15. The method of claim 13 wherein the cell is contacted in vitro.

16. A method of treating an individual having a disorder associated wit excessive bone resorption, comprising administering to the individual a therapeutically effective amount of a composition comprising an Endokine alpha fusion protein, said fusion protein consisting of amino acids 39 to 169 of SEQ ID NO:40 fused to an epitope tag.

17. The method of claim 16 wherein the disorder is osteoporosis.

18. The method of claim 16 wherein the disorder is Paget's disease.

19. The method of claim 16 wherein the disorder is arterial calcification.

20. A method of inhibiting RANK expression in a monocyte, macrophage, or osteoclast cell, comprising contacting the cell with an effective amount of a composition comprising an Endokine alpha fusion protein, said fusion protein consisting of amino acids 39 to 169 of SEQ ID NO:40 fused to an epitope tag.

21. The method of claim 20 wherein the cell is contacted in vivo.

22. The method of claim 20 wherein the cell is contacted in vitro.

23. A method of increasing TNF alpha production in a monocyte, macrophage, or osteoclast cell, comprising contacting the cell with an effective amount of a composition comprising an Endokine alpha fusion protein, said fusion protein consisting of amino acids 39 to 169 of SEQ ID NO:40 fused to an epitope tag.

24. The method of claim 23 wherein the cell is contacted in vivo.

25. The method of claim 23 wherein the cell is contacted in vitro.

* * * * *

UNITED STATES PATENT AND TRADEMARK OFFICE
CERTIFICATE OF CORRECTION

| | | |
|---|---|---|
| PATENT NO. | : 7,087,225 B2 | Page 1 of 1 |
| APPLICATION NO. | : 10/218547 | |
| DATED | : August 8, 2006 | |
| INVENTOR(S) | : Yu et al. | |

It is certified that error appears in the above-identified patent and that said Letters Patent is hereby corrected as shown below:

<u>On the title Page:</u> item (56),
    Under "References Cited, U.S. PATENT DOCUMENTS," line 4 should read "6,521,742 B2 2/2003 Yu, et al."
    Under "References Cited, FOREIGN PATENT DOCUMENTS," line 3 should read "EP 0 288 088 A2 10/1988."

Col. 248, Claim 16, line 2, delete "wit excessive bone resorption," and insert -- with excessive bone resorption,--.

Signed and Sealed this

Nineteenth Day of December, 2006

JON W. DUDAS
*Director of the United States Patent and Trademark Office*

SEQUENCE LISTING

```
<160> NUMBER OF SEQ ID NOS: 57
<210> SEQ ID NO 1
<211> LENGTH: 1325
<212> TYPE: DNA
<213> ORGANISM: human

<400> SEQUENCE: 1
gaggtttatt gggcctcggt cctcctgcac ctgctgcctg gatcccggc  ctgcctgggc    60 ctgggccttg gttctcccca tgacaccacc tgaacgtctc ttcctcccaa gggtgtgtgg   120 caccaccta  cacctcctcc ttctggggct gctgctggtt ctgctgcctg ggcccaggg    180 gctccctggt gttggcctca caccttcagc tgcccagact gcccgtcagc acccaagat    240 gcatcttgcc cacagcaccc tcaaacctgc tgctcacctc attggagacc ccagcaagca   300
gaactcactg ctctggagag caaacacgga ccgtgccttc ctccaggatg gtttctcctt   360
gagcaacaat tctctcctgg tccccaccag tggcatctac ttcgtctact cccaggtgg    420 cttctctggg aaagcctact ctcccaaggc cacctcctcc ccactctacc tggcccatga   480
ggtccagctc ttctcctccc agtacccctt ccatgtgcct ctcctcagct cccagaagat   540
ggtgtatcca gggctgcagg aaccctggct gcactcgatg taccacgggg ctgcgttcca   600
gctcacccag ggagaccagc tatccaccca cacagatggc atcccccacc tagtcctcag   660
ccctagtact gtcttctttg gagccttcgc tctgtagaac ttggaaaaat ccagaaagaa   720
aaaataattg atttcaagac cttctcccca ttctgcctcc attctgacca tttcaggggt   780
cgtcaccacc tctcctttgg ccattccaac agctcaagtc ttccctgatc aagtcaccgg   840
agctttcaaa gaaggaattc taggcatccc aggggaccca cactccctga accatccctg   900
atgtctgtct ggctgaggat ttcaagcctg cctaggaatt cccagcccaa agctgttggt   960
cttgtccacc agctaggtgg ggcctagatc cacacacaga ggaagagcag gcacatggag  1020
gagcttgggg gatgactaga ggcagggagg ggactattta tgaaggcaaa aaaattaaat  1080
tatttattta tggaggatgg agagagggaa taatagaaga acatccaagg agaaacagag  1140
acaggcccaa gagatgaaga gtgagagggc atgcgcacaa ggctgaccaa gagagaaaga  1200
agtaggcatg agggatcaca gggccccaga aggcagggaa aggctctgaa agccagctgc  1260
cgaccagagc cccacacgga ggcatctgca ccctcgatga agcccaataa acctcttttc  1320
tctga                                                              1325

<210> SEQ ID NO 2
<211> LENGTH: 205
<212> TYPE: PRT
<213> ORGANISM: human

<400> SEQUENCE: 2

Met Thr Pro Pro Glu Arg Leu Phe Leu Pro Arg Val Cys Gly Thr Thr
1               5                   10                  15

Leu His Leu Leu Leu Gly Leu Leu Leu Val Leu Leu Pro Gly Ala
            20                  25                  30
```

```
Gln Gly Leu Pro Gly Val Gly Leu Thr Pro Ser Ala Ala Gln Thr Ala
             35                  40                  45

Arg Gln His Pro Lys Met His Leu Ala His Ser Thr Leu Lys Pro Ala
 50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                 85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
            130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
            195                 200                 205

<210> SEQ ID NO 3
<211> LENGTH: 1643
<212> TYPE: DNA
<213> ORGANISM: human

<400> SEQUENCE: 3
gcagaggacc agctaagagg gagagaagca actacagacc cccctgaaa acaaccctca      60
gacgccacat cccctgacaa gctgccaggc aggttctctt cctctcacat actgacccac    120
ggctccaccc tctctcccct ggaaaggaca ccatgagcac tgaaagcatg atccgggacg    180
tggagctggc cgaggaggcg ctccccaaga agacaggggg gccccagggc tccaggcggt    240
gcttgttcct cagcctcttc tccttcctga tcgtggcagg cgccaccacg ctcttctgcc    300
tgctgcactt tggagtgatc ggccccccaga gggaagagtt ccccagggac ctctctctaa    360
tcagccctct ggcccaggca gtcagatcat cttctcgaac cccgagtgac aagcctgtag    420
cccatgttgt agcaaaccct caagctgagg ggcagctcca gtggctgaac cgccgggcca    480
atgccctcct ggccaatggc gtggagctga gagataacca gctggtggtg ccatcagagg    540
gcctgtacct catctactcc caggtcctct tcaaggggcca aggctgcccc tccacccatg    600
tgctcctcac ccacaccatc agccgcatcg ccgtctccta ccagaccaag gtcaacctcc    660
tctctgccat caagagcccc tgccagaggg agaccccaga gggggctgag gccaagcccc    720
ggtatgagcc catctatctg ggagggtct tccagctgga aagggtgac cgactcagcg    780
ctgagatcaa tcggcccgac tatctcgact ttgccgagtc tgggcaggtc tactttggga    840
tcattgccct gtgaggagga cgaacatcca accttcccaa acgcctcccc tgccccaatc    900
cctttattac cccctcctcc agacaccctc aacctcttct ggctcaaaaa gagaattggg    960
ggcttagggt cggaacccaa gcttagaact ttaagcaaca agaccaccac ttcgaaacct   1020
gggattcagg aatgtgtggc ctgcacagtg aattgctggc aaccactaag aattcaaact   1080
ggggcctcca gaactcactg gggcctacag ctttgatccc tgacatctgg aatctggaga   1140
```

-continued

```
ccagggagcc tttggttctg gccagaatgc tgcaggactt gagaagacct cacctagaaa    1200
ttgacacaag tggaccttag gccttcctct ctccagatgt ttccagactt ccttgagaca    1260
cggagcccag ccctccccat ggagccagct ccctctattt atgtttgcac ttgtgattat    1320
ttattattta tttattattt atttatttac agatgaatgt atttatttgg gagaccgggg    1380
tatcctgggg gacccaatgt aggagctgcc ttggctcaga catgttttcc gtgaaaacgg    1440
agctgaacaa taggctgttc ccatgtagcc ccctggcctc tgtgccttct tttgattatg    1500
ttttttaaaa tatttatctg attaagttgt ctaaacaatg ctgatttggt gaccaactgt    1560
cactcattgc tgagcctctg ctccccaggg gagttgtgtc tgtaatcgcc ctactattca    1620
gtggcgagaa ataaagtttg ctt                                             1643
```

<210> SEQ ID NO 4
<211> LENGTH: 233
<212> TYPE: PRT
<213> ORGANISM: human

<400> SEQUENCE: 4

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 5
<211> LENGTH: 894
<212> TYPE: DNA
<213> ORGANISM: human

<400> SEQUENCE: 5

-continued

```
cagtctcaat gggggcactg gggctggagg gcaggggtgg gaggctccag gggagggtt      60 ccctcctgct agctgtggca ggagccactt ctctggtgac cttgttgctg gcggtgccta   120
tcactgtcct ggctgtgctg gccttagtgc cccaggatca ggaggactg gtaacggaga    180 cggccgaccc cggggcacag gcccagcaag gactgggtt tcagaagctg ccagaggagg    240
agccagaaac agatctcagc cccgggctcc cagctgccca cctcataggc gctccgctga   300
aggggcaggg gctaggctgg gagacgacga aggaacaggc gtttctgacg agcgggacgc   360
agttctcgga cgccgagggg ctggcgctcc cgcaggacgg cctctattac ctctactgtc   420
tcgtcggcta ccggggccgg gcgccccctg gcggcgggga ccccagggc cgctcggtca    480 cgctgcgcag ctctctgtac cgggcggggg gcgcctacgg gccgggcact cccgagctgc   540
tgctcgaggg cgccgagacg gtgactccag tgctggaccc ggccaggaga caagggtacg   600
ggcctctctg gtacacgagc gtggggttcg gcggcctggt gcagctccgg aggggcgaga   660
gggtgtacgt caacatcagt caccccgata tggtggactt cgcgagaggg aagaccttct   720
ttggggccgt gatggtgggg tgagggaata tgagtgcgtg gtgcgagtgc gtgaatattg   780
ggggcccgga cgcccaggac cccatggcag tgggaaaaat gtaggagact gtttggaaat   840
tgattttgaa cctgatgaaa ataaagaatg gaaagcttca gtgctgccga taaa          894
```

<210> SEQ ID NO 6
<211> LENGTH: 244
<212> TYPE: PRT
<213> ORGANISM: human

<400> SEQUENCE: 6

```
Met Gly Ala Leu Gly Leu Glu Gly Arg Gly Gly Arg Leu Gln Gly Arg
  1               5                  10                  15

Gly Ser Leu Leu Leu Ala Val Ala Gly Ala Thr Ser Leu Val Thr Leu
                 20                  25                  30

Leu Leu Ala Val Pro Ile Thr Val Leu Ala Val Leu Ala Leu Val Pro
             35                  40                  45

Gln Asp Gln Gly Gly Leu Val Thr Glu Thr Ala Asp Pro Gly Ala Gln
         50                  55                  60

Ala Gln Gln Gly Leu Gly Phe Gln Lys Leu Pro Glu Glu Pro Glu
 65                  70                  75                  80

Thr Asp Leu Ser Pro Gly Leu Pro Ala Ala His Leu Ile Gly Ala Pro
                 85                  90                  95

Leu Lys Gly Gln Gly Leu Gly Trp Glu Thr Thr Lys Glu Gln Ala Phe
                100                 105                 110

Leu Thr Ser Gly Thr Gln Phe Ser Asp Ala Glu Gly Leu Ala Leu Pro
            115                 120                 125

Gln Asp Gly Leu Tyr Tyr Leu Tyr Cys Leu Val Gly Tyr Arg Gly Arg
        130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
```

|     |     |     |     | 210 |     |     |     | 215 |     |     |     | 220 |     |     |
| --- | --- | --- | --- | --- | --- | --- | --- | --- | --- | --- | --- | --- | --- | --- |
| His | Pro | Asp | Met | Val | Asp | Phe | Ala | Arg | Gly | Lys | Thr | Phe | Phe | Gly | Ala |
| 225 |     |     |     | 230 |     |     |     | 235 |     |     |     | 240 |     |     |

Val Met Val Gly

<210> SEQ ID NO 7
<211> LENGTH: 3362
<212> TYPE: DNA
<213> ORGANISM: human

<400> SEQUENCE: 7

```
ccatatcttc atcttccctc tacccagatt gtgaagatgg aaagggtcca accctggaa        60
gagaatgtgg gaaatgcagc caggccaaga ttcgagagga caagctatt gctggtggcc      120
tctgtaattc agggactggg gctgctcctg tgcttcacct acatctgcct gcacttctct      180
gctcttcagg tatacatcg gtatcctcga attcaaagta tcaaagtaca atttaccgaa      240
tataagaagg agaaaggttt catcctcact tcccaaaagg aggatgaaat catgaaggtg      300
cagaacaact cagtcatcat caactgtgat gggttttatc tcatctccct gaagggctac      360
ttctcccagg aagtcaacat tagccttcat taccagaagg atgaggagcc cctcttccaa      420
ctgaagaagt caggtctgt caactccttg atggtggcct ctctgactta caaagacaaa      480
gtctacttga atgtgaccac tgacaatacc tccctgatg acttccatgt gaatggcgga      540
gaactgattc ttatccatca aatcctggt gaattctgtg tcctttgagg ggctgatggc      600
aatatctaaa accaggcacc agcatgaaca ccaagctggg ggtggacagg gcatggattc      660
ttcattgcaa gtgaaggagc ctcccagctc agccacgtgg gatgtgacaa gaagcagatc      720
ctggccctcc cgcccccacc cctcagggat atttaaaact tattttatat accagttaat      780
cttatttatc cttatatttt ctaaattgcc tagccgtcac accccaagat tgccttgagc      840
ctactaggca ccctttgtgag aaagaaaaaa tagatgcctc ttcttcaaga tgcattgttt      900
ctattggtca ggcaattgtc ataataaact tatgtcattg aaaacggtac ctgactacca      960
tttgctggaa atttgacatg tgtgtggcat tatcaaaatg aagaggagca aggagtgaag     1020
gagtgggtt atgaatctgc caaggtggt atgaaccaac ccctggaagc caaagcggcc      1080
tctccaaggt taaattgatt gcagtttgca tattgcctaa atttaaactt tctcatttgg     1140
tgggggttca aagaagaat cagcttgtga aaatcagga cttgaagaga gccgtctaag      1200
aaataccacg tgctttttt ctttaccatt ttgctttccc agcctccaaa catagttaat      1260
agaaatttcc cttcaaagaa ctgtctgggg atgtgatgct ttgaaaaatc taatcagtga     1320
cttaagagag attttcttgt atacagggag agtgagataa cttattgtga agggttagct     1380
ttactgtaca ggatagcagg gaactggaca tctcagggta aaagtcagta cggattttaa     1440
tagcctgggg aggaaaacac attctttgcc acagacaggc aaagcaacac atgctcatcc     1500
tcctgcctat gctgagatac gcactcagct ccatgtcttg tacacacaga acattgctg      1560
gtttcaagaa atgaggtgat cctattatca aattcaatct gatgtcaaat agcactaaga     1620
agttattgtg ccttatgaaa aataatgatc tctgtctaga ataccatag accatatata     1680
gtctcacatt gataattgaa actagaaggg tctatatcag cctatgccag gcttcaatg      1740
gaatagtatc cccttatgtt tagttgaaat gtcccttaa cttgatataa tgtgttatgc     1800
ttatggcgct gtgacaatct gatttttcat gtcaacttcc agatgatttg taacttctct     1860
gtgccaaacc ttttataaac ataaattttt gagatatgta ttttaaaatt gtagcacatg     1920
```

-continued

```
tttccctgac attttcaata gaggatacaa catcacagaa tctttctgga tgattctgtg    1980
ttatcaagga attgtactgt gctacaatta tctctagaat ctccagaaag gtggagggct    2040
gttcgccctt acactaaatg gtctcagttg gattttttt tcctgttttc tatttcctct    2100
taagtacacc ttcaactata ttcccatccc tctattttaa tctgttatga aggaaggtaa    2160
ataaaaatgc taaatagaag aaattgtagg taaggtaaga ggaatcaagt tctgagtggc    2220
tgccaaggca ctcacagaat cataatcatg gctaaatatt tatggagggc ctactgtgga    2280
ccaggcactg gctaaatact tacatttaca agaatcattc tgagacagat attcaatgat    2340
atctggcttc actactcaga agattgtgtg tgtgtttgtg tgtgtgtgtg tgtgtgtatt    2400
tcacttttg ttattgacca tgttctgcaa aattgcagtt actcagtgag tgatatccga     2460
aaaagtaaac gtttatgact ataggtaata tttaagaaaa tgcatggttc attttaagt     2520
ttggaatttt tatctatatt tctcacagat gtgcagtgca catgcaggcc taagtatatg    2580
ttgtgtgtgt ttgtctttga cgtcatggtc ccctctctta ggtgctcact cgctttgggt    2640
gcacctggcc tgctcttccc atgttggcct ctgcaaccac acagggatat ttctgctatg    2700
caccagcctc actccacctt ccttccatca aaaatatgtg tgtgtgtctc agtccctgta    2760
agtcatgtcc ttcacaggga gaattaaccc ttcgatatac atggcagagt tttgtgggaa    2820
aagaattgaa tgaaaagtca ggagatcaga attttaaatt tgacttagcc actaactagc    2880
catgtaacct tgggaaagtc atttcccatt tctgggtctt gcttttcttt ctgttaaatg    2940
agaggaatgt taaatatcta acagtttaga atcttatgct tacagtgtta tctgtgaatg    3000
cacatattaa atgtctatgt tcttgttgct atgagtcaag gagtgtacac ttctccttta    3060
ctatgttgaa tgtatttttt tctggacaag cttacatctt cctcagccat ctttgtgagt    3120
ccttcaagag cagttatcaa ttgttagtta gatattttct atttagagaa tgcttaaggg    3180
attccaatcc cgatccaaat cataatttgt tcttaagtat actgggcagg tcccctattt    3240
taagtcataa ttttgtattt agtgctttcc tggctctcag agagtattaa tattgatatt    3300
aataatatag ttaatagtaa tattgctatt tacatggaaa caaataaaag atctcagaat    3360
tc                                                                  3362
```

<210> SEQ ID NO 8
<211> LENGTH: 183
<212> TYPE: PRT
<213> ORGANISM: human

<400> SEQUENCE: 8

```
Met Glu Arg Val Gln Pro Leu Glu Glu Asn Val Gly Asn Ala Ala Arg
1               5                   10                  15
Pro Arg Phe Glu Arg Asn Lys Leu Leu Leu Val Ala Ser Val Ile Gln
                20                  25                  30
Gly Leu Gly Leu Leu Cys Phe Thr Tyr Ile Cys Leu His Phe Ser
            35                  40                  45
Ala Leu Gln Val Ser His Arg Tyr Pro Arg Ile Gln Ser Ile Lys Val
        50                  55                  60
Gln Phe Thr Glu Tyr Lys Lys Glu Lys Gly Phe Ile Leu Thr Ser Gln
65                  70                  75                  80
Lys Glu Asp Glu Ile Met Lys Val Gln Asn Asn Ser Val Ile Ile Asn
                85                  90                  95
Cys Asp Gly Phe Tyr Leu Ile Ser Leu Lys Gly Tyr Phe Ser Gln Glu
                100                 105                 110
```

```
Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
        180

<210> SEQ ID NO 9
<211> LENGTH: 1803
<212> TYPE: DNA
<213> ORGANISM: human

<400> SEQUENCE: 9
```

| | | | | | |
|---|---|---|---|---|---|
| tgccaccttc | tctgccagaa | gataccattt | caactttaac | acagcatgat | cgaaacatac | 60 |
| aaccaaactt | ctccccgatc | tgcggccact | ggactgccca | tcagcatgaa | aatttttatg | 120 |
| tatttactta | ctgtttttct | tatcacccag | atgattgggt | cagcactttt | tgctgtgtat | 180 |
| cttcatagaa | ggttggacaa | gatagaagat | gaaaggaatc | ttcatgaaga | ttttgtattc | 240 |
| atgaaaacga | tacagagatg | caacacagga | gaaagatcct | tatccttact | gaactgtgag | 300 |
| gagattaaaa | gccagtttga | aggctttgtg | aaggatataa | tgttaaacaa | agaggagacg | 360 |
| aagaaagaaa | acagctttga | aatgcaaaaa | ggtgatcaga | tcctcaaat | tgcggcacat | 420 |
| gtcataagtg | aggccagcag | taaaacaaca | tctgtgttac | agtgggctga | aaaggatac | 480 |
| tacaccatga | gcaacaactt | ggtaaccctg | aaaatggga | aacagctgac | cgttaaaaga | 540 |
| caaggactct | attatatcta | tgcccaagtc | accttctgtt | ccaatcggga | agcttcgagt | 600 |
| caagctccat | ttatagccag | cctctgccta | aagtccccg | gtagattcga | gagaatctta | 660 |
| ctcagagctg | caaataccca | cagttccgcc | aaaccttgcg | ggcaacaatc | cattcacttg | 720 |
| ggaggagtat | ttgaattgca | accaggtgct | tcggtgtttg | tcaatgtgac | tgatccaagc | 780 |
| caagtgagcc | atggcactgg | cttcacgtcc | tttggcttac | tcaaactctg | aacagtgtca | 840 |
| ccttgcaggc | tgtggtggag | ctgacgctgg | gagtcttcat | aatacagcac | agcggttaag | 900 |
| cccaccccct | gttaactgcc | tatttataac | cctaggatcc | tccttatgga | gaactattta | 960 |
| ttatacactc | caaggcatgt | agaactgtaa | taagtgaatt | acaggtcaca | tgaaaccaaa | 1020 |
| acgggccctg | ctccataaga | gcttatatat | ctgaagcagc | aaccccactg | atgcagacat | 1080 |
| ccagagagtc | ctatgaaaag | acaaggccat | tatgcacagg | ttgaattctg | agtaaacagc | 1140 |
| agataacttg | ccaagttcag | ttttgttttct | ttgcgtgcag | tgtctttcca | tggataatgc | 1200 |
| atttgattta | tcagtgaaga | tgcagaaggg | aaatggggag | cctcagctca | cattcagtta | 1260 |
| tggttgactc | tgggttccta | tggccttgtt | ggaggggggcc | aggctctaga | acgtctaaca | 1320 |
| cagtggagaa | ccgaaacccc | cccccccccc | ccgccaccct | ctcggacagt | tattcattct | 1380 |
| ctttcaatct | ctctctctcc | atctctctct | ttcagtctct | ctctctcaac | ctctttcttc | 1440 |
| caatctctct | ttctcaatct | ctctgtttcc | ctttgtcagt | ctcttccctc | ccccagtctc | 1500 |
| tcttctcaat | ccccctttct | aacacacaca | cacacacaca | cacacacaca | cacacacaca | 1560 |
| cacacacaca | cagagtcagg | ccgttgctag | tcagttctct | tctttccacc | ctgtccctat | 1620 |
| ctctaccact | atagatgagg | gtgaggagta | gggagtgcag | ccctgagcct | gcccactcct | 1680 |

-continued cattacgaaa tgactgtatt taaaggaaat ctattgtatc tacctgcagt ctccattgtt     1740
tccagagtga acttgtaatt atcttgttat ttatttttg aataataaag acctcttaac     1800
att                                                                  1803

<210> SEQ ID NO 10
<211> LENGTH: 261
<212> TYPE: PRT
<213> ORGANISM: human

<400> SEQUENCE: 10

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 11
<211> LENGTH: 972
<212> TYPE: DNA
<213> ORGANISM: human

<400> SEQUENCE: 11
tctagactca ggactgagaa gaagtaaaac cgtttgctgg ggctggcctg actcaccagc       60
tgccatgcag cagcccttca attacccata tccccagatc tactgggtgg acagcagtgc      120
cagctctccc tgggcccctc caggcacagt tcttccctgt ccaacctctg tgcccagaag      180

```
gcctggtcaa aggaggccac caccaccacc gccaccgcca ccactaccac ctccgccgcc    240
gccgccacca ctgcctccac taccgctgcc acccctgaag aagagaggga accacagcac    300
aggcctgtgt ctccttgtga tgtttttcat ggttctggtt gccttggtag gattgggcct    360
ggggatgttt cagctcttcc acctacagaa ggagctggca gaactccgag agtctaccag    420
ccagatgcac acagcatcat ctttggagaa gcaaataggc cacccagtc caccccctga     480 aaaaaaggag ctgaggaaag tggcccattt aacaggcaag tccaactcaa ggtccatgcc    540
tctggaatgg gaagacacct atggaattgt cctgctttct ggagtgaagt ataagaaggg    600
tggccttgtg atcaatgaaa ctgggctgta ctttgtatat tccaaagtat acttccgggg    660
tcaatcttgc aacaacctgc ccctgagcca aggtctac atgaggaact ctaagtatcc      720
ccaggatctg gtgatgatgg agggaagat gatgagctac tgcactactg ggcagatgtg     780
ggcccgcagc agctacctgg gggcagtgtt caatcttacc agtgctgatc atttatatgt    840
caacgtatct gagctctctc tggtcaattt tgaggaatct cagacgtttt tcggcttata    900
taagctctaa gagaagcact ttgggattct ttccattatg attctttgtt acaggcaccg    960
agatgttcta ga                                                        972
```

<210> SEQ ID NO 12
<211> LENGTH: 281
<212> TYPE: PRT
<213> ORGANISM: human

<400> SEQUENCE: 12

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
```

```
                225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
                260                 265                 270
Gln Thr Phe Phe Gly Leu Tyr Lys Leu
                275                 280

<210> SEQ ID NO 13
<211> LENGTH: 926
<212> TYPE: DNA
<213> ORGANISM: human

<400> SEQUENCE: 13
ccagagaggg gcaggcttgt cccctgacag gttgaagcaa gtagacgccc aggagccccg      60
ggaggggggct gcagtttcct tccttccttc tcggcagcgc tccgcgcccc catcgccccct  120
cctgcgctag cggaggtgat cgccgcggcg atgccggagg agggttcggg ctgctcggtg    180
cggcgcaggc cctatgggtg cgtcctgcgg gctgctttgg tcccattggt cgcgggcttg    240
gtgatctgcc tcgtggtgtg catccagcgc ttcgcacagg ctcagcagca gctgccgctc    300
gagtcacttg gtgggacgt agctgagctg cagctgaatc acacaggacc tcagcaggac     360
cccaggctat actggcaggg ggcccagca ctggccgct ccttcctgca tggaccagag      420
ctggacaagg ggcagctacg tatccatcgt gatggcatct acatggtaca catccaggtg    480
acgctggcca tctgctcctc cacgacggcc tccaggcacc accccaccac cctggccgtg    540
ggaatctgct ctcccgcctc ccgtagcatc agcctgctgc gtctcagctt ccaccaaggt    600
tgtaccattg tctcccagcg cctgacgccc ctggcccgag ggacacact ctgcaccaac     660
ctcactggga cacttttgcc ttcccgaaac actgatgaga ccttctttgg agtgcagtgg   720
gtgcgcccct gaccactgct gctgattagg gtttttttaaa ttttatttta ttttatttaa    780
gttcaagaga aaagtgtac acacaggggc cacccggggt tggggtggga gtgtggtggg     840
gggtagtttg tggcaggaca agagaaggca ttgagctttt tctttcattt tcctattaaa    900
aaatacaaaa atcaaaacaa aaaaaa                                          926

<210> SEQ ID NO 14
<211> LENGTH: 193
<212> TYPE: PRT
<213> ORGANISM: human

<400> SEQUENCE: 14

Met Pro Glu Glu Gly Ser Gly Cys Ser Val Arg Arg Arg Pro Tyr Gly
1               5                   10                  15
Cys Val Leu Arg Ala Ala Leu Val Pro Leu Val Ala Gly Leu Val Ile
                20                  25                  30
Cys Leu Val Val Cys Ile Gln Arg Phe Ala Gln Ala Gln Gln Gln Leu
            35                  40                  45
Pro Leu Glu Ser Leu Gly Trp Asp Val Ala Glu Leu Gln Leu Asn His
        50                  55                  60
Thr Gly Pro Gln Gln Asp Pro Arg Leu Tyr Trp Gln Gly Gly Pro Ala
65                  70                  75                  80
Leu Gly Arg Ser Phe Leu His Gly Pro Glu Leu Asp Lys Gly Gln Leu
                85                  90                  95
Arg Ile His Arg Asp Gly Ile Tyr Met Val His Ile Gln Val Thr Leu
            100                 105                 110
```

```
Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
        130                 135                 140

Leu Ser Phe His Gln Gly Cys Thr Ile Val Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 15
<211> LENGTH: 1906
<212> TYPE: DNA
<213> ORGANISM: human

<400> SEQUENCE: 15
```

| | | | | | |
|---|---|---|---|---|---|
| ccaagtcaca | tgattcagga | ttcaggggga | gaatccttct | tggaacagag | atgggcccag | 60 |
| aactgaatca | gatgaagaga | gataaggtgt | gatgtgggga | agactatata | aagaatggac | 120 |
| ccagggctgc | agcaagcact | caacggaatg | gcccctcctg | gagacacagc | catgcatgtg | 180 |
| ccggcgggct | ccgtggccag | ccacctgggg | accacgagcc | gcagctattt | ctatttgacc | 240 |
| acagccactc | tggctctgtg | ccttgtcttc | acggtggcca | ctattatggt | gttggtcgtt | 300 |
| cagaggacgg | actccattcc | caactcacct | gacaacgtcc | ccctcaaagg | aggaaattgc | 360 |
| tcagaagacc | tcttatgtat | cctgaaaaga | gctccattca | agaagtcatg | ggcctacctc | 420 |
| caagtggcaa | agcatctaaa | caaaaccaag | ttgtcttgga | acaaagatgg | cattctccat | 480 |
| ggagtcagat | atcaggatgg | aatctggtg | atccaattcc | ctggtttgta | cttcatcatt | 540 |
| tgccaactgc | agtttcttgt | acaatgccca | aataattctg | tcgatctgaa | gttggagctt | 600 |
| ctcatcaaca | agcatatcaa | aaaacaggcc | ctggtgacag | tgtgtgagtc | tggaatgcaa | 660 |
| acgaaacacg | tataccagaa | tctctctcaa | ttcttgctgg | attacctgca | ggtcaacacc | 720 |
| accatatcag | tcaatgtgga | tacattccag | tacatagata | caagcacctt | tcctcttgag | 780 |
| aatgtgttgt | ccatcttctt | atacagtaat | tcagactgaa | cagtttctct | tggccttcag | 840 |
| gaagaaagcg | cctctctacc | atacagtatt | tcatccctcc | aaacacttgg | gcaaaaagaa | 900 |
| aactttagac | aagacaaac | tacacagggt | attaaatagt | atacttctcc | ttctgtctct | 960 |
| tggaaagata | cagctccagg | gttaaaaaga | gagttttttag | tgaagtatct | ttcagatagc | 1020 |
| aggcagggaa | gcaatgtagt | gtggtgggca | gagccccaca | cagaatcaga | agggatgaat | 1080 |
| ggatgtccca | gcccaaccac | taattcactg | tatggtcttg | atctatttct | tctgttttga | 1140 |
| gagcctccag | ttaaaatggg | gcttcagtac | cagagcagct | agcaactctg | ccctaatggg | 1200 |
| aaatgaaggg | gagctggtg | tgagtgttta | cactgtgccc | ttcacgggat | acttcttta | 1260 |
| tctgcagatg | gcctaatgct | tagttgtcca | agtcgcgatc | aaggactctc | tcacacagga | 1320 |
| aacttcccta | tactggcaga | tacacttgtg | actgaaccat | gcccagttta | tgcctgtctg | 1380 |
| actgtcactc | tggcactagg | aggctgatct | tgtactccat | atgaccccac | ccctaggaac | 1440 |
| ccccagggaa | aaccaggctc | ggacagcccc | ctgttcctga | gatggaaagc | acaaatttaa | 1500 |
| tacaccacca | caatgaaaaa | caagttcaaa | gactttttact | tacagatcct | ggacagaaag | 1560 |
| ggcataatga | gtctgaaggg | cagtcctcct | tctccaggtt | acatgaggca | ggaataagaa | 1620 |

```
gtcagacaga gacagcaaga cagttaacaa cgtaggtaaa gaaatagggt gtggtcactc    1680
tcaattcact ggcaaatgcc tgaatggtct gtctgaagga agcaacagag aagtggggaa    1740
tccagtctgc taggcaggaa agatgcctct aagttcttgt ctctggccag aggtgtggta    1800
tagaaccaga aacccatatc aagggtgact aagcccggct tccggtatga gaaattaaac    1860
ttgtatacaa aatggttgcc aaggcaacat aaaattataa gaattc                  1906
```

<210> SEQ ID NO 16
<211> LENGTH: 234
<212> TYPE: PRT
<213> ORGANISM: human

<400> SEQUENCE: 16

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230
```

<210> SEQ ID NO 17
<211> LENGTH: 1619
<212> TYPE: DNA
<213> ORGANISM: human

<400> SEQUENCE: 17

```
gtcatggaat acgcctctga cgcttcactg gaccccgaag ccccgtggcc tcccgcgccc     60
cgcgctcgcg cctgccgcgt actgccttgg gccctggtcg cggggctgct gctgctgctg    120
ctgctcgctg ccgcctgcgc cgtcttcctc gcctgcccct gggccgtgtc cggggctcgc    180
gcctcgcccg gctccgcggc cagcccgaga ctccgcgagg gtcccgagct tcgcccgac    240
```

```
gatcccgccg gcctcttgga cctgcggcag ggcatgtttg cgcagctggt ggcccaaaat    300
gttctgctga tcgatgggcc cctgagctgg tacagtgacc caggcctggc aggcgtgtcc    360
ctgacggggg gcctgagcta caaagaggac acgaaggagc tggtggtggc caaggctgga    420
gtctactatg tcttctttca actagagctg cggcgcgtgg tggccggcga gggctcaggc    480
tccgtttcac ttgcgctgca cctgcagcca ctgcgctctg ctgctgggc cgccgccctg     540
gctttgaccg tggacctgcc acccgcctcc tccgaggctc ggaactcggc cttcggtttc    600
cagggccgct gctgcacct gagtgccggc agcgcctgg gcgtccatct tcacactgag      660
gccagggcac gccatgcctg cagcttacc cagggcgcca cagtcttggg actcttccgg     720
gtgaccccg aaatcccagc cggactccct tcaccgaggt cggaataacg cccagcctgg    780
gtgcagccca cctggacaga gtccgaatcc tactccatcc ttcatggaga ccctggtgc    840
tgggtccctg ctgctttctc tacctcaagg ggcttggcag gggtccctgc tgctgacctc    900
cccttgagga ccctcctcac ccactccttc cccaagttgg accttgatat ttattctgag    960
cctgagctca gataatatat tatatatatt atatatatat atatatttct atttaaagag   1020
gatcctgagt ttgtgaatgg actttttag aggagttgtt ttggggggg ggtcttcgac    1080
attgccgagg ctggtcttga actcctggac ttagacgatc ctcctgcctc agcctcccaa   1140
gcaactggga ttcatccttt ctattaattc attgtactta tttgcctatt tgtgtgtatt   1200
gagcatctgt aatgtgccag cattgtgccc aggctagggg gctatagaaa catctagaaa   1260
tagactgaaa gaaaatctga gttatggtaa tacgtgagga atttaaagac tcatccccag   1320
cctccacctc ctgtgtgata cttgggggct agcttttttc tttctttctt ttttttgaga   1380
tggtcttgtt ctgtcaacca ggctagaatg cagcggtgca atcatgagtc aatgcagcct   1440
ccagcctcga cctcccgagg ctcaggtgat cctcccatct cagcctctcg agtagctggg   1500
accacagttg tgtgccacca cacttggcta actttttaat tttttttgcgg agacggtatt   1560
gctatgttgc caaggttgtt tacatgccag tacaatttat aataaacact catttttcc   1619
```

<210> SEQ ID NO 18
<211> LENGTH: 254
<212> TYPE: PRT
<213> ORGANISM: human

<400> SEQUENCE: 18

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125
```

```
Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 19
<211> LENGTH: 1769
<212> TYPE: DNA
<213> ORGANISM: human

<400> SEQUENCE: 19

```
cctcactgac tataaagaa tagagaagga agggcttcag tgaccggctg cctggctgac      60
ttacagcagt cagactctga caggatcatg gctatgatgg aggtccaggg gggacccagc    120
ctgggacaga cctgcgtgct gatcgtgatc ttcacagtgc tcctgcagtc tctctgtgtg    180
gctgtaactt acgtgtactt taccaacgag ctgaagcaga tgcaggacaa gtactccaaa    240
agtggcattg cttgtttctt aaaagaagat gacagttatt gggaccccaa tgacgaagag    300
agtatgaaca gccctgctg gcaagtcaag tggcaactcc gtcagctcgt tagaaagatg    360
attttgagaa cctctgagga aaccatttct acagttcaag aaaagcaaca aaatatttct    420
cccctagtga gagaaagagg tcctcagaga gtagcagctc acataactgg gaccagagga    480
agaagcaaca cattgtcttc tccaaactcc aagaatgaaa aggctctggg ccgcaaaata    540
aactcctggg aatcatcaag gagtgggcat tcattcctga caacttgca cttgaggaat    600
ggtgaactgg tcatccatga aaagggtttt actacatct attcccaaac atactttcga    660
tttcaggagg aaataaaaga aaacacaaag aacgacaaac aaatggtcca atatatttac    720
aaatacacaa gttatcctga ccctatattg ttgatgaaaa gtgctagaaa tagttgttgg    780
tctaaagatg cagaatatgg actctattcc atctatcaag ggggaatatt tgagcttaag    840
gaaaatgaca gaattttgt ttctgtaaca atgagcact tgatagacat ggaccatgaa    900
gccagttttt tcgggccttt tttagttggc taactgacct ggaagaaaa agcaataacc    960
tcaaagtgac tattcagttt tcaggatgat acactatgaa gatgtttcaa aaaatctgac   1020
caaaacaaac aaacagaaaa cagaaaacaa aaaacctctc tgcaatctg agtagagcag   1080
ccacaaccaa aaaattctac aacacacact gttctgaaag tgactcactt atcccaagaa   1140
aatgaaattg ctgaaagatc tttcaggact ctacctcata tcagtttgct agcagaaatc   1200
tagaagactg tcagcttcca aacattaatg caatggttaa catcttctgt ctttataatc   1260
tactccttgt aaagactgta gaagaaagcg caacaatcca tctctcaagt agtgtatcac   1320
agtagtagcc tccaggtttc cttaagggac aacatcctta agtcaaaaga gagaagaggc   1380
accactaaaa gatcgcagtt tgcctggtgc agtggctcac acctgtaatc ccaacatttt   1440
```

-continued

```
gggaacccaa ggtgggtaga tcacgagatc aagagatcaa gaccatagtg accaacatag    1500
tgaaacccca tctctactga aagtgcaaaa attagctggg tgtgttggca catgcctgta    1560
gtcccagcta cttgagaggc tgaggcagga gaatcgtttg aacccgggag gcagaggttg    1620
cagtgtggtg agatcatgcc actacactcc agcctggcga cagagcgaga cttggtttca    1680
aaaaaaaaaa aaaaaaaaaa cttcagtaag tacgtgttat ttttttcaat aaaattctat    1740
tacagtatgt caaaaaaaaa aaaaaaaaa                                      1769
```

<210> SEQ ID NO 20
<211> LENGTH: 281
<212> TYPE: PRT
<213> ORGANISM: human

<400> SEQUENCE: 20

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 21
<211> LENGTH: 2271
<212> TYPE: DNA

<213> ORGANISM: human

<400> SEQUENCE: 21

```
aagcttggta ccgagctcgg atccactact cgacccacgc gtccgcgcgc cccaggagcc      60
aaagccgggc tccaagtcgg cgccccacgt cgaggctccg ccgcagcctc cggagttggc     120
cgcagacaag aaggggaggg agcgggagag ggaggagagc tccgaagcga gagggccgag     180
cgccatgcgc cgcgccagca gagactacac caagtacctg cgtggctcgg aggagatggg     240
cggcggcccc ggagccccgc acgagggccc cctgcacgcc ccgccgccgc ctgcgccgca     300
ccagcccccc gccgcctccc gctccatgtt cgtggccctc ctggggctgg ggctgggcca     360
ggttgtctgc agcgtcgccc tgttcttcta tttcagagcg cagatggatc ctaatagaat     420
atcagaagat ggcactcact gcatttatag aatttttgaga ctccatgaaa atgcagattt    480
tcaagacaca actctggaga gtcaagatac aaaattaata cctgattcat gtaggagaat    540
taaacaggcc tttcaaggag ctgtgcaaaa ggaattacaa catatcgttg atcacagca    600
catcagagca gagaaagcga tggtggatgg ctcatggtta gatctggcca agaggagcaa    660
gcttgaagct cagccttttg ctcatctcac tattaatgcc accgacatcc catctggttc    720
ccataaagtg agtctgtcct cttggtacca tgatcggggt tgggccaaga tctccaacat    780
gactttagc aatggaaaac taatagttaa tcaggatggc ttttattacc tgtatgccaa    840
catttgcttt cgacatcatg aaacttcagg agacctagct acagagtatc ttcaactaat    900
ggtgtacgtc actaaaacca gcatcaaaat cccaagttct catacccctga tgaaaggagg    960
aagcaccaag tattggtcag ggaattctga attccatttt tattccataa acgttggtgg   1020
atttttttaag ttacggtctg gagaggaaat cagcatcgag gtctccaacc cctccttact   1080
ggatccggat caggatgcaa catactttgg ggcttttaaa gttcgagata tagattgagc   1140
cccagttttt ggagtgttat gtatttcctg gatgtttgga acattttttt aaaacaagcc   1200
aagaaagatg tatataggtg tgtgagacta ctaagaggca tggccccaac ggtacacgac   1260
tcagtatcca tgctcttgac cttgtagaga acacgcgtat ttacagccag tgggagatgt   1320
tagactcatg gtgtgttaca caatggtttt taaattttgt aatgaattcc tagaattaaa   1380
ccagattgga gcaattacgg gttgacctta tgagaaactg catgtgggct atggagggg   1440
ttggtccctg gtcatgtgcc ccttcgcagc tgaagtggag agggtgtcat ctagcgcaat   1500
tgaaggatca tctgaagggg caaattcttt tgaattgtta catcatgctg gaacctgcaa   1560
aaaatacttt ttctaatgag gagagaaaat atatgtattt ttatataata tctaaagtta   1620
tatttcagat gtaatgtttt ctttgcaaag tattgtaaat tatatttgtg ctatagtatt   1680
tgattcaaaa tatttaaaaa tgtcttgctg ttgacatatt taatgtttta aatgtacaga   1740
catatttaac tggtgcactt tgtaaattcc ctggggaaaa cttgcagcta aggaggggaa   1800
aaaaatgttg tttcctaata tcaaatgcag tatatttctt cgttcttttt aagttaatag   1860
attttttcag acttgtcaag cctgtgcaaa aaaattaaaa tggatgcctt gaataataag   1920
caggatgttg gccaccaggt gcctttcaaa tttagaaact aattgacttt agaaagctga   1980
cattgccaaa aaggatacat aatgggccac tgaaatctgt caagagtagt tatataattg   2040
ttgaacaggt gttttccac aagtgccgca aattgtacct ttttttttttt ttcaaaatag   2100
aaaagttatt agtggtttat cagcaaaaaa gtccaatttt aatttagtaa atgttatctt   2160
atactgtaca ataaaaacat tgcctttgaa tgttaatttt ttggtacaaa aataaattta   2220
tatgaaaaaa aaaaaaaaag ggcggccgct ctagagggcc ctattctata g             2271
```

<210> SEQ ID NO 22
<211> LENGTH: 317
<212> TYPE: PRT
<213> ORGANISM: human

<400> SEQUENCE: 22

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315

<210> SEQ ID NO 23
<211> LENGTH: 1306
<212> TYPE: DNA
<213> ORGANISM: human

<400> SEQUENCE: 23
cacagccccc cgcccccatg gccgcccgtc ggagccagag gcggaggggg cgccgggggg    60

-continued

```
agccgggcac cgccctgctg gtcccgctcg cgctgggcct gggcctggcg ctggcctgcc     120
tcggcctcct gctggccgtg gtcagtttgg ggagccgggc atcgctgtcc gcccaggagc     180
ctgcccagga ggagctggtg cagaggagg accaggaccc gtcggaactg aatccccaga      240
cagaagaaag ccaggatcct gcgcctttcc tgaaccgact agttcggcct cgcagaagtg     300
cacctaaagg ccggaaaaca cgggctcgaa gagcgatcgc agcccattat gaagttcatc     360
cacgacctgg acaggacgga gcgcaggcag gtgtggacgg acagtgagt ggctgggagg      420 aagccagaat caacagctcc agccctctgc gctacaaccg ccagatcggg gagtttatag     480
tcacccgggc tgggctctac tacctgtact gtcaggtgca ctttgatgag gggaaggctg     540
tctacctgaa gctggacttg ctggtggatg gtgtgctggc cctgcgctgc ctggaggaat     600
tctcagccca tgcggccagt tccctcgggc cccagctccg cctctgccag gtgtctgggc     660
tgttggccct gcggccaggg tcctccctgc ggatccgcac cctccctg gcccatctca       720 aggctgcccc cttcctcacc tacttcggac tcttccaggt tcactgaggg gccctggtct     780
ccccacagtc gtcccaggct gccggctccc ctcgacagct ctctgggcac ccggtcccct    840
ctgccccacc ctcagccgct ctttgctcca gacctgcccc tccctctaga ggctgcctgg     900
gcctgttcac gtgttttcca tcccacataa atacagtatt cccactctta tcttacaact     960 ccccaccgc ccactctcca cctcactagc tccccaatcc ctgacccttt gaggccccca     1020
gtgatctcga ctcccccctg gccacagacc cccagggcat tgtgttcact gtactctgtg    1080
ggcaaggatg ggtccagaag accccacttc aggcactaag aggggctgga cctggcggca    1140
ggaagccaaa gagactgggc ctaggccagg agttcccaaa tgtgaggggc gagaaacaag    1200
acaagctcct cccttgagaa ttccctgtgg atttttaaaa cagatattat ttttattatt    1260
attgtgacaa aatgttgata aatggatatt aaatagaata agtcag                   1306
```

<210> SEQ ID NO 24
<211> LENGTH: 249
<212> TYPE: PRT
<213> ORGANISM: human

<400> SEQUENCE: 24

```
Met Ala Ala Arg Arg Ser Gln Arg Arg Gly Arg Gly Glu Pro
1               5                   10                  15

Gly Thr Ala Leu Leu Val Pro Leu Ala Leu Gly Leu Gly Leu Ala Leu
                20                  25                  30

Ala Cys Leu Gly Leu Leu Leu Ala Val Val Ser Leu Gly Ser Arg Ala
            35                  40                  45

Ser Leu Ser Ala Gln Glu Pro Ala Gln Glu Glu Leu Val Ala Glu Glu
        50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Ser Ala Pro
                85                  90                  95

Lys Gly Arg Lys Thr Arg Ala Arg Ala Ile Ala Ala His Tyr Glu
            100                 105                 110

Val His Pro Arg Pro Gly Gln Asp Gly Ala Gln Ala Val Asp Gly
        115                 120                 125

Thr Val Ser Gly Trp Glu Glu Ala Arg Ile Asn Ser Ser Pro Leu
    130                 135                 140

Arg Tyr Asn Arg Gln Ile Gly Glu Phe Ile Val Thr Arg Ala Gly Leu
145                 150                 155                 160
```

Tyr Tyr Leu Tyr Cys Gln Val His Phe Asp Glu Gly Lys Ala Val Tyr
            165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
            195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 25
<211> LENGTH: 1348
<212> TYPE: DNA
<213> ORGANISM: human

<400> SEQUENCE: 25

| | | | | | |
|---|---|---|---|---|---|
| ggtacgaggc | ttcctagagg | gactggaacc | taattctcct | gaggctgagg | gagggtggag | 60 |
| ggtctcaagg | caacgctggc | cccacgacgg | agtgccagga | gcactaacag | tacccttagc | 120 |
| ttgctttcct | cctccctcct | ttttattttc | aagttccttt | ttatttctcc | ttgcgtaaca | 180 |
| accttcttcc | cttctgcacc | actgcccgta | cccttacccg | ccccgccacc | tccttgctac | 240 |
| cccactcttg | aaaccacagc | tgttggcagg | gtccccagct | catgccagcc | tcatctcctt | 300 |
| tcttgctagc | ccccaaaggg | cctccaggca | acatggggg | cccagtcaga | gagccggcac | 360 |
| tctcagttgc | cctctggttg | agttgggggg | cagctctggg | ggccgtggct | tgtgccatgg | 420 |
| ctctgctgac | ccaacaaaca | gagctgcaga | gcctcaggag | agaggtgagc | cggctgcagg | 480 |
| ggacaggagg | cccctcccag | aatggggaag | ggtatccctg | gcagagtctc | ccggagcaga | 540 |
| gttccgatgc | cctggaagcc | tgggagaatg | gggagagatc | ccggaaaagg | agagcagtgc | 600 |
| tcacccaaaa | acagaagaag | cagcactctg | tcctgcacct | ggttcccatt | aacgccacct | 660 |
| ccaaggatga | ctccgatgtg | acagaggtga | tgtggcaacc | agctcttagg | cgtgggagag | 720 |
| gcctacaggc | ccaaggatat | ggtgtccgaa | tccaggatgc | tggagtttat | ctgctgtata | 780 |
| gccaggtcct | gtttcaagac | gtgactttca | ccatgggtca | ggtggtgtct | cgagaaggcc | 840 |
| aaggaaggca | ggagactcta | ttccgatgta | taagaagtat | gccctcccac | ccggaccggg | 900 |
| cctacaacag | ctgctatagc | gcaggtgtct | tccatttaca | ccaagggat | attctgagtg | 960 |
| tcataattcc | ccgggcaagg | gcgaaactta | acctctctcc | acatggaacc | ttcctggggt | 1020 |
| ttgtgaaact | gtgattgtgt | tataaaaagt | ggctcccagc | ttggaagacc | agggtgggta | 1080 |
| catactggag | acagccaaga | gctgagtata | taaggagag | gaatgtgca | ggaacagagg | 1140 |
| catcttcctg | ggtttggctc | cccgttcctc | acttttccct | tttcattccc | accccctaga | 1200 |
| cttttgatttt | acggatatct | tgcttctgtt | ccccatggag | ctccgaattc | ttgcgtgtgt | 1260 |
| gtagatgagg | ggcgggggac | gggcgccagg | cattgttcag | acctggtcgg | ggcccactgg | 1320 |
| aagcatccag | aacagcacca | ccatctta | | | | 1348 |

<210> SEQ ID NO 26
<211> LENGTH: 250
<212> TYPE: PRT
<213> ORGANISM: human

```
<400> SEQUENCE: 26

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 27
<211> LENGTH: 1126
<212> TYPE: DNA
<213> ORGANISM: human

<400> SEQUENCE: 27
cccacccgtc cgcccacgcg tccgccactg cccgtaccct tacccgcccc gccacctact      60
tgctacccca ctcttgaaac cacagctgtt ggcagggtcc ccagctcatg ccagcctcat     120
ctcctttctt gctagccccc aaagggcctc caggcaacat ggggggccca gtcagagagc     180
cggcactctc agttgccctc tggttgagtt gggggcagc tctgggggcc gtggcttgtg      240
ccatggctct gctgacccaa caaacagagc tgcagagcct caggagagag gtgagccggc     300
tgcagaggac aggaggcccc tcccagaatg ggaagggta tccctggcag agtctcccgg      360
agcagagttc cgatgccctg gaagcctggg agtggggga gatcccgg aaaggagag         420 cagtgctcac ccaaaaacag aagaatgact ccgatgtgac agaggtgatg tggcaaccag     480
ctcttaggcg tgggagaggc ctacaggccc aaggatatgg tgtccgaatc caggatgctg     540
gagtttatct gctgtatagc caggtcctgt tcaagacgt gactttcacc atgggtcagg      600
tggtgtctcg agaaggccaa ggaaggcagg agactctatt ccgatgtata agaagtatgc     660
```

-continued

| | |
|---|---|
| cctcccaccc ggaccgggcc tacaacagct gctatagcgc aggtgtcttc catttacacc | 720 |
| aagggatat tctgagtgtc ataattcccc gggcaagggc gaaacttaac ctctctccac | 780 |
| atggaacctt cctggggttt gtgaaactgt gattgtgtta taaaaagtgg ctcccagctt | 840 |
| ggaagaccag ggtgggtaca tactggagac agccaagagc tgagtatata aggagaggg | 900 |
| aatgtgcagg aacagaggcg tcttcctggg tttggctccc cgttcctcac ttttcccttt | 960 |
| tcattcccac ccctagact tgattttac ggatatcttg cttctgttcc ccatggagct | 1020 |
| ccgaattctt gcgtgtgtgt agatgagggg cgggggacg ggcgccaggc attgttcaga | 1080 |
| cctggtcggg gcccactgga agcatccaga acagcaccac catcta | 1126 |

<210> SEQ ID NO 28
<211> LENGTH: 234
<212> TYPE: PRT
<213> ORGANISM: human

<400> SEQUENCE: 28

Met Pro Ala Ser Ser Pro Phe Leu Leu Ala Pro Lys Gly Pro Pro Gly
1               5                   10                  15
Asn Met Gly Gly Pro Val Arg Glu Pro Ala Leu Ser Val Ala Leu Trp
                20                  25                  30
Leu Ser Trp Gly Ala Ala Leu Gly Ala Val Ala Cys Ala Met Ala Leu
            35                  40                  45
Leu Thr Gln Gln Thr Glu Leu Gln Ser Leu Arg Arg Glu Val Ser Arg
        50                  55                  60
Leu Gln Arg Thr Gly Gly Pro Ser Gln Asn Gly Glu Gly Tyr Pro Trp
65                  70                  75                  80
Gln Ser Leu Pro Glu Gln Ser Ser Asp Ala Leu Glu Ala Trp Glu Ser
                85                  90                  95
Gly Glu Arg Ser Arg Lys Arg Arg Ala Val Leu Thr Gln Lys Gln Lys
                100                 105                 110
Asn Asp Ser Asp Val Thr Glu Val Met Trp Gln Pro Ala Leu Arg Arg
            115                 120                 125
Gly Arg Gly Leu Gln Ala Gln Gly Tyr Gly Val Arg Ile Gln Asp Ala
        130                 135                 140
Gly Val Tyr Leu Leu Tyr Ser Gln Val Leu Phe Gln Asp Val Thr Phe
145                 150                 155                 160
Thr Met Gly Gln Val Val Ser Arg Glu Gly Gln Gly Arg Gln Glu Thr
                165                 170                 175
Leu Phe Arg Cys Ile Arg Ser Met Pro Ser His Pro Asp Arg Ala Tyr
            180                 185                 190
Asn Ser Cys Tyr Ser Ala Gly Val Phe His Leu His Gln Gly Asp Ile
        195                 200                 205
Leu Ser Val Ile Ile Pro Arg Ala Arg Ala Lys Leu Asn Leu Ser Pro
    210                 215                 220
His Gly Thr Phe Leu Gly Phe Val Lys Leu
225                 230

<210> SEQ ID NO 29
<211> LENGTH: 858
<212> TYPE: DNA
<213> ORGANISM: human

<400> SEQUENCE: 29
atggatgact ccacagaaag ggagcagtca cgccttactt cttgccttaa gaaaagagaa    60

```
gaaatgaaac tgaaggagtg tgtttccatc ctcccacgga aggaaagccc ctctgtccga      120
tcctccaaag acggaaagct gctggctgca accttgctgc tggcactgct gtcttgctgc      180
ctcacggtgg tgtctttcta ccaggtggcc gccctgcaag gggacctggc cagcctccgg      240
gcagagctgc agggccacca cgcggagaag ctgccagcag gagcaggagc ccccaaggcc      300
ggcttggagg aagctccagc tgtcaccgcg ggactgaaaa tctttgaacc accagctcca      360
ggagaaggca actccagtca gaacagcaga aataagcgtg ccgttcaggg tccagaagaa      420
acagtcactc aagactgctt gcaactgatt gcagacagtg aaacaccaac tatacaaaaa      480
ggatcttaca catttgttcc atggcttctc agctttaaaa ggggaagtgc cctagaagaa      540
aaagagaata aatattggt caaagaaact ggttactttt ttatatatgg tcaggtttta      600
tatactgata agacctacgc catgggacat ctaattcaga ggaagaaggt ccatgtcttt      660
ggggatgaat tgagtctggt gactttgttt cgatgtattc aaaatatgcc tgaaacacta      720
cccaataatt cctgctattc agctggcatt gcaaaactgg aagaaggaga tgaactccaa      780
cttgcaatac aagagaaaaa tgcacaaata tcactggatg agatgtcac attttttggt       840 gcattgaaac tgctgtga                                                     858
```

<210> SEQ ID NO 30
<211> LENGTH: 285
<212> TYPE: PRT
<213> ORGANISM: human

<400> SEQUENCE: 30

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220
```

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 31
<211> LENGTH: 798
<212> TYPE: DNA
<213> ORGANISM: human

<400> SEQUENCE: 31

| | | | | | |
|---|---|---|---|---|---|
| atggatgact | ccacagaaag | ggagcagtca | cgccttactt | cttgccttaa | gaaaagagaa | 60 |
| gaaatgaaac | tgaaggagtg | tgtttccatc | ctcccacgga | aggaaagccc | tctgtccga | 120 |
| tcctccaaag | acggaaagct | gctggctgca | accttgctgc | tggcactgct | gtcttgctgc | 180 |
| ctcacggtgg | tgtctttcta | ccaggtggcc | gccctgcaag | gggacctggc | cagcctccgg | 240 |
| gcagagctgc | agggccacca | cgcggagaag | ctgccagcag | gagcaggagc | ccccaaggcc | 300 |
| ggcctggaga | agctccagc | tgtcaccgcg | ggactgaaaa | tctttgaacc | accagctcca | 360 |
| ggagaaggca | actccagtca | gaacagcaga | ataagcgtg | ccgttcaggg | tccagaagaa | 420 |
| acaggatctt | acacatttgt | tccatggctt | ctcagcttta | aaggggaag | tgccctagaa | 480 |
| gaaaagaga | ataaaatatt | ggtcaaagaa | actggttact | tttttatata | tggtcaggtt | 540 |
| ttatatactg | ataagaccta | cgccatggga | catctaattc | agaggaagaa | ggtccatgtc | 600 |
| tttggggatg | aattgagtct | ggtgactttg | tttcgatgta | ttcaaaatat | gcctgaaaca | 660 |
| ctacccaata | attcctgcta | ttcagctggc | attgcaaaac | tggaagaagg | agatgaactc | 720 |
| caacttgcaa | taccaagaga | aaatgcacaa | atatcactgg | atggagatgt | cacattttt | 780 |
| ggtgcattga | aactgctg | | | | | 798 |

<210> SEQ ID NO 32
<211> LENGTH: 266
<212> TYPE: PRT
<213> ORGANISM: human

<400> SEQUENCE: 32

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Gly Ser Tyr
    130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220

Ser Cys Tyr Ser Ala Gly Ile Ala Lys Leu Glu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Phe Gly Ala Leu Lys Leu Leu
            260                 265

<210> SEQ ID NO 33
<211> LENGTH: 1169
<212> TYPE: DNA
<213> ORGANISM: human

<400> SEQUENCE: 33
gaggttgaag gacccaggcg tgtcagccct gctccagaga ccttgggcat ggaggagagt      60
gtcgtacggc cctcagtgtt tgtggtggat ggacagaccg acatcccatt acgaggctg     120
ggacgaagcc accggagaca gtcgtgcagt gtggcccggg tgggtctggg tctcttgctg     180
ttgctgatgg gggctgggct ggccgtccaa ggctggttcc tcctgcagct gcactggcgt     240
ctaggagaga tggtcacccg cctgcctgac ggacctgcag gctcctggga gcagctgata     300
caagagcgaa ggtctcacga ggtcaaccca gcagcgcatc tcacagggc caactccagc     360
ttgaccggca gcggggggcc gctgttatgg gagactcagc tgggcctggc cttcctgagg     420
ggcctcagct accacgatgg ggcccttgtg gtcaccaaag ctggctacta ctacatctac     480
tccaaggtgc agctgggcgg tgtgggctgc ccgctgggcc tggccagcac catcacccac     540
ggcctctaca gcgcacacc ccgctacccc gaggagctgg agctgttggt cagccagcag     600
tcaccctgcg gacgggccac cagcagctcc cgggtctggt gggacagcag cttcctgggt     660
ggtgtggtac acctggaggc tgggggaggag gtgtcgtcc gtgtgctgga tgaacgcctg     720
gttcgactgc gtgatggtac ccggtcttac ttcgggcttt tcatggtgtg aaggaaggag     780
cgtggtgcat ggacatgggg tctgacacgt ggagaactca gagggtgcct caggggaaag     840
aaaactcacg aagcagaggc tgggcgtggt ggctctcgcc tgtaatccca gcactttggg     900
aggccaaggc aggcggatca cctgaggtca ggagttcgag accagcctgg ctaacatggc     960
aaaaccccat ctctactaaa aatacaaaaa ttagccggac gtggtggtgc ctgcctgtaa    1020
tccagctact caggaggctg aggcaggata attttgctta aacccgggag gcggaggttg    1080
cagtgagccg agatcacacc actgcactcc aacctgggaa acgcagtgag actgtgcctc    1140
aaaaaaaaaa aaaaaaaaaa aaaaaaaa                                      1169

<210> SEQ ID NO 34
<211> LENGTH: 240

```
<212> TYPE: PRT
<213> ORGANISM: human

<400> SEQUENCE: 34

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 35
<211> LENGTH: 2785
<212> TYPE: DNA
<213> ORGANISM: human
<220> FEATURE:
<221> NAME/KEY: misc_feature
<222> LOCATION: (49)..(49)
<223> OTHER INFORMATION: n equals a, c, g or t

<400> SEQUENCE: 35
agtgcagtat ctcatggagg tgtttggatg tctcttcctg tggggggtnc caaagcccat    60
gtctcttggc attttctttc agattctatc agccctctct ctttctctcc tgtctctctc   120
tttcattcat acactgagtc attcagagat ggcttctctc caactcggag ctgcaagtaa   180
ttctggatct ggtcacacac acaaagtccc cagagttgcc aatttatcta gttcatctgt   240
gcctgttcaa gatgatgtaa ctaaacattt accttcaggg aggtgttttcc aaagaatttt   300 catcgatata tagaaatcaa gagaaaatcc atactatcac caaatcaaga gaaattccat   360
actatcacca gttggccaac tttccaagtc tagtgcagaa atccaaggca cctcacacct   420
agagttccta tacctctgag actccagagg aagaacaag acagtgcaga aggatatgtt   480
agaacccact gaaaacctag aaggttaaaa aggaagcata ccctcctgac ctataagaaa   540
```

```
atttttcagtc tgcagggggga tatccttgtg gcccaagaca ttggtgttat catttgacta    600
agaggaaatt atttgtggtg agctctgagt gaggattagg accagggaga tgccaagttt    660
ctatcactta cctcatgcct gtaagacaag tgttttgttc caattgatga atggggataa    720
aacagttcag ccaatcactt atggggcaaa gaatgggaat ttgaagggtc tggtgcctgg    780
ccttgtcata cgtaaacaag agaggcatcg atgagtttta tctgagtcat ttgggaaagg    840
ataattcttg cagcaagcca ttttcctaaa cacagaagaa tagggggatt ccttaacctt    900
cattgttctc caggatcata ggtctcaggt aaaattaaaa attttcaggt cagaccactc    960
agtctcagaa aggcaaagta atttgccccca ggtcactagt ccaagatgtt attctctttg    1020
aacaaatgtg tatgtccagt cacatattct tcattcattc ctccccaaag cagtttttag    1080
ctgttaggta tattcgatca ctttagtcta ttttgaaaat gatatgagac gcttttaag    1140
caaagtctac agtttcccaa tgagaaaatt aatcctcttt cttgtctttc cagttgtgag    1200
acaaactccc acacagcact ttaaaaatca gttcccagct ctgcactggg aacatgaact    1260
aggcctggcc ttcaccaaga accgaatgaa ctataccaac aaattcctgc tgatcccaga    1320
gtcgggagac tacttcattt actcccaggt cacattccgt gggatgacct ctgagtgcag    1380
tgaaatcaga caagcaggcc gaccaaacaa gccagactcc atcactgtgg tcatcaccaa    1440
ggtaacagac agctaccctg agccaaccca gctcctcatg ggaccaagt ctgtatgcga    1500
agtaggtagc aactggttcc agcccatcta cctcggagcc atgttctcct tgcaagaagg    1560
ggacaagcta atggtgaacg tcagtgacat ctctttggtg gattacacaa agaagataa    1620
aaccttcttt ggagccttct tactatagga ggagagcaaa tatcattata tgaaagtcct    1680
ctgccaccga gttcctaatt ttctttgttc aaatgtaatt ataaccaggg gttttcttgg    1740
ggccgggagt aggggcatt ccacagggac aacggtttag ctatgaaatt tggggccaaa    1800
attcacact tcatgtgcct tactgatgag agtactaact ggaaaaaggc tgaagagagc    1860
aaatatatta ttaagatggg ttggaggatt ggcgagtttc taaatattaa gacactgatc    1920
actaaatgaa tggatgatct actcgggtca ggattgaaag agaaatattt caacacctcc    1980
tgctatacaa tggtcaccag tggtccagtt attgttcaat ttgatcataa atttgcttca    2040
attcaggagc tttgaaggaa gtccaaggaa agctctagaa aacagtataa actttcagag    2100
gcaaaatcct tcaccaattt ttccacatac tttcatgcct tgcctaaaaa aaatgaaaag    2160
agagttggta tgtctcatga atgttcacac agaaggagtt ggttttcatg tcatctacag    2220
catatgagaa aagctacctt tcttttgatt atgtacacag atatctaaat aaggaagtat    2280
gagtttcaca tgtatatcaa aaatacaaca gttgcttgta ttcagtagag ttttcttgcc    2340
cacctatttt gtgctgggtt ctaccttaac ccagaagaca ctatgaaaaa caagacagac    2400
tccactcaaa atttatatga acaccactag atacttcctg atcaaacatc agtcaacata    2460
ctctaaagaa taactccaag tcttggccag gcgcagtggc tcacacctgt aatcccaaca    2520
ctttgggagg ccaaggtggg tggatcatct aaggccggga gttcaagacc agcctgacca    2580
acgtggagaa accccatctc tactaaaaat acaaaattag ccgggcgtgg tagcgcatgg    2640
ctgtaatcct ggctactcag gaggccgagg cagaagaatt gcttgaactg gggaggcaga    2700
ggttgcggtg agcccagatc gcgccattgc actccagcct gggtaacaag agcaaaactc    2760
tgtccaaaaa aaaaaaaaaa aaaaa                                           2785
```

<210> SEQ ID NO 36

-continued

<211> LENGTH: 174
<212> TYPE: PRT
<213> ORGANISM: human

<400> SEQUENCE: 36

```
Met Arg Arg Phe Leu Ser Lys Val Tyr Ser Phe Pro Met Arg Lys Leu
 1               5                  10                  15

Ile Leu Phe Leu Val Phe Pro Val Val Arg Gln Thr Pro Thr Gln His
             20                  25                  30

Phe Lys Asn Gln Phe Pro Ala Leu His Trp Glu His Glu Leu Gly Leu
         35                  40                  45

Ala Phe Thr Lys Asn Arg Met Asn Tyr Thr Asn Lys Phe Leu Leu Ile
     50                  55                  60

Pro Glu Ser Gly Asp Tyr Phe Ile Tyr Ser Gln Val Thr Phe Arg Gly
 65                  70                  75                  80

Met Thr Ser Glu Cys Ser Glu Ile Arg Gln Ala Gly Arg Pro Asn Lys
                 85                  90                  95

Pro Asp Ser Ile Thr Val Val Ile Thr Lys Val Thr Asp Ser Tyr Pro
            100                 105                 110

Glu Pro Thr Gln Leu Leu Met Gly Thr Lys Ser Val Cys Glu Val Gly
        115                 120                 125

Ser Asn Trp Phe Gln Pro Ile Tyr Leu Gly Ala Met Phe Ser Leu Gln
    130                 135                 140

Glu Gly Asp Lys Leu Met Val Asn Val Ser Asp Ile Ser Leu Val Asp
145                 150                 155                 160

Tyr Thr Lys Glu Asp Lys Thr Phe Phe Gly Ala Phe Leu Leu
                165                 170
```

<210> SEQ ID NO 37
<211> LENGTH: 1116
<212> TYPE: DNA
<213> ORGANISM: human

<400> SEQUENCE: 37

```
atggccgagg atctgggact gagctttggg gaaacagcca gtgtggaaat gctgccagag      60
cacggcagct gcaggcccaa ggccaggagc agcagcgcac gctggctct cacctgctgc     120
ctggtgttgc tccccttcct tgcaggactc accacatacc tgcttgtcag ccagctccgg    180
gcccagggag aggcctgtgt gcagttccag gctctaaaag acaggagtt tgcaccttca     240
catcagcaag tttatgcacc tcttagagca gacggagata gccaagggc acacctgaca     300
gttgtgagac aaactcccac acagcacttt aaaaatcagt tcccagctct gcactgggaa    360
catgaactag gcctggcctt caccaagaac cgaatgaact ataccaacaa attcctgctg    420
atcccagagt cgggagacta cttcatttac tcccaggtca cattccgtgg gatgacctct    480
gagtgcagtg aaatcagaca gcaggccga ccaaacaagc cagactccat cactgtggtc     540
atcaccaagg taacagacag ctaccctgag ccaacccagc tcctcatggg gaccaagtct    600
gtatgcgaag taggtagcaa ctggttccag cccatctacc tcggagccat gttctccttg    660
caagaagggg acaagctaat ggtgaacgtc agtgacatct ctttggtgga ttacacaaaa    720
gaagataaaa ccttctttgg agccttctta ctataggagg agagcaaata tcattatatg    780
aaagtcctct gccaccgagt tcctaatttt ctttgttcaa atgtaattat aaccaggggt    840
tttcttgggg ccgggagtag gggcattcca cagggacaac ggtttagcta tgaaatttgg    900
ggcccaaaat ttcacacttc atgtgcctta ctgatgagag tactaactgg aaaaaggctg    960
```

```
aagagagcaa atatattatt aagatgggtt ggaggattgg cgagtttcta aatattaaga      1020
cactgatcac taaatgaatg gatgatctac tcgggtcagg attgaaagag aaatatttca      1080
acaccttcct gctatacaat ggtcaccagt ggtcca                                1116
```

<210> SEQ ID NO 38
<211> LENGTH: 251
<212> TYPE: PRT
<213> ORGANISM: human

<400> SEQUENCE: 38

```
Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250
```

<210> SEQ ID NO 39
<211> LENGTH: 534
<212> TYPE: DNA
<213> ORGANISM: human

<400> SEQUENCE: 39

```
atgtgtttga gccacttgga aaatatgcct ttaagccatt caagaactca aggagctcag      60
agatcatcct ggaagctgtg gctcttttgc tcaatagtta tgttgctatt tctttgctcc     120
ttcagttggc taatctttat ttttctccaa ttagagactg ctaaggagcc ctgtatggct     180
aagtttggac cattaccctc aaaatggcaa atgcatcttc tgaacctcc ttgcgtgaat      240 aaggtgtctg actggaagct ggagatactt cagaatggct tatatttaat ttatggccaa     300
```

```
gtggctccca atgcaaacta caatgatgta gctccttttg aggtgcggct gtataaaaac    360
aaagacatga tacaaactct aacaaacaaa tctaaaatcc aaaatgtagg agggacttat    420
gaattgcatg ttggggacac catagacttg atattcaact ctgagcatca ggttctaaaa    480
aataatacat actggggtat cattttacta gcaaatcccc aattcatctc ctag          534
```

<210> SEQ ID NO 40
<211> LENGTH: 177
<212> TYPE: PRT
<213> ORGANISM: human

<400> SEQUENCE: 40

```
Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
            100                 105                 110

Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser
```

<210> SEQ ID NO 41
<211> LENGTH: 5307
<212> TYPE: DNA
<213> ORGANISM: human
<220> FEATURE:
<221> NAME/KEY: misc_feature
<222> LOCATION: (4242)..(4242)
<223> OTHER INFORMATION: n equals a, c, g or t
<220> FEATURE:
<221> NAME/KEY: misc_feature
<222> LOCATION: (4471)..(4471)
<223> OTHER INFORMATION: n equals a, c, g or t
<220> FEATURE:
<221> NAME/KEY: misc_feature
<222> LOCATION: (4523)..(4523)
<223> OTHER INFORMATION: n equals a, c, g or t
<220> FEATURE:
<221> NAME/KEY: misc_feature
<222> LOCATION: (4529)..(4529)
<223> OTHER INFORMATION: n equals a, c, g or t
<220> FEATURE:
<221> NAME/KEY: misc_feature
<222> LOCATION: (4531)..(4531)
<223> OTHER INFORMATION: n equals a, c, g or t
<220> FEATURE:
<221> NAME/KEY: misc_feature
<222> LOCATION: (4545)..(4545)
<223> OTHER INFORMATION: n equals a, c, g or t

<400> SEQUENCE: 41

| | | | | | |
|---|---|---|---|---|---|
| attccctcgg | cgggccgagc | ctcccctctc | tcccgcccct | cctcctccct | ttcccacccc | 60 |
| tcggagtaga | gctgcacatg | cggctgctcc | ctgctccgtc | ccgcccagcc | actgtcgcgc | 120 |
| aggaacgggt | ccctgcagcc | cccagccgat | ggcaggacag | tagccgcctg | tcagaggtcg | 180 |
| tgaacggctg | aggcagacgc | agcggctccc | gggcctcaag | agagtggatg | tctccggagg | 240 |
| ccatgggcta | cccggaggtg | gagcgcaggg | aactcctgcc | tgcagcagcg | ccgcgggagc | 300 |
| gagggagcca | gggctgcggg | tgtggcgggg | ccctgcccg | gcgggcgaa | gggaacagct | 360 |
| gcctgctctt | cctgggtttc | tttggcctct | cgctggccct | ccacctgctg | acgttgtgct | 420 |
| gctacctaga | gttcgctcg | gagttgcggc | gggaacgtgg | agccgagtcc | cgccttggcg | 480 |
| gctcgggcac | ccctggcacc | tctggcaccc | taagcagcct | cggtggcctc | gaccctgaca | 540 |
| gccccatcac | cagtcacctt | gggcagccgt | cacctaagca | gcagccattg | gaaccgggag | 600 |
| aagccgcact | ccactctgac | tcccaggacg | ggcaccagat | ggccctattg | aatttcttct | 660 |
| tccctgatga | aaagccatac | tctgaagaag | aaagtaggcg | tgttcgccgc | aataaaagaa | 720 |
| gcaaaagcaa | tgaaggagca | gatggcccag | ttaaaaacaa | gaaaaaggga | aagaagcag | 780 |
| gacctcctgg | acccaatggc | cctccaggac | ccccaggacc | tccaggaccc | cagggacccc | 840 |
| caggaattcc | agggattcct | ggaattccag | gaacaactgt | tatgggacca | cctggtcctc | 900 |
| caggtcctcc | tggtcctcaa | ggaccccctg | gcctccaggg | accttctggt | gctgctgata | 960 |
| aagctggaac | tcgagaaaac | cagccagctg | tggtgcatct | acagggccaa | gggtcagcaa | 1020 |
| ttcaagtcaa | gaatgatctt | tcaggtggag | tgctcaatga | ctggtctcgc | atcactatga | 1080 |
| accccaaggt | gtttaagcta | catccccgca | gcggggagct | ggaggtactg | gtggacggca | 1140 |
| cctacttcat | ctatagtcag | gtagaagtat | actacatcaa | cttcactgac | tttgccagct | 1200 |
| atgaggtggt | ggtggatgag | aagcccttcc | tgcagtgcac | acgcagcatc | gagacgggca | 1260 |
| agaccaacta | caacacttgc | tataccgcag | gcgtctgcct | cctcaaggcc | cggcagaaga | 1320 |
| tcgccgtcaa | gatggtgcac | gctgacatct | ccatcaacat | gagcaagcac | accacgttct | 1380 |
| ttggggccat | caggctgggt | gaagccctg | catcctagat | tccccccatt | ttgcctctgt | 1440 |
| ccgtgcccct | tccctgggtt | tgggagccag | gactcccaga | acctctaagt | gctgctgtgg | 1500 |
| agtgaggtgt | attggtgttg | cagccgcaga | gaaatgcccc | agtgttattt | attccccagt | 1560 |
| gactccaggg | tgacaaggcc | tgcttgactt | tccagaatga | ccttgagtta | acaggacagt | 1620 |
| tgatggagcc | ccagggttta | catgaagcag | aaccttcttt | ggttccatgt | tgactgactt | 1680 |
| atggcatgac | tcttcaaccc | cgaggtccct | gttgtcagat | ctattgtttg | ttgcactaaa | 1740 |
| atgaggatcc | agggcagcag | gccagagaaa | gcaaaggtgc | actccagact | ctggggtgg | 1800 |
| acatctgacc | ccaaggggc | tgctgctcct | ctcttgggta | gggtagtggc | tggggtggag | 1860 |
| tgggaagkga | gcattgcagc | ctaagaagaa | ggccagagag | ggaaaaggca | ggtgcttttg | 1920 |
| gcagagacca | taagagaaac | ctgccaagga | gcatccttgg | cagtgggaat | gttctttctg | 1980 |
| ctctatactg | tggcctgcag | gagggttgga | gtgctcttcc | cactccagct | gacagccaca | 2040 |
| ccgtggcagc | ttgctgggct | ttgggaagtt | tgctgtgctt | tggaacaatc | acagggaatg | 2100 |
| gccacaaacc | tgcccgccta | agaccctgaa | tccgtacttg | ggtcacatga | ctctcatttt | 2160 |
| atttacagct | gtgctccaca | ctcagaaaat | tccctggggt | caccttctag | ttgccccat | 2220 |

-continued

```
tcccagcctg actagaactc ctgtcttctt tctccatgga gcctacctct gtctgagaca    2280
ggtgcctaac ctgggacctg tggtcatgtg agtctgggat attctttagc ttacctgggc    2340
acagacagaa ttttccattt attaagcagt acagatgttt ttcatccatt cctaatcaaa    2400
ttctgtctgg ggacgaaggg ttggacggga tgacctccag aagtcccttc aatttctagt    2460
acctgtgact cttagccctc accacagcct tctaaattcc caaatcctag actgctcctg    2520
ggcattagca aggcagagcc ttttttacctg gcctagaaag gcaagggg t gaggatagga    2580
cagagggatt tgttcaagt ttgctgcaac ccaagtggac gttaggccag gccttatctg    2640
aaaggccagc agctgatgct gtactaaccc agtctttctt cactctggct tcaaaaagcc    2700
acagcagagc attgtcaccg caggtcccca tgctgctccc ctaaagccag gctcaggaga    2760
agccagtgtc taggcactga gcagggatct gcccctagt tcaggtccaa attccacttc    2820
ccctaaaccc caagcttccc aacagatcat atggtaggac cctcgagagc cttacttcaa    2880
agtgcctggg ctcagcctgg tttctgggtg ctagatccag cccaaacctg ggaaggccag    2940
ccttgtacag tctgctcctc ttgttcctga aatgtgtttc cttttcagga gatggggaat    3000
aatttccttc aggcagctga aattccacca gaacagcggg tacttattc tcaagctgtg    3060
ccttcccttt ctaagcaacc acactgcttg gcccttcaag ggtcagggtg agacgtgatg    3120
ggctaggcct ccgttgtctg gttgctaatg acagccttgc aacccaaggt gaggtgaact    3180
ccagcatgt gtctggccct aactcctata agtgcctcg gacagtccgc agttgtagca    3240
gaaaccaaca agaaccactc cttcatgttt ggaaaataat ttctcttgta ttatctcctt    3300
tgaagaaggc aaggctgata atatgacaaa catcattgtt tagatgaggc tcagagaggt    3360
agcactctca gagtgttttg accagtttaa gccgcagacc tggagcttca gccaggtctg    3420
actccaaagc tgttccatta caccacagca ttgtgtggaa tttgaggtct agagagaacc    3480
aataaaagtg gtaattggga actgaaatcc ttgagagttc cggggagaaa cccagagatg    3540
cctgatttca ttcctcgatg gtaatacccg tcctctcggc tgccaggggc tctgtggcaa    3600
aaagagtcag acatttcttt ggaaaacagc gaacagcctt agagctcttg tgttcagaag    3660
aatcttcctg gcacaatgtt ggagcagcag gcctctggga cccacagaac ttgtggcctt    3720
tatgttcttt cacccatcct aggaaccagc caaccatcat gtgtagagcc cctactgtgg    3780
gcaaagtcct cctttcatta ccctacagac agcttacagg agccagcctg cttcccacaa    3840
ctactagtgt gactccttat ctctttccac cataccttag agactttgat actaccaggg    3900
tctctcaggg atggagggaa gacctgaaag agaggactgg ttctgaggcc agaaaggtgt    3960
gaggagagag gaggaaaagt cttcctaatt gtgcccctaa agagcatcct gataccattc    4020
tattctccag acatggaggg gatgataaag gaaataggat ctccactgga cccttgattc    4080
attctgaacc ctccaaagga actctaagag ggcgagggat gatgagggaa gcaataggta    4140
gctggggagc cctattgctg ctaagtcatt ggcaaagtgc aaagcaattt actgatgaga    4200
gaatgtggaa atagatgtgc agtttggaat tatgttggtg tnaatttgcc agaggaccaa    4260
tgcttgcatg gagaatggac gaggacattt gtgggcaagc agatgacaga ggtttgaagg    4320
agaatggcat ggcaggagtc tctgccagtt acttgggctt caacagccaa gctggcacaa    4380
aagacagctg gcgaggctg ctcggctact ggttacctgg agaagtagta tttgcctatt    4440
tcccccttca tccatcctga gccaaatttc ntttgctgaa caggaaagag cyaggaaccc    4500
tggaggtaaa caaagacttt ganccctgtnt nagtgtatgt gttntgtaa cttcctgtgg    4560
agtgcaaata gattcagaga aatttagagc taaaaaggcc cttagaggga atctagccca    4620
```

-continued

```
acctacattc caccctgtta cttatgtaga aactgaggcc cagagaggga agatgacctg    4680
ccccaagtgg tgagcaagca ccaacctcca gactcagcag agtgaggggg taaagcagtt    4740
cctgtcccac atggccatct tctttcttcc acccacaaac tccaggctgg aagtacttgg    4800
cccccttcag gagcctggcc aggcagggag agagtagctg cagccttcat cagaactctt    4860
cctcctccca aggcattctc ccagctctag cctctggact ggaaagcaca agactggccc    4920
agtgccagca agtccttagg ctactgtaat gctgcctcag acccatccc tgcctggagg      4980 ctcctctagg ccctgtgagc acaaagaaga aagctgattt ttgtctttta atccatttca    5040
ggactctctc caggagggct cggggtgtgt catttctata ttcctccagc tgggattggg    5100
gggtgggctt tgttgtgaga atggcctgga gcaggcccaa tgctgctttt ggggtcagc     5160 atccagtgtg agatactgtg tatataaact atatataatg tatataaact gggatgtaag    5220
tttgtgtaaa ttaatgtttt attctttgca aataaaacgc tttccccgtc aaaaaaaaaa    5280
aaaaaaaaaa aaaaaaaaaa aaaaaaa                                        5307
```

<210> SEQ ID NO 42
<211> LENGTH: 391
<212> TYPE: PRT
<213> ORGANISM: human

<400> SEQUENCE: 42

```
Met Gly Tyr Pro Glu Val Glu Arg Arg Glu Leu Leu Pro Ala Ala Ala
1               5                   10                  15

Pro Arg Glu Arg Gly Ser Gln Gly Cys Gly Cys Gly Gly Ala Pro Ala
            20                  25                  30

Arg Ala Gly Glu Gly Asn Ser Cys Leu Leu Phe Leu Gly Phe Phe Gly
        35                  40                  45

Leu Ser Leu Ala Leu His Leu Leu Thr Leu Cys Cys Tyr Leu Glu Leu
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
    130                 135                 140

Pro Tyr Ser Glu Glu Ser Arg Arg Val Arg Arg Asn Lys Arg Ser
145                 150                 155                 160

Lys Ser Asn Glu Gly Ala Asp Gly Pro Val Lys Asn Lys Lys Gly
                165                 170                 175

Lys Lys Ala Gly Pro Pro Gly Pro Asn Gly Pro Gly Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Gly Pro Pro Gly Pro Pro Gly Pro
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
```

```
              245                 250                 255
Gly Ser Ala Ile Gln Val Lys Asn Asp Leu Ser Gly Val Leu Asn
            260                 265                 270

Asp Trp Ser Arg Ile Thr Met Asn Pro Lys Val Phe Lys Leu His Pro
            275                 280                 285

Arg Ser Gly Glu Leu Glu Val Leu Val Asp Gly Thr Tyr Phe Ile Tyr
            290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
            355                 360                 365

Ile Ser Ile Asn Met Ser Lys His Thr Thr Phe Phe Gly Ala Ile Arg
    370                 375                 380

Leu Gly Glu Ala Pro Ala Ser
385                 390

<210> SEQ ID NO 43
<211> LENGTH: 24
<212> TYPE: DNA
<213> ORGANISM: human

<400> SEQUENCE: 43
gcgccatggc taagtttgga ccat                                          24

<210> SEQ ID NO 44
<211> LENGTH: 27
<212> TYPE: DNA
<213> ORGANISM: human

<400> SEQUENCE: 44
gcgaagcttt caagtctcta ggagatg                                       27

<210> SEQ ID NO 45
<211> LENGTH: 26
<212> TYPE: DNA
<213> ORGANISM: human

<400> SEQUENCE: 45
gcggatcccg agactgctaa ggagcc                                        26

<210> SEQ ID NO 46
<211> LENGTH: 31
<212> TYPE: DNA
<213> ORGANISM: human

<400> SEQUENCE: 46
gcggatccct aggagatgaa ttggggattt g                                  31

<210> SEQ ID NO 47
<211> LENGTH: 32
<212> TYPE: DNA
<213> ORGANISM: human

<400> SEQUENCE: 47
gcgggatccg ccatcatgcc tttaagccat tc                                 32
```

<210> SEQ ID NO 48
<211> LENGTH: 31
<212> TYPE: DNA
<213> ORGANISM: human

<400> SEQUENCE: 48
gcggatccct aggagatgaa ttggggattt g            31

<210> SEQ ID NO 49
<211> LENGTH: 35
<212> TYPE: DNA
<213> ORGANISM: human

<400> SEQUENCE: 49
ctagctagct agvvvagcgc cccaccgggg gtccc        35

<210> SEQ ID NO 50
<211> LENGTH: 61
<212> TYPE: DNA
<213> ORGANISM: human

<400> SEQUENCE: 50
ctagctagct agctatccat atgatgttcc agattatgct cagcgcccca ccgggggtcc    60
c                                                                   61

<210> SEQ ID NO 51
<211> LENGTH: 40
<212> TYPE: DNA
<213> ORGANISM: human

<400> SEQUENCE: 51
aaggaaaaaa gcgggccgct cacacccaca ggtctcccag        40

<210> SEQ ID NO 52
<211> LENGTH: 35
<212> TYPE: DNA
<213> ORGANISM: human

<400> SEQUENCE: 52
agacccaagc ttgtgggctc ttgaaacccg gcatg        35

<210> SEQ ID NO 53
<211> LENGTH: 36
<212> TYPE: DNA
<213> ORGANISM: human

<400> SEQUENCE: 53
gaaagatctg ggctctgccg gcggggaccc tgggac       36

<210> SEQ ID NO 54
<211> LENGTH: 35
<212> TYPE: DNA
<213> ORGANISM: human

<400> SEQUENCE: 54
agacccaagc ttgtgggctc ttgaaacccg gcatg        35

<210> SEQ ID NO 55
<211> LENGTH: 36
<212> TYPE: DNA
<213> ORGANISM: human

<400> SEQUENCE: 55

```
-continued gaaagatctg ggctctgccg gcggggaccc tgggac                              36

<210> SEQ ID NO 56
<211> LENGTH: 61
<212> TYPE: DNA
<213> ORGANISM: human

<400> SEQUENCE: 56
ctagctagcc cagcgccccg actacaagga cgacgatgac aaggagactg ctaaggagcc    60
c                                                                    61

<210> SEQ ID NO 57
<211> LENGTH: 27
<212> TYPE: DNA
<213> ORGANISM: human

<400> SEQUENCE: 57
ccgctcgagc tatagtaaga aggctcc                                        27
```